(12) United States Patent
Montrasio et al.

(10) Patent No.: US 10,392,447 B2
(45) Date of Patent: Aug. 27, 2019

(54) HUMAN-DERIVED ANTI-DIPEPTIDE REPEATS (DPRS) ANTIBODY

(71) Applicant: Neurimmune Holding AG, Schlieren (CH)

(72) Inventors: Fabio Montrasio, Schindellegi (CH); Jan Grimm, Dübendorf (CH)

(73) Assignee: Neurimmune Holding AG, Schlieren (CH)

( * ) Notice: Subject to any disclaimer, the term of this patent is extended or adjusted under 35 U.S.C. 154(b) by 0 days.

(21) Appl. No.: 15/508,343

(22) PCT Filed: Sep. 30, 2015

(86) PCT No.: PCT/EP2015/072516
§ 371 (c)(1),
(2) Date: Mar. 2, 2017

(87) PCT Pub. No.: WO2016/050822
PCT Pub. Date: Apr. 7, 2016

(65) Prior Publication Data
US 2017/0247471 A1    Aug. 31, 2017

(30) Foreign Application Priority Data

Sep. 30, 2014  (EP) ................................ 14187180
Aug. 7, 2015   (EP) ................................ 15180310

(51) Int. Cl.
*C07K 16/44*     (2006.01)
*G01N 33/68*     (2006.01)

(52) U.S. Cl.
CPC ......... *C07K 16/44* (2013.01); *G01N 33/6896* (2013.01); *C07K 2317/21* (2013.01); *C07K 2317/33* (2013.01); *C07K 2317/76* (2013.01); *C07K 2317/92* (2013.01); *G01N 2800/2814* (2013.01)

(58) Field of Classification Search
None
See application file for complete search history.

(56) References Cited

U.S. PATENT DOCUMENTS

| | | | |
|---|---|---|---|
| 2004/0110938 A1* | 6/2004 | Parekh .................. | C07K 14/47 536/23.5 |
| 2010/0040606 A1* | 2/2010 | Lantto ................ | C07K 16/1027 424/133.1 |
| 2011/0027268 A1* | 2/2011 | Kahnert ................ | C07K 16/30 424/133.1 |
| 2013/0164293 A1* | 6/2013 | Florio .................. | C07K 16/18 424/136.1 |
| 2013/0315821 A1* | 11/2013 | D'Souza .......... | A61K 47/48746 424/1.53 |
| 2014/0206102 A1 | 7/2014 | Petrucelli et al. | |
| 2014/0303033 A1* | 10/2014 | Ehricht ............ | G01N 33/56938 506/9 |
| 2017/0355756 A1* | 12/2017 | Julien .................... | C07K 16/18 |
| 2017/0369590 A1* | 12/2017 | De Goeij ............. | A61K 39/395 |

FOREIGN PATENT DOCUMENTS

| | | | |
|---|---|---|---|
| WO | WO 2008068048 | * | 6/2008 |
| WO | WO-2014/114303 A1 | | 7/2014 |
| WO | WO 2014/114660 | | 7/2014 |
| WO | WO 2016/050822 | | 4/2016 |

OTHER PUBLICATIONS

Chen "Enhancement and destruction of antibody function by somatic mutation: unequal occurrence is controlled by V gene combinatorial associations" The EMBO Journal vol. 14 No. 1 2 pp. 2784-2794 (Year: 1995).*
Kussie "A Single Engineered Amino Acid Substitution Changes Antibody Fine Specificity" J immunol 152(1):146-52 (Year: 1994).*
USCAFC "Abbvie v Janssen" Abbvie v Janssen 759 F.3d 1285 (Fed. Cir. 2014) (Year: 2014).*
Biology-online "Expression vector". accessed on Mar. 8, 2019 (Year: 2019).*
Lodish "DNA Cloning with plasmid vectors" Molecular cell biology 4th edition (excerpt) (Year: 2000).*
Mackenzie et al., "Dipeptide repeat protein pathology in C9ORF72 mutation cases: clinico-pathological correlations," Acta Neuropathol. 126(6):859-79 (2013).
Mann et al., "Dipeptide repeat proteins are present in the p62 positive inclusions in patients with frontotemporal lobar degeneration and motor neurone disease associated with expansions in C9ORF72," Acta Neuropathologica Communications. 1:68 (2013) (13 pages).
Mizielinska et al., "C9orf72 repeat expansions cause neurodegeneration in *Drosophila* through arginine-rich proteins," Science. 345(6201):1192-4 (2014).
Mori et al., "The C9orf72 GGGGCC repeat is translated into aggregating dipeptide-repeat proteins in FTLD/ALS," Science. 339(6125):1335-8 (2013) supplementary materials (13 pages).
Mori et al., "The C9orf72 GGGGCC repeat is translated into aggregating dipeptide-repeat proteins in FTLD/ALS," Science. 339(6125):1335-8 (2013).
Steinitz, "Three decades of human monoclonal antibodies: past, present and future developments," Hum Antibodies. 18(1-2):1-10 (2009).
Zu et al., "RAN proteins and RNA foci from antisense transcripts in C9ORF72 ALS and frontotemporal dementia," Proc Natl Acad Sci U S A. 110(51):E4968-77 (2013).

(Continued)

*Primary Examiner* — Adam Weidner
(74) *Attorney, Agent, or Firm* — Fish & Richardson P.C.

(57) ABSTRACT

Provided are novel human-derived dipeptide repeat (DPR) specific antibodies as well as synthetic variants and biotechnological derivatives thereof, preferably capable of binding C9ORF72 DPRs, as well as methods related thereto. Assays, kits, and solid supports related to antibodies specific for DPRs and DPR proteins such C9ORF72 DPRs are also disclosed. The antibody of the present invention can be used in pharmaceutical and diagnostic compositions for DPR protein-targeted immunotherapy and diagnostics.

120 Claims, 35 Drawing Sheets

Specification includes a Sequence Listing.

(56) References Cited

OTHER PUBLICATIONS

International Search Report and Written Opinion for International Patent Application No. PCT/EP2015/072516, dated Apr. 19, 2016 (22 pages).

International Preliminary Report on Patentability for International Patent Application No. PCT/EP2015/072516, dated Apr. 4, 2017 (15 pages).

Vajdos et al., "Comprehensive Functional Maps of the Antigen-binding Site of an Anti-ErbB2 Antibody Obtained with Shotgun Scanning Mutagenesis," J. Mol. Biol., 2002; 320 (2): 415-428.

Rajpal et al., "A general method for greatly improving the affinity of antibodies by using combinatorial libraries," PNAS, 2005; 102, 8466-8471.

Lippow et al., "Computational design of antibody affinity improvement beyond in vivo maturation," Nature Biotechnology, 2007; 25 (10): 1171-1176.

Beck et al., "Strategies and challenges for the next generation of therapeutic antibodies," Nature reviews immunology, 2010, 10(5):345-352.

Freibaum et al., "The role of dipeptide repeats in C9ORF72-related ALS-FTD," Frontiers in molecular neuroscience, 2017, 10:35.

Extended European Search Report in European Application No. 14187180.6, dated Jul. 28, 2015, 14 pages.

Hazenbos et al., "Novel staphylococcal glycosyltransferases SdgA and SdgB mediate immunogenicity and protection of virulence-associated cell wall proteins," PLoS pathogens, 2013, 9(10):e1003653.

Partial European Search Report in European Application No. 14187180.6, dated Mar. 19, 2015, 9 pages.

May et al., "C9orf72 FTLD/ALS-associated Gly-Ala dipeptide repeat proteins cause neuronal toxicity and Unc119 sequestration", ACTA Neuropathologica, Springer Verlag, Berlin, DE., 2014, 128(4):485-503.

\* cited by examiner

FIG. 1A NI-308.18F7 VH (variable heavy chain sequence VH) (SEQ ID NO: 2)
```
FR1------------------------------CDR1-FR2-----------CDR2--------
CQVQLQESGPGLVKPSETLSVTCTVSGGSINDYYWNWIRQPAGKGLEWIGRIYASGTINYNP
-----FR3-------------------------------CDR3-----------FR4--------
SLQSRVTMSIDTSKNQFSLDLISVSAADTAVYYCARWGQVVGDYYGMDVWGQGTTVTVSS
```

NI-308.18F7 VK (variable light chain sequence VK) (SEQ ID NO: 4)
```
FR1-------------------------CDR1------------FR2-------------CDR2---
CEIVLTQSPLSLSVTPGEPASISCKSSQSLQHTNGYNYLDWYLLKPGQSPQLLIFLTSNRAS
FR3-------------------------------CDR3--FR4---------
GVPDRFSGSGSGTNFTLKISRVEAEDVGVYYCMEGIQLWTFGQGTKLEIK
```

NI-308.18F7 VK - PIMC (variable light chain sequence VK) (SEQ ID NO: 6)
```
FR1-------------------------CDR1------------FR2-------------CDR2---
CDIVMTQSPLSLSVTPGEPASISCKSSQSLQHTNGYNYLDWYLLKPGQSPQLLIFLTSNRAS
FR3-------------------------------CDR3--FR4----------
GVPDRFSGSGSGTNFTLKISRVEAEDVGVYYCMEGIQLWTFGQGTKVEIK
```

FIG. 1B NI-308.15O7 VH (variable heavy chain sequence VH) (SEQ ID NO: 8)
```
FR1-----------------------------CDR1-FR2-----------CDR2----------
CQVQLVESGGGVVQPGRSLRLSCAASGFTFSNHAMHWVRQAPGKGLEWVAVISYDGENTYYA
-----FR3-------------------------------CDR3-----------FR4--------
DSIEGRFTISRDNFKNTLFLQMYSLTADDTAMYFCARGGRRGHFTSYYLDYWGQGTLVTVSS
```

NI-308.15O7 VK (variable light chain sequence VK) (SEQ ID NO: 10)
```
FR1-----------------------CDR1-------FR2-------------CDR2---FR3--
CDIQMTQSPSSLSASVGDRVTITCRASQNIDKYLNWYQQIPGKAPKLLIYAASSLHSGVPSR
------------------------------CDR3-----FR4---------
FSGSGSGTDFSLTISSLQPEDFAIYYCQQSYSSFRTFGQGTKLEIK
```

NI-308.15O7 VK - PIMC (variable light chain sequence VK) (SEQ ID NO: 12)
```
FR1-----------------------CDR1-------FR2-------------CDR2---FR3--
CDIQMTQSPSSLSASVGDRVTITCRASQNIDKYLNWYQQIPGKAPKLLIYAASSLHSGVPSR
------------------------------CDR3-----FR4-------
FSGSGSGTDFSLTISSLQPEDFAIYYCQQSYSSFRTFGQGTKVEIK
```

FIG. 1C NI-308.28G1 VH (variable heavy chain sequence VH) (SEQ ID NO: 22)
```
FR1------------------------------CDR1------FR2------------CDR2---------
CQVQLQESGPRLVKPSETLSLTCTVAGGSVNSYYWTWIQQSPGKGLEWLGRIYIAGRTNYNP
----FR3---------------------------------CDR3----------FR4--------
SLTSRIALSVDTSRNQLSLKLTSVTAADTAIYYCARWGAESGDYYYGVDVWGPGTLVTVSS
```

NI-308.28G1 VK (variable light chain sequence VK) (SEQ ID NO: 24)
```
FR1----------------------CDR1-----------FR2------------CDR2----
CEIVMTQSPLSLPVTGEPASISCKSSEGLLHSNGYTYLDWYLQKPGQAPQLLIFLASNRAA
FR3---------------------------CDR3-----FR3--------
GVPDRFSGSGSGTDFTLKISRVEAEDVGVYYCMQAIQSPWTFGPGTKVEIK
```

NI-308.28G1 VH - PIMC (variable heavy chain sequence VH) (SEQ ID NO: 26)
```
FR1------------------------------CDR1------FR2------------CDR2---------
CQVQLQESGPRLVKPSETLSLTCTVAGGSVNSYYWTWIQQSPGKGLEWLGRIYIAGRTNYNP
----FR3---------------------------------CDR3----------FR4--------
SLTSRIALSVDTSRNQLSLKLTSVTAADTAIYYCARWGAESGDYYYGVDVWGPGTTVTVSS
```

NI-308.28G1 VK - PIMC (variable light chain sequence VK) (SEQ ID NO: 28)
```
FR1----------------------CDR1-----------FR2------------CDR2----
CDIVMTQSPLSLPVTGEPASISCKSSEGLLHSNGYTYLDWYLQKPGQAPQLLIFLASNRAA
FR3---------------------------CDR3-----FR3--------
GVPDRFSGSGSGTDFTLKISRVEAEDVGVYYCMQAIQSPWTFGPGTKVEIK
```

FIG. 1D NI-308.45C2 VH (variable heavy chain sequence VH) (SEQ ID NO: 30)
```
FR1----------------------------CDR1---------FR2------------CDR2------
CQLQLQESGPGLVKPSQILSLTCAISGDSVFSNSAAWNWIRQSPSRGLEWLGRTYYRSKWDN
---------FR3-------------------------------CDR3-------------FR4---
DYAPSVKSRISINPDTSKNQFSLQLNSVTPEDTAVYYCAREVAYCGGDCYSVSFDYWGQGTL
------
VTVSS
```

NI-308.45C2 VK (variable light chain sequence VK) (SEQ ID NO: 32)
```
FR1----------------------CDR1-----------FR2------------CDR2---
CEIVMTQSPLSLPVTGEPASISCRSSQSLLQSNGYTYLDWYLQKPGQSPQLLIYLGSNRAS
FR3---------------------------CDR3-----FR4--------
GVPDRFSGSGSGTDFTLKISRVEAEDVGVYYCMQALQTPLTFGGGTKVEIK
```

NI-308.45C2 VH - PIMC (variable heavy chain sequence VH) (SEQ ID NO: 34)
```
FR1----------------------------CDR1---------FR2------------CDR2------
CQLQLQQSGPGLVKPSQILSLTCAISGDSVFSNSAAWNWIRQSPSRGLEWLGRTYYRSKWDN
---------FR3-------------------------------CDR3-------------FR4---
DYAPSVKSRISINPDTSKNQFSLQLNSVTPEDTAVYYCAREVAYCGGDCYSVSFDYWGQGTL
------
VTVSS
```

FIG. 1D Cont. NI-308.45C2 VK - PIMC (variable light chain sequence VK) (SEQ ID NO: 36)
```
FR1-----------------------------CDR1------------FR2------------CDR2---
CDIVMTQSPLSLPVTPGEPASISCRSSQSLLQSNGYTYLDWYLQKPGQSPQLLIYLGSNRAS
FR3-------------------------------CDR3-----FR4-------
GVPDRFSGSGSGTDFTLKISRVEAEDVGVYYCMQALQTPLTFGGGTKVEIK
```

FIG. 1E NI-308.24E11 VH (variable heavy chain sequence VH) (SEQ ID NO: 38)
```
FR1------------------------------CDR1------FR2------------CDR2--------
CQVQLQESGPGLVKPSETLSLTCTVSTTSLRSYFWSWIRQPPGKGLEWIGYVYYSGSTIYNP
----FR3-------------------------------CDR3---------------FR3------
SLKNRVTISIDTSKNQFSLNLRSVTAADTAMYFCARGVPAETDARDFPPYYFDHWGQGTLVT
---
VSS
```

NI-308.24E11 VK (variable light chain sequence VK) (SEQ ID NO: 40)
```
FR1--------------------------CDR1--------FR2------------CDR2---FR3---
CDIQLTQSPSSLSASVGNRITFTCQASQDIRYYLNWYQQKPGKAPKLLIYDVSNLDTGVPPR
-----------------------------CDR3-----FR4-------
FSGSGSGTNFTFTISSLQPEDIAVYYCQQYEGLPVTFGGGTKVEIK
```

NI-308.24E11 VK - PIMC (variable light chain sequence VK) (SEQ ID NO: 42)
```
FR1--------------------------CDR1--------FR2------------CDR2---FR3---
CDIQMTQSPSSLSASVGNRITFTCQASQDIRYYLNWYQQKPGKAPKLLIYDVSNLDTGVPPR
-----------------------------CDR3-----FR4-------
FSGSGSGTNFTFTISSLQPEDIAVYYCQQYEGLPVTFGGGTKVEIK
```

FIG. 1F NI-308.5G2 VH (variable heavy chain sequence VH) (SEQ ID NO: 14)
```
FR1-----------------------------CDR1------FR2------------CDR2---------
CEVQLVQSGADLRNPGASVTVSCTASGYHFADNAINWLRQAPGQRLEWMGWINIYSGNTKYS
------FR3---------------------------------CDR3-----------FR4---------
QNFQGRVTFTRNTSASTAFMHLRSLRSEDTAVYFCARDPDSSGYYLPYFDYWGQGTLVTVSS
```

NI-308.5G2 VK (variable light chain sequence VK) (SEQ ID NO: 16)
```
FR1------------------------CDR1-------------FR2------------CDR2---
CDIQLTQSPDSLTLSLGERATINCKSSQSVFYNSNNKNYLAWYQQKPGQPPKLLMYWASTRE
-FR3-------------------------------CDR3-----FR4-------
SGVTDRFSGSGSGTDFTLTITNLQAEDVAVYYCQQFYSSPLTFGGGTKVEIK
```

NI-308.5G2 VH - PIMC (variable heavy chain sequence VH) (SEQ ID NO: 18)
```
FR1-----------------------------CDR1------FR2------------CDR2---------
CQVQLVQSGADLRNPGASVTVSCTASGYHFADNAINWLRQAPGQRLEWMGWINIYSGNTKYS
------FR3---------------------------------CDR3-----------FR4---------
QNFQGRVTFTRNTSASTAFMHLRSLRSEDTAVYFCARDPDSSGYYLPYFDYWGQGTLVTVSS
```

FIG. 1F Cont. NI-308.5G2 VK-PIMC (variable light chain sequence VK) (SEQ ID NO: 20)
```
FR1-----------------------------CDR1-----------------FR2------------CDR2---
CDIVMTQSPDSLTLSLGERATINCKSSQSVFYNSNNKNYLAWYQQKPGQPPKLLMYWASTRE
-FR3---------------------------------CDR3-----FR4-------
SGVTDRFSGSGSGTDFTLTITNLQAEDVAVYYCQQFYSSPLTFGGGTKVEIK
```

FIG. 1G NI-308.46E9 VH (variable heavy chain sequence VH) (SEQ ID NO: 44)
```
FR1-------------------------CDR1---------FR2-----------CDR2------
CQVQLQESGPGLVKPSETLSLTCTVSGASISGSTYYWGIRQPPGKGLEYIGRIYYSGSTYY
------FR3---------------------------------CDR3---------FR4--------
NPSLKSRATISVDTSKNQLSLTLSSVTAADTAVYYCVRPFYAGSGNSPFDYWGQGTLVTVSS
```

NI-308.46E9 VK (variable light chain sequence VK) (SEQ ID NO: 46)
```
FR1------------------------CDR1-------FR2------------CDR2---FR3--
CEIVLTQSPATVSVSPGERATLSCRASQSVSTNLAWYQQKPGQPPRLLIYGASTRATGIPAR
-----------------------------CDR3-----FR4--------
FSGSGSGAEFTLTISSLQSEDFVVYYCQQYNNWPPAFGGGTKVEIK
```

NI-308.46E9 VH - PIMC (variable heavy chain sequence VH) (SEQ ID NO: 48)
```
FR1-------------------------CDR1---------FR2-----------CDR2------
CQLQLQESGPGLVKPSETLSLTCTVSGASISGSTYYWGIRQPPGKGLEYIGRIYYSGSTYY
------FR3---------------------------------CDR3---------FR4--------
NPSLKSRATISVDTSKNQLSLTLSSVTAADTAVYYCVRPFYAGSGNSPFDYWGQGTLVTVSS
```

NI-308.46E9 VK - PIMC (variable light chain sequence VK) (SEQ ID NO: 50)
```
FR1------------------------CDR1-------FR2------------CDR2---FR3--
CEIVMTQSPATVSVSPGERATLSCRASQSVSTNLAWYQQKPGQPPRLLIYGASTRATGIPAR
-----------------------------CDR3-----FR4--------
FSGSGSGAEFTLTISSLQSEDFVVYYCQQYNNWPPAFGGGTKVEIK
```

FIG. 1H NI-308.6B11 VH (variable heavy chain sequence VH) (SEQ ID NO: 52)
```
FR1---------------------------CDR1------FR2------------CDR2---------
CEVQLVQSGAEVKRPGASVKVSCKVSGYTLTELSMHWVRQAPGKGLEWMGGFDPEDGETVYA
-----FR3---------------------------------CDR3---------FR4---
QKFQGRVTMTEDTSTDTAYMELSSLRSEDTALYHCATYGSSWHWNEGNEGSYYFDYWGQGTL
------
VTVSS
```

NI-308.6B11 VK (variable light chain sequence VK) (SEQ ID NO: 54)
```
FR1------------------------CDR1-------FR2------------CDR2---FR3--
CDIQMTQSPSSLSASVGDRVTITCQASQDISIYLNWYQQKPGKAPKLLIYDASNLETGVPSR
-----------------------------CDR3-----FR4--------
FSGSGSGTDFTFTISGLQPEDVARYYCQQYDDLPITFGQGTRLEIK
```

FIG. 1H Cont. NI-308.6B11 VH - PIMC (variable heavy chain sequence VH) (SEQ ID NO: 56)
```
FR1------------------------CDR1------FR2----------CDR2--------
CQVQLVQSGAEVKRPGASVKVSCKVSGYTLTELSMHWVRQAPGKGLEWMGGFDPEDGETVYA
-----FR3-------------------------------CDR3---------------FR4---
QKFQGRVTMTEDTSTDTAYMELSSLRSEDTALYHCATYGSSWHWNEGNEGSYYFDYWGQGTL
-----
VTVSS
```

FIG. 1I NI-308.46F8 VH (variable heavy chain sequence VH) (SEQ ID NO: 58)
```
FR1-----------------------CDR1------FR2-----------CDR2---------
CQVQLVESGGGVVRPGGSLRLSCTASGFTFDEYGMSWVRQVPGKGLEWVSGINWNGATTRYA
-----FR3------------------------------CDR3------------FR4------
DSVKGRFTISRDNAKNSLYLQMNSLRAEDTALYHCARDGCRNTSCYIWDWFDPWGQGTLVTV
--
SS
```

NI-308.46F8 VL (variable light chain sequence VL) (SEQ ID NO: 60)
```
FR1-------------------CDR1---------FR2-------------CDR2---FR3-
CQSVLTQPPSVSAAPGQKVTISCSGSSSNIGNNYVCWYQNLPGTAPKLLIYDDNKRPSGIPD
------------------------------CDR3--------FR4--------
RFSGSKSGTSATLGITGLQTGDEADYYCGTWDSSLSVVVFGGGTKLTVL
```

NI-308.46F8 VH - PIMC (variable heavy chain sequence VH) (SEQ ID NO: 62)
```
FR1-----------------------CDR1------FR2-----------CDR2---------
CEVQLVESGGGVVRPGGSLRLSCTASGFTFDEYGMSWVRQVPGKGLEWVSGINWNGATTRYA
-----FR3------------------------------CDR3------------FR4------
DSVKGRFTISRDNAKNSLYLQMNSLRAEDTALYHCARDGCRNTSCYIWDWFDPWGQGTLVTV
--
SS
```

FIG. 1J NI-308.4M1 VH (variable heavy chain sequence VH) (SEQ ID NO: 64)
```
FR1-------------------------CDR1-FR2-----------CDR2--------
CEVQLVETGGGVVQPGGSLRLSCEASGFTIGTYAMHWVRQFPGKGLDWVAVISFDGTTEYYT
---FR3-----------------------------CDR3-------------FR4-----
DAVKGRFTISRDNAKNTLYLQMNYLRGDDTAIYFCARDFTSSGETGSWTQVPDLWGQGTLVT
---
VSS
```

NI-308.4M1 VK (variable light chain sequence VK) (SEQ ID NO: 66)
```
FR1--------------------CDR1-------FR2-------------CDR2---FR3--
CEIVMTQSPATLSLSPGERATLSCRASQSVTKYLAWYQQKPGQAPRLLIYDVSYRAAGTPAR
---------------------------CDR3-------FR4--------
FSGSGSGTDFTLTISSLEPEDFAVYYCHQRSSWPPVTFGGGTKVEIK
```

FIG. 1J Cont. NI-308.4M1 VH - PIMC (variable heavy chain sequence VH) (SEQ ID NO: 68)
```
FR1-------------------------------CDR1-FR2-----------CDR2--------
CQVQLVESGGGVVQPGGSLRLSCEASGFTIGTYAMHWVRQFPGKGLDWVAVISFDGTTEYYT
---FR3--------------------------------CDR3--------------FR4-----
DAVKGRFTISRDNAKNTLYLQMNYLRGDDTAIYFCARDFTSSGETGSWTQVPDLWGQGTLVT
---
VSS
```

NI-308.4M1 VK - PIMC (variable light chain sequence VK) (SEQ ID NO: 70)
```
FR1-----------------------CDR1-------FR2-----------CDR2---FR3---
CEIVLTQSPATLSLSPGERATLSCRASQSVTKYLAWYQQKPGQAPRLLIYDVSYRAAGTPAR
--------------------------------CDR3------FR4-------
FSGSGSGTDFTLTISSLEPEDFAVYYCHQRSSWPPVTFGGGTKVEIK
```

FIG. 1K NI-308.12A3 VH (variable heavy chain sequence VH) (SEQ ID NO: 72)
```
FR1-------------------------------CDR1-FR2-----------CDR2--------
CEVQLVETGGGLVQPGGSLRLSCVGSGFLFSDFEMDWVRQAPGKGLEWISYISGDGNIIYQT
------FR3----------------------------CDR3--------------FR4------
DSVKGRFTISRDNAKNSLFLQMDSLTVEDTAVYYCARDARENCGGDCYSTSFDFWGQGTLVT
---
VSS
```

NI-308.12A3 VK (variable light chain sequence VK) (SEQ ID NO: 74)
```
FR1---------------------CDR1-------------FR2-------------CDR2--
CDIQMTQSPDSLAVSLGERATINCKSSQSLLYTANNRNYLAWYQKKAGQPPKLLIHWASTRA
-FR3-------------------------------CDR3-----FR4--------
SGVPDRFSGSGSGTDFILTISSLQAEDVAVYFCQHYYNSPRTFGQGTKVEIK
```

NI-308.12A3 VH - PIMC (variable heavy chain sequence VH) (SEQ ID NO: 76)
```
FR1-------------------------------CDR1-FR2-----------CDR2--------
CEVQLVESGGGLVQPGGSLRLSCVGSGFLFSDFEMDWVRQAPGKGLEWISYISGDGNIIYQT
------FR3----------------------------CDR3--------------FR4------
DSVKGRFTISRDNAKNSLFLQMDSLTVEDTAVYYCARDARENCGGDCYSTSFDFWGQGTLVT
---
VSS
```

NI-308.12A3 VK - PIMC (variable light chain sequence VK) (SEQ ID NO: 78)
```
FR1---------------------CDR1-------------FR2-------------CDR2--
CDIVMTQSPDSLAVSLGERATINCKSSQSLLYTANNRNYLAWYQKKAGQPPKLLIHWASTRA
-FR3-------------------------------CDR3-----FR4--------
SGVPDRFSGSGSGTDFILTISSLQAEDVAVYFCQHYYNSPRTFGQGTKVEIK
```

FIG. 1L NI-308.16C10 VH (variable heavy chain sequence VH) (SEQ ID NO: 80)
```
FR1-------------------------------CDR1--FR2-----------CDR2--------
CEVQLVETGGGVVQPGMSLSLSCAATGFTFSSYGMHWVRQGPGKGPEWVAGIWYDGTNKYYG
-----FR3-----------------------------CDR3-----------FR4-------
DSVTGRVTISRDNSKNTLFLQMINVRVEDTAVYYCVKDAERVQKWASYIMDVWGQGTTVTVS
-
S
```

NI-308.16C10 VK (variable light chain sequence VK) (SEQ ID NO: 82)
```
FR1---------------------CDR1---------FR2-------------CDR2---FR3--
CEIVLTQSPGILSLSRGNRVALSCRASRSVNSSYLNWYQQKPGQAPRLLIYGASKRATGISD
--------------------------CDR3--FR4-------
RFRGTGSGTDFTLTVARLEPEDIAVYYCQHYGAFGQGTKLEIK
```

NI-308.16C10 VH - PIMC (variable heavy chain sequence VH) (SEQ ID NO: 84)
```
FR1-------------------------------CDR1--FR2-----------CDR2--------
CQVQLVESGGGVVQPGMSLSLSCAATGFTFSSYGMHWVRQGPGKGPEWVAGIWYDGTNKYYG
-----FR3-----------------------------CDR3-----------FR4-------
DSVTGRVTISRDNSKNTLFLQMINVRVEDTAVYYCVKDAERVQKWASYIMDVWGQGTTVTVS
-
S
```

NI-308.16C10 VK - PIMC (variable light chain sequence VK) (SEQ ID NO: 86)
```
FR1---------------------CDR1---------FR2-------------CDR2---FR3--
CEIVLTQSPGILSLSRGNRVALSCRASRSVNSSYLNWYQQKPGQAPRLLIYGASKRATGISD
--------------------------CDR3--FR4-------
RFRGTGSGTDFTLTVARLEPEDIAVYYCQHYGAFGQGTKVEIK
```

FIG. 2A

| Antibody | EC$_{50}$ [nM] | | | | |
|---|---|---|---|---|---|
| | (GA)$_{15}$ | (GP)$_{15}$ | (GR)$_{15}$ | (PR)$_{15}$ | (PA)$_{15}$ |
| NI-308.15O7 | 0.48 | - | - | - | - |
| NI-308.28G1 | 1.1 | - | - | - | - |
| NI-308.45C2 | 1.1 | - | - | - | - |
| NI-308.18F7 | 1.5 | - | - | - | - |
| NI-308.24E11 | - | - | - | 12.8 | - |
| NI-308.16C10 | 55.1 | - | - | 3.5 | - |
| NI-308.5G2 | 15.3 | 0.88 | - | - | - |
| NI-203.12A3 | 19.0 | 2.2 | - | - | - |
| NI-308.46E9 | > 200 | 13.9 | - | - | - |
| NI-308.6B11 | 38.4 | - | 0.94 | 119 | - |
| NI-308.46F8 | 108 | - | 40.6 | > 200 | - |
| NI-308.4M1 | > 200 | - | - | - | 0.10 |

FIG. 2B NI-308.15O7
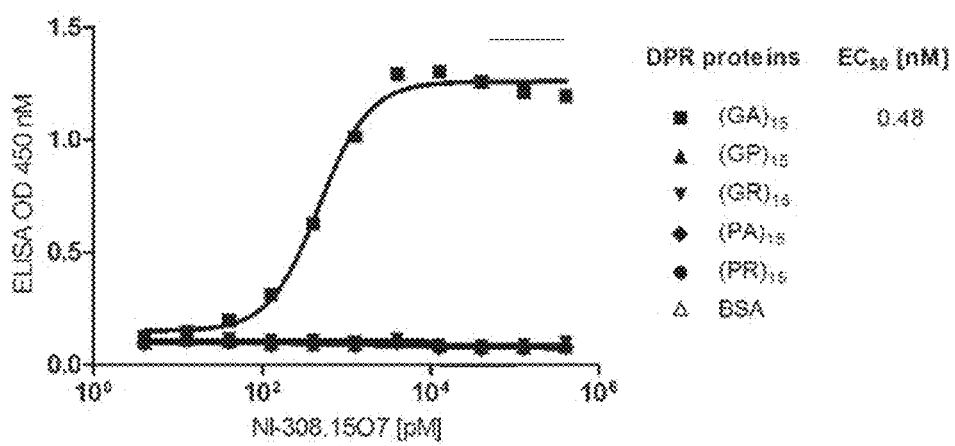
FIG. 2C NI-308.28G1
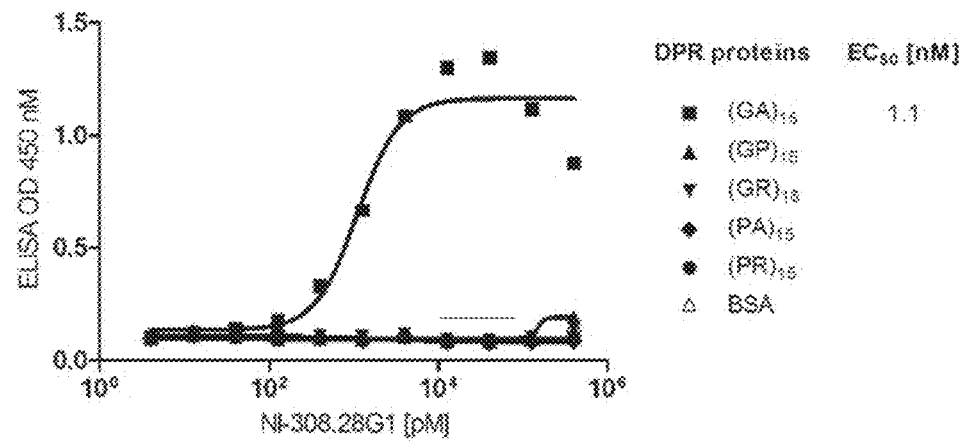
FIG. 2D NI-308.45C2
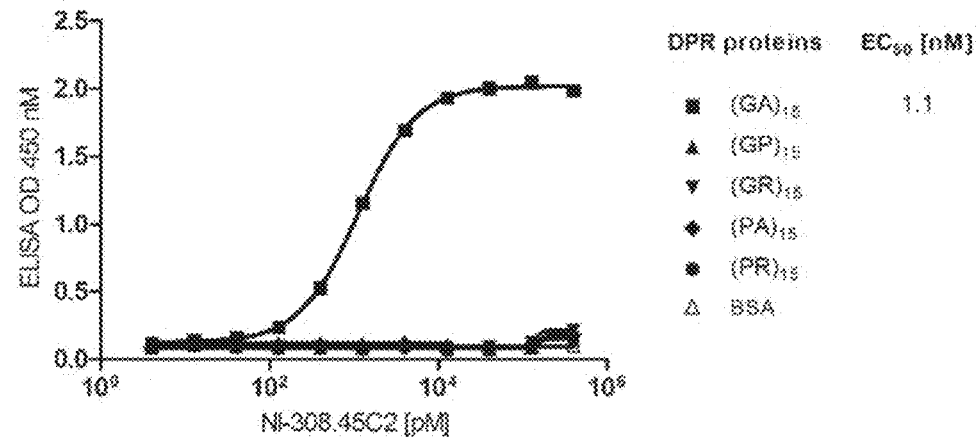

FIG. 2E NI-308.18F7
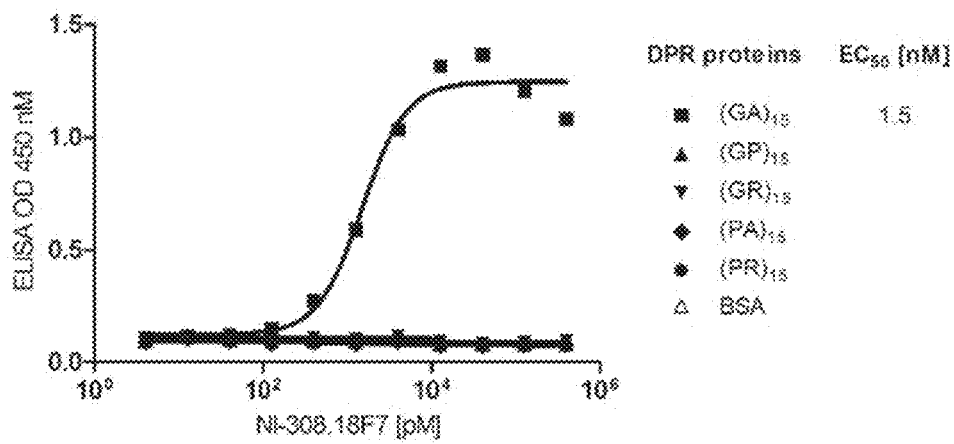
FIG. 2F NI-308.24E11
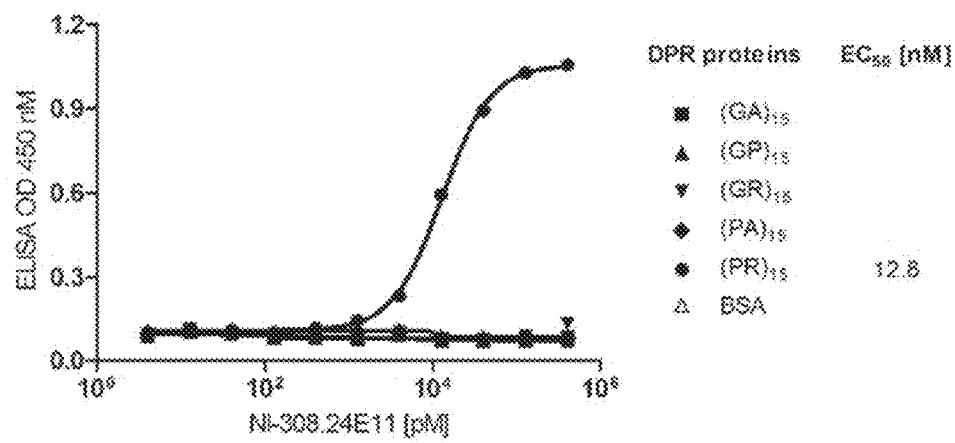
FIG. 2G NI-308.5G2
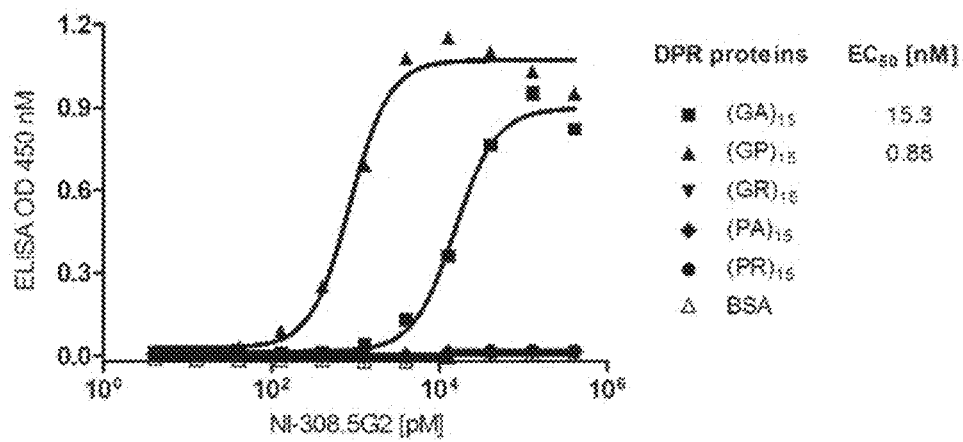

FIG. 2H NI-308.46E9
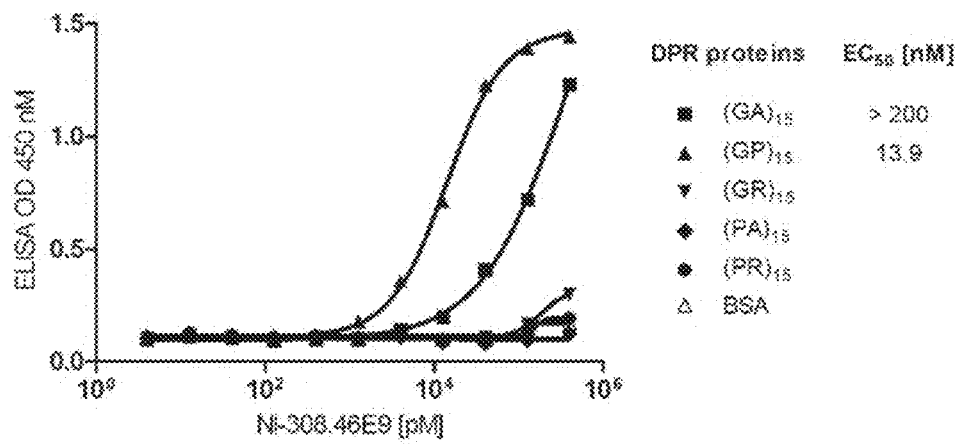
FIG. 2I NI-308.6B11
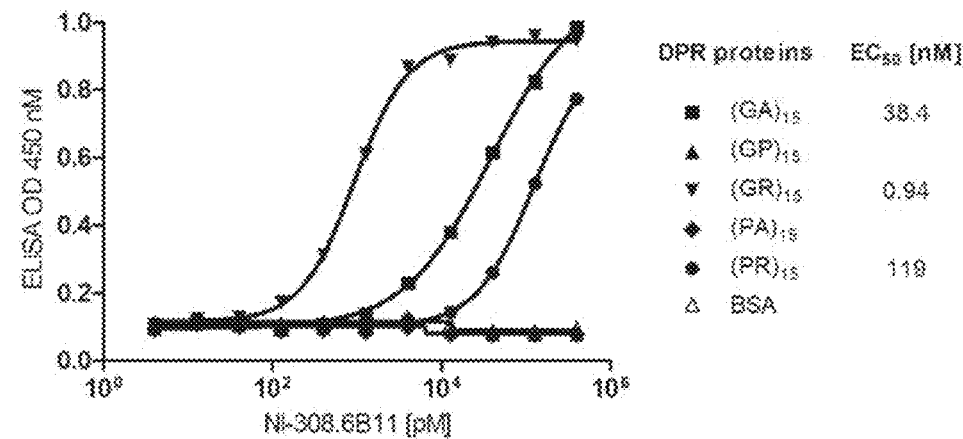
FIG. 2J NI-308.46F8
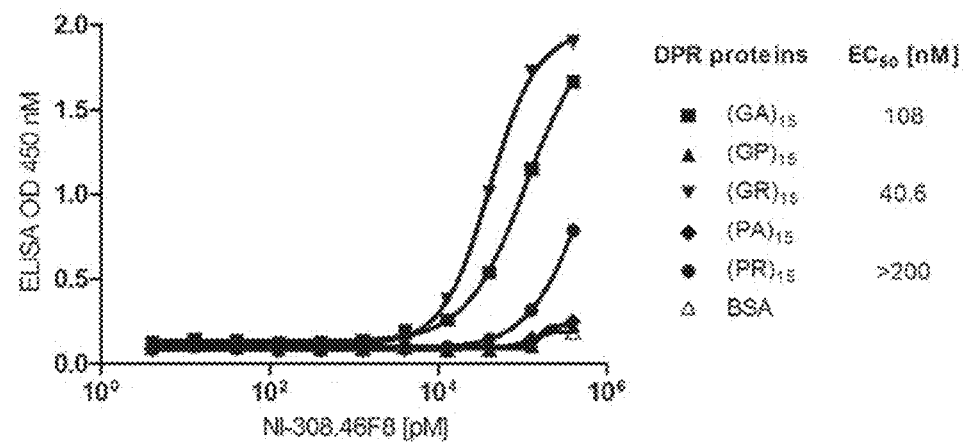

FIG. 2K NI-308.4M1
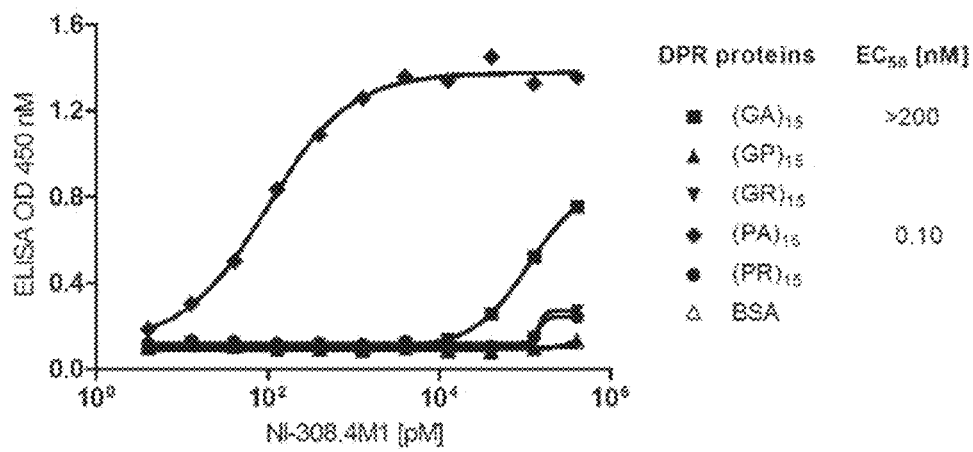
FIG. 2L NI-308.12A3
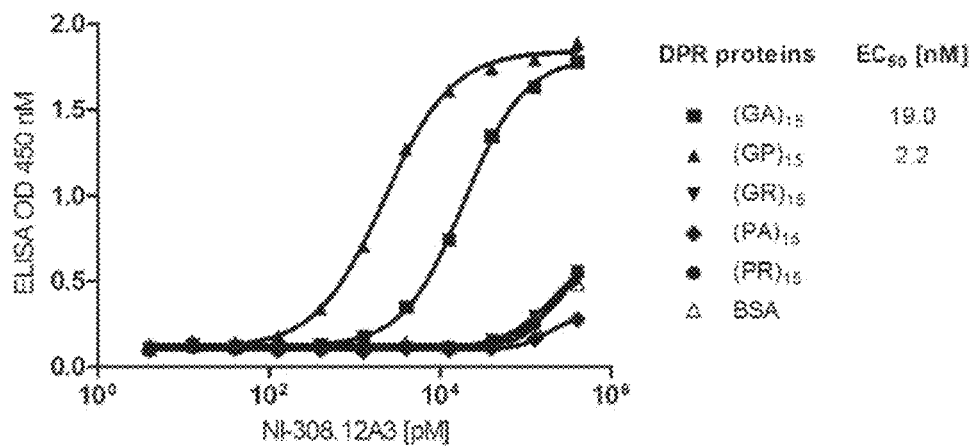
FIG. 2M NI-308.16C10
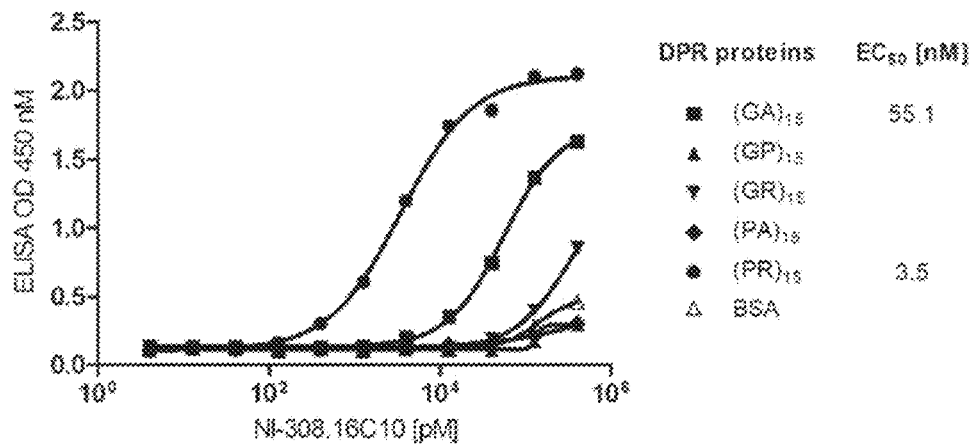

FIG. 3A
| Antibody | Peptide | EC50 [nM] | |
|---|---|---|---|
| | | BSA-coupled peptide | Uncoupled peptide |
| NI-308.18F7 | (GA)15 | 0.11 | 0.34 |
| NI-308.15O7 | (GA)15 | 0.41 | 0.18 |
| NI-308.28G1 | (GA)15 | 0.66 | 2.0 |
| NI-308.45C2 | (GA)15 | 15.2 | 1.1 |
| NI-308.24E11 | (PR)15 | > 200 | 11.3 |
| NI-308.16C10 | (PR)15 | 91.1 | 3.5 |
| NI-308.5G2 | (GP)15 | 0.21 | 0.40 |
| NI-308.12A3 | (GP)15 | 6.1 | 2.2 |
| NI-308.46E9 | (GP)15 | 12.1 | 22.0 |
| NI-308.68I1 | (GR)15 | NA | 1.3 |
| NI-308.45F8 | (GR)15 | NA | 90.3 |
| NI-308.4M1 | (PA)15 | 0.14 | 0.10 |
FIG. 3B NI-308.18F7
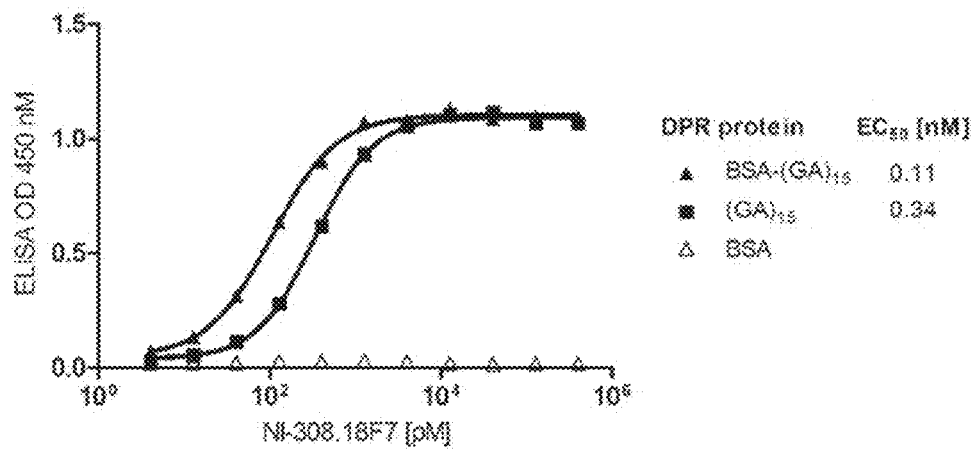
FIG. 3C NI-308.15O7
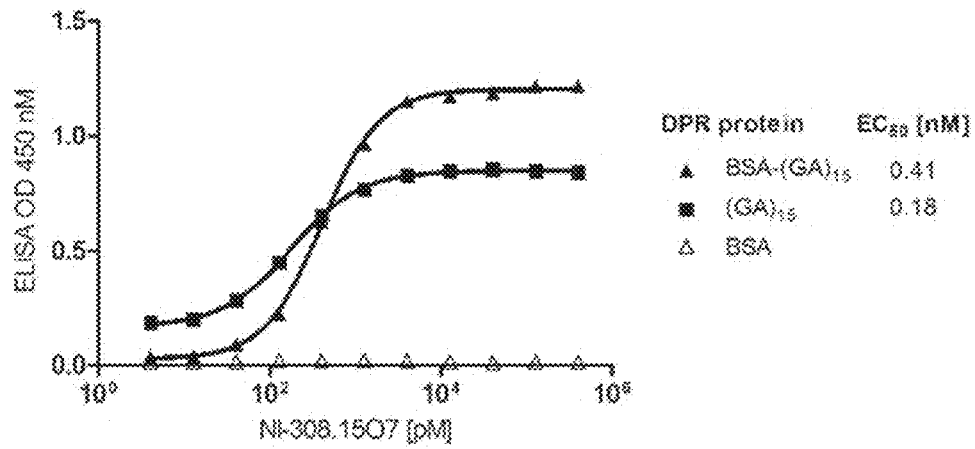

FIG. 3D NI-308.28G1
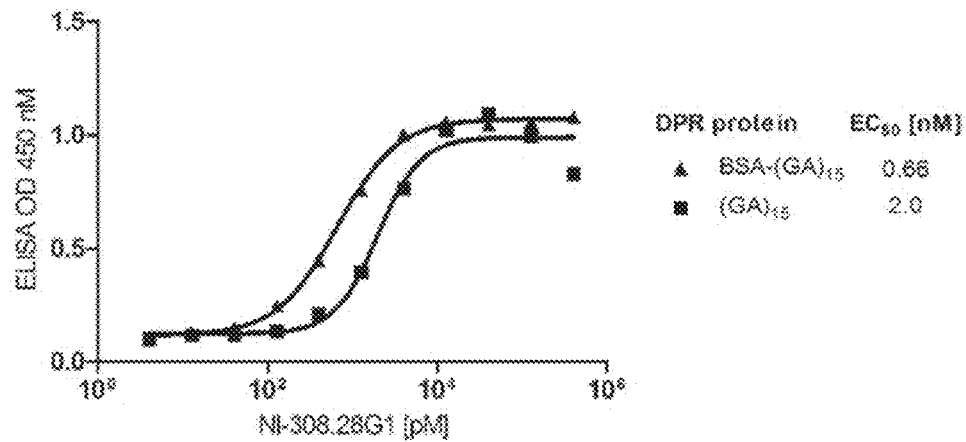
FIG. 3E NI-308.45C2
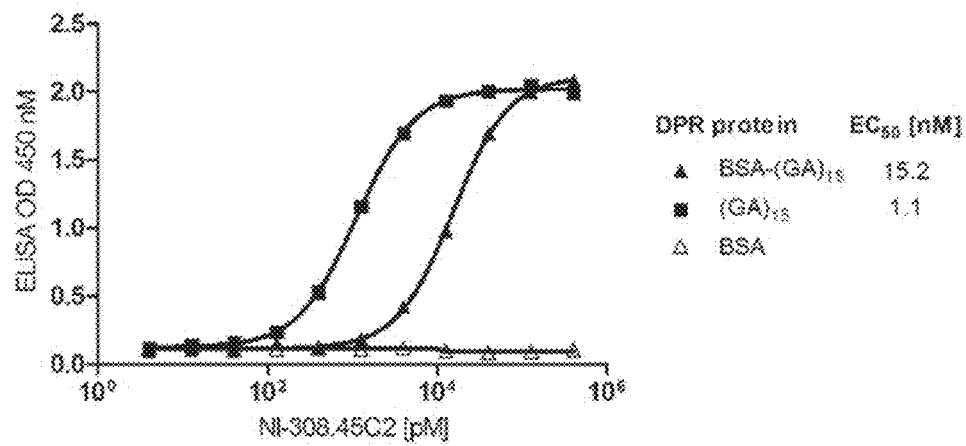
FIG. 3F NI-308.24E11
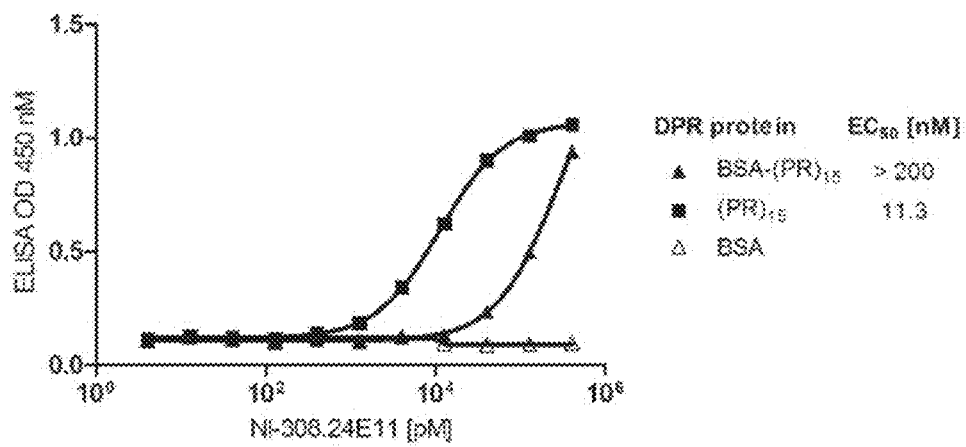

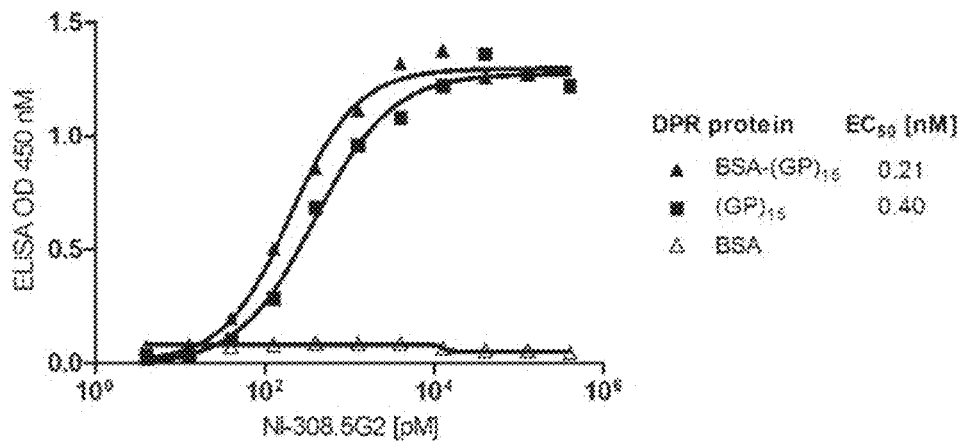
FIG. 3G NI-308.5G2
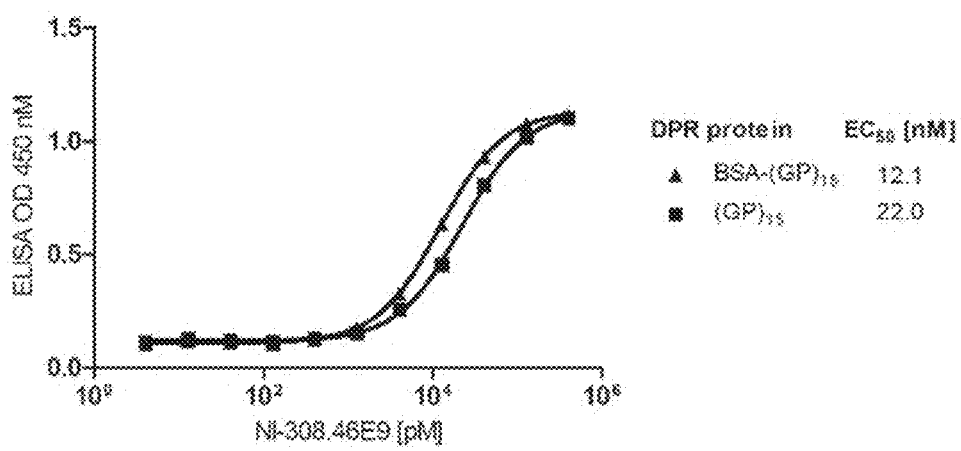
FIG. 3H NI-308.46E9
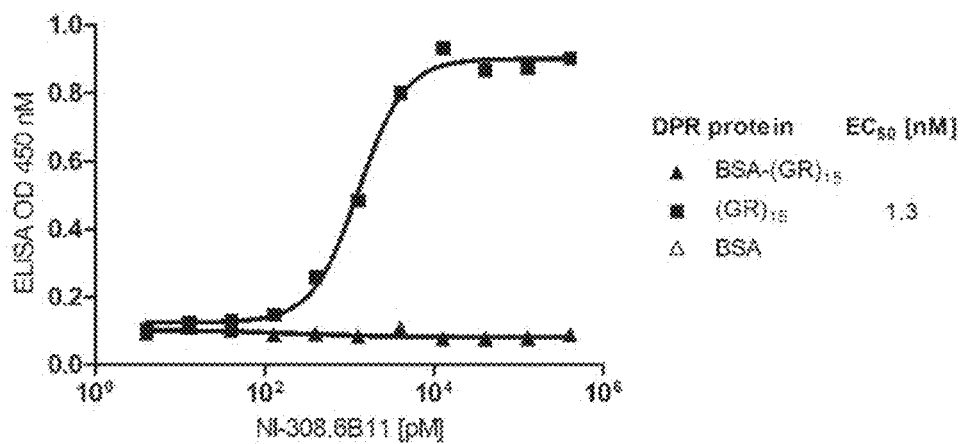
FIG. 3I NI-308.6B11

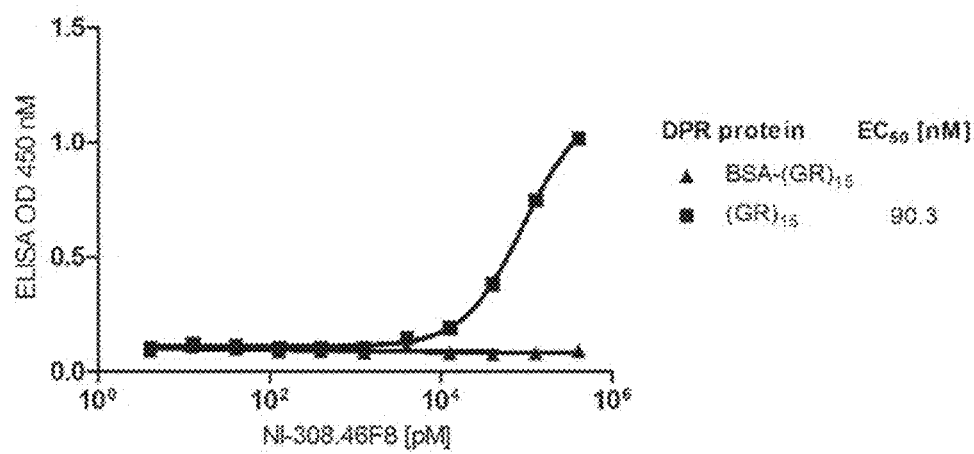
FIG. 3J  NI-308.46F8
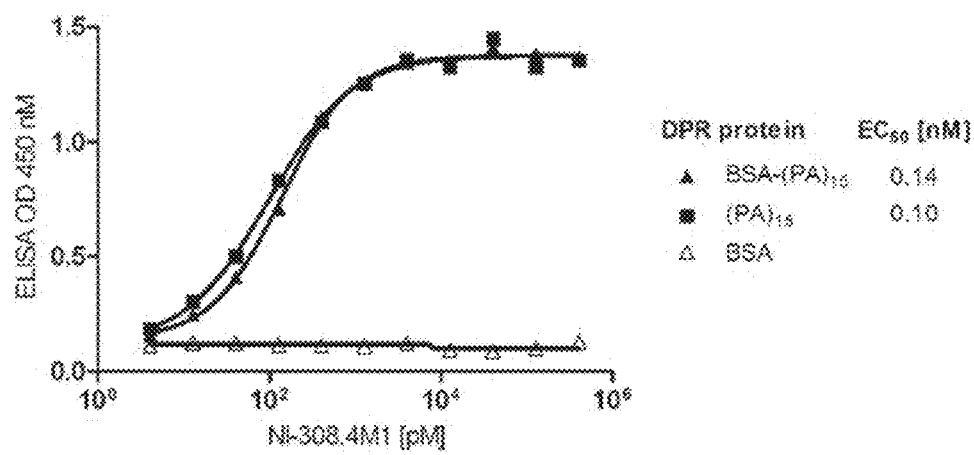
FIG. 3K  NI-308.4M1
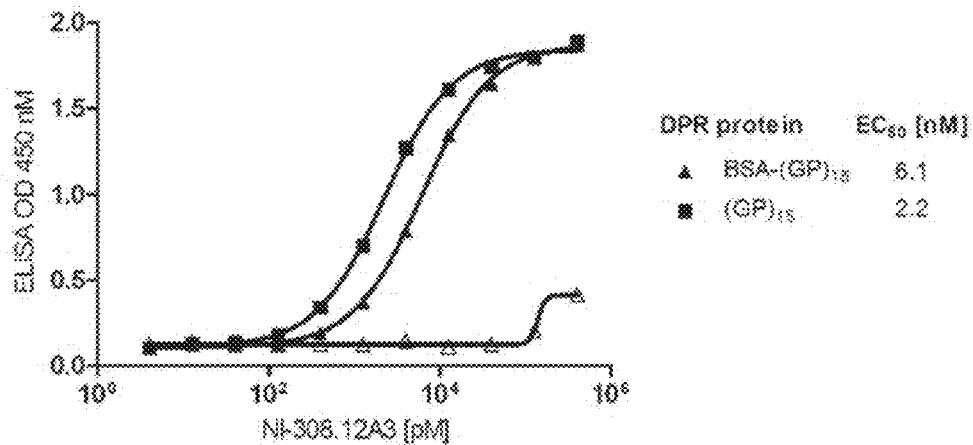
FIG. 3L  NI-308.12A3

FIG. 3M  NI-308.16C10
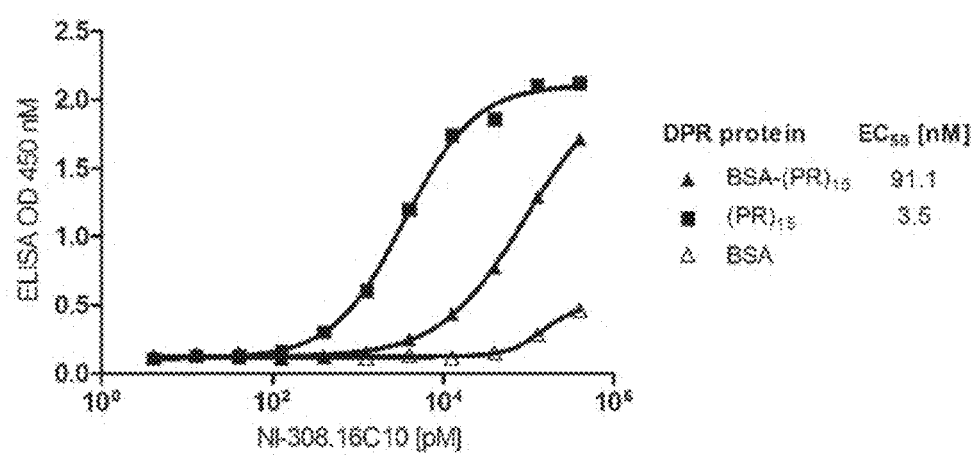

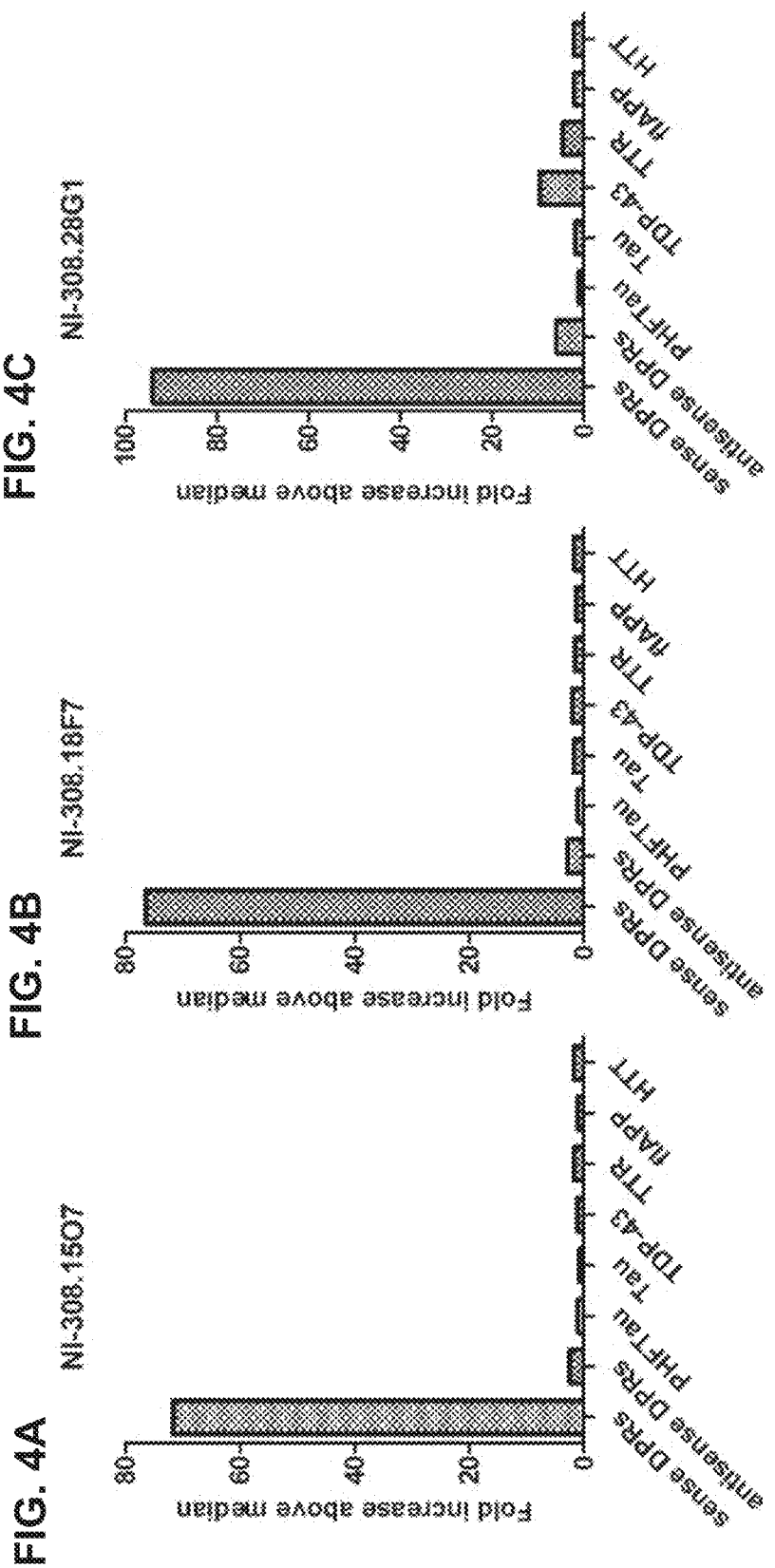

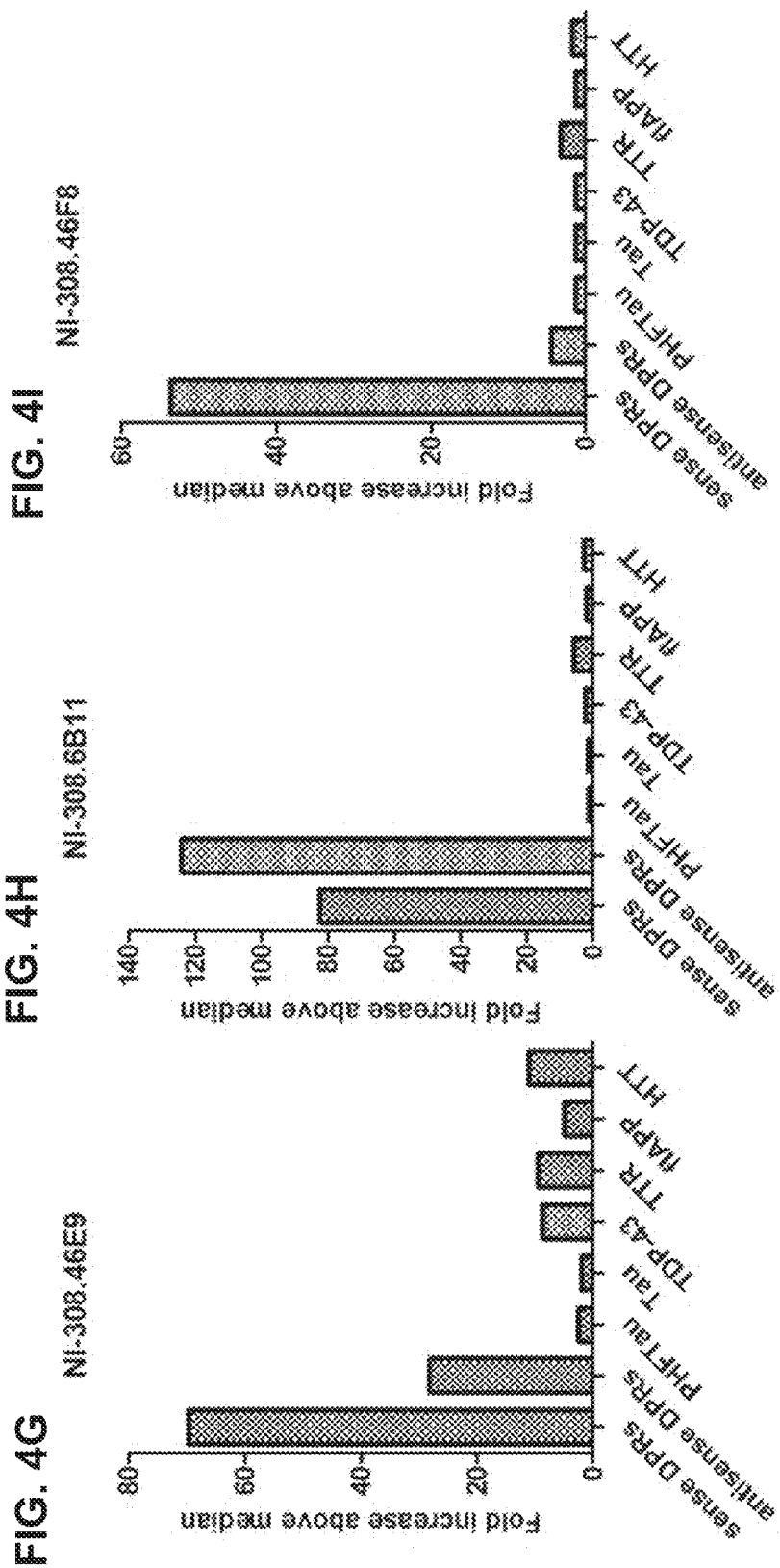

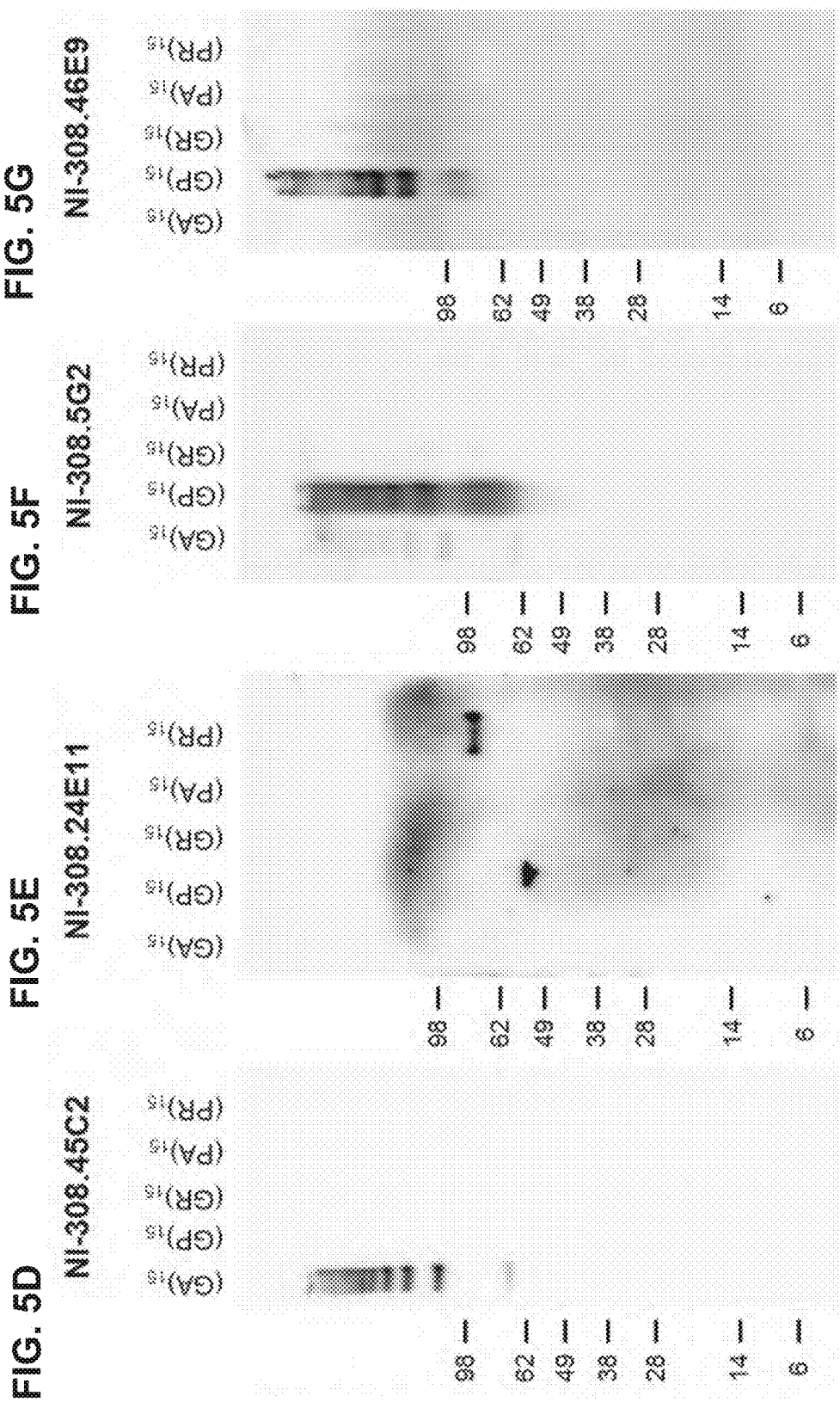

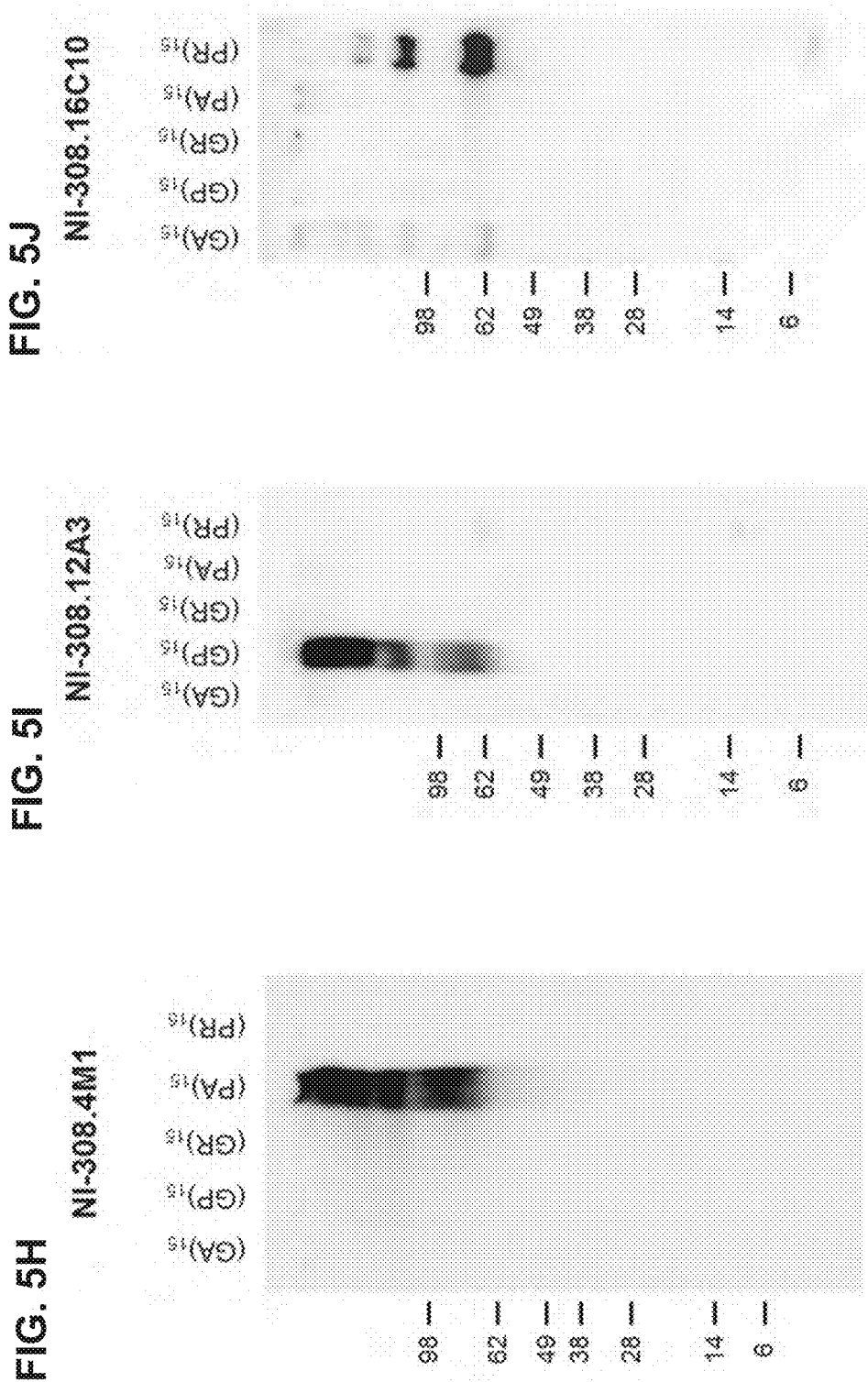

| Antibody | (GA)₂ | (GA)₃ | (GA)₄ | (GA)₅ | (GA)₆ | (GA)₁₀ | (GA)₂₀ |
|---|---|---|---|---|---|---|---|
| NI-308.15O7 | - | - | - | >150 | 7.9 | 0.37 | 0.54 |
| NI-308.18F7 | - | - | - | - | >200 | 0.78 | 0.83 |
| NI-308.28G1 | - | - | - | >200 | 6.3 | 0.9 | 1.1 |
| NI-308.45C2 | - | - | - | - | >200 | 7.6 | 9.6 |
| NI-308.6B11 | - | - | - | - | >200 | 27.7 | 33.6 |
| NI-308.5G2 | - | - | - | - | >200 | 5.7 | 18.2 |

EC₅₀ [nM]

| Antibody | (GP)₂ | (GP)₃ | (GP)₄ | (GP)₅ | (GP)₆ | (GP)₁₀ | (GP)₂₀ |
|---|---|---|---|---|---|---|---|
| NI-308.5G2 | - | - | - | >200 | 26.8 | 0.94 | 0.47 |
| NI-308.46E9 | - | - | - | - | - | 63.3 | 15.5 |

EC₅₀ [nM]

| Antibody | (GR)₂ | (GR)₃ | (GR)₄ | (GR)₅ | (GR)₆ | (GR)₁₀ | (GR)₂₀ |
|---|---|---|---|---|---|---|---|
| NI-308.6B11 | - | 14.3 | 13.2 | 0.47 | 0.33 | 1.3 | 0.25 |

EC₅₀ [nM]

| Antibody | (PR)₂ | (PR)₃ | (PR)₄ | (PR)₅ | (PR)₆ | (PR)₁₀ | (PR)₂₀ |
|---|---|---|---|---|---|---|---|
| NI-308.24E11 | - | - | - | - | >200 | 31.7 | 11.3 |

EC₅₀ [nM]

| Antibody | (PA)₂ | (PA)₃ | (PA)₄ | (PA)₅ | (PA)₆ | (PA)₁₀ | (PA)₂₀ |
|---|---|---|---|---|---|---|---|
| NI-308.4M1 | - | - | - | 26.9 | 4.3 | 0.06 | 0.06 |

| DPR proteins | EC₅₀ [nM] |
|---|---|
| (GA)₂ | |
| (GA)₃ | |
| (GA)₄ | |
| (GA)₅ | >150 |
| (GA)₆ | 7.9 |
| (GA)₁₀ | 0.37 |
| (GA)₂₀ | 0.54 |

FIG. 7P
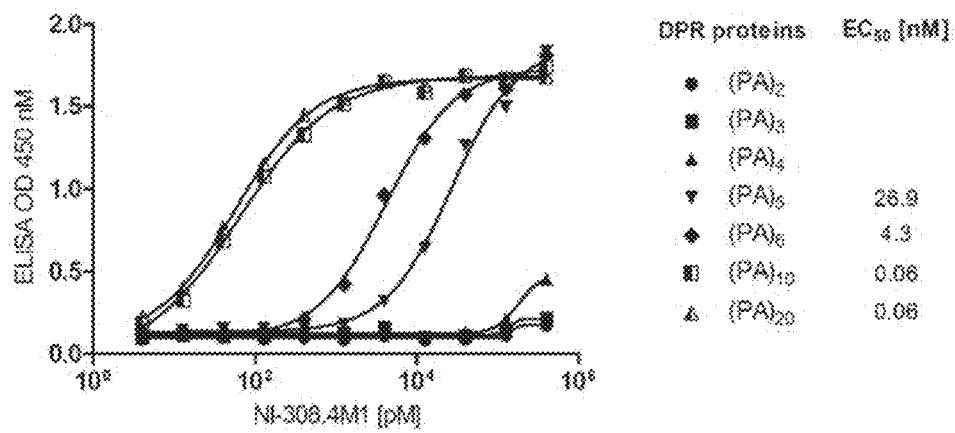
FIG. 8A
| Antibody | EC50 [nM] | | | | | | |
| --- | --- | --- | --- | --- | --- | --- | --- |
| | (GA)2 | (GA)3 | (GA)4 | (GA)5 | (GA)6 | (GA)10 | (GA)20 |
| NI-308.15O7 | - | - | - | - | - | >400 | 9.0 |
| NI-308.18F7 | - | - | - | - | - | 0.34 | 0.45 |
| NI-308.28G1 | - | - | - | - | - | 0.46 | 0.40 |
FIG. 8B
| Antibody | EC50 [nM] | | | | | | |
| --- | --- | --- | --- | --- | --- | --- | --- |
| | (GA)2 | (GA)3 | (GA)4 | (GA)5 | (GA)6 | (GA)10 | (GA)20 |
| NI-308.5G2 | - | - | - | - | - | - | 38.2 |
FIG. 8C  NI-308.15O7
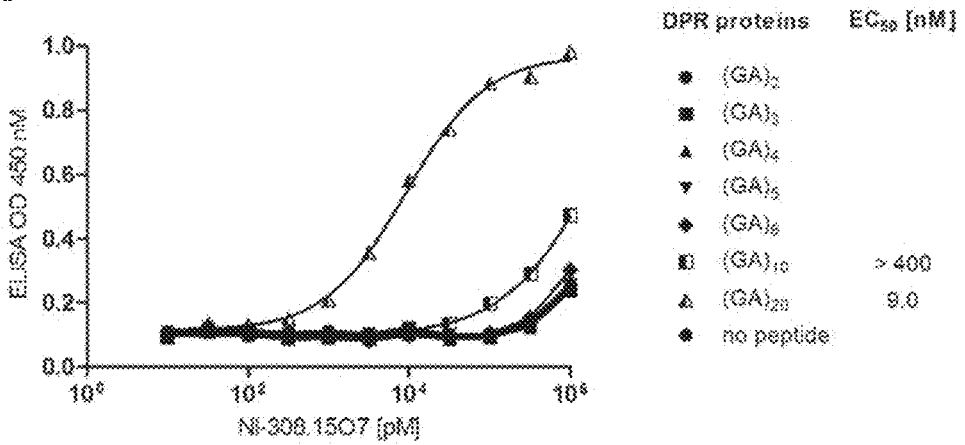

FIG. 9
| Antibody | EC50 [nM] | | | |
|---|---|---|---|---|
| | Indirect ELISA | | Sandwich ELISA | |
| | monomeric (GA)15 | aggregated (GA)15 | monomeric (GA)15 | aggregated (GA)15 |
| NI-308.18F7 | 0.87 | 0.89 | 0.64 | 2.9 |
| NI-308.15O7 | 0.53 | 0.78 | 6.3 | 8.1 |
FIG. 10A
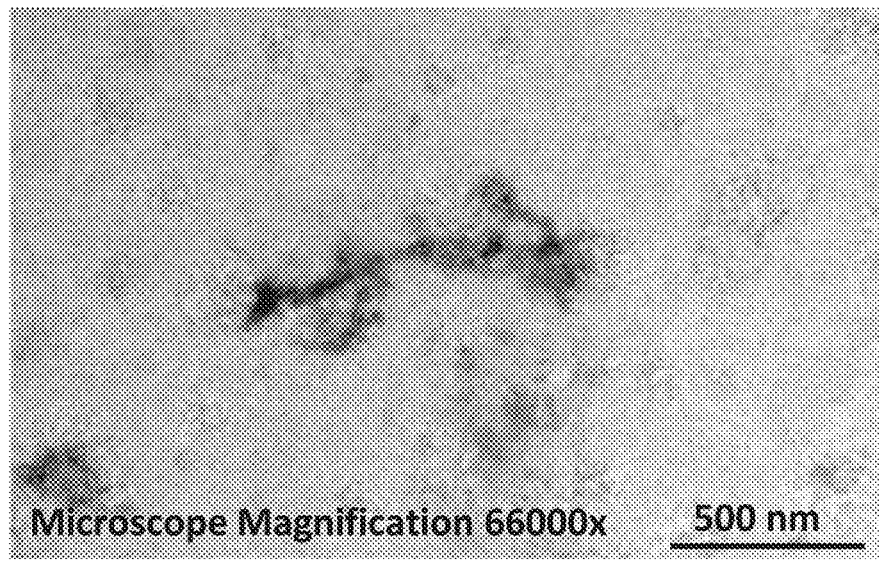
FIG. 10B
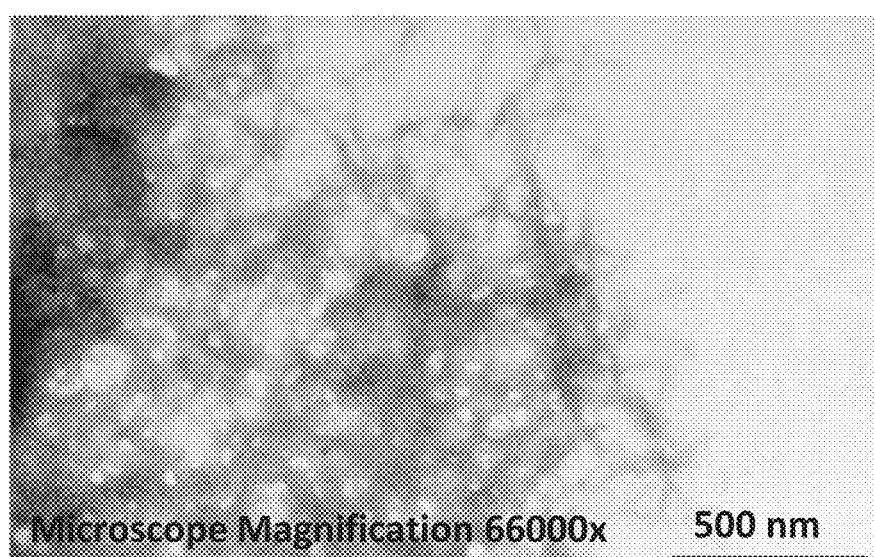

NI-308.15O7

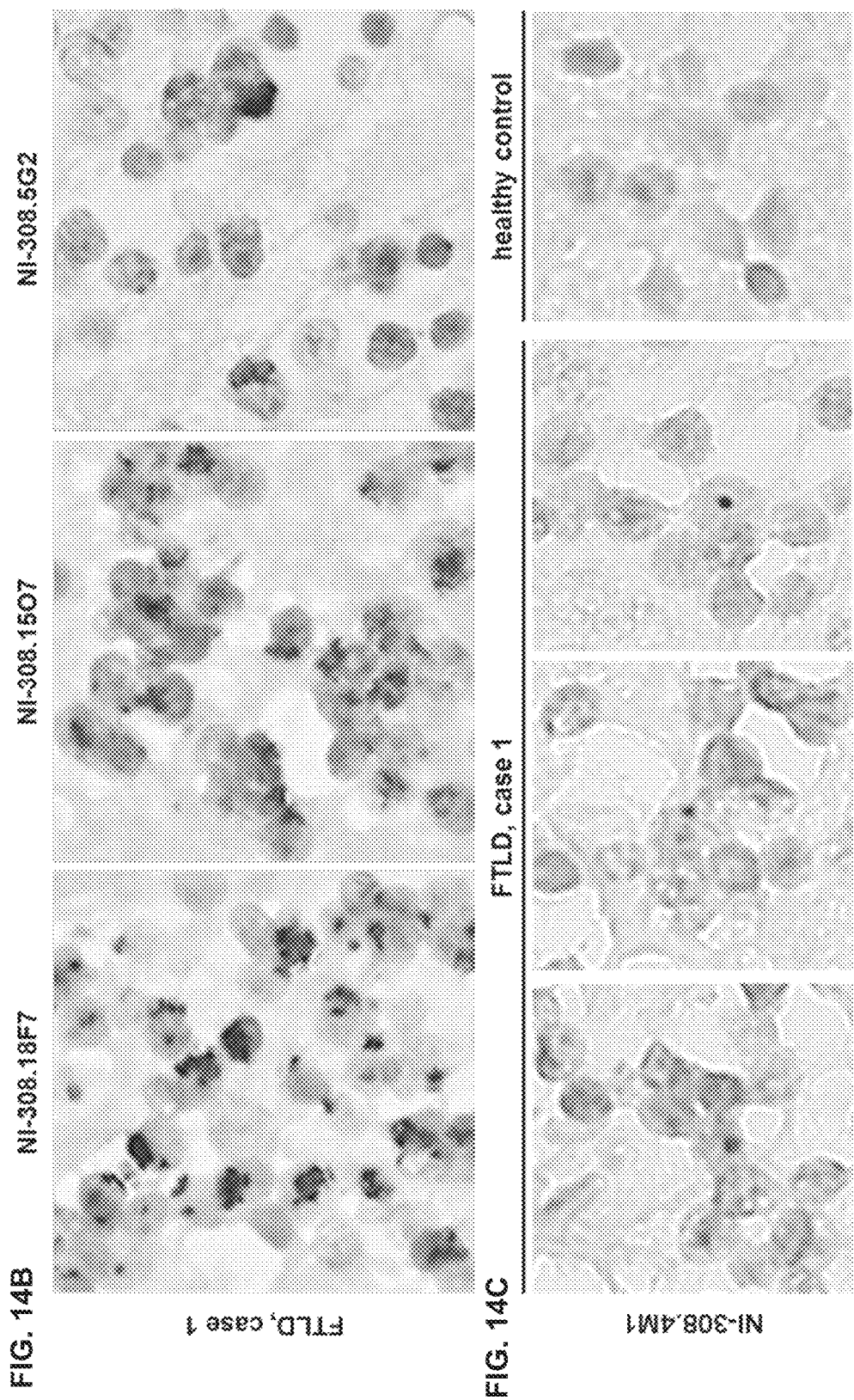

HUMAN-DERIVED ANTI-DIPEPTIDE REPEATS (DPRS) ANTIBODY

FIELD OF THE INVENTION

The present invention generally relates to antibody-based therapies and diagnostic methods. In particular, the present invention relates to novel molecules specifically binding to unconventional non-ATG translations, in particular hexanucleotide repeats forming dipeptide repeats (DPRs) and antigens comprising such DPRs, which are useful in the diagnosis of diseases and conditions induced by aggregated DPRs and DPRs containing proteins, respectively. In one embodiment the present invention provides human-derived antibodies as well as fragments, derivatives and biotechnological variants thereof that recognize DPRs as found in chromosome 9 open reading frame 72 (C9ORF72) such as poly-glycine-alanine repeats, poly-glycine-proline repeats, poly-glycine-arginine repeats, poly-proline-alanine repeats or poly proline-arginine repeats, and which are useful in the treatment and diagnosis of diseases and conditions induced by aggregated C9ORF72-DPRs. In addition, the present invention relates to pharmaceutical and diagnostic compositions comprising such binding molecules, antibodies and mimics thereof valuable both as a diagnostic tool to identify diseases associated with DPRs or its aggregates and also as a passive vaccination strategy for treating such diseases, for example Frontotemporal lobar degeneration (FTLD), amyotrophic lateral sclerosis (ALS), FTLD-ALS, and spinocerebellar ataxia type 36.

BACKGROUND OF THE INVENTION

Frontotemporal lobar degeneration (FTLD) belongs to a group of clinically, pathologically and genetically heterogeneous disorders associated with atrophy in the frontal lobe and temporal lobe of the brain. It is the second most common cause of early-onset of dementia. Cognitive symptoms are variable and include dementia, changes of the behavior as well as personality, language dysfunctions, and/or psychosis with are due to the degeneration of the frontal and temporal cortex. Due to its symptoms FTLD can be divided into three groups (i) behavioral-variant frontotemporal dementia (bvFTLD), (ii) semantic dementia (SD), or (iii) progressive nonfluent aphasia (PNFA). Patients with FTLD die 5-10 years after symptom onset, since no suitable therapy is available. However, 50% of FTLD patient were shown to have a positive family history and compared to amyotrophic lateral sclerosis (ALS) seems to represent a disease continuum with a shared underlying pathogenesis. Although both autosomal dominant disorders were shown to be genetically and pathologically heterogeneous, see, e.g., Vance et al., Brain 129 (2006), 868-876, genetic analysis identified a heterozygous expanded hexanucleotide repeat (GGGGCC) located between the noncoding exons 1a and 1b of the C9ORF72 gene as the most common genetic cause of FTLD and ALS; see, e.g., DeJesus-Hernandez et al., Neuron 72 (2011), 245-256 and Renton et al., Neuron 72 (2011), 257-268. In particular, it was shown that the unconventional non-ATG translation of the sense transcript in the three alternate reading frames, i.e. of the expanded hexanucleotide repeats, resulted in the production, generation and aggregation of three different polypeptides, each composed of repeating units of two amino acids (dipeptide repeats, DPRs), i.e. poly-(Gly-Ala; GA), poly-(Gly-Pro; GP) and poly-(Gly-Arg; GR). Furthermore, translation of corresponding antisense transcripts results in the generation of poly-(Pro-Arg; PR), poly-(Pro-Ala; PA), and poly-(Gly-Pro; GP). These C9ORF72-dipeptide repeat (DPR) expansions were shown to account for up to 30% of FTLD, 50% of ALS and 80% of FTLD-ALS patients with the highest mutation frequencies observed in US and EU Caucasian populations. Additionally, patients with C9ORF72-DPR expansion with more than 19 repeats had a lower age of onset, increased incidence of neurological disorders, and a propensity towards psychosis or hallucinations compared to patients with other forms of FTLD and/or ALS; see, e.g., Harms et al., Neurobiol. Aging 34 (2013), e13-e19.

However, also other diseases and/or disorders have been reported which seem to be associated with a hexanucleotide repeat expansions, e.g., spinocerebellar ataxia type 36. Indeed, such tandem repeats (either as microsatellites or minisatellites) are mutation-prone DNA in both eukaryotic and prokaryotic organisms. For example, the cell surface adhesins of bacteria often contain the minisatellite SD repeats, encoding the amino acid pair of serine-aspartate with an array of 18-nucleotide repeats, whose elements follow the consensus GAYTCNGAYTCN GAYAGY, where N is any base and Y is T or C, especially in Staphylococcal strains. It has been found that serine-aspartate repeats (SDR) are present in a variable repetitive region of these adhesins, such as the R domain of clumping factor A (C1fA); see, e.g., Hazenbos et al., PLOS Pathogens 9 (2013), e1003653.

Treatments for diseases and/or disorders associated with a dipeptide repeat (DPR) expansion, e.g. medicaments which slow down the progression of the disease, are missing. The major focus of medical care so far lies in the provision of pharmaceuticals for the treatment of the often very stressful accompanying symptoms. However, so far there is no evidence for an effective treatment.

This technical problem is solved by the embodiments characterized in the claims and described further below and illustrated in the Examples and Figures.

SUMMARY OF THE INVENTION

The present invention provides human-derived monoclonal antibodies capable of binding dipeptide repeats (DPRs) and DPR containing proteins (DPR proteins) as well as equivalent DPR protein-binding molecules such as DPR-binding fragments, synthetic variants and biotechnological derivatives of the antibodies exemplified herein which are particularly useful in the prophylactic or therapeutic treatment of diseases and conditions associated with DPR proteins and aggregated forms thereof. More specifically, therapeutically useful human-derived antibodies and equivalent DPR protein-binding molecules are provided that recognize DPRs consisting of poly-glycine-alanine (Gly-Ala; GA), poly-glycine-proline (Gly-Pro; GP), poly-glycine-arginine (Gly-Arg; GR), poly-proline-arginine (Pro-Arg; PR), or poly-proline-alanine (Pro-Ala; PA), repeats and proteins comprising such DPRs.

Experiments performed in accordance with the present invention were successful in the isolation of human-derived monoclonal anti-DPR-specific antibodies which matured in the human body and are capable of specifically recognizing non-aggregated and aggregated C9ORF72-DPR protein species and fragments thereof. The human subjects being the source of the B cells from which the human-derived monoclonal anti-DPR protein antibodies and the cDNA encoding their variable domain, respectively, have been isolated, were symptom-free of neurological and neurodegenerative conditions. However, in another embodiment of the present invention, the source of the B cells from which the human-derived monoclonal anti-DPR antibodies and the cDNA encoding their variable domain, respectively, might be isolated are patients showing symptoms of a disease and/or disorder associated with the DPR proteins. Since the antibodies of the present invention are isolated from the human body and as demonstrated in the Examples, were shown to specifically bind to DPR proteins in FTLD patients, it is prudent to expect that the human monoclonal anti-DPR protein antibodies of the present invention and derivatives thereof besides being non-immunogenic also exhibit a therapeutically beneficial effect in human.

Frontotemporal dementia (FTD), also known as Pick's disease, is a group of disorders associated with the progressive nerve cell degeneration in the frontal and/or temporal lobes of the brain. The symptoms associated with the reduced function of the brain due to cell damage and the tissue shrinkage were termed as Frontotemporal lobar degeneration (FTLD). As already explained in the background section which disclosure content is incorporated herein, a heterozygous expanded hexanucleotide repeat (GGGGCC), i.e. dipeptide repeat (DPR), located between the noncoding exons 1a and 1b of the C9ORF72 (NC_000009.12, 27546545-27573866, complement; NG_031977.1, 5001-32322 RefSeqGene) was identified as the most common cause of FTLD and amyotrophic lateral sclerosis (ALS). The expanded hexanucleotide repeat results in the production, generation and/or aggregation of different polypeptides consisting of repeating units of two amino acids (dipeptide repeats, DPRs), in particular poly-(Gly-Ala; GA), poly-(Gly-Pro; GP), poly-(Pro-Arg; PR), or poly-(Pro-Ala, PA), and/or poly-(Gly-Arg; GR).

The present invention is generally directed to human-derived antibodies, antigen-binding fragments, synthetic and biotechnological variants thereof and equivalent antigen-binding molecules which are capable of specifically recognizing DPR proteins, in particular those wherein the DPR consists of poly-(Gly-Ala; GA), poly-(Gly-Pro; GP), poly-(Pro-Arg; PR), poly-(Pro-Ala, PA), and/or poly-(Gly-Arg; GR). Thus, the present invention relates to both, antibodies which selectively recognize one particular dipeptide repeat, for example poly-GA as well as to antibodies which are capable of recognizing more than one dipeptide repeat, for example poly-GA and poly-GP or poly-GR, poly-GA and poly-PR with either substantially the same or different affinity but still significantly over background. If not indicated otherwise, by "specifically recognizing DPRs", "antibody specific to/for DPRs" and "anti-DPR antibody" antibodies are meant which specifically, generally, and collectively bind to the native or aggregated form of "DPR proteins", "dipeptide repeats", "DPRs" which are used interchangeably herein. DPRs are a results of an expanded hexanucleotide repeat and comprises repeating units of two amino acids. The repeating units can comprise any amino acid. However, in a preferred embodiment of the present invention the DPR comprise glycine and alanine (Gly-Ala; GA), glycine and proline (Gly-Pro; GP), glycine and arginine (Gly-Arg; GR), proline and arginine (Pro-Arg; PR), or proline and alanine (Pro-Ala, PA). Therefore, provided herein are human-derived antibodies, protein-binding fragments, synthetic and biotechnological variants thereof selective for DPR proteins consisting of GA, GP, GR, PR, or PA. In a preferred embodiment the DPR binding molecules of the present invention bind to DPR proteins containing higher number of repeats, i.e. DPRs consisting of $(GA)_X$, $(GP)_X$, $(GR)_X$, $(PR)_X$, or $(PA)_X$. Particularly the X denotes the number of repeats, e.g. a DPR protein with 15 repeats of will be denoted $(GA)_{15}$, also meaning that the e.g. hexanucleotide expansion $G_4C_2$ is repeated 15 times. In one embodiment of the present invention the antibody preferably recognize a DPR protein of $(GA)_{15}$.

Typically, the ability of an antibody to bind a DPR protein is assessed using a DPR peptide bound to a carrier protein such as BSA or GST; see, e.g., Mori et al., Science 339 (2013), 1335-1338 and Mackenzie et al., Acta Neuropathol. 126 (2013), 859-879 describing inter alia the use of recombinant GST-$GA_{15}$ protein in the generation and characterization mouse monoclonal anti-GA antibody. However, experiments performed in accordance with the present invention surprisingly revealed that some anti-DPR antibodies which lacked significant binding to BSA-coupled DPR peptides or displayed only rather low affinity bind the uncoupled DPR peptide and with substantially higher affinity than the BSA-coupled DPR peptide; compare, e.g., $EC_{50}$ values summarized in FIGS. 3A-3M for anti-poly GA antibody NI-308.45C2, anti-poly PR antibody NI-308.24E11 and in particular of anti-poly GR antibodies NI-308.6B11 and NI-308.46F8 which did not bind to BSA-coupled $(GR)_{15}$ peptide at all and thus most likely would have been missed in the ELISA methods used in the prior art for the generation of mouse monoclonal anti-DPR antibodies.

For example, international application WO 2014/114303 A1 and WO 2014/114660 A1, respectively, describe polyclonal antibodies raised in rabbit against poly-GA $(GA)_{15}$ and poly-GP $(GP)_{15}$ fused to maltose binding protein (MBP) and mouse monoclonal antibodies raised against aggregated poly-GA $(GA)_{10}$ linked to polyethylene glycol (PEG) and recognizing poly-GA $(GA)_{15}$ fused to glutathione S-transferase (GST). However, no data as to the binding specificity towards unrelated amyloidogenic proteins and binding to pathologic DPR aggregates in human C9orf72-FTLD brain tissue are disclosed. Therefore, the diagnostic and therapeutic utility of those antibodies has not been substantiated and remains to be seen.

International application WO 2014/116865A1 describes the generation of polyclonal antibodies raised in rabbit against a mixture of poly-GA $(GA)_8$, poly-GP $(GP)_8$, and poly-GR $(GR)_8$ each coupled to aminohexanoic acid (Ahx) and conjugated to m-maleimidobenzoyl-N-hydroxysuccinimide ester (MBS) as an immune carrier. One polyclonal rabbit antibody termed MC-001 is described to bind poly-GP $(GP)_8$ but not to the other DPRs. The polyclonal MC-001 antibody is described to detect immunoreactivity in cerebrospinal fluid (CSF) of $C9^+$ ALS patients and insoluble inclusions of poly-GP polypeptides in the brains of patients with the C9ORF72 genetic expansion. Furthermore, attempts for the generation of polyclonal anti-poly-GA, poly-GP, poly-GR and poly-PA antibodies in rabbit and goat, respectively, using individual DPR peptides with different repeat numbers and immune carriers are described as well as one experiment of producing mouse monoclonal anti-poly-GP antibodies with the approach used for the generation of the polyclonal MC-001 antibody. However, though it is described that three monoclonal antibody clones G2, G3 and G4 have been obtained which bind poly-GP $(GP)_8$ only, no data as to the binding specificity towards unrelated amyloidogenic proteins and binding to pathologic DPR aggregates in human C9orf72-FTLD brain tissue are disclosed. Moreover, besides the cryptic description of the protocol of producing the monoclonal antibody no sequence information on the variable region of the antibody or deposit of the same are provided. Therefore, also here the diagnostic and therapeutic utility of monoclonal antibodies possibly obtainable by the immunization protocol taught in WO 2014/116865A1 remains to be investigated.

International application WO2014/159247 A1 describes polyclonal rabbit and mouse antibodies which have been raised against synthetic DPR peptides with different repeat numbers and N- and/or C-terminal modifications, e.g. acetylation and amidation. However, the generation of monoclonal anti-DPR antibodies is not described. Furthermore, WO2014/159247 A1 inter alia describes a transgenic mouse model of C9ORF72 ALS to test the hypothesis that both sense and antisense transcripts contribute to ALS/FTD. In accordance with the present invention, this mouse model may be used for testing the therapeutic utility of the antibodies of the present invention.

In summary, the prior does not teach or suggest, let alone provide anti-DPR antibodies which selectively bind one or more of the DPRs derived from the different reading frames of the C9orf72 gene, which are capable of binding pathologic DPR aggregates in human C9orf72-FTLD brain tissue and have utility in both the diagnosis and therapy of disorders associated with the accumulation and aggregation of DPR proteins such as in ALS/FTD. In contrast, the present invention for the first time provides a set of monoclonal human-derived anti-DPR antibodies from human memory B cells, which specifically recognize one or more DPRs as translated from the C9orf72 gene in it sense and/or antisense direction. As demonstrated in the Examples, the monoclonal human-derived anti-DPR antibodies of the present invention have high affinity, do not substantially recognize unrelated amyloidogenic proteins and are capable binding to pathologic DPR aggregates in human C9orf72-FTLD brain tissue.

Therefore, and in view of the fact that the anti-DPR antibodies of the present invention are derived from human autoantibodies and thus are supposed to be substantially non-immunogenic in humans it is prudent to expect that besides their diagnostic value illustrated in the Examples they have therapeutic utility as well. In this context, it has to be noted that the prior art is silent as to the possible existence of human autoantibodies against DPR proteins but teaches to apply immunization of laboratory animals with synthetic and modified DPR peptides only, and that the generation of mouse monoclonal ant-DPR antibodies is rather difficult since common immunization methods failed and only immunization with a PEG-conjugated poly GA $(GA)_{10}$ peptide resulted in stable antibody clones; see, e.g., international application WO 2014/114660 A1 in Example 10 at page 80, lines 5 to 15. Hence, this makes the findings of the present invention, i.e. provision of human-derived anti-DPR antibodies all the more surprising since of course the memory B cells providing the source of the antibodies of the present invention were obtained from non-immunized human patients/volunteers.

Accordingly, the present invention generally relates to the following embodiments:

[1] A human-derived monoclonal antibody capable of binding a dipeptide (XX') repeat (DPR), or a DPR-binding fragment, synthetic variant or biotechnological derivative thereof which recognize at least on DPR as translated from the chromosome 9 open reading frame 72 (C9orf72) gene in it sense and/or antisense direction, preferably wherein at least one, preferably two and most preferably all three CDRs of one or preferably both the variable light and heavy chain of the antibody are derived from a human antibody as expressed by a human memory B cell (human autoantibody). Preferably, the antibody recognizes at least two different DPRs, preferably at least one DPR as translated from the C9orf72 gene in its sense direction and at least one DPR as translated from the C9orf72 gene in its antisense direction; see, e.g., subject antibody NI-308.6B11 illustrated in the Examples and the Table in FIG. 2A. For the sake of clarity it is to be understood that unless indicated otherwise reference to the antibody in the following items only is made for the sake of conciseness and of course includes the mentioned DPR-binding fragment, synthetic variant and biotechnological derivative of the antibody.

[2] The antibody of [1], wherein the DPR is contained in or conjugated to a protein (DPR-protein), preferably wherein the protein is bovine serum albumin (BSA) and conjugated to the DPR.

[3] The antibody of [1] or [2], wherein the DPR consists of poly-Glycine-Alanine (Gly-Ala; GA), poly-Glycine-Proline (Gly-Pro; GP), poly-(Gly-Arg; GR), poly-(Pro-Arg; PR), and/or poly-(Pro-Ala, PA) repeats, preferably wherein the repeat number is $(XX')_{15}$.

[4] The antibody of any one of [1] to [3], which recognizes a combination of DPR proteins, preferably wherein the DPR proteins consist of poly-(GA) or poly-(PA), poly-(GP) or poly-(PA), or poly-(GR) or poly-(PR), preferably wherein the antibody recognizes poly-(GA) and poly-(GP); poly-(GA) and poly-(GR); poly-(PA) and poly-(GA); poly-(GA), poly-(GR) and optionally poly-(PR); poly-(PA), poly-(PR) and optionally poly-(GR); or poly-(PA), poly-(GR), poly-(PR) and optionally poly-(GA).

[5] The antibody of any one of [1] to [4], wherein the antibody is capable of binding a DPR peptide consisting of $(XX')_{15}$, optionally wherein the antibody does not bind or at least a magnitude less to the peptide coupled to BSA or to another carrier protein such as chitin binding protein (CBP), maltose binding protein (MBP), or glutathione-S transferase (GST).

[6] The antibody of any one of [1] to [5], which is capable of binding aggregated forms of the DPR and DPR protein, respectively.

[7] The antibody of any one of [1] to [6], wherein the DPR-protein is C9ORF72-DPR.

[8] The antibody of any one of [1] to [7] recognizing a DPR comprising a GA repeat, comprising in its variable region
  (a) at least one complementarity determining region (CDR) of the $V_H$ and/or $V_L$ variable region amino acid sequence of any one of antibodies NI-308.18F7, NI-308.15O7, NI-308.28G1, and NI-308.45C2 shown in any one of FIGS. 1A-1D, and depicted in
    (i) $V_H$ sequence (SEQ ID NOs: 2, 8, 22, 26, 30, 34); and
    (ii) $V_L$ sequence (SEQ ID NOs: 4, 6, 10, 12, 24, 28, 32, 36), respectively;
  (b) an amino acid sequence of the $V_H$ and/or $V_L$ region as depicted in any one of FIGS. 1A-1D;
  (c) at least one CDR consisting of an amino acid sequence resulted from a partial alteration of any one of the amino acid sequences of (a);
  (d) a heavy chain and/or a light variable region comprising an amino acid sequence resulted from a partial alteration of the amino acid sequence of (b); and/or
  (e) the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

[9] The antibody of any one of [1] to [7] recognizing a DPR comprising a GP repeat comprising in its variable region
  (a) at least one complementarity determining region (CDR) of the $V_H$ and/or $V_L$ variable region amino acid sequence of any one of antibodies NI-308.5G2, NI-308.46E9 and NI.308-12A3 shown in FIGS. 1F, 1G and 1K and depicted in
   (i) $V_H$ sequence (SEQ ID NOs: 14, 18, 44, 48, 72, 76); and
   (ii) $V_L$ sequence (SEQ ID NOs: 16, 20, 46, 50, 74, 78), respectively;
(b) an amino acid sequence of the $V_H$ and/or $V_L$ region as depicted in FIG. 1F, 1G or 1K;
(c) at least one CDR consisting of an amino acid sequence resulted from a partial alteration of any one of the amino acid sequences of (a);
(d) a heavy chain and/or a light variable region comprising an amino acid sequence resulted from a partial alteration of the amino acid sequence of (b); and/or
(e) the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

[10] The antibody of any one of [1] to [7] recognizing a DPR comprising a GR repeat comprising in its variable region
   (a) at least one complementarity determining region (CDR) of the $V_H$ and/or $V_L$ variable region amino acid sequence of antibody NI-308.6B11 or NI-308.46F8 shown in FIGS. 1H and 1I and depicted in
      (i) $V_H$ sequence (SEQ ID NOs: 52, 56, 58, 62); and
      (ii) $V_L$ sequence (SEQ ID NOs: 54, 60), respectively;
   (b) an amino acid sequence of the $V_H$ and/or $V_L$ region as depicted in FIG. 1H or 1I;
   (c) at least one CDR consisting of an amino acid sequence resulted from a partial alteration of any one of the amino acid sequences of (a);
   (d) a heavy chain and/or a light variable region comprising an amino acid sequence resulted from a partial alteration of the amino acid sequence of (b); and/or
   (e) the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

[11] The antibody of any one of [1] to [7] recognizing a DPR comprising a PR repeat comprising in its variable region
   (a) at least one complementarity determining region (CDR) of the $V_H$ and/or $V_L$ variable region amino acid sequence of antibody NI-308.24E11 shown in FIG. 1E and depicted in
      (i) $V_H$ sequence (SEQ ID NOs: 38); and
      (ii) $V_L$ sequence (SEQ ID NOs: 40, 42), respectively;
   (b) an amino acid sequence of the $V_H$ and/or $V_L$ region as depicted in FIG. 1E;
   (c) at least one CDR consisting of an amino acid sequence resulted from a partial alteration of any one of the amino acid sequences of (a);
   (d) a heavy chain and/or a light variable region comprising an amino acid sequence resulted from a partial alteration of the amino acid sequence of (b); and/or
   (e) the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

[12] The antibody of any one of [1] to [7] recognizing a DPR comprising a PA repeat comprising in its variable region
   (a) at least one complementarity determining region (CDR) of the $V_H$ and/or $V_L$ variable region amino acid sequence of antibody NI-308.4M1 shown in FIG. 1J and depicted in
      (i) $V_H$ sequence (SEQ ID NOs: 64, 68); and
      (ii) $V_L$ sequence (SEQ ID NOs: 66, 70), respectively;
   (b) an amino acid sequence of the $V_H$ and/or $V_L$ region as depicted in FIG. 1J;
   (c) at least one CDR consisting of an amino acid sequence resulted from a partial alteration of any one of the amino acid sequences of (a);
   (d) a heavy chain and/or a light variable region comprising an amino acid sequence resulted from a partial alteration of the amino acid sequence of (b); and/or
   (e) the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

[13] The antibody of any one of [1] to [7] recognizing a DPR comprising a PR repeat comprising in its variable region
   (a) at least one complementarity determining region (CDR) of the $V_H$ and/or $V_L$ variable region amino acid sequence of antibody NI-308.16C10 shown in FIG. 1L and depicted in
      (i) $V_H$ sequence (SEQ ID NOs: 80, 84); and
      (ii) $V_L$ sequence (SEQ ID NOs: 82, 86), respectively;
   (b) an amino acid sequence of the $V_H$ and/or $V_L$ region as depicted in FIG. 1L;
   (c) at least one CDR consisting of an amino acid sequence resulted from a partial alteration of any one of the amino acid sequences of (a);
   (d) a heavy chain and/or a light variable region comprising an amino acid sequence resulted from a partial alteration of the amino acid sequence of (b); and/or
   (e) the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

[14] The antibody of [9], which is also capable of binding a poly GA repeat, preferably wherein the antibody is or is derived from antibody NI-308.5G2.

[15] The antibody of [10], which is also capable of binding a poly GA repeat, preferably wherein the antibody is or is derived from antibody NI-308.6B11.

[16] The antibody of [10] or [14], which is also capable of binding a poly PR repeat, preferably wherein the antibody is or is derived from antibody NI-308.6B11.

[17] The antibody of [12], which is also capable of binding a poly GA repeat, preferably wherein the antibody is or is derived from antibody NI-308.4M1.

[18] The antibody of [13], which is also capable of binding a poly GA repeat, preferably wherein the antibody is or is derived from antibody NI-308.16C10.

[19] The antibody of any one of [1] to [18], which selectively or preferentially binds uncoupled DPR peptide.

[20] The antibody of any one of [1] to [19], which binds to the DPR only if the repeat number n is ≥6, preferably ≥10, more preferably ≥15.

[21] The antibody of any one of [1] to [20], which is capable of binding uncoupled and BSA-coupled DPR with substantially equal affinity or within the same order of magnitude, preferably wherein the $EC_{50}$ (half maximal effective concentration) value for binding the uncoupled and the BSA-coupled DPR differs no more than a factor of ≤20, preferably ≤15, more preferably ≤10, still more preferably ≤5, and most preferably no more than about ≤2 o or 3 as determined by indirect ELISA, wherein the repeat number n is 15.

[22] The anti-DPR antibody of any one of [1] to [22], which is capable of binding two or more different DPRs with substantially equal affinity or within the same order of magnitude, preferably wherein the $EC_{50}$ for binding any one of the DPRs is at least ≤200 nM, preferably ≤150 nM, more preferably ≤100 nM, still more preferably ≤50 nM and most preferably ≤25 nM for binding DPRn or DPRn protein as determined by indirect ELISA, wherein the repeat number n is 15. For example, antibody NI-308.5G2 binds $(GA)_{15}$ with $EC_{50}$ of about 15.3 and $(GP)_{15}$ with an $EC_{50}$ of about 0.88, and antibody NI-308.6B11which binds $(GA)_{15}$ with $EC_{50}$ of about 38.4, $(GR)_{15}$ with an $EC_{50}$ of about 0.94 and $(PR)_{15}$ with an $EC_{50}$ of about 119; see Example 3 and FIGS. 2A-2M.

[23] The antibody of any one of [1] to [22], which has a binding affinity to at least one $DPR_n$ or $DPR_n$ protein corresponding to an $EC_{50}$ (half maximal effective concentration) value of ≤25 nM, preferably ≤2 nM, more preferably ≤1 nM and most preferably ≤0.5 nM as determined by indirect ELISA, wherein the repeat number n is 15.

[24] The antibody of any one of [1] to [23], which is a chimeric murine-human or a murinized antibody.

[25] An antibody or antigen-binding molecule which competes with an antibody of any one of [1] to [24] for specific binding to a DPR or DPR-protein as defined in any one of [1] to [24].

[26] The antibody of any one of [1] to [25], which is selected from the group consisting of a single chain Fv fragment (scFv), an F(ab') fragment, an F(ab) fragment, and an F(ab')$_2$ fragment.

[27] A polynucleotide encoding at least the binding domain or variable region of an immunoglobulin chain of the antibody of any one of [1] to [26], preferably wherein the polynucleotide is a cDNA.

[28] A vector comprising the polynucleotide of [7], optionally in combination with a polynucleotide of [27] that encodes the variable region of the other immunoglobulin chain of said binding molecule.

[29] A host cell comprising a polynucleotide of [27] or a vector of [28].

[30] Use of the cDNA of [27], the vector of [28], or the host cell of [29] for the production of an anti-DPR antibody.

[31] A method for preparing an anti-DPR antibody or a biotechnological derivative or immunoglobulin chain(s) thereof, said method comprising
   (a) culturing the cell of [30]; and
   (b) isolating the antibody or immunoglobulin chain(s) thereof from the culture.

[32] An antibody or immunoglobulin chain(s) thereof encoded by a polynucleotide of [27] or obtainable by the method of [31].

[33] The antibody of any one of [1] to [26] or [32], which is detectably labeled.

[34] The antibody of [33], wherein the detectable label is selected from the group consisting of an enzyme, a radioisotope, a fluorophore, and a heavy metal.

[35] The antibody of any one of claims [1] to [26] or [32], which is attached to a drug.

[36] A composition comprising the antibody of any one of [1] to [26] or [32] to [34], the polynucleotide of [27], the vector of [28] or the cell of [29].

[37] The composition of [36], which is a pharmaceutical composition and further comprises a pharmaceutically acceptable carrier.

[38] The composition of [37], which is a vaccine.

[39] A method of preparing a pharmaceutical composition for use in the treatment of a disorder associated with or caused by DPR and DPR-protein aggregates, the method comprising:
   (a) culturing the cell of [29];
   (b) purifying the antibody, biotechnological derivative or immunoglobulin chain(s) thereof from the culture to pharmaceutical grade; and
   (c) admixing the antibody or biotechnological derivative thereof with a pharmaceutically acceptable carrier

[40] The pharmaceutical composition of [36] or [37] further comprising an additional agent useful for treating diseases and/or symptoms associated with aggregated DPR proteins, for example C9ORF72-DPR.

[41] The composition of [40], which is a diagnostic composition.

[42] The diagnostic composition of [41], which comprises reagents conventionally used in immuno or nucleic acid based diagnostic methods.

[43] An antibody of any one of [1] to [26] or [32] to [34], or DPR protein-binding molecule having substantially the same binding specificities of any one thereof, the polynucleotide of [27], the vector of [28] or the cell of [29] for use in the preparation of a pharmaceutical or diagnostic composition for prophylactic and therapeutic treatment of diseases associated with DPR protein and aggregated forms thereof.

[44] The antibody of [43] for use in the preparation of a pharmaceutical or diagnostic composition for prophylactic and therapeutic treatment, wherein the disease is selected from the group consisting of Frontotemporal lobar degeneration (FTLD), amyotrophic lateral sclerosis (ALS), and FTLD-ALS.

[45] DPR protein-binding molecule comprising at least one CDR of an antibody of any one of claims [1] to [26] or [32] to [35] for use in in vivo detection of or targeting a therapeutic and/or diagnostic agent to aggregated in the human or animal body.

[46] DPR protein-binding molecule of [45], wherein said in vivo imaging comprises positron emission tomography (PET), single photon emission tomography (SPECT), near infrared (NIR), optical imaging or magnetic resonance imaging (MRI).

[47] A method for diagnosing disorders associated with DPR protein, comprising steps of determining the presence of an antibody according to any one of claims [1] to [26] or [32] to [35] in a biological sample of said subject.

[49] A kit useful in the diagnosis or monitoring of disorders associated with DPR protein, said kit comprising at least one antibody of any one of claims [1] to [27] or [32] to [35] or a DPR protein-binding molecule having substantially the same binding specificities of any one thereof, the polynucleotide of [27], the vector of [28] or the cell of [29], optionally with reagents and/or instructions for use.

The toxic properties of repeat expansion were shown in several diseases including but not limited to Frontotemporal lobar degeneration (FTLD), amyotrophic lateral sclerosis (ALS), FTLD-ALS, and spinocerebellar ataxia type 36. Therefore, in one embodiment of the present invention the antibody of the present invention is capable of binding DPRs in any one of the diseases and/or disorders selected from the group consisting of Frontotemporal lobar degeneration (FTLD), amyotrophic lateral sclerosis (ALS), FTLD-ALS, and/or spinocerebellar ataxia type 36. Since C9ORF72-DPRs were shown to be associated with FTLD, see supra, in a preferred embodiment, the antibody of the present invention binds to C9ORF72 dipeptide repeats (DPRs).

As demonstrated in the Examples and Figures antibodies obtained in accordance with the present invention bind aggregated forms of C9ORF72-DPRs in human C9ORF72-FTLD patients; see e.g. Examples 10 and 12 as well as FIGS. 9 to 12A and 12B and 14A-14C. Therefore, in one embodiment the antibody of the present invention is capable of binding aggregated forms of C9ORF72-DPRs. Interestingly, antibodies obtained in accordance with the present invention also bind co-aggregated forms of C9ORF72-DPRs in human C9ORF72-FTLD patients; see Example 13 and FIG. 15. Thus, in another embodiment the antibody of the present invention is capable of binding co-aggregated forms of C9ORF72-DPRs.

In one embodiment of the present invention, the antibody or binding fragment, synthetic or biotechnological derivative thereof demonstrates the immunological binding characteristics of an antibody characterized by any one of the variable regions VH and/or VL as set forth in FIGS. 1A-1L. In a preferred embodiment, the antibody of the present invention comprises in its variable region at least one complementarity determining region (CDR) of the $V_H$ and/or $V_L$ variable region amino acid sequence depicted in (i) $V_H$ sequence (SEQ ID NOs: 2, 8, 14, 18, 22, 26, 30, 34, 38, 44, 48, 52, 56, 58, 62, 64, 68, 72, 76, 80, 84); and (ii) $V_L$ sequence (SEQ ID NOs: 4, 6, 10, 12, 16, 20, 24, 28, 32, 36, 40, 42, 46, 50, 54, 60, 66, 70, 74, 82, 86, 88).

In addition or alternatively, in one embodiment of the present invention the antibody comprises an amino acid sequence of the $V_H$ and/or $V_L$ region as depicted in any one of FIGS. 1A-1L.

In one embodiment the antibody of the present invention additionally or alternatively comprises at least one CDR consisting of an amino acid sequence resulted from a partial alteration of any one of the amino acid sequences of $V_H$ sequence (SEQ ID NOs: 2, 8, 14, 18, 22, 26, 30, 34, 38, 44, 48, 52, 56, 58, 62, 64, 68, 72, 76, 80, 84); and (ii) $V_L$ sequence (SEQ ID NOs: 4, 6, 10, 12, 16, 20, 24, 28, 32, 36, 40, 42, 46, 50, 54, 60, 66, 70, 74, 82, 86, 88). In another embodiment, the antibody comprises a heavy chain and/or a light variable region comprising an amino acid sequence resulted from a partial alteration of the amino acid sequence described above.

In a further embodiment of the present invention, the antibody or antigen binding fragment thereof additionally or alternatively optionally further comprises a polypeptide sequence which is heterologous to the $V_H$ and/or $V_L$ region or the least one CDR, preferably wherein polypeptide sequence comprises a human constant domain.

In a preferred embodiment, infra, the antibody or biotechnological derivative thereof is a human IgG isotype antibody, preferably of the IgG1 class or isotype.

As illustrated in the Examples and Figures, it was shown that the anti-DPR protein antibodies bind specifically to C9ORF72-DPRs with a $(GA)_{15}$ or $(GP)_{15}$ or $(GR)_{15}$ or $(PA)_{15}$ or $(PR)_{15}$ repeat. Therefore, in one embodiment of the present invention, the antibody of the present invention or biotechnological derivative thereof has a binding affinity corresponding to an $EC_{50}$ (half maximal effective concentration) value of ≤2 nM, preferably ≤1 nM and most preferably ≤0.5 nM for binding a DPR consisting of $(XX')_{15}$, preferably wherein the DPR is DPR protein $(GA)_{15}$ or DPR protein $(GP)_{15}$ DPR protein $(GR)_{15}$ or DPR protein $(PA)_{15}$ or DPR protein $(PR)_{15}$.

Since anti-DPR antibodies with high affinity and specificity towards individual dipeptide repeats are of interest in general and the subject antibodies illustrated in the Examples provide a means for arriving at equivalent antibodies and like DPR binding molecules, the present invention also relates to an antibody or antigen-binding molecule which competes with an antibody, supra, for specific binding to a DPR protein.

The antigen-binding fragment of the antibody can be a single chain Fv fragment, an F(ab') fragment, an F(ab) fragment, and an F(ab')2 fragment, or any other antigen-binding fragment. Alternatively, the antibody is a chimeric human-rodent or rodentized antibody such as murine-human, murine or murinized, rat or ratinized antibody, the rodent versions being particularly useful for diagnostic methods and studies in animals.

Furthermore, the present invention relates to compositions comprising the antibody of the present invention or antigen-binding fragment, synthetic or biotechnological derivative thereof and to immunotherapeutic and immunodiagnostic methods using such compositions in the prevention, diagnosis or treatment of diseases and/or disorders associated with DPR proteins and/or aggregated C9ORF72, wherein an effective amount of the composition is administered to a patient in need thereof.

The present invention also relates to polynucleotides encoding at least a variable region of an immunoglobulin chain of the antibody of the invention. Preferably, said variable region comprises at least one complementarity determining region (CDR) of the VH and/or VL of the variable region as set forth in any one of FIGS. 1A-1L.

Accordingly, the present invention also encompasses vectors comprising said polynucleotides and host cells transformed therewith as well as their use for the production of an antibody and equivalent binding molecules which are specific for DPRs and preferably are capable of binding C9ORF72-DPR proteins or fragments thereof. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human-derived antibody in the sense that application of said antibody is substantially free of an immune response directed against such antibody otherwise observed for chimeric and even humanized antibodies.

Furthermore, disclosed herein are compositions and methods that can be used to identify DPRs, in particular C9ORF72-DPRs or fragments in vitro, e.g. in samples and/or in vivo. The disclosed anti-DPR protein antibodies and binding fragments thereof can be used to screen human blood, plasma, serum, saliva, peritoneal fluid, cerebrospinal fluid ("CSF"), and urine for the presence of DPRs and/or C9ORF72-DPRs species or fragments thereof in samples, for example, by using ELISA-based or surface adapted assay. In one embodiment the present invention relates to a method of diagnosing or monitoring the progression of a disease and/or disorder related to DPR protein species or fragments thereof in a subject, the method comprising determining the presence of DPR protein species or fragments in a sample from the subject to be diagnosed with at least one antibody of the present invention or equivalent DPR-binding molecule, wherein the presence of DPR protein species or fragments is indicative of the disorder. Furthermore, in one embodiment of the present invention the disclosed anti-DPR antibodies and DPR-binding molecules comprising at least one CDR of an antibody of the present invention are provided for the preparation of a composition for in vivo detection (also called in vivo imaging) of or targeting a therapeutic and/or diagnostic agent to DPRs, in particular C9ORF72-DPR species in the human or animal body. The methods and compositions disclosed herein can aid in diseases and/or disorders associated with DPR proteins and characterized, e.g., by the occurrence of aggregated forms of DPRs and can be used to monitor disease progression and therapeutic efficacy of the therapy provided to the subject, for example in in vivo imaging related diagnostic methods. In one embodiment the in vivo detection (imaging) comprises scintigraphy, positron emission tomography (PET), single photon emission tomography (SPECT), near infrared (NIR) optical imaging or magnetic resonance imaging (MRI).

Hence, it is a particular object of the present invention to provide methods for treating, diagnosing or preventing a disease and/or disorder associated with DPR proteins, preferably with C9ORF72-DPRs. The methods comprise administering an effective concentration of a preferably human-derived antibody or biotechnological antibody derivative to the subject where the antibody targets DPRs and DPR proteins, preferably C9ORF72-DPR protein species or fragments thereof.

Further embodiments of the present invention will be apparent from the description and Examples that follow.

BRIEF DESCRIPTION OF THE DRAWINGS

FIGS. 1A-1L: Amino acid sequences of the variable regions of human antibodies NI-308.18F7, NI-308.15O7, NI-308.28G1, NI-308.45C2, NI.308.24E11, NI-308.5G2, NI-308.46E9, NI308-6B11, NI-308.46F8, NI-308.4M1, NI-308.12A3 and NI-308.16C10. Framework (FR) and complementarity determining regions (CDRs) are indicated with the CDRs being underlined. The Kabat numbering scheme was used (cf. bioinf.org.uk/abs/). Boxes indicate the VH CDR1 as defined by Kabat et al., U.S. Dept. of Health and Human Services, "Sequence of Proteins of Immunological Interest" (1983) referred to in the mentioned web reference and given in Table 1, infra.

FIGS. 2A-2M: Binding specificity and $EC_{50}$ determination for C9orf72 dipeptide repeat proteins. (FIG. 2A) Summary of NI-308.15O7, NI-308.28G1, NI308.45C2, NI-308.18F7, NI-308.24E11, NI-308.16C10, NI-308.5G2, NI-308.12A3, NI-308.46E9, NI-308.6B11, NI-308.46F8, and NI-308.4M1 binding specificity and affinity for C9orf72 dipeptide repeat proteins. $EC_{50}$s of human-derived NI-308 antibodies for C9orf72 dipeptide repeat protein peptides $(GA)_{15}$ (■), $(GP)_{15}$ (▲), $(GR)_{15}$ (▼), $(PA)_{15}$ (◆), $(PR)_{15}$ (●) and BSA control (Δ) were determined by indirect ELISA. Antibodies NI-308.15O7 (FIG. 2B), NI-308.28G1 (FIG. 2C), NI-308.45C2 (FIG. 2D) and NI-308.18F7 (FIG. 2E) specifically recognized the C9orf72 DPR protein peptide $(GA)_{15}$ with binding affinity of 0.48 nM, 1.1 nM, 1.1 nM and 1.5 nM, respectively. Antibody NI-308.24E11 (FIG. 2F) specifically targeted the C9orf72 DPR protein peptide $(PR)_{15}$ with an $EC_{50}$ of 12.8 nM whereas antibody NI-308.16C10 (FIG. 2M) showed preferential binding to the C9orf72 DPR protein peptide $(PR)_{15}$ with binding affinity of 3.5 nM but also recognized with lower binding affinity the C9orf72 DPR protein peptide $(GA)_{15}$. Antibodies NI-308.5G2 (FIG. 2G), NI-308.12A3 (FIG. 2L) and NI-308.46E9 (FIG. 2H) showed preferential binding to the C9orf72 DPR protein peptide $(GP)_{15}$ with binding affinity of 0.88 nM, 2.2 nM and 13.9 nM, respectively but also recognized with lower binding affinity the C9orf72 DPR protein peptide $(GA)_{15}$. Antibodies NI-308.6B11 (FIG. 2I) and NI-308.46F8 (FIG. 2J) targeted preferentially the C9orf72 DPR protein peptide $(GR)_{15}$ with binding affinity of 0.94 nM and 40.6 nM, respectively but also recognized with lower binding affinity the C9orf72 DPR protein peptides $(GA)_{15}$ and $(PR)_{15}$. Antibody NI-308.4M1 (FIG. 2K) showed preferential binding to the C9orf72 DPR protein peptide $(PA)_{15}$ with binding affinity of 0.10 nM but also recognized with lower binding affinity the C9orf72 DPR protein peptide $(GA)_{15}$.

FIGS. 3A-3M: $EC_{50}$ determination for BSA-coupled and uncoupled C9orf72 dipeptide repeat protein peptides. (FIG. 3A) Summary of NI-308.18F7, NI-308.15O7, NI-308.28G1, NI308.45C2, NI-308.24E11, NI-308.5G2, NI-308.46E9, NI-308.6B11, NI-308.46F8, NI-308.4M1, NI-308.12A3 and NI-308.16C10 binding affinities to BSA-coupled and uncoupled C9orf72 DPR peptides. Determination of the half maximal effective concentration ($EC_{50}$) of human-derived NI-308 antibodies for BSA-coupled (▲) and uncoupled (■) C9orf72 dipeptide repeat protein peptides $(GA)_{15}$, $(GP)_{15}$, $(GR)_{15}$, $(PR)_{15}$, $(PA)_{15}$ or BSA control (Δ), using indirect ELISA. Antibodies NI-308.18F7 (FIG. 3B), NI-308.15O7 (FIG. 3C), NI-308.28G1 (FIG. 3D), NI-308.5G2 (FIG. 3G), NI-308.46E9 (FIG. 3H), NI-308.4M1 (FIG. 3K) and NI-308.12A3 (FIG. 3L) recognized with similar binding affinities BSA-coupled and uncoupled C9orf72 DPR protein peptides. Antibodies NI-308.45C2 (FIG. 3E), NI-308.24E11 (FIG. 3F) and NI-308.16C10 (FIG. 3M) targeted BSA-coupled DPR protein peptides with lower $EC_{50}$ as compared to the uncoupled peptides. No binding to BSA-coupled DPR protein peptide $(GR)_{15}$ was detected for antibodies NI-308.6B11 (FIG. 3I) and NI-308.46F8 (FIG. 3J).

FIGS. 4A-4I: Binding specificity analysis of human-derived DPR antibodies to unrelated aggregating proteins Antibody binding to sense $((GA)_{15}, (GP)_{15}$ and $(GR)_{15})$ and antisense $((PA)_{15}$ and $(PR)_{15})$ DPR protein peptides mixtures and six unrelated amyloidogenic proteins was determined by indirect ELISA. Antibodies NI-308.15O7 (FIG. 4A), NI-308.18F7 (FIG. 4B), NI-308.28G1 (FIG. 4C), NI-308.45C2 (FIG. 4D), NI-308.5G2 (FIG. 4F) and NI-308.46F8 (FIG. 4I) showed binding to the sense DPR protein peptides mixture with absence of significant off-target binding to the unrelated analytes. Antibody NI-308.46E9 (FIG. 4G) also targeted the sense DPR protein peptides mixture and additionally showed moderate off-target binding to unrelated analytes. Antibody NI-308.24E11 (FIG. 4E) showed specific binding to the antisense DPR protein peptides mixture whereas antibody NI-308.6B11 (FIG. 4H) targeted both sense and antisense DPR peptides mixtures. For both antibodies, no significant off-target binding to the unrelated amyloidogenic proteins was determined. NI-308 antibodies were tested at 20 nM concentration.

FIGS. 5A-5J: NI-308 antibody binding selectivity for C9orf72 dipeptide repeat proteins Determination of human-derived C9orf72 DPR antibody binding selectivity for BSA-coupled C9orf72 dipeptide repeat protein peptides $(GA)_{15}$, $(GP)_{15}$, $(GR)_{15}$, $(PA)_{15}$ and $(PR)_{15}$ by Western blot analysis. The C9orf72 poly-GA DPR protein was recognized by antibodies NI-308.15O7 (FIG. 5A), NI-308.18F7 (FIG. 5B), NI-308.28G1 (FIG. 5C) and NI-308.45C2 (FIG. 5D). The poly-PR DPR protein was specifically recognized by antibodies NI-308.24E11 (FIG. 5E) and NI-308.16C10 (FIG. 5J), with antibody NI-308.16C10 showing a weaker binding also to the poly-GA DPR protein. Antibodies NI-308.5G2 (FIG. 5F), NI-308.46E9 (FIG. 5G) and NI-308.12A3 (FIG. 5I) targeted the poly-GP DPR protein with NI-308.5G2 showing a weaker binding also to the poly-GA DPR protein. Antibody NI-308.4M1 (FIG. 5H) specifically recognized the C9orf72 poly-PA DPR protein.

(FIG. 7A) Summary of C9orf72 poly-GA repeat-length dependent binding of selected NI-308 antibodies.

FIGS. 8A-8F: C9orf72 poly-GA and poly-GP DPR protein repeat-length dependent binding of selected NI-308 antibodies. (FIG. 8A) Summary of C9orf72 poly-GA repeat-length dependent binding of selected NI-308 antibodies. (FIG. 8B) Summary of C9orf72 poly-GP repeat-length dependent binding of selected NI-308 antibodies. Determination of dipeptide repeat-length dependent binding specificity and the half maximal effective concentration ($EC_{50}$) of human-derived NI-308 antibodies for C9orf72 poly-GA or poly-GP dipeptide repeat protein peptides by sandwich ELISA. Antibody NI-308.15O7 (FIG. 8C) bound in solution to DPR protein peptides $(GA)_{10}$ and $(GA)_{20}$ with binding affinity at $EC_{50}$ of >400 nM and 9.0 nM, respectively. Antibody NI-308.18F7 (FIG. 8D) recognized in solution the DPR protein peptides $(GA)_{10}$ and $(GA)_{20}$ with binding affinity at $EC_{50}$ of 0.34 nM and 0.45 nM, respectively. Antibody NI-308.28G1 (FIG. 8E) targeted in solution the DPR protein peptides $(GA)_{10}$ and $(GA)_{20}$ with binding affinity at $EC_{50}$ of 0.46 nM and 0.40 nM, respectively. Antibody NI-308.5G2 (FIG. 8F) recognized in solution only the single DPR protein peptide $(GP)_{20}$ with a binding affinity at $EC_{50}$ of 38.2 nM.

FIG. 9: NI-308.18F7 and NI-308.15O7 antibodies binding specificity and affinity for C9orf72 $(GA)_{20}$ dipeptide repeat protein peptide monomeric and aggregated preparations.

FIGS. 10A and 10B: Characterization of in vitro C9orf72 $(GA)_{20}$ DPR protein peptide preparations by transmission electron microscopy. Representative images of non-aggregated (monomeric, FIG. 10A.) and amyloid-fibril like aggregated (aggregated, FIG. 10B.) $(GA)_{20}$ DPR protein peptide preparations. Magnification: 66 k. Scale bar: 0.5 µm.

FIGS. 14A-14C: NI-308.18F7, NI-308.15O7, NI-308.5G2 and NI-308.4M1 detect pathologic C9orf72 dipeptide repeat protein aggregates in FTLD patients. (FIG. 14A) Human-derived NI-308.18F7, NI-308.15O7 and NI-308.5G2 antibodies revealed pathologic neuronal cytoplasmic inclusions, neuronal intranuclear inclusions and dystrophic neurites in the granule cell layer of the cerebellum of all three tested C9orf72-FTLD cases. In contrast, non-neurological control cerebellum was negative for NI-308.18F7, NI-308.15O7 and NI-308.5G2 staining. Commercial available antibody C9RANT was used as control antibody. Representative images are shown. (FIG. 14B) Representative high magnification images of neuronal C9orf72 DPR inclusions in the granule cell layer of the cerebellum of a selected C9orf72-FTLD case detected by antibodies NI-308.18F7, NI-308.15O7 and NI-308.5G2. (FIG. 14C) Representative high magnification images of neuronal cytoplasmatic and intranuclear C9orf72 DPR inclusions in the granule cell layer of the cerebellum of a selected C9orf72-FTLD case detected by antibody NI-308.4M1. In contrast, non-neurological control cerebellum was negative for NI-308.4M1 staining.

DETAILED DESCRIPTION OF THE INVENTION

Figures 4D, 4E, 4F:
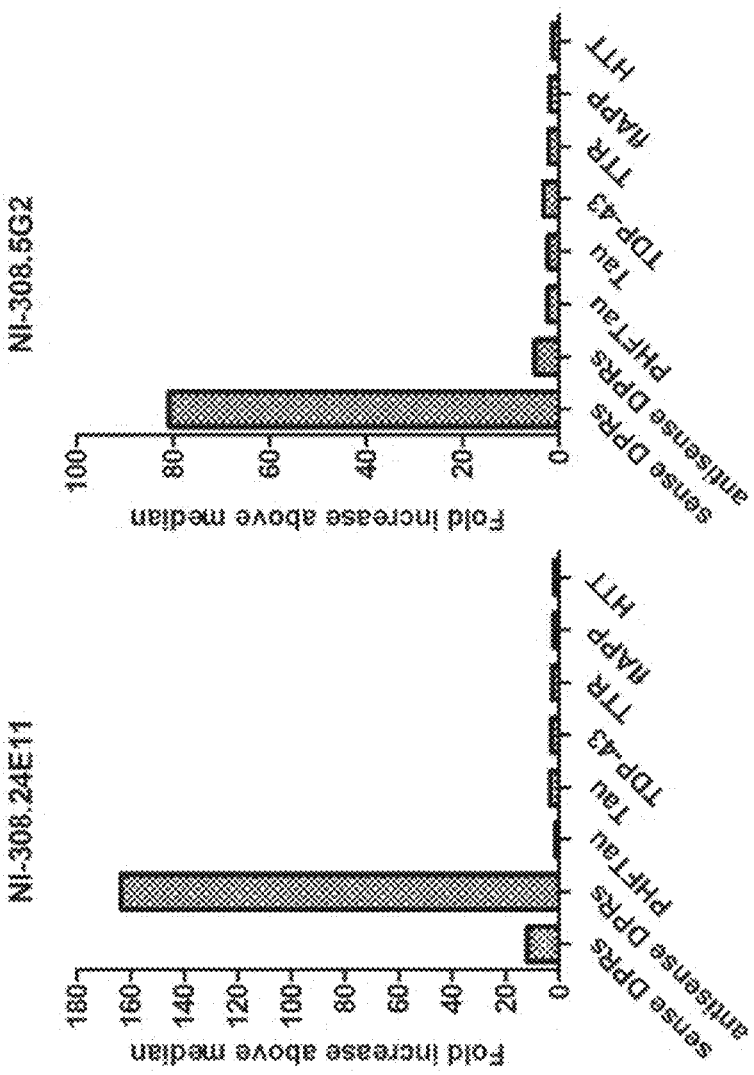

The present invention generally relates to immunotherapy and non-invasive methods for the detection of diseases and conditions associated with the presence of dipeptide repeats (DPR) proteins and in particular aggregated forms thereof. More specifically, the present invention relates to recombinant human-derived monoclonal antibodies and antigen-binding fragments thereof, which have been generated based on sequence information obtained from selected human donor populations and are capable of binding to such DPRs, in particular poly-glycine-alanine (Gly-Ala; GA)-DPRs, poly-glycine-proline (Gly-Pro; GP)-DPRs, poly-Glycine-Arginine (Gly-Arg; GR)-DPRs, poly-Proline-Arginine (Pro-Arg; PR)-DPRs, and/or poly-proline-alanine (Pro-Ala; PA)-DPRs and antigens thereof. The recombinant human-derived monoclonal antibodies of the present invention as well as synthetic and biotechnological derivatives thereof are advantageously characterized by specifically binding to altered C9ORF72 with expanded hexanucleotide repeats forming C9ORF72-dipeptide repeats (DPRs). As shown in the Examples, the recombinant antibodies of the present invention are highly specific as a diagnostic reagent for the detection of DPRs and/or pathological C9ORF72 without giving false positives and due to the human origin of the sequences encoding at least the variable region and CDRs, respectively, and maturation of the original antibodies in the human body can be reasonably expected to be efficacious and safe as therapeutic agent.

In addition, the present invention relates to human-derived monoclonal antibodies including any biotechnological derivatives thereof as described herein for use in the treatment of patients either alone or in combination with other agents utilized for diseases, disorders, and/or symptoms associated with DPRs, preferably wherein the antibody of the present invention is designed to be administered concomitantly with the agent suppressing further side effects or sequentially before or after administration of the same. In this context, the anti-DPR antibody of the present invention is preferably substantially non-immunogenic in human. In one embodiment of the present invention, pharmaceutical compositions are provided comprising both a human-derived monoclonal antibody of the present invention and one or more drugs utilized for diseases, disorders, and/or symptoms associated with DPRs.

I. Definitions

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

If not specifically indicated otherwise, the term "DPR", i.e. "dipeptide repeat" proteins, is used hereinto specifically refer to repeating units of two amino acids, in particular due to an expanded hexanucleotide repeat in a gene. The term "DPR" and "DPRs" is also used to refer collectively to all types and forms of DPRs, such as GA, GR, GP, PA, PR etc. In the following, the present invention will mainly be described with respect to antibodies specifically recognizing DPRs comprising or consisting of either GA, preferably with 15 repeats ($GA_{15}$), GP, preferably with 15 repeats ($GP_{15}$), GR, preferably with 15 repeats ($GR_{15}$), or PR, preferably with 15 repeats ($PR_{15}$), or PA, preferably with 15 repeats ($PA_{15}$) commonly observed in C9ORF72-DPR proteins found in brain tissue of patients suffering from FLTD or ALS. However, though anti-C9ORF72-DPR antibodies represent a preferred embodiment, the present invention generally provides anti-DPR protein antibodies and corresponding embodiments. Accordingly, it is emphasized that in principle any embodiment and corresponding features disclosed herein and illustrated in the Examples and Figures, unless specifically applicable to the anti-C9ORF72-DPR only, is also meant to apply to any anti-DPR protein antibody in general.

Another example for a DPR related disease is spinocerebellar ataxia type 36, a slowly progressive neurodegenerative disorder and a subtype of the autosomal dominant cerebellar ataxia type 1 (ADCA type 1) characterized by adult-onset gait and limb ataxia, lower limb spasticity, dysarthria, muscle fasiculations, tongue atrophy and hyperreflexia. Some affected individuals can also develop hearing loss; see, e.g., Garcia-Murias et al., Brain 135 (2012), 1423-1435. It was shown that spinocerebellar ataxia type 36 is caused by a heterozygous expansion of the intronic GGCCTG hexanucleotide repeat in the NOP56 gene on chromosome 20p13; see, e.g., Garcia-Murias et al., Brain 135 (2012), 1423-1435. Ikeda et al., Neurology 79 (2012), 333-341, Kobayashi et al., Am. J. Hum. Genet. 89 (2011), 121-130.

The term "C9ORF72", if not specifically indicated otherwise, refers to the altered forms of chromosome 9 open reading frame 72 (C9ORF72). The term "C9ORF72" is also used to generally identify C9ORF72 hexanucleotide expansions, leading to C9ORF72-dipeptide repeats (DPRs). Therefore, the term is also used to indicate C9ORF72-DPRs. The term "C9ORF72" is also used to refer collectively to all types and forms of C9ORF72, such as mutated C9ORF72. Added letters in front of the terms C9ORF72 are used to indicate the organism the particular ortholog is originating from, e.g. hC9ORF72 for human C9ORF72 or mC9ORF72 for murine origin.

The anti-DPR antibodies disclosed herein preferably bind C9ORF72-dipeptide repeats (DPRs) and epitopes thereof. For example, disclosed herein are antibodies that specifically bind pathologically altered C9ORF72 species or fragments thereof, i.e. dipeptide repeats that are unconventionally translated from C9ORF72 transcripts of the expanded intronic C9ORF72 hexanucleotide repeats, as well as aggregated forms of C9ORF72-DPRs or fragments thereof. The term (pathologically) aggregated/aggregates of C9ORF72-DPRs is used herein to specifically refer to the aforementioned forms. The term (pathological) "aggregated forms" or "aggregates" as used herein describes the products of an accumulation or cluster formation due to C9ORF72 erroneous/pathological translation from C9ORF72 transcripts of the expanded intronic C9ORF72 hexanucleotide repeats. These aggregates, accumulations or cluster forms may be, substantially consist or consist of both C9ORF72-DPR protein and/or fragments thereof. As used herein, reference to an antibody that "specifically binds", "selectively binds", or "preferentially binds" C9ORF72-DPRs refers to an antibody that does not bind other unrelated proteins; see, e.g., FIGS. 4A-4I. As shown in FIGS. 4A-4I and Example 5, the antibodies of the present invention do not substantially recognize unrelated amyloid-forming proteins selected from the group consisting of paired helical filament (PHF)-tau, TAU, transactive response DNA binding protein 43 (TDP-43), transthyrethin (TTR), full-length amyloid precursor protein (flAPP), and/or Huntingtin (HTT).

In one example, a C9ORF72-DPR antibody disclosed herein can bind DPRs and/or C9ORF72-DPRs or an epitope thereof and shows no binding above about 2 times background for other proteins. An antibody that "specifically binds" or "selectively binds" a DPR and/or a C9ORF72-DPR protein variant refers to an antibody that does not bind all variants of C9ORF72-DPR proteins, i.e., does not bind at least one other C9ORF72 conformer. For example, disclosed herein are antibodies that can preferentially bind to forms of C9ORF72 showing expanded hexanucleotide repeats forming DPRs both in vitro and in tissues obtained from patients with diseases associated with C9ORF72 or with a risk to develop diseases associated with C9ORF72; see, e.g., Example 8 and FIGS. 7A-7P.

Since the anti-DPR antibodies of the present invention have been isolated from human subjects, the DPR antibodies of the present invention may also be called "human autoantibodies" or "human-derived antibodies" in order to emphasize that those antibodies were indeed expressed initially by the subjects and are not synthetic constructs generated, for example, by means of human immunoglobulin expressing phage libraries or xenogeneic antibodies generated in a transgenic animal expressing part of the human immunoglobulin repertoire which hitherto represented one common method for trying to provide human-like antibodies. On the other hand, the human-derived antibody of the present invention may be denoted synthetic, recombinant, and/or biotechnological in order distinguish it from human serum antibodies per se, which may be purified via protein A or affinity column.

A particular advantage of the therapeutic approach of the present invention lies in the fact that the antibodies of the present invention are derived from B cells or B memory cells from healthy human subjects with no signs of a disease showing the occurrence of, or related to DPR proteins and aggregated forms thereof and thus are, with a certain probability, capable of preventing a clinically manifest disease related to aggregated DPR proteins such as C9ORF72-DPR, or of diminishing the risk of the occurrence of the clinically manifest disease, or of delaying the onset or progression of the clinically manifest disease.

Typically, the antibodies of the present invention also have already successfully gone through somatic maturation, i.e. the optimization with respect to selectivity and effectiveness in the high affinity binding to the target DPR molecules by means of somatic variation of the variable regions of the antibody. The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human-derived anti-DPR antibodies of the present invention, both its target structure-specific efficiency as therapeutic agent and its decreased probability of side effects significantly increase its clinical probability of success.

In contrast, antibodies derived from cDNA library's or phage displays are artificial molecules such as a humanized antibody which is still of murine origin and thus foreign to the human body. Therefore the clinical utility and efficacy of the therapeutic antibodies can be limited by the production of anti-drug antibodies (ADAs), which can influence the efficacy and pharmacokinetics of the antibodies and sometimes lead to serious side effects; see, e.g., Igawa et al., MAbs. 3 (2011), 243-252. In particular, humanized antibodies or antibodies generated with recent human-antibody-generation technologies are in contrast to the human-derived antibodies such as those of the present invention prone to induce an antibody response and these human-like antibodies derived from e.g. phage display such as adalimumab have been reported to induce ADA production; see, e.g., Mansour, Br. J. Ophthalmol 91 (2007), 274-276 and Igawa et al., MAbs. 3 (2011), 243-252. Therefore, human-derived antibodies which are not prone to undesired immune response are more beneficial for the patient than artificial molecules derived from libraries or displays.

The term "peptide" is understood to include the terms "polypeptide" and "protein" (which, at times, may be used interchangeably herein) within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Included as polypeptides of the present invention are fragments, derivatives, analogs or variants of the foregoing polypeptides as well as synthetic or biological variants and any combinations thereof. The terms "fragment," "variant," "derivative", and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to altered C9ORF72 protein, such as pathological C9ORF72-DPRs as well as DPR proteins alone, variants, derivatives or analogs of either of them. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

Furthermore, the terms "fragment," "variant," "derivative", and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of DPR protein specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Determination of similarity and/or identity of molecules:
"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

"Similarity" between two polynucleotides is determined by comparing the nucleic acid sequence of one polynucleotide to the sequence of a polynucleotide. A nucleic acid of one polynucleotide is similar to the corresponding nucleic acid of a second polynucleotide if it is identical or, if the nucleic acid is part of a coding sequence, the respective triplet comprising the nucleic acid encodes for the same amino acid or for a conservative amino acid substitution. The determination of percent identity or similarity between two sequences is preferably accomplished using the mathematical algorithm of Karlin and Altschul (1993) Proc. Natl. Acad. Sci USA 90: 5873-5877. Such an algorithm is incorporated into the BLASTn and BLASTp programs of Altschul et al. (1990) J. Mol. Biol. 215: 403-410 available at NCBI (ncbi.nlm.nih.gov/Blast.cge).

The determination of percent identity or similarity is performed with the standard parameters of the BLASTn programs for BLAST polynucleotide searches and BLASTp programs for BLAST protein search, as recommended on the NCBI webpage and in the "BLAST Program Selection Guide" in respect of sequences of a specific length and composition.

BLAST polynucleotide searches are performed with the BLASTn program.

For the general parameters, the "Max Target Sequences" box may be set to 100, the "Short queries" box may be ticked, the "Expect threshold" box may be set to 1000 and the "Word Size" box may be set to 7 as recommended for short sequences (less than 20 bases) on the NCBI webpage. For longer sequences the "Expect threshold" box may be set to 10 and the "Word Size" box may be set to 11. For the scoring parameters the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "DUST Filter Settings" may be ticked and the "Mask lower case letters" box may not be ticked. In general the "Search for short nearly exact matches" may be used in this respect, which provides most of the above indicated settings. Further information in this respect may be found in the "BLAST Program Selection Guide" published on the NCBI webpage.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Modifications of both programs, e.g., in respect of the length of the searched sequences, are performed according to the recommendations in the "BLAST Program Selection Guide" published in a HTML and a PDF version on the NCBI webpage.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" as used in the context of the present invention relates primarily to antibodies, and fragments thereof, but may also refer to other non-antibody molecules that bind dipeptide repeat (DPR) proteins, preferably which bind to altered C9ORF72, in particular (pathologically) altered C9ORF72-DPRs, including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is a binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to DPRs, in particular to altered C9ORF72 forming C9ORF72-DPRs is denoted herein interchangeably as a "binding fragment" or an "immunospecific fragment."

Figure 13:
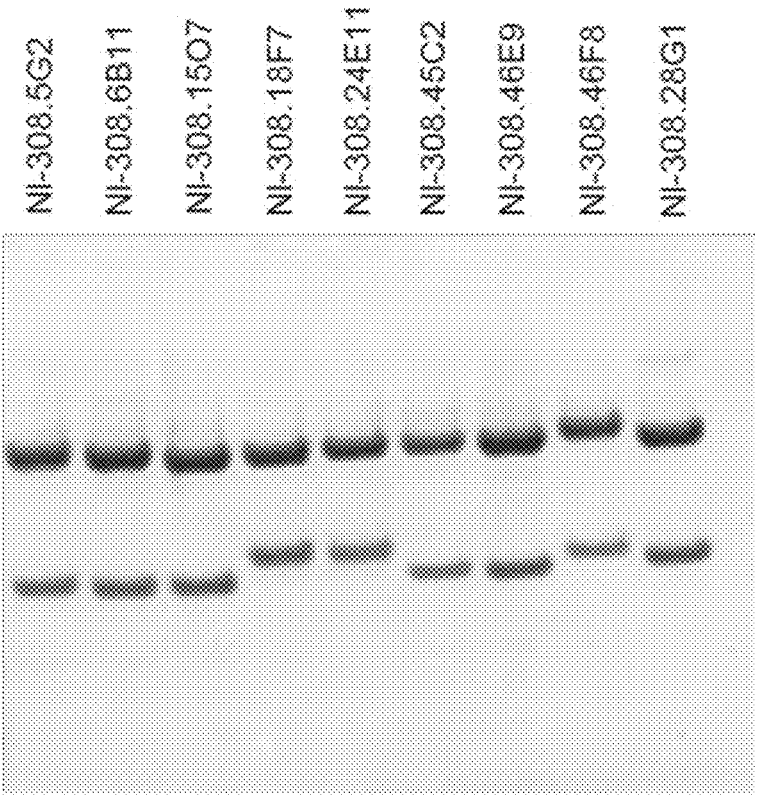
FIG. 13: NI-308 antibody integrity analysis. SDS-PAGE analysis followed by Coomassie blue staining of 5 µg recombinant human-derived NI-308 anti-C9orf72 DPRs antibodies. Two major bands corresponding to the antibody heavy and light chains at the expected size were detected.

As described in Example 11 and shown in FIG. 13 antibodies of the present invention when expressed as IgG, preferably IgG1 in mammalian cells, in particular CHO-S cells demonstrated high integrity with respect to both the light ($V_L$) and heavy ($V_H$) chain portions whereas no significant contaminations or proteolytic degradation products could be detected.

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarily determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE I

| CDR Definitions[1] | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table I is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019 Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity. In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are DPR binding fragments which comprise any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural DPRs and DPR proteins, preferably C9ORF72-DPRs in its relevant conformation in the human body, (ii) having protected the individual or is at least significant for the presence of DPRs, preferably C9ORF72-DPRs, and (iii) since the antibody is of human origin the risks of cross-reactivity against self-antigens is minimized; see also supra. Thus, in accordance with the present invention the terms "human monoclonal antibody", "human monoclonal autoantibody", "human antibody" and the like are used to denote a DPR-binding molecule which is of human origin, i.e. which has been isolated from a human cell such as a B cell or hybridoma thereof or the cDNA of which has been directly cloned from mRNA of a human cell, for example a human memory B cell. A human antibody is still "human", i.e. human-derived even if amino acid substitutions are made in the antibody, e.g., to improve binding characteristics. In this context, contrary to humanized antibodies and otherwise human-like antibodies, see also the discussion infra, the human-derived antibodies of the present invention are characterized by comprising CDRs which have been seen by human body and therefore are substantially devoid of the risk of being immunogenic. Therefore, the antibody of the present invention may still be denoted human-derived if at least one, preferably two and most preferably all three CDRs of one or both the variable light and heavy chain of the antibody are derived from the human antibodies illustrated herein.

In one embodiment the human-derived antibodies of the present invention comprises heterologous regions compared to the natural occurring antibodies, e g amino acid substitutions in the framework region, constant region exogenously fused to the variable region, different amino acids at the C- or N-terminal ends and the like.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention. For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability. In contrast, the present invention provides isolated affinity-matured antibodies from selected human subjects, which are characterized by their therapeutic utility and their tolerance in man.

As used herein, the term "rodentized antibody" or "rodentized immunoglobulin" refers to an antibody comprising one or more CDRs from a human antibody of the present invention; and a human framework region that contains amino acid substitutions and/or deletions and/or insertions that are based on a rodent antibody sequence. When referred to rodents, preferably sequences originating in mice and rats are used, wherein the antibodies comprising such sequences are referred to as "murinized" or "ratinized" respectively. The human immunoglobulin providing the CDRs is called the "parent" or "acceptor" and the rodent antibody providing the framework changes is called the "donor". Constant regions need not be present, but if they are, they are usually substantially identical to the rodent antibody constant regions, i.e. at least about 85% to 90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody. The above explanations in respect of "murinized" antibodies apply analogously for oder "rodentized" antibodies, such as "ratinized antibodies", wherein rat sequences are used instead of the murine.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a VL or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of DPRs such as $GA_{15}$ as found in. C9ORF72-DPRs. Put in other words, the antibody of the present invention or biotechnological derivative thereof preferably recognizes a DPR with a repeat number of the dipeptide consisting of two different amino acids X and X' (XXX and XXX'; XaaXaa') of for example 3 to 50, preferably 10 to 40, more preferably 15 to 30 and most preferably 15. Thus, the epitope or antigen recognized by the antibody of the present invention or biotechnological derivative thereof if consisting of a DPR with a repeat number of 15 generally may be designated $(XX')_{15}$.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant (KD) that is less than the antibody's KD for the second epitope. In another non-limiting example, an antibody may be considered to bind a first antigen preferentially if it binds the first epitope with an affinity that is at least one order of magnitude less than the antibody's KD for the second epitope. In another non-limiting example, an antibody may be considered to bind a first epitope preferentially if it binds the first epitope with an affinity that is at least two orders of magnitude less than the antibody's KD for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind DPRs or a fragment, variant or specific conformation thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind DPR proteins or a fragment, variant or specific conformation thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$. In a particularly preferred embodiment, the DPR is a DPR associated with C9ORF72, i.e. C9ORF72-DPR.

A binding molecule, e.g., an antibody or antigen-binding fragment, variant, or derivative disclosed herein may be said to bind DPR, or a fragment, variant or specific conformation thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind DPR or a fragment, variant or specific conformation thereof with an on rate (k(on)) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$. In one embodiment, the binding molecule may be said to bind C9ORF72-DPR, or a fragment, variant or specific conformation thereof with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. More preferably, an antibody of the invention may be said to bind C9ORF72-DPR or a fragment, variant or specific conformation thereof with an on rate (k(on)) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., KD, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to DPRs and/or mutated C9ORF72 species showing C9ORF72-DPRs and/or fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art.

Diseases:

Unless stated otherwise, the terms "disorder" and "disease" are used interchangeably herein and comprise any undesired physiological change in a subject, an animal, an isolated organ, tissue or cell/cell culture.

Frontotemporal lobar degeneration (FTLD) is a pathogenesis associated with an atrophy in the frontal lobe and temporal lobe of the brain. Additionally 50% of FTLD patient were also shown to have a positive family history and compared to amyotrophic lateral sclerosis (ALS). As already described above, the shared underlying cause of pathogenesis seems to be a heterozygous expanded hexanucleotide repeat located in the C9ORF72 of FTLD and ALS patients. In particular, it was shown that resulting repeating units of two amino acids (dipeptide repeats, DPRs).

However, expanded hexanucleotide repeats resulting in the repetition of two amino acids (DPRs) have also been reported in several other diseases and/or disorders. The diseases including but are not limited to Frontotemporal lobar degeneration (FTLD), amyotrophic lateral sclerosis (ALS), FTLD-ALS, and/or spinocerebellar ataxia type 36, and symptoms associated therein.

Figure 14A:
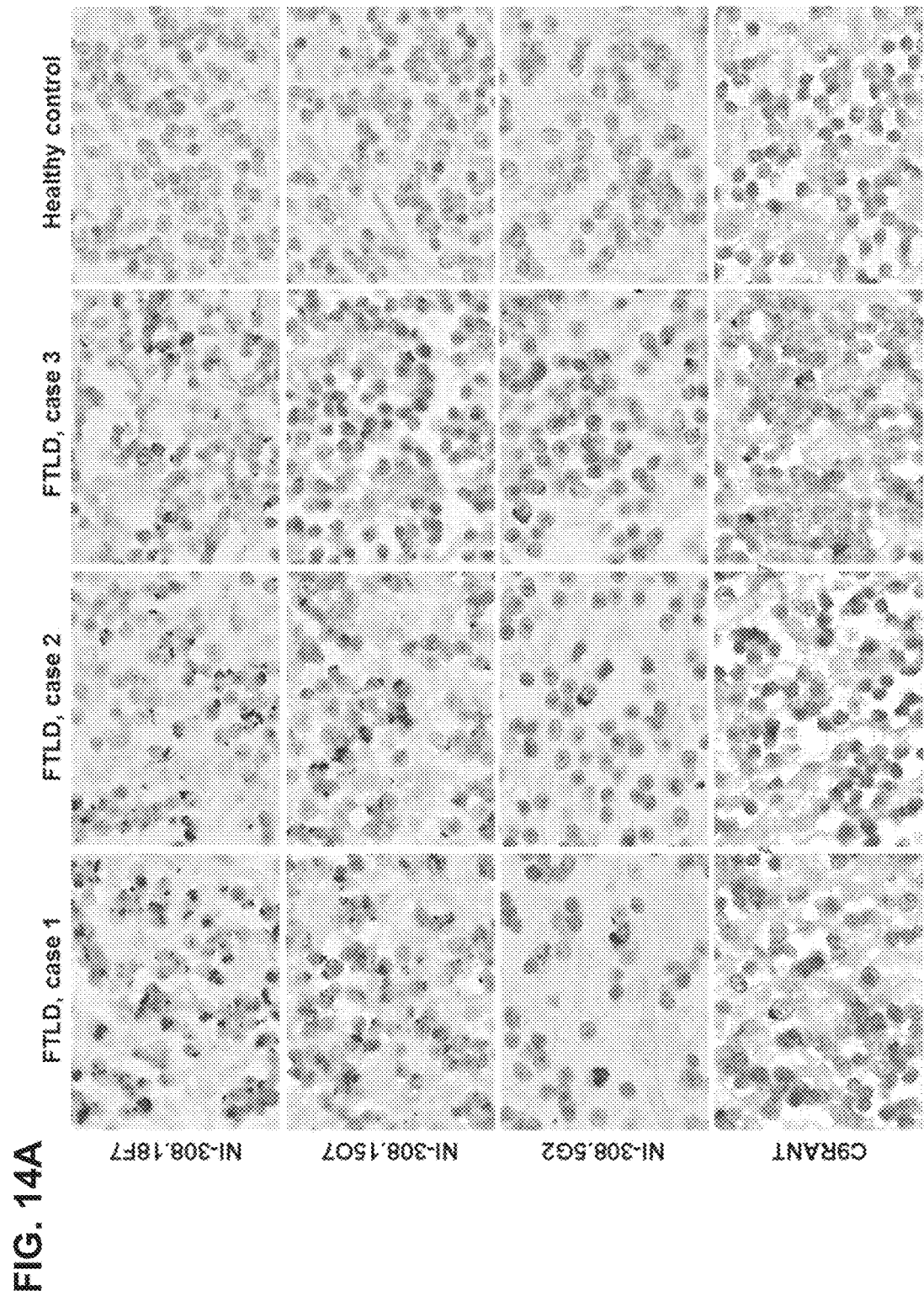

Since the antibodies of the present invention have been shown to be capable of binding to DPRs, in particular C9ORF72-DPRs in tissue sections of FTLD patients, see e.g. Example 12 and FIGS. 14A-14C, the human-derived antibodies and biotechnological derivatives thereof are useful in both the treatment and diagnosis of FTLD, and other diseases and/or disorders associated with DPRs, and symptoms thereof. In particular, the in-vitro and in vivo therapeutic potential of antibodies of the present invention in modulating disease progression is evaluated either in cell-based models or in selected C9orf72 hexanucleotide repeat expansion mouse models, respectively; see, e.g., Examples 14 and 15.

Therefore, in one embodiment of the present invention the antibodies of the present invention, binding molecules having substantially the same binding specificities of any one thereof, the polynucleotides, the vectors or the cells of the present invention are used for preparation of a pharmaceutical or diagnostic composition for prophylactic and/or therapeutic treatment of diseases associated with DPRs, for monitoring disease progression and/or treatment response, and for the diagnosis of diseases associated with DPRs amyloidosis comprising Frontotemporal lobar degeneration (FTLD), amyotrophic lateral sclerosis (ALS), FTLD-ALS, and/or spinocerebellar ataxia type 36.

As shown in Examples 12 and 13 as well as FIGS. 14A-14C and 15, the antibodies of the present invention binds to pathologic C9ORF72-dipeptide repeat protein aggregates in FTLD patients. Therefore, in a one embodiment of the present invention the antibodies, binding molecules having substantially the same binding specificities of any one thereof, the polynucleotides, the vectors or the cells of the present invention are used for preparation of a pharmaceutical or diagnostic composition for prophylactic and/or therapeutic treatment of diseases associated with C9ORF72-DPRs, for monitoring disease progression and/or treatment response, and for the diagnosis of diseases associated with C9ORF72-DPRs aggregates comprising Frontotemporal lobar degeneration (FTLD), amyotrophic lateral sclerosis (ALS), and/or FTLD-ALS, and symptoms associated therein.

Treatment:

As used herein, the terms "treat" or "treatment" refer to both therapeutic treatment and prophylactic or preventative measures, wherein the object is to prevent or slow down (lessen) an undesired physiological change or disorder, such as the development of cardiac deficiency. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound", or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington: The Science and Practice of Pharmacy (2000) by the University of Sciences in Philadelphia, ISBN 0-683-306472, Vaccine Protocols 2nd Edition by Robinson et al., Humana Press, Totowa, N.J., USA, 2003; Banga, Therapeutic Peptides and Proteins: Formulation, Processing, and Delivery Systems. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc. are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., Nature Reviews, Drug Discovery 2(9) (2003), 727-735. Further guidance regarding formulations that are suitable for various types of administration can be found in Remington's Pharmaceutical Sciences, Mace Publishing Company, Philadelphia, Pa., 17th ed. (1985) and corresponding updates. For a brief review of methods for drug delivery see Langer, Science 249 (1990), 1527-1533.

II. Antibodies of the Present Invention

The present invention generally relates to human-derived anti-DPR, preferably anti-C9ORF72-DPR antibodies and antigen-binding fragments as well as biotechnological derivatives thereof which preferably demonstrate the immunological binding characteristics and/or biological properties as outlined for the antibodies illustrated in the Examples. In accordance with the present invention human monoclonal antibodies specific for DPRs were cloned from a pool of healthy human subjects. However, in another embodiment of the present invention, the human monoclonal anti-DPR antibodies might also be cloned from patients showing symptoms of a disease and/or disorder associated with DPR aggregation.

In the course of the experiments performed in accordance with the present invention, recombinant IgG antibodies derived from antibodies present in the conditioned media of cultured human memory B cell initially screened for DPR binding were evaluated for their capacity to bind to DPRs and to other proteins including bovine serum albumin (BSA); see Examples 3 to 7 as well as FIGS. 2A-2M to 6A-6C. Only the B-cell supernatants able to bind to the DPR protein but not to any of the other proteins in the screen were selected for further analysis, including determination of the antibody class and light chain subclass. The selected B-cells were then processed for antibody cloning; see Examples 1 and 12 as well as FIGS. 14A-14C.

In brief, the cloning method consisted in the extraction of messenger RNAs from the selected B-cells, retro-transcription by RT-PCR, amplification of the antibody-coding regions by PCR, cloning into plasmid vectors and sequencing. Selected human antibodies were then produced by recombinant expression in HEK293 or CHO cells and purification, and subsequently characterized for their capacity to bind human DPR protein. The combination of various tests, e.g. recombinant expression of the antibodies in HEK293 or CHO cells and the subsequent characterization of their binding specificities towards human DPR protein, and their distinctive binding to pathologically mutated and/or aggregated forms thereof confirmed that for the first time human antibodies have been cloned that are highly specific for DPR and distinctively recognize and selectively bind the pathologically aggregated forms of DPR protein, for example C9ORF72-DPRs. In some cases, mouse chimeric antibodies were also generated on the basis of the variable domains of the human antibodies of the present invention.

Thus, the present invention generally relates to recombinant human-derived monoclonal anti-DPR antibodies and DPR-binding fragments, synthetic and biotechnological derivatives and variants thereof. In one embodiment of the invention, the antibody is capable of binding human C9ORF72-DPRs.

In one embodiment of the present invention, the antibody binds a DPR protein or peptide, wherein the repeat number is about 10 to 20, preferably 15 as used in the Examples for the GA, GP, GR, PR and PA repeat of C9ORF72; see, e.g., Examples 8 and 9 as well as FIGS. 7A-7P and 8A-8F. The DPR protein may essentially consist of the DPR only or comprise the DPR within a larger polypeptide, for example at the N-terminus, C-terminus or in between like the GA or GP repeat in exon 1 in C9ORF72.

Furthermore, as demonstrated in the Examples 12 and 13 and shown in FIGS. 14A-14C and 15, the human-derived monoclonal NI-308.18F7, NI-308.15O7, NI-308.5G2 and NI-308.4M1 anti-DPR antibodies of the present invention are preferably characterized in specifically binding to pathological mutated and/or aggregated C9ORF72-DPRs and not substantially recognizing C9ORF72 in the physiological form; see, e.g., FIGS. 14A-14C and 15. Hence, the present invention provides a set of human anti-DPR antibodies with binding properties particularly useful for diagnostic and therapeutic purposes. Thus, in one embodiment the present invention provides antibodies which are capable of specifically binding pathologically aggregated forms of DRP proteins, for example C9ORF72-DPRs.

In one embodiment, the antibody of the present invention exhibits the binding properties of any one of the exemplary NI-308.18F7, NI-308.15O7, NI-308.28G1, NI-308.45C2, NI.308.24E11, NI-308.5G2, NI-308.46E9, NI-308.6B11, NI-308.46F8, NI-308.4M1, NI-308.12A3 and NI-308.16C10 antibodies as described in the Examples. The anti-DPR antibody of the present invention preferentially recognizes pathologically altered C9ORF72, such as C9ORF72-DPR species and fragments thereof rather than physiological C9ORF72. Thus, in one embodiment, the antibody of the present invention does not substantially recognize physiological C9ORF72 species.

The term "does not substantially recognize" when used in the present application to describe the binding affinity of a molecule of a group comprising an antibody, a fragment thereof or a binding molecule for a specific target molecule, antigen and/or conformation of the target molecule and/or antigen means that the molecule of the aforementioned group binds said molecule, antigen and/or conformation with a binding affinity which is at least 2-fold, 3-fold, 4-fold, 5-fold, 6-fold, 7-fold, 8-fold or 9-fold less than the binding affinity of the molecule of the aforementioned group for binding another molecule, antigen and/or conformation. Very often the dissociation constant (KD) is used as a measure of the binding affinity. Sometimes, it is the $EC_{50}$ on a specific assay as for example an ELISA assay that is used as a measure of the binding affinity. Preferably the term "does not substantially recognize" when used in the present application means that the molecule of the aforementioned group binds said molecule, antigen and/or conformation with a binding affinity which is at least or 10-fold, 20-fold, 50-fold, 100-fold, 1000-fold or 10000-fold less than the binding affinity of said molecule of the aforementioned group for binding to another molecule, antigen and/or conformation.

As described above, the most common genetic cause of the aggregation of C9ORF72 in FTLD and ALS were shown to be due to a heterozygous expanded hexanucleotide repeat (GGGGCC) located between the noncoding exons 1a and 1b of the C9ORF72 gene. In particular, it was shown that these unconventional non-ATG translation of the sense transcript in the three alternate reading frames, i.e. of the expanded hexanucleotide repeats, resulted in the production, generation and aggregation of different polypeptides, each comprising repeating units of two amino acids (dipeptide repeats, DPRs), i.e. poly-(Gly-Ala; GA), poly-(Gly-Pro; GP), and/or poly-(Gly-Arg; GR). Therefore, in one embodiment of the present invention the DPR comprises poly-glycine-alanine (Gly-Ala; GA), poly-glycine-proline (Gly-Pro; GP), or poly-glycine-arginine (Gly-Arg; GR) repeats.

In a preferred embodiment the DPR consists of poly-glycine-alanine (Gly-Ala; GA) or poly-glycine-proline (Gly-Pro; GP) repeats.

Despite the fact that the expanded hexanucleotide repeat is located between the noncoding exons 1a and 1b of C9ORF72, and the fact that the mutated C9ORF72 lack a start codon, all reading frames are translated into the dipeptide-repeat (DPR) proteins, i.e. poly-(Gly-Ala; GA), poly-(Gly-Pro; GP), and/or poly-(Gly-Arg; GR). Preliminary studies also show that antibodies have been identified and cloned in the experiments performed in accordance with the present invention do not only stain neuronal cytoplasmic inclusions, neuronal intranuclear inclusions, and dystrophic neuritis in the granule cell layer of the cerebellum associated with C9ORF72-DPRs of GA, GP, or GP-type, i.e. translated in sense strand direction (sense DPRs), as shown in Examples 12 and 13 as wells as FIGS. 14A-14C and 15, but also antibodies which are capable of recognizing bi-directionally translated DPRs, i.e. dipeptide repeat proteins which are translated in its antisense direction, i.e. poly-(Pro-Arg; PR), and/or poly-(Pro-Ala, PA). Accordingly, antibodies are provided which are capable of identifying and binding aggregation of C9ORF72 protein products derived from both strands, i.e. DPRs resulting from expanded hexanucleotide repeat of the noncoding region between exons 1a and 1b of C9ORF72 translated in sense and antisense direction. Therefore, in one embodiment, the anti-DPR antibodies, DPR-binding molecules or fragments, synthetic, or biotechnological variants thereof recognize DPRs as translated from the C9ORF72 gene in it sense and/or antisense direction. In a preferred embodiment, the DPR antibodies recognize DPRs of poly-(Gly-Ala; GA), poly-(Gly-Pro; GP), poly-(Gly-Arg; GR), poly-(Pro-Arg; PR), and/or poly-(Pro-Ala, PA) type.

In addition, in preliminary experiments DPR antibodies were identified which can bind to different constellations of DPRs, i.e. different amino acid compositions of the DPR proteins. In particular, DPR antibodies recognizing DPR proteins consisting of both $(PA)_n$ and $(GA)_n$, $(GP)_n$ and $(GA)_n$, $(PR)_n$ and $(GA)_n$, or $(GR)_n$ and $(GA)_n$ and $(PR)_n$ were observed. Accordingly, in one embodiment of the present invention, the DPR antibody can recognize DPR proteins consisting of a combination of DPR proteins showing a different amino acid composition. Hence, as demonstrated in the Examples and shown in FIGS. 2A to 2M and 7A to 7P human-derived antibodies are obtained which recognize two or even three different dipeptide repeats with a specificity in the same order of magnitude. In a preferred embodiment, the anti-DPR antibody can recognize DPR proteins consisting of a combination of DPR proteins, wherein the DPR proteins are $(PA)_n$ or $(GA)_n$, $(GP)_n$ or $(GA)_n$, $(PR)_n$ or $(GA)_n$, or $(GR)_n$ or $(GA)_n$ or $(PR)_n$, i.e. the anti-DPR antibody of the present invention may recognize any combination of DPRs, preferably $(GP)_n$ and $(GA)_n$ as shown for antibody NI-308.5G2 (see FIGS. 2A and 2G and FIGS. 7A, 7B, 7J and 7K) or $(GR)_n$, $(GA)_n$ and $(PR)_n$ as shown for antibody NI-308.6B11 (see FIGS. 2A and 2I and FIGS. 7A, 7C, 7L and 7M) or $(PA)_n$ and $(GA)_n$ as shown for antibody NI-308.4M1 (see FIGS. 2A and 2K and FIGS. 7E and 7P) or $(PR)_n$ and $(GA)_n$ as shown for antibody NI-308.16C10 (see FIGS. 2A and 2M).

Alternatively, or in addition the antibody of the present invention may be engineered to comprise at least a first and second antigen-binding site, i.e. variable domain from two different antibodies of the present invention with distinct epitopes, preferably wherein one or both variable regions are derived from any one of the subject antibodies illustrated in the appended Examples and Figures, and as further described herein. For example, the combination of the variable region of antibody NI-308.6B11 and NI-308.4M1 would result in an antibody capable of binding a combination of DPRs consisting of $(GA)_n$, $(GR)_n$, $(PR)_n$ and $(PA)_n$. Hence, the subject antibodies enable the provision of antibodies capable of recognizing any combination of DPRs. Bi- and multispecific antibodies can be generated by methods well known in the art, for example by chemical recombination of monoclonal immunoglobulin G1 fragments as described, e.g., by Brennan et al., Science. 229 (1985), 81-83, or recombinant simultaneously co-expression of the appropriate heavy and light chain and corresponding pairing; see, e.g., Lewis et al., Nature Biotechnology 32 (2014), 191-198; for review see, e.g., Kontermann, mAbs 4 (2012), 182-197 and Kontermann and Brinkmann, Drug Discovery Today 20 (2015), 838-847.

In several studies it has been demonstrated that the aggregation of DPRs in patients occurs mainly in patients with a higher number of dipeptide repeats. Therefore, in one embodiment of the present invention, the DPR binding molecules bind to DPR proteins containing higher number of repeats, i.e. DPRs consisting of $(GA)_n$, $(GP)_n$, $(GR)_n$, $(PR)_n$, or $(PA)_n$. Here the n denotes the number of repeats, e.g., a DPR protein with 15 repeats of will be denoted $(XX)_{15}$, also meaning that the, e.g., hexanucleotide expansion G4C2 is repeated 15 times. In a preferred embodiment the repeat number is 10 to 30 $(XX')_{10-30}$. In a particular preferred embodiment the repeat number is $(XX')_{15}$.

However, without be bound to theory, a smaller repeat size, i.e. <15 repeats, preferably <10 repeats, more preferably <5 repeats, may mimic larger peptides upon dense coating at a surface. Thus, in one embodiment of the present invention, the DPR antibodies bind to DPRs consisting of $(GA)_n$, $(GP)_n$, $(GR)_n$, $(PR)_n$, or $(PA)_n$, wherein the number of repeats (n) is under 15 repeats. In a preferred embodiment the DPR antibodies bind to DPRs consisting of $(GA)_n$, $(GP)_n$, $(GR)_n$, $(PR)_n$, or $(PA)_n$, wherein the number of repeats (n) is below 10 repeats. In a particularly preferred embodiment the DPR antibodies bind to DPRs consisting of $(GA)_n$, $(GP)_n$, $(GR)_n$, $(PR)_n$, or $(PA)_n$, wherein the number of repeats (n) is below 5 repeats. Preliminary experiments show that a binding of DPR antibodies of the present invention is also possible to DPR proteins showing just 3 to 4 repeats; see, e.g., FIGS. 7A-7P. Accordingly, in one embodiment of the present invention 3 to 4 repeats are sufficient for a binding of the DPR antibody. In one embodiment, the antibody of the present invention does not substantially or only to a significant lesser extent bind to an epitope with less than 3 of any one of the above described dipeptide repeats (n<3); see, e.g., Examples 8 and 9 as well as FIGS. 7A-7P and 8A-8F.

As shown in the Examples, in particular Examples 3 and 4, different DPR constructs were designed showing a higher number of dipeptide repeats. In particular, DPR-constructs showing 15 repeats, i.e. $(GA)_{15}$, $(GP)_{15}$, $(GR)_{15}$, $(PA)_{15}$ and $(PR)_{15}$ were constructed. Utilizing these constructs characterization studies of the antibodies identified in accordance with the present invention were performed; see, e.g. Example 3 and 4. The results revealed that antibodies NI-308.18F7, NI-308.15O7, NI-308.28G1 and NI-308.45C2 specifically bind with high affinity to C9ORF72-DPR $(GA)_{15}$, but not to the DPRs consisting of $(GP)_{15}$, $(GR)_{15}$, $(PA)_{15}$ or $(PR)_{15}$; see, e.g. FIGS. 2A, 2B, 2C, 2D and 2E as well as FIGS. 3A, 3B, 3C, 3D and 3E. In contrast, antibodies NI-308.5G2, NI-308.12A3 and NI-308.46E9 specifically recognize with high affinity the C9ORF72-DPR $(GA)_{15}$ and $(GP)_{15}$, but not the DPRs consisting of $(GR)_{15}$, $(PA)_{15}$ or $(PR)_{15}$; see, e.g. FIGS. 2A, 2G, 2H and 2L, and FIGS. 3A, 3G, 3H and 3L. Antibody NI-308.24E11 recognizes the C9ORF72-DPR $(PR)_{15}$ only, but not the DPRs consisting of $(GP)_{15}$, $(GR)_{15}$, $(GA)_{15}$ or $(PA)_{15}$; see, e.g. FIGS. 2A and 2F as well as FIGS. 3A and 3F. In contrast, antibody NI-308.16C10 preferentially recognized the C9ORF72-DPR $(PR)_{15}$ and also bound to $(GA)_{15}$ but not the DPRs consisting of $(GP)_{15}$, $(GR)_{15}$ or $(PR)_{15}$; see FIGS. 2A and 2M as well as FIGS. 3A and 3M. Surprisingly, antibodies NI-308.6B11 and NI.308.46F8 showed a high affinity to $(GR)_{15}$, $(GA)_{15}$ and $(PR)_{15}$, but not the DPR consisting of $(GP)_{15}$ or $(PA)_{15}$; see, e.g., FIGS. 2A, 2I, and 2J as well as FIGS. 3A, 3I and 3J. Antibody NI-308.4M1 recognizes the C9ORF72-DPR $(PA)_{15}$ and $(GA)_{15}$, but not the DPRs consisting of $(GP)_{15}$, $(GR)_{15}$, or $(PR)_{15}$; see, e.g. FIGS. 2A and 2K as well as FIGS. 3A and 3K. Therefore, in one embodiment, the antibody of the present invention preferably recognizes a DPR protein consisting of $(GA)_{15}$. In another embodiment, the antibody of the present invention recognizing a DPR protein consisting of $(GA)_{15}$ does not substantially recognize a DPR protein consisting of $(GP)_{15}$ or $(GR)_{15}$ or $(PA)_{15}$ or $(PR)_{15}$. In a further embodiment, the antibody of the present invention preferably recognizes a DPR protein consisting of $(GP)_{15}$ or $(GA)_{15}$, preferably the antibody recognizing a DPR protein consisting of $(GP)_{15}$ or $(GA)_{15}$ does not substantially recognize a DPR protein consisting of $(GR)_{15}$ or $(PR)_{15}$ or $(PA)_{15}$. In a further embodiment, the antibody of the present invention recognizing a DPR protein consisting of $(PR)_{15}$ does not substantially recognize a DPR protein consisting of $(GA)_{15}$, $(GP)_{15}$ or $(GR)_{15}$ or $(PA)_{15}$. In yet a further embodiment, the antibody of the present invention recognizing a DPR protein consisting of $(GA)_{15}$, $(GR)_{15}$ or $(PR)_{15}$ does not substantially recognize a DPR protein consisting of $(GP)_{15}$ or $(PA)_{15}$. In a further embodiment, the antibody of the present invention preferably recognizes a DPR protein consisting of $(PA)_{15}$ or $(GA)_{15}$, preferably the antibody recognizing a DPR protein consisting of $(PA)_{15}$ or $(GA)_{15}$ does not substantially recognize a DPR protein consisting of $(GP)_{15}$ or $(GR)_{15}$ or $(PR)_{15}$. In still a further embodiment, the antibody of the present invention preferably recognizes a DPR protein consisting of $(GA)_{15}$ or $(PR)_{15}$, preferably the antibody recognizing a DPR protein consisting of $(PR)_{15}$ or $(GA)_{15}$ does not substantially recognize a DPR protein consisting of $(GP)_{15}$ or $(GR)_{15}$ or $(RA)_{15}$. Put in other words, the antibodies in those embodiments are able to bind either a single or at least two different DPR proteins, see, e.g., exemplary antibodies NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI.308-16C10 as illustrated in Examples 3 and 4 as well as in FIGS. 2A-2M and FIGS. 3A-3M.

Utilizing the constructs as described in the Examples, it could be shown that the anti-DPR antibody of the present invention binds to human C9ORF72-DPRs $(GA)_{15}$ or $(GP)_{15}$, or $(GR)_{15}$, or $(PR)_{15}$, or $(PA)_{15}$. In this context, the binding affinities of any one of the anti-DPR antibodies of the present invention or biotechnological derivative thereof may be in the range as shown for the exemplary NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI-308.16C10 antibodies in FIGS. 2A-2M, i.e. having half maximal effective concentrations ($EC_{50}$) of about 0.1 nM to 200 nM, preferably 1 pM to 100 nM, more preferably an $EC_{50}$ of about 50 pM to 50 nM, most preferably an $EC_{50}$ of about 0.1 nM to 0.5 nM for BSA-(GA)$_{15}$, BSA-(GP)$_{15}$ or BSA-(PA)$_{15}$ constructs and most preferably an EC$_{50}$ of about 10 nM to 200 nM for BSA-(PR)$_{15}$ constructs; see, e.g., FIGS. 3A-3M.

Preferably, the anti-DPR antibody, DPR-binding fragment or biotechnological derivative thereof has a binding affinity corresponding to an EC$_{50}$ (half maximal effective concentration) value of >200 nM, preferably ≤100 nM, more preferably ≤50 nM, even more preferably ≤10 nM and most preferably ≤0.5 nM for binding DPR protein (GA)$_{15}$, (GR)$_{15}$ or (PR)$_{15}$, or ≤10 nM, preferably ≤2 nM, even more preferably ≤1 nM and most preferably ≤0.5 nM for binding DPR protein (GP)$_{15}$ or (PA)$_{15}$; see, e.g. FIGS. 2A-2M.

Some antibodies are able to bind to a wide array of biomolecules, e.g., proteins. As the skilled artisan will appreciate, the term specific is used herein to indicate that other biomolecules than DPR do not significantly bind to the antigen-binding molecule, e.g., one of the antibodies of the present invention. Preferably, the level of binding to a biomolecule other than DPRs results in a binding affinity which is at most only 20% or less, 10% or less, only 5% or less, only 2% or less or only 1% or less (i.e. at least 5, 10, 20, 50 or 100 fold lower, or anything beyond that) of the affinity to DPRs, respectively; see, e.g., Examples 3 to 5 as well as FIGS. 2A-2M to 4A-4I.

In one embodiment, the anti-DPR antibody of the present invention binds preferentially to aggregated forms of DPRs, for example C9ORF72-DPR and/or fragments, derivatives, fibrils and/or oligomers thereof. In another embodiment, the anti-DPR antibody of the present invention preferentially binds to both C9ORF72-DPRs not associated with a disease and/or disorder and pathologically aggregated forms of C9ORF72-DPR; see, e.g., Example 10 as well as FIGS. 9 to 12A and 12B. In yet another embodiment, the anti-DPR antibody of the present invention is able to bind to forms of DPRs, for example C9ORF72-DPR and/or fragments, derivatives, fibrils and/or oligomers thereof in solution; see Example 7 as well as FIGS. 6A-6C. In this context, any one of the anti-DPR antibodies of the present invention or biotechnological derivative thereof may be capable of capturing poly-GA DPR protein peptides in solution as shown for the exemplary antibodies NI-308.15O7, NI-308.18F7, NI-308.45C2 and NI-308.28G1 or any one of the anti-DPR antibodies of the present invention or biotechnological derivative thereof may be capable of precipitating poly-PR and poly-GR as shown for the exemplary antibodies NI-308.24E11 and NI-308.6B11; see, e.g., FIGS. 6A to 6C.

In FIGS. 14A-14C and 15 as well as Examples 12 and 13, it was shown that the antibodies of the present invention are capable of staining pathologic neuronal cytoplasmic inclusions, neuronal intranuclear inclusions, and dystrophic neurites in the granule cell layer of the cerebellum in FTLD patients which are associated with aggregates of DPRs, in particular of C9ORF72-DPR proteins. Therefore, in one embodiment, the antibody of the present invention is capable of binding aggregated C9ORF72 in human tissue. In a particular preferred embodiment, the antibody is capable of binding aggregated C9ORF72 in human FTLD tissue. As mentioned, aggregated C9ORF72 means mutated C9ORF72 which shows as described above an expanded hexanucleotide repeat in its non-coding region. This repeat leads to a loss of the ATG start side and a translation of the repeats into DPRs as described supra.

As mentioned before, accumulation of DPR protein aggregates in the frontal and temporal lobe of the brain is a hallmark of the neurodegenerative disorder FTLD. Patients with DPR aggregates in neuronal cytoplasmic inclusions, neuronal intranuclear inclusions and dystrophic neurites in the granule cell layer of the cerebellum, as shown in FIGS. 14A-14C and 15 as well as Examples 12 and 13 of the present invention, often show an altered cognitive function. In particular, patients with FTLD show dementia, changes of the behavior as well as personality, language dysfunctions, and/or psychosis with are due to the degeneration of the frontal and temporal cortex, as described supra. Therefore, in one embodiment the antibody of the present invention is useful for the treatment of diseases and/or disorders associated with DPRs. In a preferred embodiment, the antibody of the present invention is useful in the treatment of FTLD and symptoms thereof.

The present invention is also drawn to an antibody, antigen-binding fragment, biotechnological variants and derivatives thereof, where the antibody comprises an antigen-binding domain identical to that of an antibody selected from the group consisting of NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI-308.16C10 or being capable of competing with either or all antibodies for binding DPR, e.g., (GA)$_{15}$ or (GP)$_{15}$ or (GR)$_{15}$ or (PR)$_{15}$ or (PA)$_{15}$.

The present invention further exemplifies several binding molecules, e.g., antibodies and binding fragments thereof, recognizing DPRs, which may be characterized by comprising in their variable region, e.g., binding domain at least one complementarity determining region (CDR) of the V$_H$ and/or V$_L$ variable region comprising any one of the amino acid sequences depicted in any one of FIGS. 1A-1L.

The corresponding nucleotide sequences encoding the above-identified variable regions are set forth in Table II below. Exemplary sets of CDRs of the above amino acid sequences of the V$_H$ and/or V$_L$ region are depicted in any one of FIGS. 1A-1L. However, as discussed in the following the person skilled in the art is well aware of the fact that in addition or alternatively CDRs may be used, which differ in their amino acid sequence from those set forth in any one of FIGS. 1A-1L by one, two, three or even more amino acids in case of CDR2 and CDR3. Therefore, in one embodiment the antibody of the present invention, biotechnological derivative or a DPR-binding fragment thereof is provided comprising in its variable region at least one complementarity determining region (CDR) as depicted in in any one of FIGS. 1A-1L and/or one or more CDRs thereof comprising one or more amino acid substitutions.

In one embodiment, the antibody of the present invention is any one of the antibodies comprising an amino acid sequence of the V$_H$ and/or V$_L$ region as depicted in any one of FIGS. 1A-1L or a V$_H$ and/or V$_L$ region thereof comprising one or more amino acid substitutions. Preferably, the antibody of the present invention is characterized by the preservation of the cognate pairing of the heavy and light chain as was present in the human B-cell.

In a further embodiment of the present invention the anti-DPR antibody, DPR-binding fragment, synthetic or biotechnological variant thereof can be optimized to have appropriate binding affinity to the target and pharmacokinetic and stability properties. Therefore, at least one amino acid in the CDR or variable region, which is prone to modifications selected from the group consisting of glycosylation, oxidation, deamination, peptide bond cleavage, iso-aspartate formation and/or unpaired cysteine is substituted by a mutated amino acid that lack such alteration or wherein at least one carbohydrate moiety is deleted or added chemically or enzymatically to the antibody, see, e.g. Liu et al., J. Pharm. Sci. 97(7) (2008), 2426-2447; Beck et al., Nat. Rev. Immunol. 10 (2010), 345-352; Haberger et al., MAbs. 6 (2014), 327-339.

Alternatively, the antibody of the present invention is an antibody or antigen-binding fragment, biotechnological derivative or variant thereof, which competes for binding to DPRs with at least one of the antibodies having the $V_H$ and/or $V_L$ region as depicted in any one of FIGS. 1A-1L.

Experimental results provided in FIGS. 4A-4I and Example 5 suggest that some of the anti-DPR antibodies of the present invention preferentially bind to disease causing aggregated forms of DPRs such as C9ORF72-DPRs over the other amyloid forming proteins. Accordingly, in one embodiment the antibody of the present invention preferentially recognizes C9ORF72-DPRs over amyloid forming proteins.

In one embodiment of the present invention the anti-DPR antibody, DPR-binding fragment, synthetic or biotechnological derivative thereof does preferentially recognize mutated and/or aggregated forms of C9ORF72-DPR over physiological C9ORF72.

The antibody of the present invention may be human-derived, in particular for therapeutic applications. Alternatively, the antibody of the present invention is a rodent, rodentized or chimeric rodent-human antibody, preferably a murine, murinized or chimeric murine-human antibody or a rat, ratinized or chimeric rat-human antibody which is particularly useful for diagnostic methods and studies in animals. In one embodiment the antibody of the present invention is a chimeric rodent-human or a rodentized antibody.

Furthermore, in one embodiment, the chimeric antibody of the present invention, i.e. comprising the variable domains of a human antibody and generic murine light and heavy constant domains bind with a high affinity to human DPRs. Preferably, the binding affinity of chimeric antibodies is similar to their human-derived counterparts.

In one embodiment the antibody of the present invention is provided by cultures of single or oligoclonal B-cells that are cultured and the supernatant of the culture which contains antibodies produced by said B-cells, is screened for presence and affinity of anti-DPR antibodies therein. The screening process comprises screening for binding to native monomeric, fibrilar or non-fibrilar aggregates like oligomers of hDPRs derived from a synthetic full-length hDPR peptide or e.g. purified from human plasma or recombinant expression. The respective hDPR peptides can be used in their pure form or alternatively coupled or conjugated to a suitable carrier such as BSA.

In a preferred embodiment the present invention also extends generally to anti-DPR antibodies and DPR-binding molecules which compete with the human monoclonal antibodies of the present invention for specific binding to mutated and/or aggregated C9ORF72-DPR species or fragments thereof.

Competition between antibodies is determined by an assay in which the immunoglobulin under test inhibits specific binding of a reference antibody to a common antigen, such as DPRs. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al., Molec. Immunol. 25 (1988), 7-15 and Moldenhauer et al., Scand. J. Immunol. 32 (1990), 77-82. Typically, such an assay involves the use of purified DPRs or mutated and/or aggregated C9ORF72-DPRs, such as oligomers and/or fibrils thereof bound to a solid surface or cells bearing either of these, an unlabeled test immunoglobulin and a labeled reference immunoglobulin, i.e. the human-derived monoclonal antibody of the present invention. Competitive inhibition is measured by determining the amount of label bound to the solid surface or cells in the presence of the test immunoglobulin. Usually the test immunoglobulin is present in excess. Preferably, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI-308.16C10 from binding to DPRs. The present invention is further drawn to an antibody, or antigen-binding fragment, variant or derivatives thereof, where the antibody competitively inhibits a reference antibody selected from the group consisting of NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI-308.16C10 from binding to mutated and/or aggregated C9ORF72-DPR species or fragments thereof.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90% or 95% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90% or 95% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in any one of FIGS. 1A-1L respectively. While FIGS. 1A-1L show $V_H$-CDRs defined by the Kabat system, other CDR definitions, e.g., $V_H$-CDRs defined by the Chothia system, are also included in the present invention, and can be easily identified by a person of ordinary skill in the art using the data presented in any one of FIGS. 1A-1L.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in any one of FIGS. 1A-1L respectively.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in any one of FIGS. 1A-1L respectively, except for one, two, three, four, five, or six amino acid substitutions in any one $V_H$-CDR. In certain embodiments the amino acid substitutions are conservative.

In another embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2 or $V_L$-CDR3 amino acid sequences from antibodies disclosed herein. Alternatively, the $V_L$-CDR1, $V_L$—CDR2 and $V_L$—CDR3 regions of the $V_L$ are at least 80%, 85%, 90% or 95% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in any one of FIGS. 1A-1J respectively. While in any one of FIGS. 1A-1L show $V_L$-CDRs defined by the Kabat system, other CDR definitions, e.g., $V_L$-CDRs defined by the Chothia system, are also included in the present invention.

In another embodiment, the present invention provides an isolated polypeptide comprising, consisting essentially of, or consisting of an immunoglobulin light chain variable region ($V_L$) in which the $V_L$-CDR1, $V_L$—CDR2 and $V_L$—CDR3 regions have polypeptide sequences which are identical to the $V_L$-CDR1, $V_L$—CDR2 and $V_L$—CDR3 groups shown in any one of FIGS. 1A-1L respectively.

In another embodiment, the present invention provides an isolated polypeptide comprising, consisting essentially of, or consisting of an immunoglobulin heavy chain variable region ($V_L$) in which the $V_L$-CDR1, $V_L$—CDR2 and $V_L$—CDR3 regions have polypeptide sequences which are identical to the $V_L$-CDR1, $V_L$-CDR2 and $V_L$-CDR3 groups shown in any one of FIGS. 1A-1L respectively, except for one, two, three, four, five, or six amino acid substitutions in any one $V_L$-CDR. In certain embodiments the amino acid substitutions are conservative.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO 89/09622. Methods for the production of humanized antibodies are described in, e.g., European application EP-A1 0 239 400 and international application WO 90/07861. Further sources of antibodies to be utilized in accordance with the present invention are so-called xenogeneic antibodies. The general principle for the production of xenogeneic antibodies such as human-like antibodies in mice is described in, e.g., international applications WO 91/10741, WO 94/02602, WO 96/34096 and WO 96/33735. As discussed above, the antibody of the invention may exist in a variety of forms besides complete antibodies; including, for example, Fv, Fab and F(ab)$_2$, as well as in single chains; see e.g. international application WO 88/09344. In one embodiment therefore, the antibody of the present invention is provided, which is selected from the group consisting of a single chain Fv fragment (scFv), a F(ab') fragment, a F(ab) fragment, and a F(ab')$_2$ fragment.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

The antibodies of the present invention may also include additional modifications which optimize their therapeutic potential. These modifications comprise but are not limited to modifications to the amino acid sequence of the antibody (e.g., the variable regions) and post-translational modifications. Post-translational modifications (PTMs) are chemical modifications that play a key role in functional proteomics, because they regulate activity, localization and interaction with other cellular molecules such as proteins, nucleic acids, lipids, and cofactors. Therefore, the optimization of the antibodies may provide several advantages such as an improved stability during storage as well as pharmacokinetics and/or pharmacodynamics profile such as the in vivo or in vitro circulating time of the antibody, increased solubility, stability, increased affinity to the target, decreased off-rate, an improved effector function of the constant region (Fc region) and safety profile of the antibody, such as a decreased immunogenicity, or reduced susceptibility to post-translational modifications, as shown e.g. in Igawa et al., MAbs 3 (2011), 243-52. Accordingly, in one embodiment of the present invention the anti-DPR antibody, DPR-binding fragment, synthetic or biotechnological variant thereof can be optimized, wherein at least one amino acid in the CDR or variable region, which is prone to modifications including but are not limited to acetylation, acylation, ADP-ribosylation, amidation, deamidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, isomerization, demethylation, formation of covalent cross-links, formation of cysteine, formation of pyroglutamate, formylation, γ-carboxylation, glycosylation, GPI anchor formation, hydroxylation, hydrolysis, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., Creighton, "Proteins: Structures and Molecular Properties," 2nd eds., Freeman and Co., N.Y., 1992; "Postranslational Covalent Modification of Proteins," Johnson, eds., Academic Press, New York, 1983; Seifter et al., Meth. Enzymol. 182 (1990), 626-646; Rattan et al., Ann. NY. Acad. Sci. 663 (1992) 48-62) is substituted by a mutated amino acid that lack such alteration or wherein at least one carbohydrate moiety is deleted or added chemically or enzymatically to the antibody. In a preferred embodiment the modifications are selected from the group consisting of glycosylation, oxidation, deamination, peptide bond cleavage, iso-aspartate formation and/or unpaired cysteine. Additional modification that optimize the utility of the anti-DPR-antibodies or equivalent binding molecules as a therapeutic agent are well known in the art and described e.g., in Igawa et al., MAbs 3 (2011), 243-52 which disclosure content is incorporated herein. Means of adding or deleting carbohydrate moieties can be achieved chemically or enzymatically and is described in detail in e.g., Berg et al. "Biochemistry" 5th eds W H Freeman, New York 2002; WO 87/05330; Aplin et al., CRC Crit. Rev. Biochem., 22 (1981), 259-306; Hakimuddin et al., Arch. Biochem. Biophys. 259 (1987), 10-52; Edge et al., Anal. Biochem. 118 (1981), 131; Thotakura et al., Meth. Enzymol. 138. (1987), 350.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the anti-DPR antibodies of the present invention and is capable of binding aggregated DPRs which may be present in an otherwise normal protein, for example C9ORF72-DPR species and/or fragments thereof. Such antibodies and binding molecules can be tested for their binding specificity and affinity by ELISA, SDS-PAGE and immunohistochemistry as described herein, see, e.g., the Examples 3 to 13. These characteristics of the antibodies and binding molecules can be tested by Western Blot as well; see, in particular Example 6 and FIGS. 5A-5J.

As an alternative to obtaining immunoglobulins directly from the culture of B cells or memory B cells, the cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in any one of FIGS. 1A-1L.

Binding molecules, e.g., antibodies, or antigen-binding fragments, synthetic or biotechnological variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of DPR protein aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO 2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing DPR protein localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as DPR protein localization, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences binding to DPRs as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced", i.e., are produced using recombinant DNA technology. Exemplary techniques for making antibody molecules or fragments thereof are discussed in more detail elsewhere herein.

Antibodies, or antigen-binding fragments, biotechnological variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO 98/52976 and WO 00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., DPR-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been induced for antibody production via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press (1986), 59-103. It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

In one embodiment, an antibody of the invention comprises at least one CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an $IgG_1$ human constant domain, see, e.g., international applications WO 02/060955 and WO 02/096948A2. This vector is engineered to delete the CH2 domain and provide a synthetic vector expressing a domain deleted $IgG_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817. In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase DPR protein localization. Similarly, it may be desirable to simply delete that part of one or more constant region domains that control the effector function (e.g., complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to DPRs. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$—CDR1, $V_H$—CDR2, $V_H$—CDR3, $V_L$ region, $V_L$—CDR1, $V_L$-CDR2, or $V_L$—CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind DPRs and/or mutated and/or aggregated C9ORF72-DPR species and/or fragments thereof).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of DPRs and/or mutated and/or aggregated C9ORF72-DPR species and/or fragments thereof) can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single-stranded and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In this context, the present invention also relates to a polynucleotide encoding at least the binding domain or variable region of an immunoglobulin chain of the antibody of the present invention. In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90%, or 95% identical to reference heavy chain $V_H$-CDR1, $V_H$—CDR2, or $V_H$-CDR3 amino acid sequences from the antibodies disclosed herein. Alternatively, the $V_H$-CDR1, $V_H$—CDR2, or $V_H$—CDR3 regions of the $V_H$ are at least 80%, 85%, 90%, or 95% identical to reference heavy chain $V_H$-CDR1, $V_H$—CDR2, and $V_H$—CDR3 amino acid sequences from the antibodies disclosed herein. Thus, according to this embodiment a heavy chain variable region of the invention has $V_H$-CDR1, $V_H$—CDR2, or $V_H$—CDR3 polypeptide sequences related to the polypeptide sequences shown in FIGS. 1A-1L.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90%, or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90%, or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$—CDR3 polypeptide sequences related to the polypeptide sequences shown in any one of FIGS. 1A-1L.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in any one of FIGS. 1A-1L.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90%, or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In a preferred embodiment of the present invention, the polynucleotide comprises, consists essentially of, or consists of a nucleic acid having a polynucleotide sequence of the $V_H$ or $V_L$ region of an anti-DPR antibody as depicted in and Table II. In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-DPR antibody and/or fragments thereof as depicted in Table II.

TABLE II

Nucleotide sequences of the $V_H$ and $V_L$ region of antibodies recognizing DPRs, preferably C9ORF72-DPRs.

| Antibody | Nucleotide sequences of variable heavy ($V_H$) and variable light ($V_L$) chains |
|---|---|
| NI-308.18F7 $V_H$ | TGCCAGGTGCAGCTGCAGGAGTCGGGCCCAGGACTGGTGAAGCCTTCGGAGACCCTGTC<br>CGTCACGTGCACTGTCTCTGGTGGCTCCATCAATGATTACTACTGGAACTGGATCCGGC<br>AGCCCGCCGGGAAGGGACTGGAGTGGATTGGGCGTATATATGCCAGTGGGACCATCAAT<br>TACAACCCTTCCCTCCAGAGTCGAGTCACCATGTCAATTGACACGTCCAAGAACCAGTT<br>CTCCCTAGACCTCATCTCTGTGTCCGCCGCGGACACGGCCGTCTACTATTGTGCAGAT<br>GGGGCCAGGTGGTCGGGACTACTACTACGGGATGGACGTCTGGGGCCAGGGGACCACG<br>GTCACCGTCTCCTCG<br>SEQ ID NO: 1 |
| NI-308.18F7 $V_K$ | TGCGAAATTGTGCTGACTCAGTCTCCACTCTCCCTGTCCGTCACCCCTGGAGAGCCGGC<br>CTCCATCTCCTGCAAGTCTAGTCAGAGCCTCCAACATACAAATGGATACAATTACTTGG<br>ATTGGTACCTGCTGAAGCCAGGGCAGTCTCCACAACTCCTAATCTTCTTGACTTCTAAT<br>CGGGCCTCCGGGGTCCCTGACAGGTTCAGTGGCAGTGGATCAGGCACAAATTTTACACT<br>GAAAATCAGCAGAGTGGAGGCTGAGGATGTTGGGGTCTATTATTGCATGGAAGGTATAC<br>AATTGTGGACGTTCGGCCAAGGGACCAAGCTGGAGATCAAA<br>SEQ ID NO: 3 |
| NI-308.18F7 $V_K$-PIMC | TGCGACATCGTGATGACCCAGTCTCCACTCTCCCTGTCCGTCACCCCTGGAGAGCCGGC<br>CTCCATCTCCTGCAAGTCTAGTCAGAGCCTCCAACATACAAATGGATACAATTACTTGG<br>ATTGGTACCTGCTGAAGCCAGGGCAGTCTCCACAACTCCTAATCTTCTTGACTTCTAAT<br>CGGGCCTCCGGGGTCCCTGACAGGTTCAGTGGCAGTGGATCAGGCACAAATTTTACACT<br>GAAAATCAGCAGAGTGGAGGCTGAGGATGTTGGGGTCTATTATTGCATGGAAGGTATAC<br>AATTGTGGACGTTCGGCCAAGGGACCAAGGTGGAGATCAAA<br>SEQ ID NO: 5 |
| NI-308.1507 $V_H$ | TGCCAGGTGCAGCTGGTGGAGTCTGGGGGAGGCGTAGTCCAGCCTGGGAGGTCCCTGAG<br>ACTGTCCTGTGCAGCCTCTGGATTCACCTTCAGTAATCATGCTATGCACTGGGTCCGCC<br>AGGCTCCAGGCAAGGGGCTGGAGTGGGTGGCAGTTATATCATATGATGGCGAGAACACA<br>TATTATGCAGACTCCATTGAGGGCCGATTCACCATTTCCAGAGACAATTTCAAGAACAC<br>ACTCTTTCTACAAATGTACAGCCTGACAGCTGATGACACGGCTATGTACTTCTGTGCGA<br>GAGGGGGCCGTCGGGGGCACTTCACCTCATACTACCTTGACTACTGGGGCCAGGGAACC<br>CTGGTCACCGTCTCCTCG<br>SEQ ID NO: 7 |
| NI-308.1507 $V_K$ | TGCGACATCCAGATGACCCAGTCTCCATCCTCCCTGTCTGCATCTGTAGGAGACAGAGT<br>CACCATCACTTGCCGGGCAAGCCAGAACATAGACAAGTACTTAAATTGGTATCAGCAGA<br>TACCGGGGAAAGCCCCTAAGCTCCTGATCTATGCTGCATCGAGTTTGCACAGTGGGGTC<br>CCATCAAGGTTCAGTGGCAGTGGATCTGGGACAGATTTCTCTCTCACCATCAGCAGTCT<br>GCAACCTGAAGATTTTGCAATTTACTACTGTCAACAGAGTTACAGTTCCTTCCGGACGT<br>TCGGCCAAGGGACCAAGCTGGAGATCAAA<br>SEQ ID NO: 9 |
| NI-308.1507 $V_K$-PIMC | TGCGACATCCAGATGACCCAGTCTCCGTCCTCCCTGTCTGCATCTGTAGGAGACAGAGT<br>CACCATCACTTGCCGGGCAAGCCAGAACATAGACAAGTACTTAAATTGGTATCAGCAGA<br>TACCGGGGAAAGCCCCTAAGCTCCTGATCTATGCTGCATCGAGTTTGCACAGTGGGGTC<br>CCATCAAGGTTCAGTGGCAGTGGATCTGGGACAGATTTCTCTCTCACCATCAGCAGTCT<br>GCAACCTGAAGATTTTGCAATTTACTACTGTCAACAGAGTTACAGTTCCTTCCGGACGT<br>TCGGCCAAGGGACCAAGGTGGAGATCAAA<br>SEQ ID NO: 11 |
| NI-308.5G2 $V_H$ | TGCGAGGTGCAGCTGGTGCAGTCTGGGGCTGACTTGCGGAACCCTGGGGCCTCAGTGAC<br>GGTTTCCTGCACGGCTTCTGGATACCATTTCGCTGACAATGCTATAAACTGGCTGCGCC<br>AGGCCCCCGGACAAAGGCTTGAGTGGATGGGTGGATCAACATTTACAGTGGTAACACA<br>AAATATTCACAGAACTTCCAGGGCAGAGTCACCTTTACCAGAAACACATCCGCGAGCAC<br>AGCCTTCATGCACCTGCGCAGCCTGAGATCAGAAGACACGGCTGTGTATTTCTGTGCGA<br>GAGACCCTGATAGCAGTGGATATTACTTGCCCTATTTTGACTACTGGGGCCAAGGAACC<br>CTGGTCACCGTCTCCTCG<br>SEQ ID NO: 13 |
| NI-308.5G2 $V_K$ | TGCGACATCCAGTTGACCCAGTCTCCAGACTCCCTGACTTTGTCTCTGGGCGAGAGGGC<br>CACCATCAACTGCAAGTCCAGCCAGAGTGTTTTCTACAACTCCAACAATAAGAACTACT<br>TAGCTTGGTATCAGCAGAAACCAGGACAGCCTCCTAAGTTGCTCATGTACTGGGCATCT<br>ACCCGGGAGTCCGGGGTCACTGACCGATTCAGTGGCAGCGGGTCTGGGACAGATTTTAC<br>TCTCACCATTACCAACCTGCAGGCTGAAGATGTGGCAGTCTATTATTGTCAGCAATTTT<br>ATAGTTCTCCTCTCACTTTCGGCGGAGGGACCAAGGTGGAGATCAAA<br>SEQ ID NO: 15 |

TABLE II-continued

Nucleotide sequences of the $V_H$ and $V_L$ region of antibodies recognizing DPRs, preferably C9ORF72-DPRs.

| Antibody | Nucleotide sequences of variable heavy ($V_H$) and variable light ($V_L$) chains |
|---|---|
| NI-308.5G2 $V_H$-PIMC | TGCCAGGTGCAGCTGGTGCAATCTGGGGCTGACTTGCGGAACCCTGGGGCCTCAGTGAC<br>GGTTTCCTGCACGGCTTCTGGATACCATTTCGCTGACAATGCTATAAACTGGCTGCGCC<br>AGGCCCCCGGACAAAGGCTTGAGTGGATGGGGTGGATCAACATTTACAGTGGTAACACA<br>AAATATTCACAGAACTTCCAGGGCAGAGTCACCTTTACCAGAAACACATCCGCGAGCAC<br>AGCCTTCATGCACCTGCGCAGCCTGAGATCAGAAGACACGGCTGTGTATTTCTGTGCGA<br>GAGACCCTGATAGCAGTGGATATTACTTGCCCTATTTTGACTACTGGGGCCAAGGAACC<br>CTGGTCACCGTCTCCTCG<br>SEQ ID NO: 17 |
| NI-308.5G2 $V_K$-PIMC | TGCGACATCGTGATGACCCAGTCTCCAGACTCCCTGACTTTGTCTCTGGGCGAGAGGGC<br>CACCATCAACTGCAAGTCCAGCCAGAGTGTTTTCTACAACTCCAACAATAAGAACTACT<br>TAGCTTGGTATCAGCAGAAACCAGGACAGCCTCCTAAGTTGCTCATGTACTGGGCATCT<br>ACCCGGGAGTCCGGGGTCACTGACCGATTCAGTGGCAGCGGGTCTGGGACAGATTTTAC<br>TCTCACCATTACCAACCTGCAGGCTGAAGATGTGGCAGTCTATTATTGTCAGCAATTTT<br>ATAGTTCTCCTCTCACTTTCGGCGGAGGGACCAAGGTGGAGATCAAA<br>SEQ ID NO: 19 |
| NI-308.28G1 $V_H$ | TGCCAGGTGCAGCTGCAGGAGTCGGGCCCAAGACTGGTGAAGCCCTCGGAGACCCTGTC<br>GCTCACGTGCACTGTCGCTGGCGGCTCCGTCAATAGTTACTATTGGACCTGGATCCAGC<br>AGTCCCCCGGGAAGGGACTGGAGTGGCTTGGGCGTATCTATATCGCTGGGAGGACCAAC<br>TATAACCCCTCCCTCACGAGTCGAATCGCCCTGTCAGTGGACACGTCCAGGAACCAGTT<br>GTCCCTGAAGCTGACGTCTGTGACCGCCGCGGAACACGGCCATATATTATTGTGCGAGAT<br>GGGGAGCGGAGAGTGGTGACTACTACTATGGAGTGGACGTCTGGGGCCCAGGCACCCTG<br>GTCACCGTCTCCTCG<br>SEQ ID NO: 21 |
| NI-308.28G1 $V_K$ | TGCGAAATTGTGATGACGCAGTCTCCACTCTCCCTGCCCGTCACCCCTGGAGAGCCGGC<br>CTCCATCTCCTGCAAGTCTAGTGAGGGACTCCTGCATAGTAATGGTTACACCTATTTGG<br>ATTGGTACCTGCAGAAGCCAGGGCAGGCTCCGCAGCTCCTGATCTTTCTGGCTTCTAAT<br>CGGGCCGCCGGGGTCCCTGACAGGTTCAGTGGCAGTGGATCAGGCACAGATTTTACACT<br>GAAGATCAGCAGAGTGGAGGCTGAGGATGTTGGCGTTTATTACTGCATGCAGGCTATAC<br>AAAGTCCTTGGACGTTCGGCCCAGGGACCAAGGTGGAAATCAAA<br>SEQ ID NO: 23 |
| NI-308.28G1 $V_H$-PIMC | TGCCAGGTGCAGCTGCAGGAGTCGGGCCCAAGACTGGTGAAGCCCTCGGAGACCCTGTC<br>GCTCACGTGCACTGTCGCTGGCGGCTCCGTCAATAGTTACTATTGGACCTGGATCCAGC<br>AGTCCCCCGGGAAGGGACTGGAGTGGCTTGGGCGTATCTATATCGCTGGGAGGACCAAC<br>TATAACCCCTCCCTCACGAGTCGAATCGCCCTGTCAGTGGACACGTCCAGGAACCAGTT<br>GTCCCTGAAGCTGACGTCTGTGACCGCCGCGGAACACGGCCATATATTATTGTGCGAGAT<br>GGGGAGCGGAGAGTGGTGACTACTACTATGGAGTGGACGTCTGGGGCCCAGGGACCACG<br>GTCACCGTCTCCTCA<br>SEQ ID NO: 25 |
| NI-308.28G1 $V_K$-PIMC | TGCGATATTGTGATGACTCAGTCTCCACTCTCCCTGCCCGTCACCCCTGGAGAGCCGGC<br>CTCCATCTCCTGCAAGTCTAGTGAGGGACTCCTGCATAGTAATGGTTACACCTATTTGG<br>ATTGGTACCTGCAGAAGCCAGGGCAGGCTCCGCAGCTCCTGATCTTTCTGGCTTCTAAT<br>CGGGCCGCCGGGGTCCCTGACAGGTTCAGTGGCAGTGGATCAGGCACAGATTTTACACT<br>GAAGATCAGCAGAGTGGAGGCTGAGGATGTTGGCGTTTATTACTGCATGCAGGCTATAC<br>AAAGTCCTTGGACGTTCGGCCCAGGGACCAAGGTGGAAATCAAA<br>SEQ ID NO: 27 |
| NI-308.45C2 $V_H$ | TGCCAGCTGCAGCTGCAGGAGTCGGGTCCAGGACTGGTGAAGCCCTCGCAGATCCTCTC<br>ACTCACCTGTGCCATCTCCGGGGACAGTGTCTTCAGCAACAGTGCTGCTTGGAACTGGA<br>TCAGGCAGTCCCCATCGAGAGGCCTTGAGTGGCTGGGAAGGACATACTACAGGTCCAAG<br>TGGGATAATGATTATGCACCATCTGTGAAAAGTCGAATAAGTATCAACCCAGACACATC<br>CAAGAACCAGTTCTCCCTGCAGTTGAATTCTGTGACTCCCGAGGACACGGCTGTGTATT<br>ATTGTGCAAGAGAGGTCGCATATTGTGGTGGTGACTGCTATTCTGTTTCCTTTGACTAC<br>TGGGGCCAGGGAACCCTGGTCACCGTCTCCTCG<br>SEQ ID NO: 29 |
| NI-308.45C2 $V_K$ | TGCGAAATTGTGATGACACAGTCTCCACTCTCCCTGCCCGTCACCCCTGGAGAGCCGGC<br>CTCCATCTCCTGCAGGTCTAGTCAGAGCCTCCTCCAGAGTAATGGATACACCTATTTGG<br>ATTGGTACCTGCAGAAGCCAGGGCAGTCTCCACAGCTCCTGATCTATTTGGGTTCTAAT<br>CGGGCCTCCGGGGTCCCTGACAGGTTCAGTGGCAGTGGATCAGGCACAGATTTTACACT<br>GAAAATCAGCAGAGTGGAGGCTGAGGATGTTGGGGTTTATTACTGCATGCAAGCTCTAC<br>AAACTCCGCTCACTTTCGGCGGAGGGACCAAGGTGGAGATCAAA<br>SEQ ID NO: 31 |
| NI-308.45C2 $V_H$-PIMC | TGCCAGCTGCAGCTGCAGCAGTCAGGTCCAGGACTGGTGAAGCCCTCGCAGATCCTCTC<br>ACTCACCTGTGCCATCTCCGGGGACAGTGTCTTCAGCAACAGTGCTGCTTGGAACTGGA<br>TCAGGCAGTCCCCATCGAGAGGCCTTGAGTGGCTGGGAAGGACATACTACAGGTCCAAG<br>TGGGATAATGATTATGCACCATCTGTGAAAAGTCGAATAAGTATCAACCCAGACACATC<br>CAAGAACCAGTTCTCCCTGCAGTTGAATTCTGTGACTCCCGAGGACACGGCTGTGTATT |

TABLE II-continued

Nucleotide sequences of the V$_H$ and V$_L$ region of antibodies recognizing DPRs, preferably C9ORF72-DPRs.

| Antibody | Nucleotide sequences of variable heavy (V$_H$) and variable light (V$_L$) chains |
|---|---|
| | ATTGTGCAAGAGAGGTCGCATATTGTGGTGGTGACTGCTATTCTGTTTCCTTTGACTAC<br>TGGGGCCAGGGAACCCTGGTCACCGTCTCCTCG<br>SEQ ID NO: 33 |
| NI-308.45C2 V$_K$-PIMC | TGCGATATTGTGATGACTCAGTCTCCACTCTCCCTGCCCGTCACCCCTGGAGAGCCGGC<br>CTCCATCTCCTGCAGGTCTAGTCAGAGCCTCCTCCAGAGTAATGGATACACCTATTTGG<br>ATTGGTACCTGCAGAAGCCAGGGCAGTCTCCACAGCTCCTGATCTATTTGGGTTCTAAT<br>CGGGCCTCCGGGGTCCCTGACAGGTTCAGTGGCAGTGGATCAGGCACAGATTTTACACT<br>GAAAATCAGCAGAGTGGAGGCTGAGGATGTTGGGGTTTATTACTGCATGCAAGCTCTAC<br>AAACTCCGCTCACTTTCGGCGGAGGGACCAAGGTGGAGATCAAA<br>SEQ ID NO: 35 |
| NI-308.24E11 V$_H$ | TGCCAGGTGCAGCTGCAGGAGTCGGGCCCAGGACTGGTGAAGCCTTCGGAGACCCTGTC<br>CCTCACCTGCACTGTCTCTACTACTTCCCTCAGAAGTTATTTCTGGAGTTGGATCCGGC<br>AGCCCCCAGGGAAGGGGCTGGAGTGGATTGGGTATGTCTATTACAGTGGGAGTACCATC<br>TACAATCCGTCCCTCAAGAATCGAGTCACCATATCCATAGACACGTCCAAGAACCAGTT<br>CTCCCTGAACCTGCGCTCTGTGACCGCTGCGGATACGGCCATGTATTTCTGTGCGAGAG<br>GCGTCCCGGCTGAGACTGATGCGCGGGACTTCCCGCCCTACTACTTTGATCACTGGGGC<br>CAGGGAACCCTGGTCACCGTCTCCTCG<br>SEQ ID NO: 37 |
| NI-308.24E11 V$_K$ | TGCGACATCCAGTTGACCCAGTCTCCATCCTCCCTGTCTGCGTCAGTAGGAAACAGAAT<br>CACCTTCACTTGCCAGGCGAGTCAGGACATTAGATATTATTTAAATTGGTATCAGCAGA<br>AACCAGGGAAAGCCCCTAAACTCCTGATCTACGATGTGTCCAATTTGGATACAGGGGTG<br>CCACCAAGGTTCAGTGGAAGTGGATCTGGGACAAATTTCACTTTCACCATCAGCAGCCT<br>GCAGCCTGAAGATATTGCAGTTTATTACTGTCAACAGTATGAAGGACTCCCTGTGACCT<br>TCGGCGGGGGGACCAAGGTGGAGATCAAA<br>SEQ ID NO: 39 |
| NI-308.24E11 V$_K$-PIMC | TGCGACATCCAGATGACCCAGTCTCCATCCTCCCTGTCTGCGTCAGTAGGAAACAGAAT<br>CACCTTCACTTGCCAGGCGAGTCAGGACATTAGATATTATTTAAATTGGTATCAGCAGA<br>AACCAGGGAAAGCCCCTAAACTCCTGATCTACGATGTGTCCAATTTGGATACAGGGGTG<br>CCACCAAGGTTCAGTGGAAGTGGATCTGGGACAAATTTCACTTTCACCATCAGCAGCCT<br>GCAGCCTGAAGATATTGCAGTTTATTACTGTCAACAGTATGAAGGACTCCCTGTGACCT<br>TCGGCGGGGGGACCAAGGTGGAGATCAAA<br>SEQ ID NO: 41 |
| NI-308.46E9 V$_H$ | TGCCAGGTGCAGCTGCAGGAGTCGGGCCCAGGACTGGTGAAGCCTTCGGAGACCCTGTC<br>CCTCACTTGCACTGTCTCTGGTGCCTCCATCAGCGGTAGTACCTACTACTGGGGCTGGA<br>TCCGCCAGCCCCCAGGGAAGGGGCTGGAGTATATTGGGAGAATCTACTATAGTGGGAGC<br>ACCTACTACAACCCGTCCCTCAAGAGTCGAGCCACCATATCTGTAGACACGTCCAAGAA<br>CCAGCTCTCCCTGACACTGAGTTCTGTGACCGCCGCAGATACGGCTGTGTATTATTGTG<br>TGAGACCCTTTTACGCTGGTTCGGGGAACTCCCCCTTTGACTACTGGGGCCAGGGAACC<br>CTGGTCACCGTCTCCTCG<br>SEQ ID NO: 43 |
| NI-308.46E9 V$_K$ | TGCGAAATTGTGCTGACTCAGTCTCCAGCCACCGTGTCTGTGTCTCCAGGGGAGAGAGC<br>CACCCTCTCCTGCAGGGCCAGCCAGAGTGTTAGCACCAACTTAGCCTGGTACCAGCAGA<br>AACCTGGCCAGCCTCCCAGGCTCCTCATTTATGGTGCATCCACCAGGGCCACTGGTATC<br>CCAGCCAGGTTCAGTGGCAGTGGGTCTGGGGCAGAGTTCACCCTCACCATCAGCAGCCT<br>GCAGTCTGAAGATTTTGTTGTTTATTACTGTCAGCAATATAATAACTGGCCTCCGGCTT<br>TCGGCGGAGGGACCAAGGTGGAAATCAAA<br>SEQ ID NO: 45 |
| NI-308.46E9 V$_H$-PIMC | TGCCAGCTGCAGCTGCAGGAGTCGGGCCCAGGACTGGTGAAGCCTTCGGAGACCCTGTC<br>CCTCACTTGCACTGTCTCTGGTGCCTCCATCAGCGGTAGTACCTACTACTGGGGCTGGA<br>TCCGCCAGCCCCCAGGGAAGGGGCTGGAGTATATTGGGAGAATCTACTATAGTGGGAGC<br>ACCTACTACAACCCGTCCCTCAAGAGTCGAGCCACCATATCTGTAGACACGTCCAAGAA<br>CCAGCTCTCCCTGACACTGAGTTCTGTGACCGCCGCAGATACGGCTGTGTATTATTGTG<br>TGAGACCCTTTTACGCTGGTTCGGGGAACTCCCCCTTTGACTACTGGGGCCAGGGAACC<br>CTGGTCACCGTCTCCTCG<br>SEQ ID NO: 47 |
| NI-308.46E9 V$_K$-PIMC | TGCGAAATAGTGATGACGCAGTCTCCAGCCACCGTGTCTGTGTCTCCAGGGGAGAGAGC<br>CACCCTCTCCTGCAGGGCCAGCCAGAGTGTTAGCACCAACTTAGCCTGGTACCAGCAGA<br>AACCTGGCCAGCCTCCCAGGCTCCTCATTTATGGTGCATCCACCAGGGCCACTGGTATC<br>CCAGCCAGGTTCAGTGGCAGTGGGTCTGGGGCAGAGTTCACCCTCACCATCAGCAGCCT<br>GCAGTCTGAAGATTTTGTTGTTTATTACTGTCAGCAATATAATAACTGGCCTCCGGCTT<br>TCGGCGGAGGGACCAAGGTGGAGATCAAA<br>SEQ ID NO: 49 |
| NI-308.6B11 V$_H$ | TGCGAGGTGCAGCTGGTGCAGTCTGGGGCTGAGGTGAAGAGGCCTGGGGCCTCAGTGAA<br>GGTCTCCTGCAAGGTTTCCGGATACACCCTCACTGAATTATCCATGCACTGGGTGCGAC<br>AGGCTCCTGGAAAAGGGCTTGAGTGGATGGGAGGTTTTGATCCTGAAGATGGTGAAACA |

TABLE II-continued

Nucleotide sequences of the V$_H$ and V$_L$ region of antibodies recognizing DPRs, preferably C9ORF72-DPRs.

| Antibody | Nucleotide sequences of variable heavy (V$_H$) and variable light (V$_L$) chains |
|---|---|
| | GTCTACGCACAGAAGTTCCAGGGCAGAGTCACCATGACCGAGGACACATCTACAGACAC<br>AGCCTACATGGAGCTGAGCAGCCTGAGATCTGAGGACACGGCCTTGTATCACTGTGCAA<br>CATACGGCAGCAGCTGGCACTGGAATGAGGGAAATGAGGGGTCCTACTACTTTGACTAC<br>TGGGGCCAGGGAACCCTGGTCACCGTCTCCTCG<br>SEQ ID NO: 51 |
| NI-308.6B11 V$_K$ | TGCGACATCCAGATGACCCAGTCTCCATCCTCCCTGTCTGCATCTGTAGGAGACAGAGT<br>CACCATCACTTGCCAGGCGAGTCAGGACATTAGCATTTATTTAAATTGGTATCAGCAAA<br>AACCAGGGAAAGCCCCTAAGCTCCTGATCTACGATGCATCCAATTTGGAAACAGGGGTC<br>CCATCAAGGTTCAGTGGAAGTGGATCTGGGACAGATTTTACTTTCACCATCAGCGGCCT<br>GCAGCCTGAAGATGTTGCAAGATATTATTGTCAACAGTATGATGATCTCCCCATCACCT<br>TCGGCCAAGGGACACGACTGGAGATTAAA<br>SEQ ID NO: 53 |
| NI-308.6B11 V$_H$-PIMC | TGCCAGGTCCAGCTGGTACAGTCTGGGGCTGAGGTGAAGAGGCCTGGGGCCTCAGTGAA<br>GGTCTCCTGCAAGGTTTCCGGATACACCCTCACTGAATTATCCATGCACTGGGTGCGAC<br>AGGCTCCTGGAAAAGGGCTTGAGTGGATGGGAGGTTTTGATCCTGAAGATGGTGAAACA<br>GTCTACGCACAGAAGTTCCAGGGCAGAGTCACCATGACCGAGGACACATCTACAGACAC<br>AGCCTACATGGAGCTGAGCAGCCTGAGATCTGAGGACACGGCCTTGTATCACTGTGCAA<br>CATACGGCAGCAGCTGGCACTGGAATGAGGGAAATGAGGGGTCCTACTACTTTGACTAC<br>TGGGGCCAGGGAACCCTGGTCACCGTCTCCTCG<br>SEQ ID NO: 55 |
| NI-308.46F8 V$_H$ | TGCCAGGTGCAGCTGGTGGAGTCTGGGGGAGGTGTGGTACGGCCTGGGGGGTCCCTGAG<br>ACTCTCCTGTACAGCCTCTGGATTCACGTTTGATGAATATGGCATGAGCTGGGTCCGCC<br>AAGTTCCAGGGAAGGGGCTGGAGTGGGTCTCTGGCATTAATTGGAATGGAGCAACCACA<br>CGTTATGCAGACTCTGTGAAGGGCCGATTCACCATCTCCAGAGACAACGCCAAGAACTC<br>CCTCTATCTGCAAATGAACAGTCTGAGAGCCGAGGACACGGCCTTGTATCACTGTGCGA<br>GAGATGGGTGTAGGAATACCAGCTGCTATATCTGGGACTGGTTCGATCCCTGGGGCCAG<br>GGAACCCTGGTCACCGTCTCCTCG<br>SEQ ID NO: 57 |
| NI-308.46F8 V$_L$ | TGCCAGTCTGTGTTGACGCAGCCGCCCTCAGTGTCTGCGGCCCCAGGACAGAAGGTCAC<br>CATCTCCTGCTCTGGAAGCAGCTCCAACATTGGAAATAATTATGTATGCTGGTACCAGA<br>ACCTCCCAGGAACAGCCCCCAAACTCCTCATTTATGACGATAATAAGCGACCCTCAGGG<br>ATTCCTGACCGATTCTCTGGCTCCAAGTCTGGCACGTCAGCCACCCTGGGCATCACCGG<br>ACTCCAGACTGGGGACGAGGCCGATTATTACTGCGGAACATGGGACAGCAGCCTGAGTG<br>TTGTGGTATTCGGCGGAGGGACCAAGCTGACCGTCCTA<br>SEQ ID NO: 59 |
| NI-308.46F8 V$_H$-PIMC | TGCGAGGTGCAGCTGGTGGAGTCTGGGGGAGGTGTGGTACGGCCTGGGGGGTCCCTGAG<br>ACTCTCCTGTACAGCCTCTGGATTCACGTTTGATGAATATGGCATGAGCTGGGTCCGCC<br>AAGTTCCAGGGAAGGGGCTGGAGTGGGTCTCTGGCATTAATTGGAATGGAGCAACCACA<br>CGTTATGCAGACTCTGTGAAGGGCCGATTCACCATCTCCAGAGACAACGCCAAGAACTC<br>CCTCTATCTGCAAATGAACAGTCTGAGAGCCGAGGACACGGCCTTGTATCACTGTGCGA<br>GAGATGGGTGTAGGAATACCAGCTGCTATATCTGGGACTGGTTCGATCCCTGGGGCCAG<br>GGAACCCTGGTCACCGTCTCCTCG<br>SEQ ID NO: 61 |
| NI-308.4M1 V$_H$ | TGCGAGGTGCAGCTGGTGGAGACTGGGGGAGGCGTGGTCCAGCCGGGGGGGTCCCTGCG<br>ACTCTCCTGTGAAGCCTCTGGATTCACCATCGGCACCTATGCCATGCACTGGGTCCGCC<br>AGTTTCCAGGCAAGGGCCTGGATTGGGTGGCAGTAATATCGTTCGATGGAACTACTGAG<br>TACTACACAGACGCCGTGAAGGGCCGATTCACCATCTCCAGAGACAATGCCAAGAACAC<br>ACTGTATCTGCAAATGAACTACTTGAGAGGTGACGACACGGCTATATATTTCTGTGCGC<br>GAGATTTCACCTCCTCGGGGGAGACCGGTTCGTGGACACAAGTACCTGATCTCTGGGGC<br>CAGGGCACCCTGGTCACCGTCTCCTCG<br>SEQ ID NO: 63 |
| NI-308.4M1 V$_K$ | TGCGAAATTGTGATGACACAGTCTCCAGCCACCCTGTCTCTGTCTCCAGGGGAAAGAGC<br>CACGCTCTCCTGCAGGGCCAGTCAGAGTGTTACTAAATACTTAGCCTGGTACCAACAGA<br>AACCTGGCCAGGCTCCCAGGCTCCTCATCTATGATGTATCTTACAGGGCCGCTGGCACC<br>CCAGCCAGGTTCAGTGGCAGTGGGTCTGGGACAGACTTCACTCTCACCATCAGCAGCCT<br>AGAGCCTGAAGATTTTGCAGTTTATTACTGTCACCAACGTAGCAGCTGGCCTCCGGTCA<br>CTTTCGGCGGAGGGACCAAGGTGGAGATCAAA<br>SEQ ID NO: 65 |
| NI-308.4M1 V$_H$-PIMC | TGCCAGGTGCAGCTGGTGGAGTCTGGGGGAGGCGTGGTCCAGCCGGGGGGGTCCCTGCG<br>ACTCTCCTGTGAAGCCTCTGGATTCACCATCGGCACCTATGCCATGCACTGGGTCCGCC<br>AGTTTCCAGGCAAGGGCCTGGATTGGGTGGCAGTAATATCGTTCGATGGAACTACTGAG<br>TACTACACAGACGCCGTGAAGGGCCGATTCACCATCTCCAGAGACAATGCCAAGAACAC<br>ACTGTATCTGCAAATGAACTACTTGAGAGGTGACGACACGGCTATATATTTCTGTGCGC<br>GAGATTTCACCTCCTCGGGGGAGACCGGTTCGTGGACACAAGTACCTGATCTCTGGGGC<br>CAGGGCACCCTGGTCACCGTCTCCTCG<br>SEQ ID NO: 67 |

TABLE II-continued

Nucleotide sequences of the V_H and V_L region of antibodies recognizing DPRs, preferably C9ORF72-DPRs.

| Antibody | Nucleotide sequences of variable heavy (V_H) and variable light (V_L) chains |
|---|---|
| NI-308.4M1 V_K-PIMC | TGCGAAATTGTGTTGACACAGTCTCCAGCCACCCTGTCTCTGTCTCCAGGGGAAAGAGC<br>CACGCTCTCCTGCAGGGCCAGTCAGAGTGTTACTAAATACTTAGCCTGGTACCAACAGA<br>AACCTGGCCAGGCTCCCAGGCTCCTCATCTATGATGTATCTTACAGGGCCGCTGGCACC<br>CCAGCCAGGTTCAGTGGCAGTGGGTCTGGGACAGACTTCACTCTCACCATCAGCAGCCT<br>AGAGCCTGAAGATTTTGCAGTTTATTACTGTCACCAACGTAGCAGCTGGCCTCCGGTCA<br>CTTTCGGCGGAGGGACCAAGGTGGAGATCAAA<br>SEQ ID NO: 69 |
| NI-308.12A3 V_H | TGCGAGGTGCAGCTGGTGGAGACTGGGGGAGGCTTGGTACAGCCTGGAGGGTCCCTGAG<br>ACTCTCCTGCGTAGGCTCTGGATTTCTCTTCAGTGATTTTGAAATGGACTGGGTCCGCC<br>AGGCTCCAGGGAAGGGGCTGGAGTGGATTTCATATATTAGTGGTGACGGTAATATCATA<br>TATCAGACAGACTCTGTGAAGGGCCGATTCACCATCTCCAGAGACAACGCCAAGAATTC<br>ACTGTTTCTACAAATGGACAGCCTGACCGTCGAGGACACGGCTGTATATTACTGTGCGA<br>GAGACGCCCGTGAAAACTGTGGTGGTGACTGCTATTCCACGTCCTTTGATTTTTGGGGC<br>CAGGGCACCCTGGTCACCGTCTCCTCG<br>SEQ ID NO: 71 |
| NI-308.12A3 V_K | TGCGACATCCAGATGACCCAGTCTCCAGACTCCCTGGCTGTGTCTCTGGGCGAGAGGGC<br>CACCATCAACTGCAAGTCCAGCCAGAGTCTTTTATACACTGCCAACAATAGGAACTACT<br>TAGCCTGGTACCAGAAAAAAGCAGGACAGCCTCCTAAGCTCCTCATTCACTGGGCATCT<br>ACCCGGGCATCCGGGGTCCCTGACCGATTCAGTGGCAGCGGGTCTGGGACAGATTTCAT<br>TCTCACCATCAGCAGCCTGCAGGCTGAAGATGTGGCAGTTTATTTTTGTCAACATTATT<br>ATAATTCTCCCCGGACGTTCGGCCAAGGGACCAAGGTGGAGATCAAA<br>SEQ ID NO: 73 |
| NI-308.12A3 V_H-PIMC | TGCGAGGTGCAGCTGGTGGAGTCTGGGGGAGGCTTGGTACAGCCTGGAGGGTCCCTGAG<br>ACTCTCCTGCGTAGGCTCTGGATTTCTCTTCAGTGATTTTGAAATGGACTGGGTCCGCC<br>AGGCTCCAGGGAAGGGGCTGGAGTGGATTTCATATATTAGTGGTGACGGTAATATCATA<br>TATCAGACAGACTCTGTGAAGGGCCGATTCACCATCTCCAGAGACAACGCCAAGAATTC<br>ACTGTTTCTACAAATGGACAGCCTGACCGTCGAGGACACGGCTGTATATTACTGTGCGA<br>GAGACGCCCGTGAAAACTGTGGTGGTGACTGCTATTCCACGTCCTTTGATTTTTGGGGC<br>CAGGGCACCCTGGTCACCGTCTCCTCG<br>SEQ ID NO: 75 |
| NI-308.12A3 V_K-PIMC | TGCGACATCGTGATGACCCAGTCTCCAGACTCCCTGGCTGTGTCTCTGGGCGAGAGGGC<br>CACCATCAACTGCAAGTCCAGCCAGAGTCTTTTATACACTGCCAACAATAGGAACTACT<br>TAGCCTGGTACCAGAAAAAAGCAGGACAGCCTCCTAAGCTCCTCATTCACTGGGCATCT<br>ACCCGGGCATCCGGGGTCCCTGACCGATTCAGTGGCAGCGGGTCTGGGACAGATTTCAT<br>TCTCACCATCAGCAGCCTGCAGGCTGAAGATGTGGCAGTTTATTTTTGTCAACATTATT<br>ATAATTCTCCCCGGACGTTCGGCCAAGGGACCAAGGTGGAGATCAAA<br>SEQ ID NO: 77 |
| NI-308.16C10 V_H | TGCGAGGTGCAGCTGGTGGAGACTGGGGGAGGCGTGGTCCAGCCTGGGATGTCCCTGAG<br>CCTCTCCTGTGCAGCGACTGGATTCACCTTCAGCAGTTATGGCATGCACTGGGTCCGCC<br>AAGGTCCAGGCAAGGGGCCGGAGTGGGTGGCGGGTATATGGTACGATGGAACAAATAAG<br>TATTATGGAGACTCCGTGACGGGCAGAGTCACCATCTCCAGAGACAACTCCAAGAACAC<br>GCTGTTTCTGCAAATGATCAACGTGAGAGTCGAGGACACGGCTGTGTATTACTGTGTGA<br>AGGATGCAGAGCGCGTCCAGAAATGGGCTAGTTACATTATGGACGTGTGGGGCCAAGGG<br>ACCACGGTCACCGTCTCCTCG<br>SEQ ID NO: 79 |
| NI-308.16C10 V_K | TGCGAAATTGTGCTGACTCAGTCTCCAGGCATCCTGTCTTTGTCTCGAGGGAATCGGGT<br>CGCCCTCTCCTGCAGGGCCAGTCGGAGTGTTAATAGCAGCTACTTAAATTGGTACCAGC<br>AAAAACCAGGCCAGGCTCCCAGACTCCTCATCTATGGTGCATCTAAAAGGGCCACTGGC<br>ATCTCAGACAGGTTCCGTGGCACTGGGTCTGGGACAGACTTCACTCTCACCGTCGCCAG<br>ACTGGAGCCTGAAGATATTGCGGTTTACTACTGTCAGCACTATGGTGCCTTCGGCCAAG<br>GGACCAAGCTGGAGATCAAA<br>SEQ ID NO: 81 |
| NI-308.16C10 V_H-PIMC | TGCCAGGTGCAGCTGGTGGAGTCTGGGGGAGGCGTGGTCCAGCCTGGGATGTCCCTGAG<br>CCTCTCCTGTGCAGCGACTGGATTCACCTTCAGCAGTTATGGCATGCACTGGGTCCGCC<br>AAGGTCCAGGCAAGGGGCCGGAGTGGGTGGCGGGTATATGGTACGATGGAACAAATAAG<br>TATTATGGAGACTCCGTGACGGGCAGAGTCACCATCTCCAGAGACAACTCCAAGAACAC<br>GCTGTTTCTGCAAATGATCAACGTGAGAGTCGAGGACACGGCTGTGTATTACTGTGTGA<br>AGGATGCAGAGCGCGTCCAGAAATGGGCTAGTTACATTATGGACGTGTGGGGCCAAGGG<br>ACCACGGTCACCGTCTCCTCG<br>SEQ ID NO: 83 |
| NI-308.16C10 V_K-PIMC | TGCGAAATTGTGTTGACGCAGTCTCCAGGCACCCTGTCTTTGTCTCGAGGGAATCGGGT<br>CGCCCTCTCCTGCAGGGCCAGTCGGAGTGTTAATAGCAGCTACTTAAATTGGTACCAGC<br>AAAAACCAGGCCAGGCTCCCAGACTCCTCATCTATGGTGCATCTAAAAGGGCCACTGGC<br>ATCTCAGACAGGTTCCGTGGCACTGGGTCTGGGACAGACTTCACTCTCACCGTCGCCAG<br>ACTGGAGCCTGAAGATATTGCGGTTTACTACTGTCAGCACTATGGTGCCTTCGGCCAAG |

TABLE II-continued

Nucleotide sequences of the $V_H$ and $V_L$ region of antibodies recognizing DPRs, preferably C9ORF72-DPRs.

| Antibody | Nucleotide sequences of variable heavy ($V_H$) and variable light ($V_L$) chains |
|---|---|
| | GGACCAAGGTGGAAATCAAA<br>SEQ ID NO: 85 |

The present invention also includes fragments of the polynucleotides of the invention, as described elsewhere. Additionally polynucleotides which encode fusion polynucleotides, Fab fragments, and other biotechnological derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing the DPR-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative, or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses, and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics), or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. In one embodiment, this is accomplished using a proprietary expression vector of Biogen IDEC, Inc., referred to as NEOSPLA, and disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene, and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application. Therefore, in one embodiment the present invention provides a vector comprising the polynucleotide encoding at least the binding domain or variable region of an immunoglobulin chain of the antibody, optionally in combination with a polynucleotide that encodes the variable region of the other immunoglobulin chain of said binding molecule.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells comprising a polynucleotide encoding an antibody of the invention, or a heavy or light chain thereof, or at least the binding domain or variable region of an immunoglobulin thereof, which preferably are operable linked to a heterologous promoter. In addition or alternatively the invention also includes host cells comprising a vector, as defined hereinabove, comprising a polynucleotide encoding at least the binding domain or variable region of an immunoglobulin chain of the antibody, optionally in combination with a polynucleotide that encodes the variable region of the other immunoglobulin chain of said binding molecule. In preferred embodiments for the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *Escherichia coli, Bacillus subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as E. coli, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAH (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska and Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan and Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981), which are incorporated by reference herein in their entireties. The expression levels of an antibody molecule can be increased by vector amplification, for a review; see Bebbington and Hentschel, The use of vectors based on gene amplification for the expression of cloned genes in mammalian cells in DNA cloning, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or antigen-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of E. coli or Salmonella; Bacillaceae, such as B. subtilis; Pneumococcus; Streptococcus, and Haemophilus influenzae. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO 02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye and Inouye, Nucleic Acids Res. 13 (1985), 3101-3109; Van Heeke and Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e g ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1. In one embodiment therefore, the present invention also provides a method for preparing an anti-DPR antibody or an antibody recognizing mutated and/or aggregated C9ORF72-DPR species and/or fragments thereof or immunoglobulin chain(s) thereof, said method comprising:
(a) culturing the host cell as defined hereinabove, which cell comprised a polynucleotide or a vector as defined hereinbefore; and
(b) isolating said antibody or immunoglobulin chain(s) thereof from the culture.

Furthermore, the present invention also relates to an antibody or immunoglobulin chain(s) thereof encoded by a polynucleotide as defined hereinabove or obtainable by said method for preparing an anti-DPR antibody or an antibody recognizing mutated and/or aggregated C9ORF72-DPR species and/or fragments thereof or immunoglobulin chain(s) thereof.

V. Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like).

An antibody polypeptide of the invention may comprise, consist essentially of, or consist of a fusion protein. Fusion proteins are chimeric molecules which comprise, for example, an immunoglobulin DPR-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO 92/08495; WO 91/14438; WO 89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, (1983) 1-12; Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to DPR proteins or peptides. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds DPRs. In yet another embodiment, a fusion protein for use in the diagnostic and treatment methods disclosed herein comprises a polypeptide having the amino acid sequence of any one, two, three, or more of the $V_H$ CDRs of an antibody and the amino acid sequence of any one, two, three, or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, synthetic variants, or biotechnological derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767), GST, c-myc and the "flag" tag; see, e.g., Bill Brizzard, BioTechniques 44 (2008) 693-695 for a review of epitope tagging techniques, and Table 1 on page 694 therein listing the most common epitope tags usable in the present invention, the subject matter of which is hereby expressly incorporated by reference.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression, which is performed as described herein before.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared, e.g., by reacting a DPR-binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a DPRs to indicate the risk of getting a disease or disorder associated with DPRs, preferably associated with mutated C9ORF72 forming DPRs, i.e. C9ORF72-DPRs, to monitor the development or progression of such a disease, i.e. a disease showing the occurrence of, or related to aggregated DPRs, or as part of a clinical testing procedure to, e.g., determine the efficacy of a given treatment and/or prevention regimen. In one embodiment thus, the present invention relates to an antibody, which is detectably labeled. Furthermore, in one embodiment, the present invention relates to an antibody, which is attached to a drug. Detection can be facilitated by coupling the antibody, or antigen-binding fragment, variant, or derivative thereof to a detectable substance. The detectable substances or label may be in general an enzyme; a heavy metal, preferably gold; a dye, preferably a fluorescent or luminescent dye; or a radioactive label. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. Therefore, in one embodiment the present invention provides a detectably labeled antibody, wherein the detectable label is selected from the group consisting of an enzyme, a radioisotope, a fluorophore and a heavy metal.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, (ed.), Enzyme Immunoassay, CRC Press, Boca Raton, Fla., (1980); Ishikawa, et al., (eds.), Enzyme Immunoassay, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Anion et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., (1987) 623-53; Thorpe, "Antibody Carriers Of Cytotoxic Agents In Cancer Therapy: A Review", in Monoclonal Antibodies '84: Biological And Clinical Applications, Pinchera et al. (eds.), (1985) 475-506; "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press (1985) 303-16, and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned DPR-binding molecule of the present invention, e.g., antibody or antigen-binding fragment, variant or biotechnological derivative thereof, or the polynucleotide, vector or cell of the invention as defined hereinbefore. In one embodiment, the composition of the present invention is a pharmaceutical composition and further comprises a pharmaceutically acceptable carrier. Furthermore, the pharmaceutical composition of the present invention may comprise further agents such as interleukins or interferons depending on the intended use of the pharmaceutical composition. For use in the treatment of a disease or disorder showing the occurrence of, or related to aggregated DPRs, in particular C9ORF72-DPRs, such as FTLD, the additional agent may be selected from the group consisting of small organic molecules, anti-DPR antibodies, and combinations thereof. Hence, in a particular preferred embodiment the present invention relates to the use of the DPR-binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a disease or disorder associated with DPR proteins, monitoring the progression of a disease or disorder associated with DPR protein and/or aggregated C9ORF72 or a response to a DPR treatment in a subject or for determining a subject's risk for developing a disease or disorder associated with DPR protein and/or aggregated C9ORF72-DPRs.

Hence, in one embodiment the present invention relates to a method of treating a disease or disorder characterized by abnormal accumulation and/or deposition of DPRs and DPR proteins such as aggregated C9ORF72 due to C9ORF72-DPRs, which method comprises administering to a subject in need thereof a therapeutically effective amount of any one of the afore-described DPR-binding molecules, antibodies, polynucleotides, vectors or cells of the instant invention.

A particular advantage of the therapeutic approach of the present invention lies in the fact that the recombinant antibodies of the present invention are derived from B cells or memory B cells from healthy human subjects with no signs or symptoms of a disease, e.g. carrying an asymptomatic mutation and/or mutations, showing the occurrence of, or related to aggregated DPRs and thus are, with a certain probability, capable of preventing a clinically manifest disease related to DPRs, e.g. mutated C9ORF72 with expanded hexanucleotide repeats resulting in the formation of dipeptide repeat (DPR) in the C9ORF72 protein an aggregated C9ORF72 due to C9ORF72-DPRs, or of diminishing the risk of the occurrence of the clinically manifest disease or disorder, or of delaying the onset or progression of the clinically manifest disease or disorder. Typically, the antibodies of the present invention also have already successfully gone through somatic maturation, i.e. the optimization with respect to selectivity and effectiveness in the high affinity binding to the target DPR molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human-derived anti-DPR antibodies of the present invention, both its high target structure-specific affinity as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-DPR antibody, binding fragment, biotechnological derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disease or disorder which is accompanied with the presence of DPRs, and in particular applicable for the treatment of disorders generally characterized by presence of DPRs. In particular, the composition is useful in the treatment of disorders which are related to DPR aggregation, for example mutated C9ORF72 with expanded hexanucleotide repeats resulting in the formation of aggregated C9ORF72 due to C9ORF72-DPRs. Diseases and/or disorders associated with DPRs comprise but are not limited to Frontotemporal lobar degeneration (FTLD), amyotrophic lateral sclerosis (ALS), FTLD-ALS, and/or spinocerebellar ataxia type 36.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline, and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an anti-DPR antibody or DPR-binding fragment, or synthetic or biotechnological variant or derivative thereof for passive immunization. As mentioned in the background section aggregated DPR species are a major trigger for diseases and/or disorders such as FTLD and ALS. Accordingly, it is prudent to expect that passive immunization with human-derived anti-DPR antibodies and equivalent DPR-binding molecules of the present invention will help to circumvent several adverse effects of active immunization therapy concepts and lead to a reduced aggregation of DPRs. Therefore, the present anti-DPR antibodies and their equivalents of the present invention will be particularly useful as a vaccine for the prevention or amelioration of diseases or disorders showing the presence of, or caused by aggregated DPRs, in particular C9ORF72-DPRs, such as FTLD.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008); S1741-0134, published online ahead, describe the use of chimeric recombinant Fab (rFab) and single chain fragments (scFvs) of monoclonal antibody WO-2 which recognizes an epitope in the N-terminal region of Abeta. The engineered fragments were able to (i) prevent amyloid fibrillization, (ii) disaggregate preformed Abeta1-42 fibrils and (iii) inhibit Abeta1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a disease, disorder, or symptoms related to the occurrence of DPRs, in particular aggregated DPRs such as C9ORF72-DPRs may be desirable. In one embodiment, the additional antibody is comprised in the pharmaceutical composition of the present invention. Examples of antibodies which can be used to treat a subject include, but are not limited to, antibodies targeting CD33, SGLT2, IL-6, and IL-1.

In a further embodiment, co-administration or sequential administration of other agents useful for treating a disease, disorder, or symptoms related to DPRs, in particular aggregated DPRs such as mutated C9ORF72, i.e. C9ORF72-DPRs may be desirable. In one embodiment, the additional agent is comprised in the pharmaceutical composition of the present invention. Examples of agents which can be used to treat a subject include, but are not limited to: VMAT2 inhibitors targeting involuntary muscle movements such as anti-inflammatory agents such as diflusinal, corticosteroids, 2-(2,6-dichloranilino) phenylacetic acid (diclofenac), iso-butyl-propanoic-phenolic acid (ibuprofen); diuretics, Epigallocatechin gallate, Melphalan hydrochloride, dexamethasone, Bortezomib, Bortezomib-Melphalan, Bortezomib-dexamethasone, Melphalan-dexamethasone, Bortezomib-Melphalan-dexamethasone; antidepressants, antipsychotic drugs, neuroleptics, antidementiva (e.g. the NMDA-rezeptor antagonist memantine), acetylcholinesterase inhibitors (e.g. Donepezil, HCl, Rivastigmine, Galantamine), glutamat-antagonists and other nootropics blood pressure medication (e.g. Dihydralazin, Methyldopa), cytostatics, glucocorticoides, angiotensin-converting-enzyme (ACE) inhibitors; anti-inflammatory agents or any combination thereof.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

From the foregoing, it is evident that the present invention encompasses any use of an DPR-binding molecule comprising at least one CDR of the above described antibody, in particular for diagnosing and/or treatment of a disease or disorder related to DPRs, in particular aggregated DPR species such as C9ORF72-DPRs such as FTLD. Preferably, said binding molecule is an antibody of the present invention or a biotechnological derivative thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-DPR antibodies in a sample obtained from a subject. In one embodiment thus, the present invention provides an antibody as defined hereinabove and below or a DPR-binding molecule having substantially the same binding specificities of any one thereof, the polynucleotide, the vector or the cell as defined herein or a pharmaceutical or diagnostic composition comprising any one thereof for use in prophylactic treatment, therapeutic treatment and/or monitoring the progression or a response to treatment of a disease or disorder related to DPRs. In a preferred embodiment of the present invention, the disease and/or disorder is associated with aggregated DPRs. In a particular preferred embodiment the disease and/or disorder is associated with C9ORF72-DPRs such as in FTLD and ALS.

In another embodiment the present invention relates to a diagnostic composition comprising any one of the above described DPR-binding molecules, antibodies, antigen-binding fragments, polynucleotides, vectors or cells of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry, and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the DPR-binding molecules, in particular antibodies of the present invention may also be used in a method for the diagnosis of a disease or disorder used in an individual by obtaining a body fluid sample from the tested individual which may be a blood sample, a plasma sample, a serum sample, a lymph sample or any other body fluid sample, such as a saliva or a urine sample and contacting the body fluid sample with an antibody of the instant invention under conditions enabling the formation of antibody-antigen complexes. The level of such complexes is then determined by methods known in the art, a level significantly higher than that formed in a control sample indicating the disease or disorder in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In a further embodiment of the present invention the DPR-binding molecules, in particular antibodies of the present invention may also be used in a method for the diagnosis of a disease or disorder in an individual by obtaining a biopsy from the tested individual.

In this context, the present invention also relates to means specifically designed for this purpose. For example, an antibody-based array may be used, which is for example loaded with antibodies or equivalent antigen-binding molecules of the present invention which specifically recognize DPRs. Design of microarray immunoassays is summarized in Kusnezow et al., Mol. Cell Proteomics 5 (2006), 1681-1696. Accordingly, the present invention also relates to microarrays loaded with DPR-binding molecules identified in accordance with the present invention.

In one embodiment, the present invention relates to a method of diagnosing a disease or disorder related to DPRs, in particular aggregated DPR species such as C9ORF72-DPRs in a subject, the method comprising determining the presence of DPRs and aggregated DPRs, respectively, in a sample from the subject to be diagnosed with at least one antibody of the present invention, a DPR-binding fragment thereof or an DPR-binding molecule having substantially the same binding specificities of any one thereof, wherein the presence of pathologically aggregated DPRs, preferably of C9ORF72-DPRs is indicative for FTLD and/or ALS, and an increase of the level of the pathologically aggregated DPRs, in particular of C9ORF72-DPRs in comparison to the level of the physiological C9ORF72, i.e. which does not show a translation of the repeat region into DPR proteins, is indicative for progression of FTLD and/or ALS in said subject.

The subject to be diagnosed may be asymptomatic or preclinical for the disease. Preferably, the control subject has a disease associated with DPRs, aggregated DPRs, and/preferably C9ORF72-DPRs, e.g. FTLD, ALS and FTLD-ALS and others, as described above, wherein a similarity between the level of DPRs, e.g. aggregated C9ORF72-DPRs and the reference standard indicates that the subject to be diagnosed has a FTLD, ALS and/or FTLD-ALS or is at risk to develop a disease and/or disorder associated with DPR aggregation. Alternatively, or in addition as a second control the control subject does not have a DPR aggregation, wherein a difference between the level of physiological C9ORF72 or another protein which is prone to have DPRs inserted due to mutation in its gene like the mutated C9ORF72 gene and/or aggregated C9ORF72-DPRs and the reference standard indicates that the subject to be diagnosed has a disease and/or disorder associated with DPRs, such as FTLD, ALS and/or FTLD-ALS or is at risk to develop a disease and/or disorder associated with DPRs. Preferably, the subject to be diagnosed and the control subject(s) are age-matched. The sample to be analyzed may be any body fluid suspected to contain pathologically DPR proteins such as aggregated C9ORF72-DPRs, for example a blood, blood plasma, blood serum, urine, peritoneal fluid, saliva or cerebral spinal fluid (CSF).

The level of physiological C9ORF72 or like protein and/or aggregated DPRs such as C9ORF72-DPRs may be assessed by any suitable method known in the art comprising, e.g., analyzing DPRs and/or the protein incorporating DPRs such as C9ORF72 by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of DPRs comprises scintigraphy, positron emission tomography (PET), single photon emission tomography (SPECT), near infrared (NIR) optical imaging or magnetic resonance imaging (MRI).

In one embodiment thus, an antibody of the present invention or a DPR-binding molecule having substantially the same binding specificities of any one thereof, the polynucleotide, the vector or the cell as defined hereinabove or a pharmaceutical or diagnostic composition comprising any one thereof is provided for use in prophylactic treatment, therapeutic treatment, and/or monitoring the progression or a response to treatment of a disease or disorder related to aggregated DPR protein. Thus, the present invention also relates to a method of diagnosing or monitoring the progression of a disease or disorder related to DPR proteins (such as FTLD and ALS) in a subject, the method comprising determining the presence of DPR proteins in a sample from the subject to be diagnosed with at least one antibody of the present invention or a DPR-binding molecule having substantially the same binding specificities of any one thereof, wherein the presence of DPRs such as in mutated C9ORF72 and aggregated C9ORF72-DPR species is indicative for the disease or disorder. In one embodiment said method of diagnosing or monitoring the progression of DPR associated diseases and/or disorders in a subject is provided, the method comprising determining the presence DPRs such as in mutated C9ORF72 and aggregated forms thereof in a sample from the subject to be diagnosed with at least one antibody of the present invention or a DPR-binding molecule having substantially the same binding specificities of any one thereof, wherein the presence of DPRs such as mutated C9ORF72 and/or aggregated C9ORF72-DPRs is indicative for presymptomatic, prodromal or clinical diseases and/or disorders associated with DPRs, an increase of the level of DPR aggregates, in particular C9ORF72-DPRs in comparison to the level of the physiological C9ORF72 without DPRs or in comparison to a reference sample derived from a healthy control subject or a control sample from the same subject is indicative for progression of presymptomatic, prodromal or established diseases and/or disorders associated with DPRs such as FTLD and ALS. It would be appreciated by any person skilled in the art that in one embodiment said method is used as well for the diagnosing or monitoring the progression of any other disease or disorder from the group of disorders related to DPRs and proteins which contain DPRs, respectively, as defined hereinabove.

As indicated above, the antibodies of the present invention and molecules of the same binding specificity as the antibodies may be used not only in vitro but in vivo as well, wherein besides diagnostic, therapeutic applications as well may be pursued. In one embodiment thus, the present invention also relates to a DPR-binding molecule comprising at least one CDR of an antibody of the present invention for the preparation of a composition for in vivo detection of or targeting a therapeutic and/or diagnostic agent to DPR, preferably C9ORF72-DPRs in the human or animal body. Potential therapeutic and/or diagnostic agents may be chosen from the nonexhaustive enumerations of the therapeutic agents useful in treatment of diseases and/or disorders associated with DPRs and potential labels as indicated hereinbefore. In respect of the in vivo imaging, in one preferred embodiment the present invention provides said DPR-binding molecule comprising at least one CDR of an antibody of the present invention, wherein said in vivo imaging comprises scintigraphy, positron emission tomography (PET), single photon emission tomography (SPECT), near infrared (NIR) optical imaging or magnetic resonance imaging (MRI). In a further embodiment the present invention also provides said DPR-binding molecule comprising at least one CDR of an antibody of the present invention, or said molecule for the preparation of a composition for the above specified in vivo imaging methods, for the use in the method of diagnosing or monitoring the progression of a disease or disorder related to DPR protein in a subject, as defined hereinabove.

In this context, the present invention also relates to a kit useful in the diagnosis or monitoring the progression of diseases and/or disorders associated with DPRs and DPR containing proteins, said kit comprising at least one antibody of the present invention or a DPR-binding molecule having substantially the same binding specificities of any one thereof, the polynucleotide, the vector or the cell and/or the peptide as respectively defined hereinbefore, optionally with reagents and/or instructions for use.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Isolation and Identification of Anti-Dipeptide Repeat (DPR) Protein Antibodies Human-derived antibodies targeting dipeptide repeat (DPR) proteins, fragments thereof, C9ORF72-DPRs and/or fragments thereof were identified utilizing the method described in the international application WO 2008/081008 the disclosure content of which is incorporated herein by reference, with modifications. In particular, dipeptide repeat proteins were synthesized and purified by Schafer-N(Copenhagen, Denmark): $GA_{15}$: H-CHHHHHH$(GA)_{15}$-OH; $GP_{15}$: H-C$(GP)_{15}$-OH; $GR_{15}$: H-C$(GR)_{15}$-OH; $(PA)_{15}$: H-C$(PA)_{15}$-OH; $(PR)_{15}$: H-C$(PR)_{15}$-OH. Dipeptide repeat proteins were then conjugated via a bifunctional linker (SMCC) to bovine serum albumin (BSA). Subsequently, direct ELISA was performed using 96-well microplates (Corning) coated with either non-conjugated or BSA-conjugated dipeptide repeat proteins or with BSA (Sigma-Aldrich, Buchs, Switzerland) at a concentration of 5 μg/ml in coating buffer (15 mM $Na_2CO_3$, 35 mM $NaHCO_3$, pH 9.42). Non-specific binding sites were blocked for 1 h at room temperature with PBS/0.1% Tween®-20 containing 2% BSA (Sigma-Aldrich, Buchs, Switzerland). B cell conditioned medium was transferred from memory B cell culture plates to ELISA plates and incubated for one hour at RT, followed by incubation with a donkey anti-human IgG Fcγ-specific antibody conjugated with HRP (Jackson ImmunoResearch Laboratories, Inc., West Grove, USA) and a goat anti-human IgA specific antibody conjugated with HRP (Jackson ImmunoResearch Laboratories, Inc., West Grove, USA). Binding was determined by measurement of HRP activity in a standard colorimetric assay. Only B cell cultures which have shown binding of the antibodies contained in the medium to DPRs but not to BSA were subjected to antibody cloning.

Example 2: Determination of Antibody Sequence

The amino acid sequences of the variable regions of the above identified anti-DPR antibodies were determined on the basis of their mRNA sequences, see FIGS. 1A-1L. In brief, living B cells of selected non-immortalized memory B cell cultures were harvested. Subsequently, the mRNAs from cells producing selected anti-DPR antibodies were extracted and converted in cDNA, and the sequences encoding the antibody's variable regions were amplified by PCR, cloned into plasmid vectors and sequenced. In brief, a combination of primers representing all sequence families of the human immunoglobulin germline repertoire was used for the amplifications of leader peptides, V-segments and J-segments. The first round of amplification was performed using leader peptide-specific primers in 5'-end and constant region-specific primers in 3'-end (Smith et al., Nat Protoc. 4 (2009), 372-384). For heavy chains and kappa light chains, the second round of amplification was performed using V-segment-specific primers at the 5'-end and J-segment-specific primers at the 3'-end. For lambda light chains, the second round amplification was performed using V-segment-specific primers at the 5'-end and a C-region-specific primer at the 3'-end (Marks et al., Mol. Biol. 222 (1991), 581-597; de Haard et al., J. Biol. Chem. 26 (1999), 18218-18230).

Identification of the antibody clone with the desired specificity was performed by re-screening on ELISA upon recombinant expression of complete antibodies. Recombinant expression of complete human IgG1 antibodies was achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins were expressed by inserting the immunoglobulin heavy chain RT-PCR product in frame into a heavy chain expression vector bearing a signal peptide and the constant domains of human or mouse immunoglobulin gamma 1. Kappa light chain immunoglobulins were expressed by inserting the kappa light chain RT-PCR-product in frame into a light chain expression vector providing a signal peptide and the constant domain of human kappa light chain immunoglobulin. Lambda light chain immunoglobulins were expressed by inserting the lambda light chain RT-PCR-product in frame into a lambda light chain expression vector providing a signal peptide and the constant domain of human or mouse lambda light chain immunoglobulin.

Functional recombinant monoclonal antibodies were obtained upon co-transfection into HEK 293 or CHO cells (or any other appropriate recipient cell line of human or mouse origin) of an Ig-heavy-chain expression vector and a kappa or lambda Ig-light-chain expression vector. Recombinant human monoclonal antibody was subsequently purified from the conditioned medium using a standard Protein A column purification. Recombinant human monoclonal antibody can produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)2 and scFv can also be generated from these Ig-variable regions.

The framework and complementarity determining regions were determined by comparison with reference antibody sequences available in databases such as Abysis (bioinf.org.uk/abysis/), and annotated using the Kabat numbering scheme (bioinf.org.uk/abs/).

Example 3: ELISA $EC_{50}$ Analysis to C9orf72 Dipeptide Repeat Proteins

To determine the binding specificity and the half maximal effective concentration ($EC_{50}$) of recombinant human-derived C9orf72 antibodies NI-308.15O7, NI-308.28G1, NI-308 0.45C2, NI-308.18F7, NI-308.24E11, NI-308.5G2, NI-308.46E9, NI-308.6B11, NI-308.46F8, NI-308.4M1, NI-308.12A3 and NI-308.16C10 for C9orf72 dipeptide repeat proteins an ELISA $EC_{50}$ analysis was performed. In brief, dipeptide repeat proteins were synthesized and purified by Schafer-N(Copenhagen, Denmark): $(GA)_{15}$: H-CHHHHHH$(GA)_{15}$-OH; $(GP)_{15}$: H-C$(GP)_{15}$-OH; $(GR)_{15}$: H-C$(GR)_{15}$-OH; $(PA)_{15}$: H-C$(PA)_{15}$-OH; $(PR)_{15}$: H-C$(PR)_{15}$-OH. 96-well microplates (Corning Incorporated, Corning, USA) were coated with dipeptide repeat protein peptides at a concentration of either 5 µg/ml or 20 µg/ml in coating buffer (15 mM $Na_2CO_3$, 35 mM $NaHCO_3$, pH 9.42). Non-specific binding sites were blocked for 1 h at room temperature with PBS/0.1% Tween®-20 containing 2% BSA (Sigma-Aldrich, Buchs, Switzerland). Primary antibodies were diluted to the indicated concentrations and incubated for 1 h at room temperature, followed by incubation with a donkey anti-human IgG Fcγ-specific antibody conjugated with HRP (Jackson ImmunoResearch Laboratories, Inc., West Grove, USA). Binding was determined by measurement of HRP activity in a standard colorimetric assay. $EC_{50}$ values were estimated by non-linear regression using GraphPad Prism software (San Diego, USA). The binding specificity and $EC_{50}$ of human-derived antibodies for C9orf72 dipeptide repeat protein peptides $(GA)_{15}$, $(GP)_{15}$, $(GR)_{15}$, $(PA)_{15}$ and $(PR)_{15}$ were determined by indirect ELISA. Antibodies NI-308.15O7, NI-308.28G1, NI-308.45C2 and NI-308.18F7 exclusively recognized the poly-GA DPR protein with binding affinities in the subnanomolar or low nanomolar range (FIGS. 2A-2E). Antibody NI-308.24E11 specifically bound to poly-PR DPR protein with low nanomolar $EC_{50}$ (FIGS. 2A and 2F) whereas antibody NI-308.16C10 preferentially recognized the DPR protein poly-PR with low nanomolar $EC_{50}$ and also bound with lower affinity to poly-GA DPR protein (FIGS. 2A and 2M). Antibodies NI-308.5G2, NI-308.12A3 and NI-308.46E9 preferentially recognized the DPR protein poly-GP with subnanomolar and low nanomolar $EC_{50}$, respectively and also bound with lower affinities to poly-GA DPR (FIGS. 2A, 2G, 2L and 2H). Antibody NI-308.6B11 showed binding to multiple DPR proteins, targeting poly-GR, poly-GA and poly-PR, with the highest affinity for poly-GR DPR protein (FIGS. 2A and 2I). A similar binding pattern was observed for NI-308.46F8 albeit at a lower affinity (FIGS. 2A and 2J). Antibody NI-308.4M1 preferentially recognized the DPR protein poly-PA with subnanomolar $EC_{50}$ and also bound with lower affinity to poly-GA DPR protein (FIGS. 2A and 2K). In conclusion, high-throughput immune repertoire analyses of healthy elderly human donor populations by RTM™ screening lead to the successful cloning and recombinant production of human monoclonal antibodies targeting C9orf72 hexanucleotide expansion-associated DPRs with high affinity. The recombinant human antibodies are either selective for a single DPR or target multiple species—potentially due to a common shared amino acid in the repeats.

Example 4: Binding Affinity to BSA-Coupled DPR Peptides

To determine the binding specificity and the half maximal effective concentration ($EC_{50}$) of recombinant human-derived C9orf72 antibodies NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI-308.16C10 for C9orf72 dipeptide repeat proteins coupled to bovine serum albumin (BSA) an ELISA $EC_{50}$ analysis was performed. In brief, dipeptide repeat proteins were synthesized and purified by Schafer-N (Copenhagen, Denmark): $(GA)_{15}$: H-CHHHHHH$(GA)_{15}$-OH; $(GP)_{15}$: H-C$(GP)_{15}$-OH; $(GR)_{15}$: H-C$(GR)_{15}$-OH; $(PA)_{15}$: H-C$(PA)_{15}$-OH; $(PR)_{15}$: H-C$(PR)_{15}$-OH. DPR protein peptides were then conjugated via a bifunctional linker (SMCC) to bovine serum albumin (BSA). 96-well microplates (Corning Incorporated, Corning, USA) were coated with BSA-coupled or -uncoupled dipeptide repeat protein peptides at a concentration of either 5 µg/ml or 20 µg/ml in coating buffer (15 mM $Na_2CO_3$, 35 mM $NaHCO_3$, pH 9.42). Non-specific binding sites were blocked for 1 h at room temperature with PBS/0.1% Tween®-20 containing 2% BSA (Sigma-Aldrich, Buchs, Switzerland). Primary antibodies were diluted to the indicated concentrations and incubated 1 h at room temperature, followed by incubation with a donkey anti-human IgG Fcγ-specific antibody conjugated with HRP (Jackson ImmunoResearch Laboratories, Inc., West Grove, USA). Binding was determined by measurement of HRP activity in a standard colorimetric assay. $EC_{50}$ values were estimated by non-linear regression using GraphPad Prism software (San Diego, USA). Comparable binding affinities were determined for BSA-coupled and uncoupled DPRs for antibodies NI-308.18F7, NI-308.15O7, NI-308.28G1, NI-308.5G2, NI-308.46E9, NI-308.4M1 and NI-308.12A3 (FIGS. 3A-3D, 3G, 3H, 3K, 3L). Antibodies NI-308.45C2, NI-308.24E11 and NI-308.16C10 showed a reduced affinity for the respective BSA-coupled DPR peptides (FIGS. 3A, 3E, 3F and 3M) while antibodies NI-308.6B11 and NI-308.46F8 did not bind to BSA-coupled DPRs under these experimental conditions (FIGS. 3A, 3I and 3J). In conclusion, most of the human DPR antibodies can recognize DPR peptides coupled to BSA carrier protein with comparable affinities to hydrophobically coated peptides. The lower binding affinities observed for individual candidates could be due to a poor coupling efficiency of individual DPR peptides to BSA, a different conformation upon BSA coupling or a steric inaccessibility of the epitope following the site-directed chemical coupling to the carrier.

Example 5: Binding Specificity Analysis to Unrelated Amyloidogenic Proteins

To determine the target specificity of NI-308.15O7, NI-308.28G1, NI-308.45C2, NI-308.18F7, NI-308.24E11, NI-308.5G2, NI-308.46E9, NI-308.6B11 and NI-308.46F8 recombinant antibodies indirect ELISA was performed as follows. 96-well microplates (Corning) were coated with different target proteins at a concentration of 1-10 µg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). NI-308.15O7, NI-308.28G1, NI-308.45C2, NI-308.18F7, NI-308.24E11, NI-308.5G2, NI-308.46E9, NI-308.6B11 and NI-308.46F8 antibodies were diluted at 20 nM concentration and incubated 1 h at RT. Binding was determined using donkey anti-human IgG Fcγ-specific antibody conjugated with HRP (Jackson ImmunoResearch Laboratories, Inc., West Grove, USA) followed by measurement of HRP activity in a standard colorimetric assay. Signals for target protein were calculated in fold increase above median. The determination of target specificity of the NI-308.15O7, NI-308.28G1, NI-308.45C2, NI-308.18F7, NI-308.24E11, NI-308.5G2, NI-308.46E9, NI-308.6B11 and NI-308.46F8 human-derived antibodies by indirect ELISA assessed antibody binding to C9orf72 dipeptide repeat proteins and six unrelated amyloid-forming proteins (PHFTau, Tau, TDP-43, TTR, flAPP and HTT). As shown in FIGS. 4A-4I human-derived antibodies NI-308.15O7, NI-308.28G1, NI-308.45C2, NI-308.18F7, NI-308.24E11, NI-308.5G2, NI-308.6B11 and NI-308.46F8 revealed their high binding specificity to DPR peptides with absent or minimal cross-reactivity to unrelated amyloidogenic proteins for most candidates (FIGS. 4A-4F, 4H and 4I). For antibody NI-308.46E9 an elevated off-target signal was detected for several analytes (FIG. 4G).

Example 6: Western Blot Analysis of C9orf72 Dipeptide Repeat Proteins

To determine the binding specificity of recombinant human-derived C9orf72 antibodies NI-308.15O7, NI-308.28G1, NI-308.45C2, NI-308.18F7, NI-308.24E11, NI-308.5G2, NI-308.46E9, NI-308.6B11, NI-308.46F8, NI-308.4M1, NI-308.12A3 and NI-308.16C10 for C9orf72 dipeptide repeat proteins immunoblot analysis was performed. Dipeptide repeat protein peptides were synthesized and purified by Schafer-N(Copenhagen, Denmark): $(GA)_{15}$: H-CHHHHH$(GA)_{15}$-OH; $(GP)_{15}$: H-C$(GP)_{15}$-OH; $(GR)_{15}$: H-C$(GR)_{15}$-OH; $(PA)_{15}$: H-C$(PA)_{15}$-OH; $(PR)_{15}$: H-C$(PR)_{15}$-OH. DPR protein peptides were then conjugated via a bifunctional linker (SMCC) to bovine serum albumin (BSA). In brief, BSA-conjugated dipeptide repeat protein peptides (0.5 μg) were resolved by gradient SDS-PAGE (Novex® Bis-Tris NuPAGE® 4-12%; Life Technologies Europe B.V., Zug, Switzerland) using Novex® NuPAGE® MES SDS Running Buffer complemented with antioxidant (Life Technologies Europe B.V., Zug, Switzerland). Resolved proteins were then electroblotted (Novex® Semi-Dry Blotter, 1 h, 25V) on methanol-activated PVDF membranes (Immobilon®-P Transfer Membrane, Merck & Cie, Schaffhausen, Switzerland) by the use of Novex® NuPAGE® transfer buffer 2x (Life Technologies Europe B.V., Zug, Switzerland). Non-specific binding sites were blocked overnight at 4° C. (or alternatively for 1 h at room temperature) with PBS/0.1% Tween®-20 containing 2% BSA (Sigma-Aldrich, Buchs, Switzerland) (PBST). NI-308 antibodies were diluted at either 10 nM or 100 nM concentration and incubated for 1 h at room temperature (or alternatively overnight at 4° C.). Membranes were washed three times in PBST for 15 min at RT and then incubated with a donkey anti-human IgG Fcγ-specific antibody conjugated with HRP (1:20000 or 1:10000 dilution, Jackson ImmunoResearch Laboratories, Inc., West Grove, USA) for 1 h at room temperature. Antibody binding was determined by membrane development using ECL and ImageQuant 350 detection (GE Healthcare, Otelfingen, Switzerland).

Figure 5A:
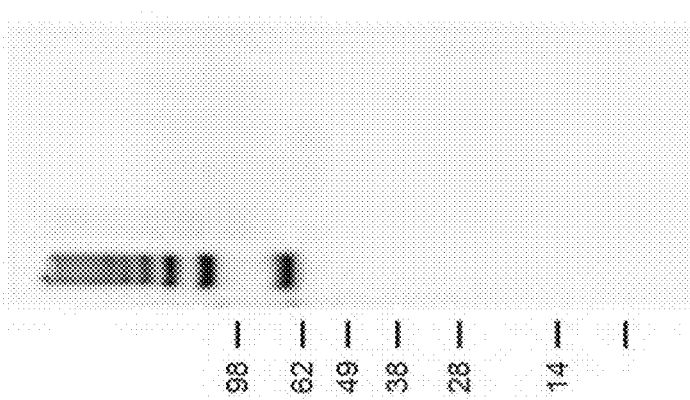
Figure 5B:
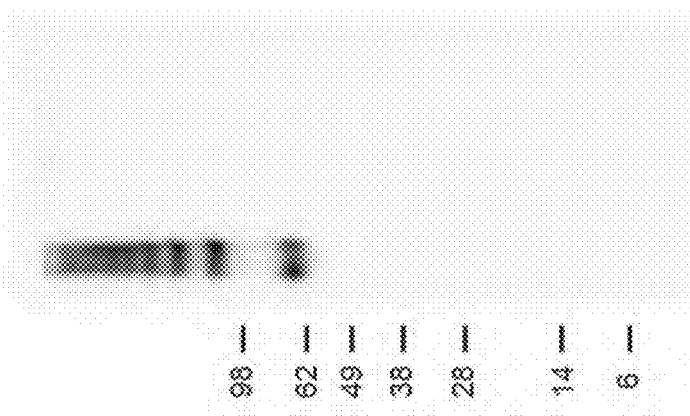
Figure 5C:
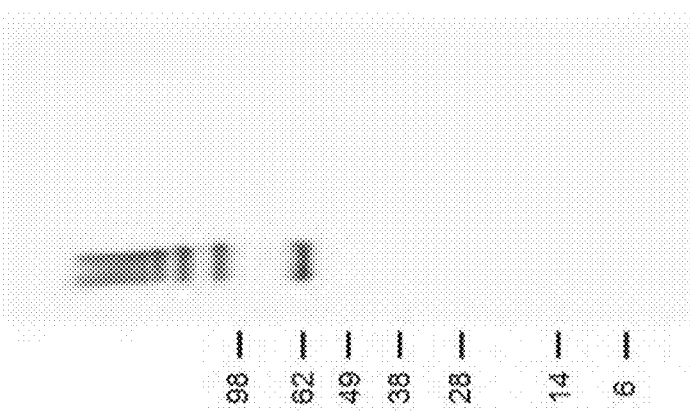

The binding specificity of the human-derived antibodies to BSA-coupled C9orf72 dipeptide repeat proteins $(GA)_{15}$, $(GP)_{15}$, $(GR)_{15}$, $(PA)_{15}$ and $(PR)_{15}$ was determined by Western blot analysis. Antibodies NI-308.15O7, NI-308.18F7, NI-308.28G1 and NI-308.45C2 exclusively recognized the DPR protein poly-GA (FIGS. 5A-5D). Antibodies NI-308.24E11 and NI.308-16C10 specifically bound to the single DPR protein poly-PR (FIGS. 5E and 5J), with antibody NI-308.16C10 additionally recognizing poly-GA DPR (FIG. 5J). Antibodies NI-308.5G2, NI.308-12A3 and NI-308.46E9 specifically targeted poly-GP (FIGS. 5F, 5G and 5I), with antibody NI-308.5G2 additionally recognizing poly-GA DPR (FIG. 5F). Antibody NI-308.4M1 exclusively recognized the DPR protein poly-PA (FIG. 5H). For antibodies NI-308.6B11 and NI-308.46F8 no binding was detected to BSA-coupled DPRs by Western blot under the selected experimental conditions (data not shown). In conclusion, most human-derived C9orf72 DPR antibodies can recognize BSA-coupled DPR peptides following SDS PAGE and Western blotting. The observed biding patterns are consistent with the results obtained by ELISA analyses.

Example 7: In Solution Binding Analysis to C9orf72 DPRs by Immunoprecipitation

Figure 6A:
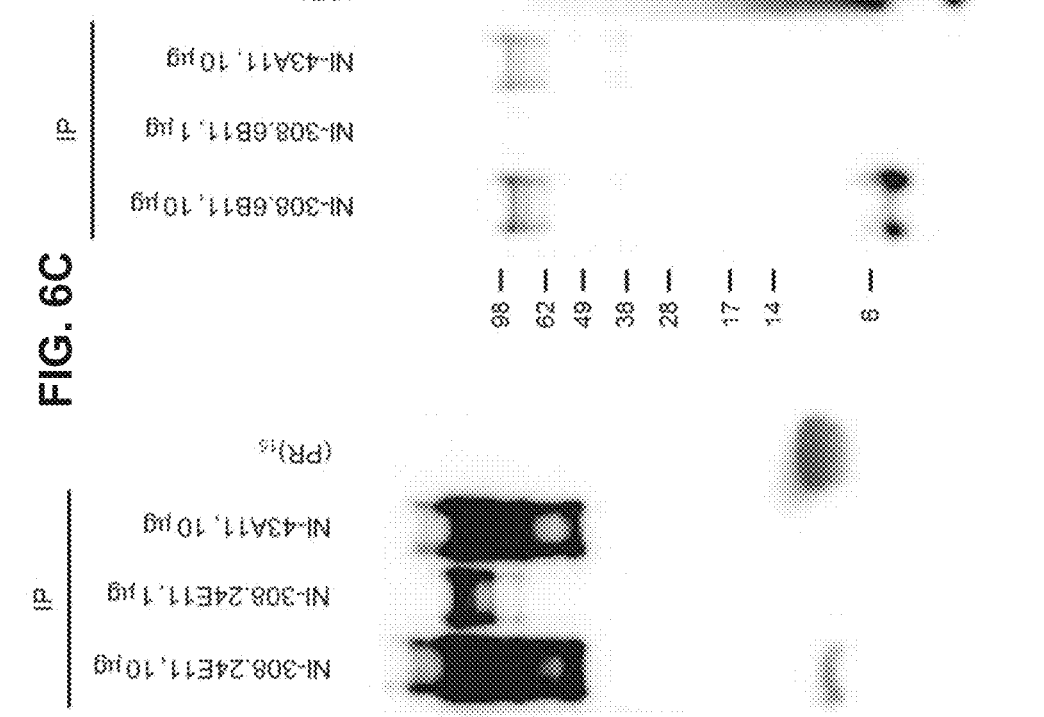
FIGS. 6A-6C: In solution binding to C9orf72 dipeptide repeat proteins. Determination of human-derived C9orf72 DPR antibody in solution binding to peptides $(GA)_{15}$, $(PR)_{15}$ and $(GR)_{15}$ by immunoprecipitation analysis. The C9orf72 poly-GA DPR protein was captured in solution by antibodies NI-308.15O7, NI-308.18F7, NI-308.45C2 and NI-308.28G1 (FIG. 6A). Poly-PR DPR protein was precipitated by antibody NI-308.24E11 (FIG. 6B) whereas antibody NI-308.6B11 captured poly-GR DPR protein. Isotype control antibody NI-43A11 did not precipitate any of the C9orf72 DPR proteins (FIGS. 6A-6C).
Figure 6B:
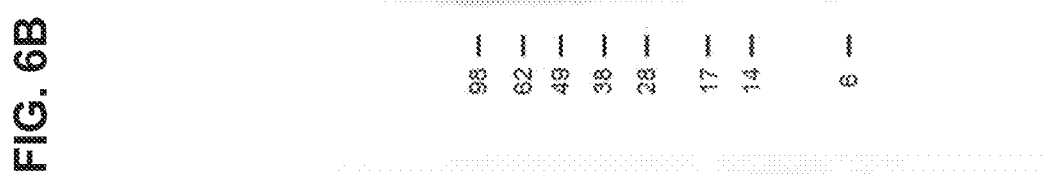
Figure 6C:
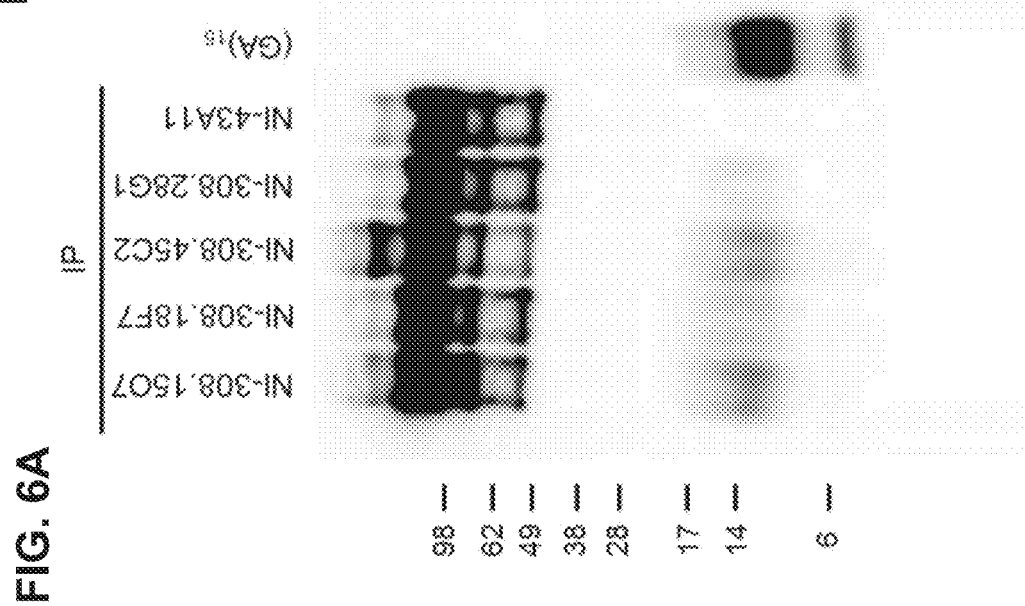

To assess in solution binding of recombinant human-derived C9orf72 DPR antibodies NI-308.15O7, NI-308.28G1, NI-308.45C2, NI-308.18F7, NI-308.24E11 and NI-308.6B11 by immunoprecipitation. In brief, dipeptide repeat proteins were synthesized and purified by Schafer-N(Copenhagen, Denmark): $(GA)_{15}$: H-CHHHHH $(GA)_{15}$-OH; $(GP)_{15}$: H-C$(GP)_{15}$-OH; $(GR)_{15}$: H-C$(GR)_{15}$-OH; $(PA)_{15}$: H-C$(PA)_{15}$-OH; $(PR)_{15}$: H-C$(PR)_{15}$-OH. Five micrograms of BSA-uncoupled dipeptide repeat protein peptides were diluted in 500 μl PBS, pH 7.4 (Gibco®, Life Technologies Europe B.V., Zug, Switzerland) to a final concentration of 10 μg/ml. DPR protein peptides samples were preadsorbed with 25 μl Dynabeads® Protein A (Novex®; Life Technologies Europe B.V., Zug, Switzerland) by incubation at 4° C. for 30 min on a rotating platform. 1 or 10 μg of selected antibodies were added to the preadsorbed samples and incubated overnight at 4° C. on a rotating platform. Immune-complexes were captured by addition of 25 μl Protein A-Dynabeads and incubation at 4° C. for 2 hours on a rotating platform. The beads were washed according to manufacturer's instructions, suspended in sample buffer and heated at 95° C. for 3 minutes. For Western Blot analysis, Immune-complexes and uncoupled DPR protein peptides (500 ng) were resolved by SDS-PAGE (Novex® Bis-Tris NuPAGE® 12%; Life Technologies Europe B.V., Zug, Switzerland) using Novex® NuPAGE® MES SDS Running Buffer (Life Technologies Europe B.V., Zug, Switzerland) under non-reducing conditions. Resolved proteins were electroblotted (Novex® Semi-Dry Blotter, 1 h, 25V) on methanol-activated PVDF membranes (Immobilon®-P Transfer Membrane, Merck & Cie, Schaffhausen, Switzerland) in Novex® NuPAGE® transfer buffer (Life Technologies Europe B.V., Zug, Switzerland). Non-specific binding sites were blocked overnight at 4° C. with PBS/0.1% Tween®-20 containing 2% BSA (Sigma-Aldrich, Buchs, Switzerland) (PBST). DPR proteins were revealed by incubation for 1 h at room temperature with the following detection antibodies: $(GA)_{15}$: NI-308.28G1, 10 nM; $(PR)_{15}$: NI-308.24E11, 100 nM; $(GR)_{15}$: anti-C9ORF72/C9RANT clone 5A5, 1:5000 dilution (MABN778, Merck & Cie, Schaffhausen, Switzerland). Membranes were washed three times in PBST for 15 min at RT and incubated with either a donkey anti-human IgG Fcγ-specific antibody conjugated with HRP (1:10000 dilution, Jackson ImmunoResearch Laboratories, Inc., West Grove, USA) or a mouse anti-rat kappa antibody conjugated with HRP (1:10000 dilution, SouthernBiotech, Birmingham, USA) for 1 h at room temperature. Membranes were developed using ECL and ImageQuant 350 detection (GE Healthcare, Otelfingen, Switzerland). Antibodies NI-308.15O7, NI-308.18F7, NI-308.45C2 and NI-308.28G1 captured in solution poly-GA DPR protein peptides (FIG. 6A) whereas antibodies NI-308.24E11 and NI-308.6B11 precipitated poly-PR and poly-GR, respectively (FIGS. 6B and 6C). The NI-43A11 isotype control antibody did precipitate any of the tested DPR protein peptides (FIGS. 6A-6C). In conclusion, the human-derived C9orf72 DPR antibodies can bind and precipitate DPR protein peptides in solution.

Example 8: Characterization of Repeat-Length Dependent Binding by Indirect ELISA To determine the binding affinity of recombinant human-derived antibodies NI-308.15O7, NI-308.28G1, NI-308.45C2, NI-308.18F7, NI-308.24E11, NI-308.5G2, NI-308.46E9, NI-308.6B11, and NI-302.4M1 to C9orf72 DRPs of different repeat sizes an ELISA $EC_{50}$ analysis was performed. In brief, dipeptide repeat proteins were synthesized and purified by Schafer-N (Copenhagen, Denmark): $GA_{20}$: H-(GA)$_{20}$HHHHHH-NH$_2$; $GA_{10}$: H-(GA)$_{10}$HHHHHH-NH$_2$; $GA_6$: H-(GA)$_6$HHHHHH-NH$_2$; $GA_5$: H-(GA)$_5$HHHHHH-NH$_2$; $GA_4$: H-(GA)$_4$HHHHHH-NH$_2$; $GA_3$: H-(GA)$_3$HHHHHH-NH$_2$; $GA_2$: H-(GA)$_2$HHHHHH-NH$_2$; $GP_{20}$: H-(GP)$_{20}$HHHHHH-NH$_2$; $GP_{10}$: H-(GP)$_{10}$HHHHHH-NH$_2$; $GP_6$: H-(GP)$_6$HHHHHH-NH$_2$; $GP_5$: H-(GP)$_5$HHHHHH-NH$_2$; $GP_4$: H-(GP)$_4$HHHHHH-NH$_2$; $GP_3$: H-(GP)$_3$HHHHHH-NH$_2$; $GP_2$: H-(GP)$_2$HHHHHH-NH$_2$. $GR_{20}$: H-(GR)$_{20}$HHHHHH-NH$_2$; GR1D: H-(GR)$_{10}$HHHHHH-NH$_2$; $GR_6$: H-(GR)$_6$HHHHHH-NH$_2$; $GR_5$: H-(GR)$_5$HHHHHH-NH$_2$; $GR_4$: H-(GR)$_4$HHHHHH-NH$_2$; $GR_3$: H-(GR)$_3$HHHHHH-NH$_2$; $GR_2$: H-(GR)$_2$HHHHHH-NH$_2$; $PA_{20}$: H-(PA)$_{20}$HHHHHH-NH$_2$; $PA_{10}$: H-(PA)$_{10}$HHHHHH-NH$_2$; $PA_6$: H-(PA)$_6$HHHHHH-NH$_2$; $PA_5$: H-(PA)$_5$HHHHHH-NH$_2$; $PA_4$: H-(PA)$_4$HHHHHH-NH$_2$; $PA_3$: H-(PA)$_3$HHHHHH-NH$_2$; $PA_2$: H-(PA)$_2$HHHHHH-NH$_2$; $PR_{20}$: H-(PR)$_{20}$HHHHHH-NH$_2$; $PR_{10}$: H-(PR)$_{10}$HHHHHH-NH$_2$; $PR_6$: H-(PR)$_6$HHHHHH-NH$_2$; $PR_5$: H-(PR)$_5$HHHHHH-NH$_2$; $PR_4$: H-(PR)$_4$HHHHHH-NH$_2$; $PR_3$: H-(PR)$_3$HHHHHH-NH$_2$; $PR_2$: H-(PR)$_2$HHHHHH-NH$_2$. 96-well microplates (Corning Incorporated, Corning, USA) were coated with dipeptide repeat protein peptides at a concentration of 50 μg/ml in coating buffer (15 mM $Na_2CO_3$, 35 mM $NaHCO_3$, pH 9.42). Non-specific binding sites were blocked for 1 h at room temperature with PBS/0.1% Tween®-20 containing 2% BSA (Sigma-Aldrich, Buchs, Switzerland). Primary antibodies were diluted to the indicated concentrations and incubated 1 h at room temperature, followed by incubation with a donkey anti-human IgG Fcγ-specific antibody conjugated with HRP (Jackson ImmunoResearch Laboratories, Inc., West Grove, USA). Binding was determined by measurement of HRP activity in a standard colorimetric assay. $EC_{50}$ values were estimated by non-linear regression using GraphPad Prism software (San Diego, USA).

Figures 7A, 7B, 7C, 7D, 7E:
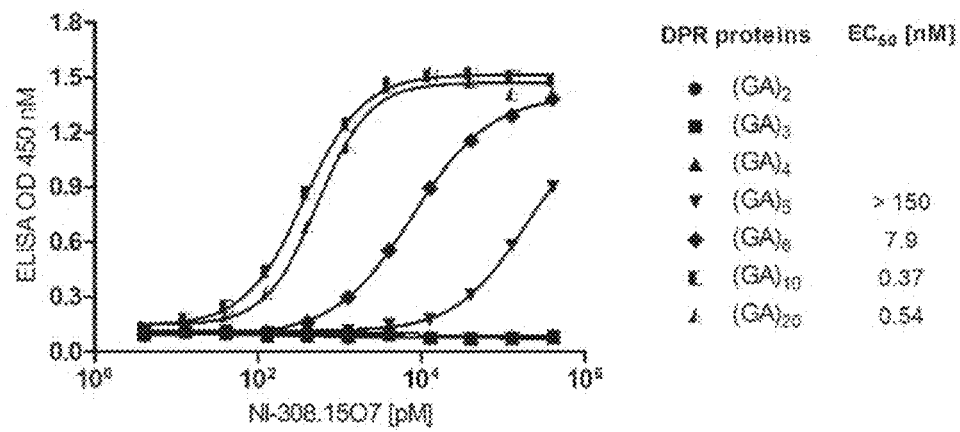
FIGS. 7A-7P: C9orf72 DPR proteins repeat-length dependent binding of selected NI-308 antibodies.
(FIG. 7B) Summary of C9orf72 poly-GP repeat-length dependent binding of selected NI-308 antibodies.
(FIG. 7C) Summary of C9orf72 poly-GR repeat-length dependent binding of selected NI-308 antibodies.
(FIG. 7D) Summary of C9orf72 poly-PR repeat-length dependent binding of selected NI-308 antibodies.
(FIG. 7E) Summary of C9orf72 poly-PA repeat-length dependent binding of selected NI-308 antibodies. Determination of dipeptide repeat-length dependent binding specificity and the half maximal effective concentration ($EC_{50}$) of human-derived NI-308 antibodies for C9orf72 dipeptide repeat protein peptides by indirect ELISA. Antibody NI-308.15O7 (FIG. 7F) bound to DPR protein peptides $(GA)_5$, $(GA)_6$, $(GA)_{10}$ and $(GA)_{20}$ with binding affinity at $EC_{50}$ of >150 nM, 7.9 nM, 0.0.37 nM and 0.54 nM, respectively. Antibody NI-308.18F7 (FIG. 7G) recognized the DPR protein peptides $(GA)_6$, $(GA)_{10}$ and $(GA)_{20}$ with binding affinity at $EC_{50}$ of >200 nM, 0.78 nM and 0.83 nM, respectively. Antibody NI-308.28G1 (FIG. 7H) targeted the DPR protein peptides $(GA)_5$, $(GA)_6$, $(GA)_{10}$ and $(GA)_{20}$ with binding affinity at $EC_{50}$ of >200 nM, 6.3 nM, 0.9 nM and 1.1 nM, respectively. Antibody NI-308.45C2 (FIG. 7I) bound to DPR protein peptides $(GA)_6$, $(GA)_{10}$ and $(GA)_{20}$ with binding affinity at $EC_{50}$ of >200 nM, 7.6 nM and 9.6 nM, respectively. Antibody NI-308.5G2 (FIGS. 7J and 7K) recognized the DPR protein peptides $(GP)_5$, $(GP)_6$, $(GP)_{10}$ and $(GP)_{20}$ with binding affinity at $EC_{50}$ of >200 nM, 26.8 nM, 0.94 nM and 0.47 nM respectively and to DPR protein peptides $(GA)_6$, $(GA)_{10}$ and $(GA)_{20}$ with binding affinity at $EC_{50}$ of >200 nM, 5.7 nM and 18.2 nM, respectively. Antibody NI-308.6B11 (FIGS. 7L and 7M) bound to the DPR protein peptides $(GR)_3$, $(GR)_4$, $(GR)_5$, $(GR)_6$, $(GR)_{10}$ and $(GR)_{20}$ with binding affinity at $EC_{50}$ of 14.3 nM, 13.2 nM, 0.47 nM, 0.33 nM, 1.3 nM and 0.25 nM, respectively and to DPR protein peptides $(GA)_6$, $(GA)_{10}$ and $(GA)_{20}$ with binding affinity at $EC_{50}$ of >200 nM, 27.7 nM and 33.6 nM, respectively. Antibody NI-308.46E9 (FIG. 7N) targeted the DPR protein peptides $(GP)_{10}$ and $(GP)_{20}$ with binding affinity at $EC_{50}$ of 63.3 nM and 15.5 nM, respectively. Antibody NI-308.24E11 (FIG. 7O) recognized the DPR protein peptides $(PR)_6$, $(PR)_{10}$ and $(PR)_{20}$ with binding affinity at $EC_{50}$ of >200 nM, 31.7 nM and 11.3 nM, respectively. Antibody NI-308.4M1 (FIG. 7P) bound to the DPR protein peptides $(PA)_5$, $(PA)_6$, $(PA)_{10}$ and $(PA)_{20}$ with binding affinity at $EC_{50}$ of 26.9 nM, 4.3 nM, 0.06 nM and 0.06 nM, respectively.
Figure 7G:
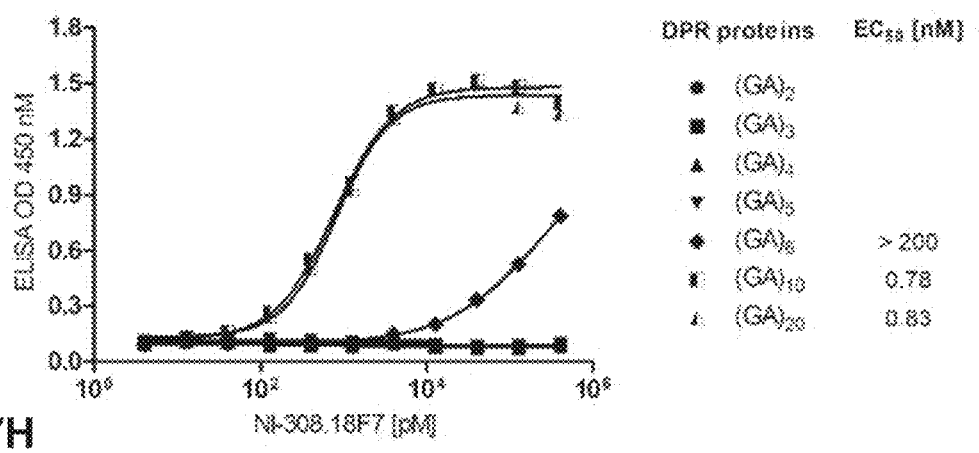
Figure 7H:
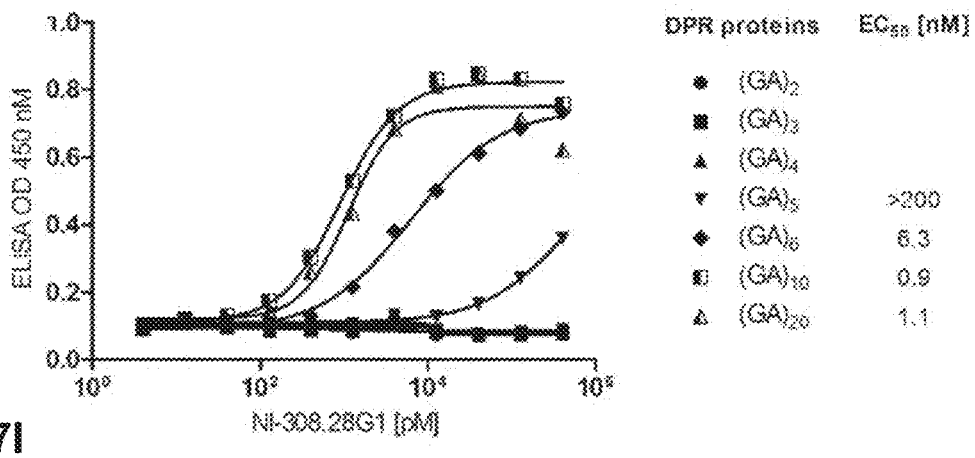
Figure 7I:
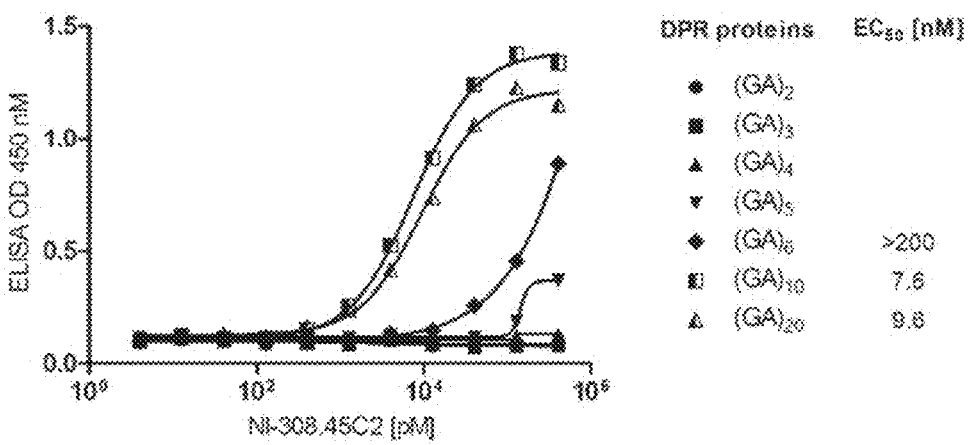
Figure 7J:
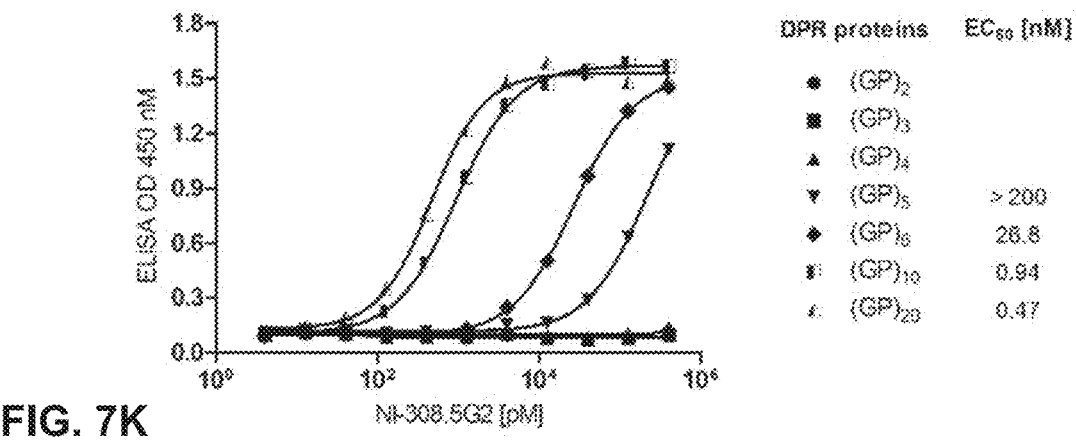
Figure 7K:
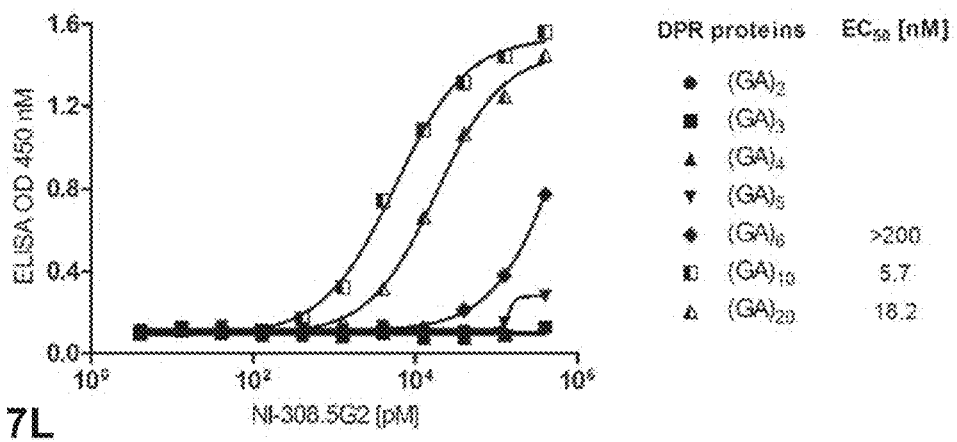
Figure 7L:
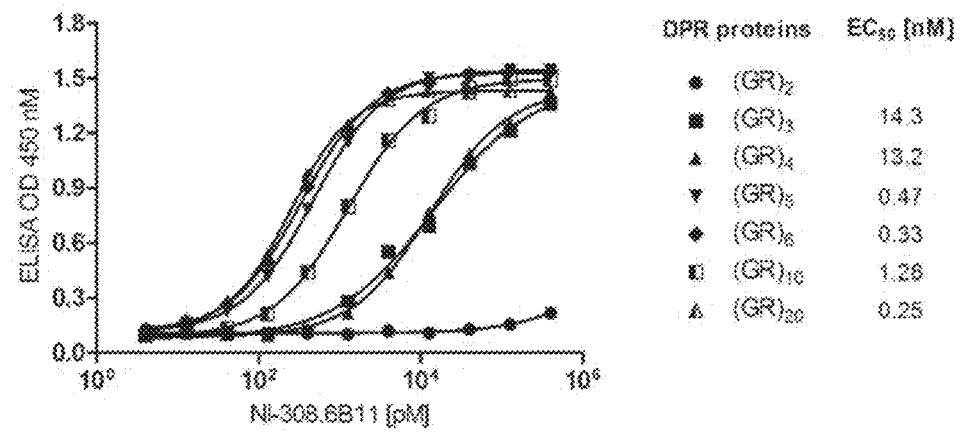
Figure 7M:
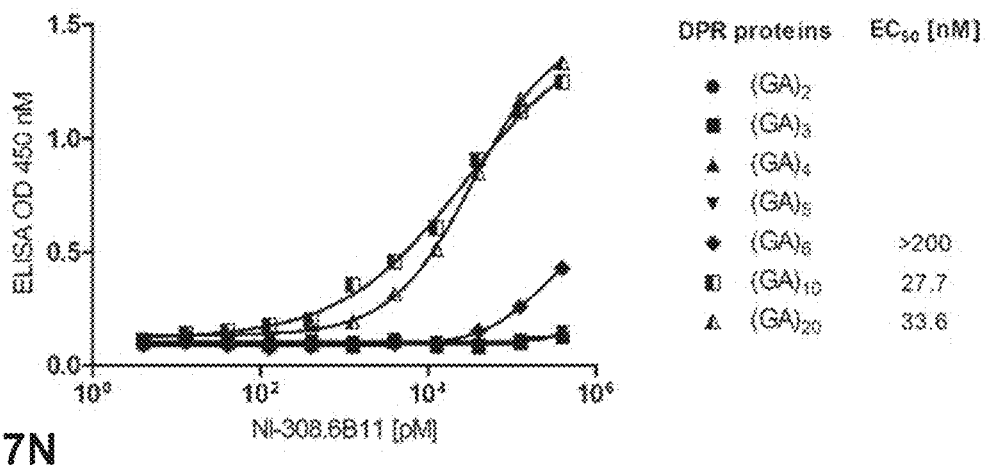
Figure 7N:
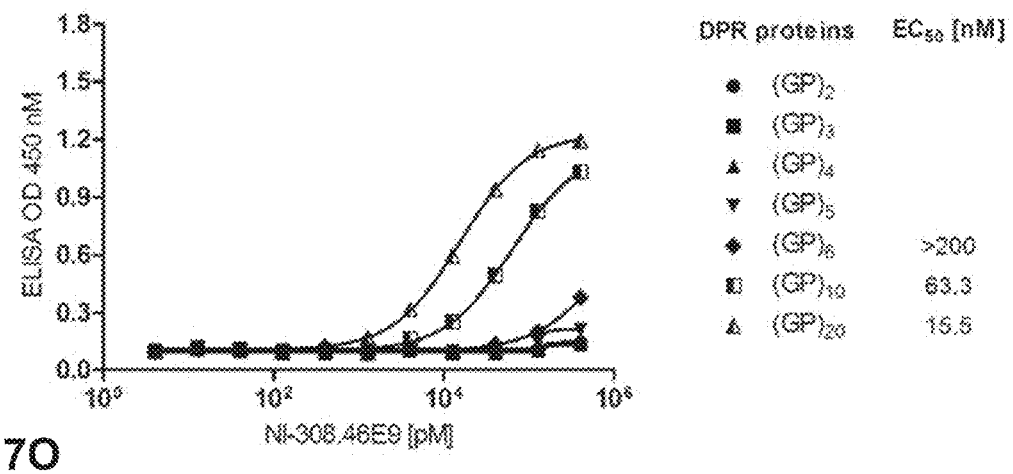
Figure 7O:
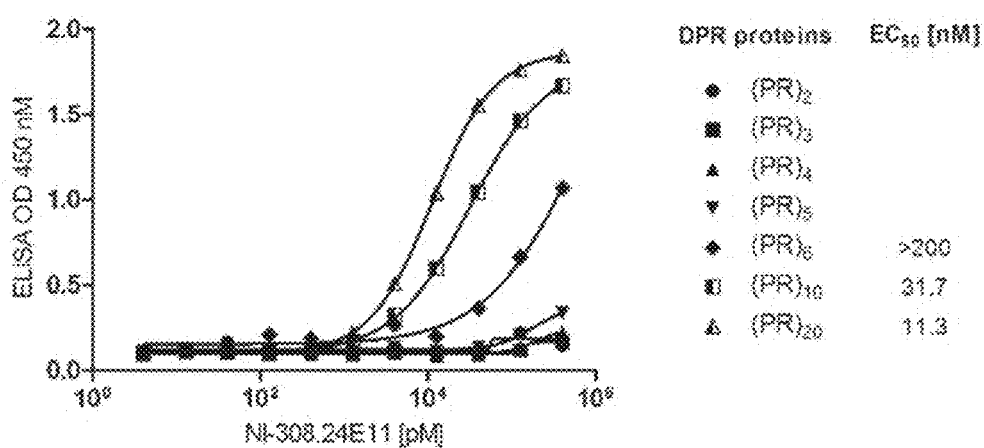

The binding affinity of selected NI-308 antibodies for C9orf72 DPR proteins with different repeat lengths was determined following hydrophobic peptide coating by indirect ELISA. Antibodies NI-308.15O7 and NI-308.28G1 required a minimum of 5 GA dipeptide repeats whereas antibodies NI-308.18F7 and NI-308.45C2 required at least 6 GA repeats for a first detectable low affinity binding at >100 nM $EC_{50}$ (FIGS. 7A, 7F-7I). High affinity binding was detected for poly-GA DPRs harboring 10 or 20 (GA)-repeats, reflected in an $EC_{50}$ in the subnanomolar or low nanomolar range (FIGS. 7A, 7C-7I). Antibodies NI-308.5G2 and NI-308.46E9 required a minimum of 5 and 10 GP-repeats, respectively (FIGS. 7B, 7J and 7N). High affinity binding for the latter 2 antibodies was detected only at expanded repeat lengths for poly-GP DPR protein peptides harboring 10 and 20 repeats. Furthermore, antibody NI-308.5G2 required a minimum of 6 GA dipeptide repeats for a first detectable low affinity binding at >100 nM $EC_{50}$ (FIGS. 7A and 7K). High affinity binding was detected for poly-GA DPRs harboring 10 or 20 (GA)-repeats, reflected in an $EC_{50}$ in the low nanomolar range (FIGS. 7A and 7K). Antibody NI-308.6B11 required a minimum of 3 GR-repeats (FIGS. 7C and 7L). High affinity binding for this antibody was detected for poly-GR DPR protein peptides harboring at least 5 GR dipeptide repeats (FIGS. 7C and 7L). In addition, antibody NI-308.6B11 required a minimum of 6 GA dipeptide repeats for a first detectable low affinity binding at >100 nM $EC_{50}$ (FIGS. 7A and 7M). High affinity binding was detected for poly-GA DPRs harboring 10 or 20 (GA)-repeats, reflected in an $EC_{50}$ in the low nanomolar range (FIGS. 7A and 7M). Antibody NI-308.24E11 required a minimum of 6 PR dipeptide repeats (FIGS. 7D and 7O) whereas antibody NI-308.4M1 required at least 5 PA repeats (FIGS. 7E and 7P) for a first detectable low affinity binding at >100 nM $EC_{50}$ or at two-digit nanomolar binding affinity, respectively. High affinity binding for the latter 2 antibodies was detected only for expanded repeat lengths for poly-PR and poly-PA DPRs harboring 10 or 20 repeats, respectively, reflected in an $EC_{50}$ in the low nanomolar or subnanomolar range (FIGS. 7D, 7E, 7O and 7P). In conclusion, human-derived C9orf72 DPR antibodies display a repeat-length dependent binding to DPRs with absent binding to short repeat sizes and preferential high affinity binding to extended dipeptide repeats.

Figure 8D:
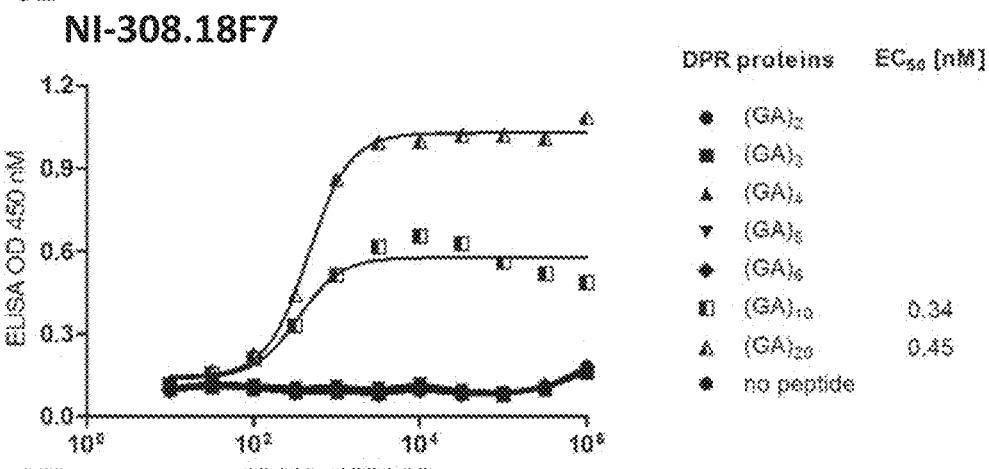
Figure 8E:
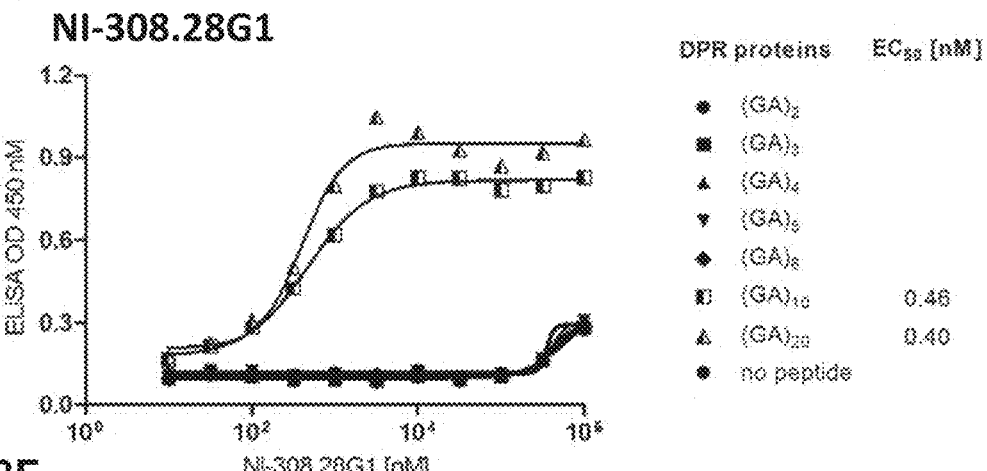
Figure 8F:
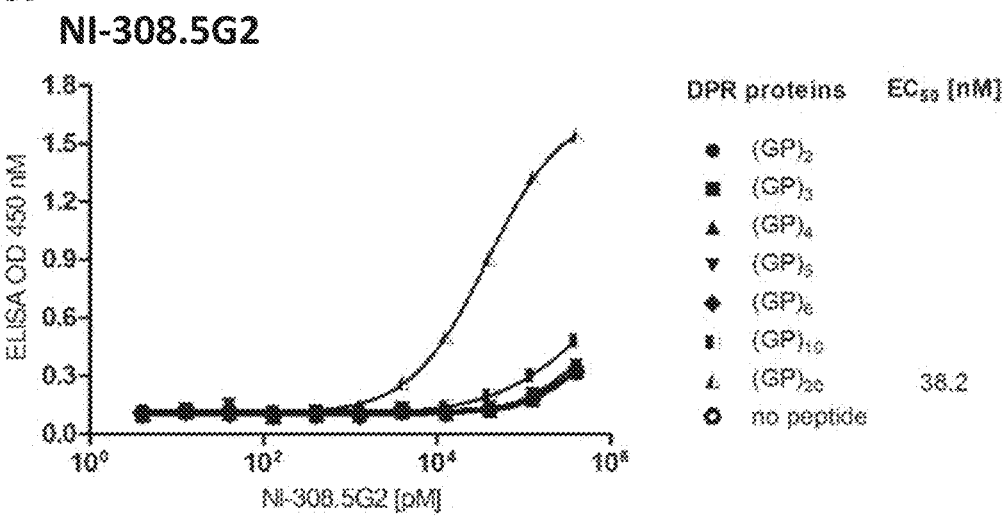
Figure 11A:
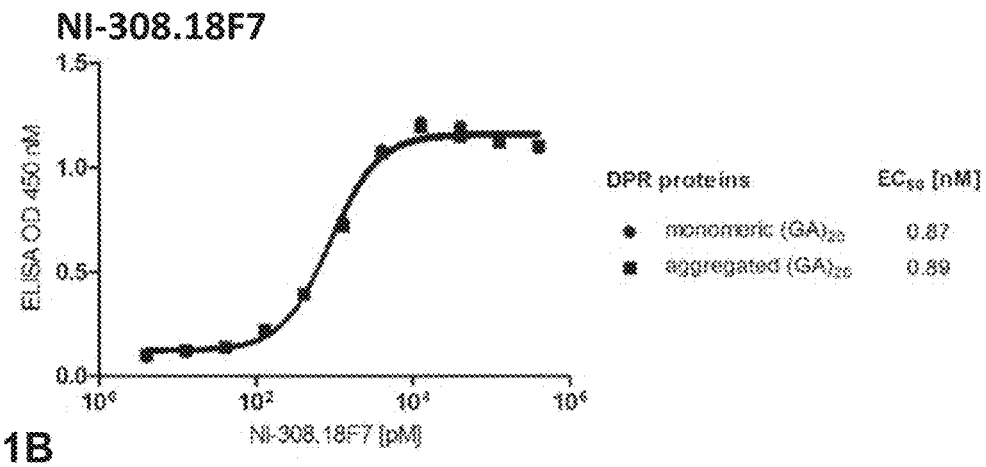
FIGS. 11A and 11B: NI-308.18F7 and NI-308.15O7 binding specificity and $EC_{50}$ determination for monomeric and aggregated C9orf72 $(GA)_{20}$ DPR protein peptide preparations by indirect ELISA binding assay. NI-308.18F7 and NI-308.15O7 antibodies binding specificity and $EC_{50}$ determination for monomeric (●) and aggregated (■) C9orf72 $(GA)_{20}$ DPR protein peptide preparations using indirect ELISA. Antibody NI-308.18F7 (FIG. 11A) recognized monomeric and aggregated $(GA)_{20}$ preparations with binding affinity at $EC_{50}$ of 0.87 nM and 0.89 nM, respectively. Antibody NI-308.15O7 (FIG. 11B) bound to monomeric and aggregated $(GA)_{20}$ preparations with binding affinity at $EC_{50}$ of 0.53 nM and 0.78 nM, respectively.
Figure 11B:
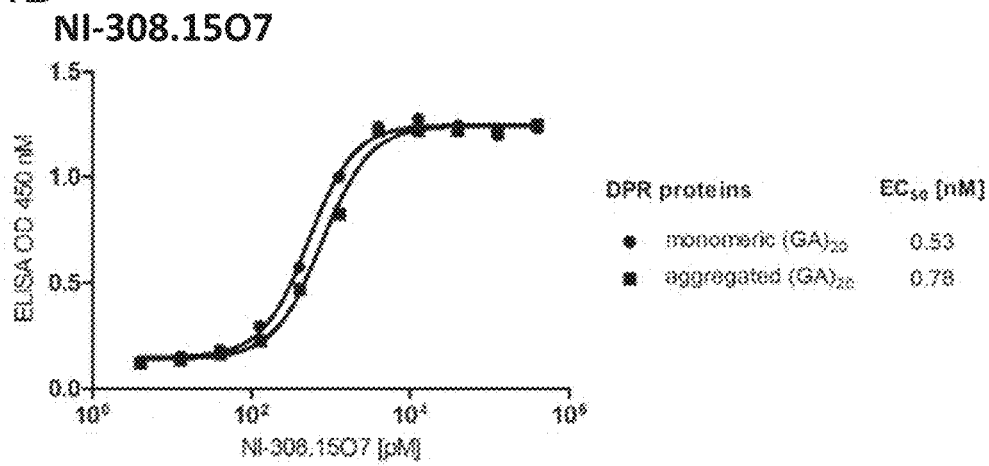
Figure 12A:
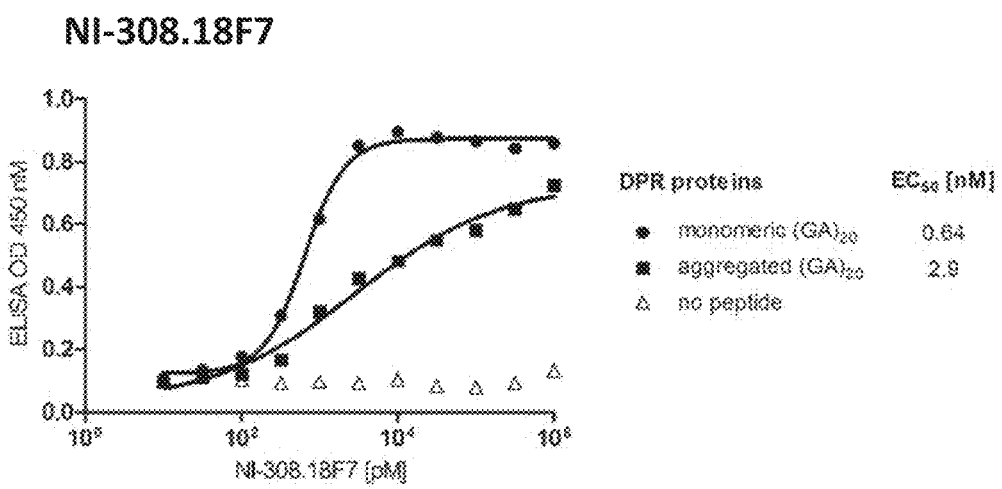
FIGS. 12A and 12B: NI-308.18F7 and NI-308.15O7 binding specificity and $EC_{50}$ determination for monomeric and aggregated C9orf72 $(GA)_{20}$ DPR protein peptide preparations by sandwich ELISA binding assay NI-308.18F7 and NI-308.15O7 antibodies binding specificity and $EC_{50}$ determination for monomeric (●) and aggregated (■) C9orf72 $(GA)_{20}$ DPR protein peptide preparations in solution using sandwich ELISA. Antibody NI-308.18F7 (FIG. 12A) recognized monomeric and aggregated $(GA)_{20}$ preparations with binding affinity at $EC_{50}$ of 0.64 nM and 2.9 nM, respectively. Antibody NI-308.15O7 (FIG. 12B) bound to monomeric and aggregated $(GA)_{20}$ preparations with an $EC_{50}$ of 6.3 nM and 8.1 nM, respectively. No antibody binding was detected in absence of his-tagged $(GA)_{20}$ preparations (A). Binding specificities and affinities are summarized in the Table of FIG. 9.
Figure 12B:
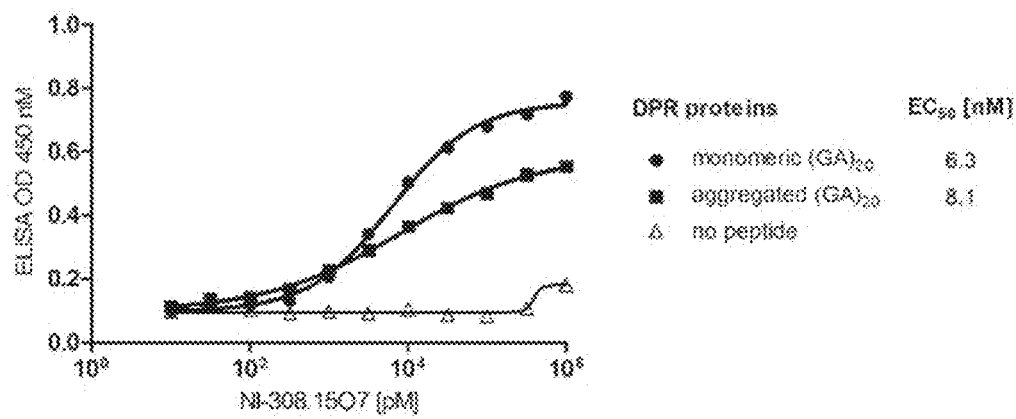

Example 9: Characterization of Repeat-Length Dependent Binding by Sandwich ELISA To determine the binding affinity of recombinant human-derived antibodies NI-308.15O7, NI-308.28G1, NI-308.18F7 and NI-308.5G2 to C9orf72 dipeptide repeat proteins of different repeat sizes. In brief, His-tagged dipeptide repeat protein peptides were synthesized and purified by Schafer-N(Copenhagen, Denmark): $GA_{20}$: H-(GA)$_{20}$HHHHHH-NH$_2$; $GA_{10}$: H-(GA)$_{10}$HHHHHH-NH$_2$; $GA_6$: H-(GA)$_6$HHHHHH-NH$_2$; $GA_5$: H-(GA)$_5$HHHHHH-NH$_2$; $GA_4$: H-(GA)$_4$HHHHHH-NH$_2$; $GA_3$: H-(GA)$_3$HHHHHH-NH$_2$; $GA_2$: H-(GA)$_2$HHHHHH-NH$_2$; $GP_{20}$: H-(GP)$_{20}$HHHHHH-NH$_2$; $GP_{10}$: H-(GP)$_{10}$HHHHHH-NH$_2$; $GP_6$: H-(GP)$_6$HHHHHH-NH$_2$; $GP_5$: H-(GP)$_5$HHHHHH-NH$_2$; $GP_4$: H-(GP)$_4$HHHHHH-NH$_2$; $GP_3$: H-(GP)$_3$HHHHHH-NH$_2$; $GP_2$: H-(GP)$_2$HHHHHH-NH$_2$. 96-well microplates (Corning Incorporated, Corning, USA) were coated with monoclonal mouse anti-His tag antibody (Takara Bio Europe/Clontech, Saint-Germain-en-Laye, France) at a concentration of 10 μg/ml in coating buffer (15 mM $Na_2CO_3$, 35 mM $NaHCO_3$, pH 9.42) overnight at 4° C. Non-specific binding sites were blocked for 1 h at room temperature with PBS/0.1% Tween®-20 containing 2% BSA (Sigma-Aldrich, Buchs, Switzerland). After a washing step, His-tagged C9orf72 DPR protein peptides at equal concentration of either 1 μM or 5 μM in PBS (pH 7.4) were added for target-trapping by the anti-His tag antibody for 1 h at room temperature. After a further washing step, NI-308 antibodies were diluted in PBS/0.1% Tween®-20 containing 2% BSA (Sigma-Aldrich, Buchs, Switzerland) to the indicated concentrations and incubated 1 h at room temperature. Antibody binding to DPR protein peptides was detected by a donkey anti-human IgG Fcγ-specific antibody conjugated with HRP at 1:5000 dilution (Jackson ImmunoResearch Laboratories, Inc., West Grove, USA) for 1h at RT. Binding was determined by measurement of HRP activity in a standard colorimetric assay. $EC_{50}$ values were estimated by non-linear regression using GraphPad Prism software (San Diego, USA). The binding affinity of selected NI-308 antibodies for C9orf72 DPR proteins with different repeat lengths was determined following His-tag capture of DPR proteins by sandwich ELISA. Antibodies NI-308.15O7, NI-308.18F7, NI-308.28G1 required a minimum of 10 GArepeats for in solution binding to the poly-GA DPR protein peptides (FIGS. 8A, 8C-8E). Binding affinities for antibodies NI-308.18F7 and NI-308.28G1 were in the subnanomolar range and equivalent for both $(GA)_{10}$ and $(GA)_{20}$ DPR protein peptides (FIGS. 8A, 8D and 8E). Antibody NI-308.15O7 showed high affinity binding only for the expanded $(GA)_{20}$ DPR protein peptide (FIGS. 8A and 8C). Antibody NI-308.5G2 showed a similar binding dependence on expanded poly-GP DPR repeat lengths with significant binding starting only at 20 GP-repeats (FIGS. 8B and 8F). In conclusion, human-derived C9orf72 DPR antibodies display a pronounced repeat-length dependent binding to DPRs with absent binding to short repeats and preferential high affinity binding to extended dipeptide repeats. The observed selectivity for expanded DPRs was even more pronounced following antigen capture compared to hydrophobically coated peptides (Example 9).

Example 10: Binding Analysis to Monomeric and Aggregated C9orf72 DPRs

To determine the binding specificity and the half maximal effective concentration ($EC_{50}$) of recombinant human-derived NI-308.18F7 and NI-308.15O7 antibodies to monomeric and aggregated GA C9orf72 dipeptide repeat proteins.
Methods
C9orf72 Dipeptide Repeat Protein Peptide Dipeptide repeat protein $(GA)_{20}$ (H-$(GA)_{20}$HHHHHH-$NH_2$) was synthesized and purified by Schafer-N(Copenhagen, Denmark). Lyophilized peptide was dissolved at 10 mg/ml concentration in DMSO (Sigma-Aldrich, Buchs, Switzerland).
Generation of Monomeric and Fibrillary Aggregated Preparations of $(GA)_{20}$ DPR Protein Peptide To obtain a monomeric DPR protein preparation, $(GA)_{20}$ peptides were dissolved at a concentration of 200 µg/ml in carbonate buffer (15 mM $Na_2CO_3$, 35 mM $NaHCO_3$, pH 9.42) and immediately frozen at −80° C. To obtain DPR aggregates, $(GA)_{20}$ peptides were dissolved at a concentration of 200 µg/ml in sodium acetate buffer (50 mM $C_2H_3O_2Na$, 100 mM KCl and 1 mM EDTA, pH 3.0) and incubated for 72 hrs at room temperature with shaking (600 rpm). Peptide preparations were stored at −80° C. until used.
Transmission Electron Microscopy Samples were adsorbed onto glow-discharged carbon-coated copper grids. Excess sample was removed by blotting on filter paper. Grids were stained with 2% (w/v) uranyl acetate for 1 min and excess uranyl acetate was washed with distilled deionized water. Grids were air-dried and imaged using a Philips CM100 transmission electron microscope with an acceleration voltage of 100 kV.
Indirect ELISA 96-well microplates (Corning Incorporated, Corning, USA) were coated with monomeric and aggregated $(GA)_{20}$ DPR protein peptide preparations at a concentration of 5 µg/ml in coating buffer (15 mM $Na_2CO_3$, 35 mM $NaHCO_3$, pH 9.42). Non-specific binding sites were blocked for 1 h at room temperature with PBS/0.1% Tween®-20 containing 2% BSA (Sigma-Aldrich, Buchs, Switzerland). Primary antibodies were diluted to the indicated concentrations and incubated 1 h at room temperature, followed by incubation with a donkey anti-human IgG Fcγ-specific antibody conjugated with HRP (Jackson ImmunoResearch Laboratories, Inc., West Grove, USA). Binding was determined by measurement of HRP activity in a standard colorimetric assay. $EC_{50}$ values were estimated by non-linear regression using GraphPad Prism software (San Diego, USA).

Sandwich ELISA 96-well microplates (Corning Incorporated, Corning, USA) were coated with monoclonal mouse anti-His tag antibody (Takara Bio Europe/Clontech, Saint-Germain-en-Laye, France) at a concentration of 10 µg/ml in coating buffer (15 mM $Na_2CO_3$, 35 mM $NaHCO_3$, pH 9.42) overnight at 4° C. Non-specific binding sites were blocked for 1 h at room temperature with PBS/0.1% Tween®-20 containing 2% BSA (Sigma-Aldrich, Buchs, Switzerland). After a washing step, his-tagged $(GA)_{20}$ DPR protein peptide preparations at equal concentration of 5 µM in PBS (pH 7.4) were added for target-trapping by the anti-His tag antibody for 1 h at room temperature. After a further washing step, NI-308 antibodies were diluted in PBS/0.1% Tween®-20 containing 2% BSA (Sigma-Aldrich, Buchs, Switzerland) to the indicated concentrations and incubated 1 h at RT. Antibody binding to DPR protein peptides was detected by a donkey anti-human IgG Fcγ-specific antibody conjugated with HRP at 1:5000 dilution (Jackson ImmunoResearch Laboratories, Inc., West Grove, USA) for 1h at RT. Binding was determined by measurement of HRP activity in a standard colorimetric assay. $EC_{50}$ values were estimated by non-linear regression using GraphPad Prism software (San Diego, USA).

As a result C9orf72 $(GA)_{20}$ dipeptide repeat proteins readily aggregated into structures reassembling amyloid fibrils upon aging under acidic conditions, as revealed by transmission electron microscopy analysis (FIG. 10B). In contrast, under basic conditions the $(GA)_{20}$ DPR protein peptide did not form fibrillar aggregates and likely remained in a monomeric state (FIG. 10A). The binding specificity and binding affinity ($EC_{50}$) of the human-derived antibodies NI-308.18F7 and NI-308.15O7 for monomeric and aggregated C9orf72 $(GA)_{20}$ DPR protein peptide preparations were determined by indirect and sandwich ELISA binding assays. Both antibodies recognized with comparable binding affinities the monomeric as well as the aggregated $(GA)_{20}$-DPR protein peptide preparations (FIGS. 9, 11A-11B and 12A-12B). The poly-GA dipeptide repeat protein was reported to be the most prevalent peptide species in C9orf72-FTLD (Mori et al., Acta Neuropathol. 2013). $(GA)_{20}$ dipeptide repeat proteins readily aggregated into amyloid-like fibrillar structures upon aging under acidic but not basic conditions. Human-derived antibodies NI-308.18F7 and NI-308.15O7 recognize with comparable binding affinities monomeric as well as the aggregated $(GA)_{20}$-DPR preparations in two independent binding assays. These antibodies are therefore suitable candidates to target pathological GA DPR proteins in a soluble as well as insoluble conformation.

Example 11: Antibody Integrity Analyses by SDS PAGE

To assess the purity and integrity of recombinant human NI-308 antibodies. In brief, human NI-308 antibodies were expressed by transient transfections of CHO-S cells and purified by protein A affinity purification on an FPLC system (ÄKTApurifier; GE Healthcare Life Sciences). After PD-10 column (GE Healthcare Life Sciences) desalting, antibodies were formulated in PBS. Five µg of purified recombinant human NI-308 antibodies were resolved under reducing conditions by gradient SDS-PAGE (Novex® Bis-Tris NuPAGE® 4-12%; Life Technologies Europe B.V., Zug, Switzerland) using Novex® NuPAGE® MES SDS Running Buffer complemented with antioxidant (Life Technologies Europe B.V., Zug, Switzerland) followed by Coomassie blue staining (Novex® SimplyBlue™ SafeStain, Life Technologies Europe B.V., Zug, Switzerland). As a result, SDS-PAGE analysis under reducing conditions of the recombinant human NI-308 antibodies revealed two major bands corresponding to the antibody heavy and light chains at the expected size. No significant contaminations or proteolytic degradation products were detectable (FIG. 13).

Example 12: Binding Analysis to DPR Aggregate Pathology in Post Mortem Human C9orf72-FTLD and Non-Neurological Control Brain Tissues To assess the binding of antibodies NI-308.18F7, NI-308.15O7, NI-308.5G2 and NI-308.4M1 to C9orf72 dipeptide repeat proteins in post-mortem cerebellar tissues derived from human C9orf72-FTLD patients and non-neurological controls. In brief, formalin fixed, paraffin-embedded 5 pin sections of cerebellum from 3 FTLD patients with C9orf72 hexanucleotide repeat expansions and 1 non-neurological control subjects (BiOBANC HCB-IDIBAPS, Barcelona, Spain) were pretreated for antigen retrieval by cooking in 1 mM EDTA buffer, pH 8.3, and microwave irradiation for 12 mM (600 W). Quenching of endogenous peroxidase activity was achieved by treatment with 3% $H_2O_2$ in methanol for 10 mM at RT. Non-specific binding sites were blocked for 1 h at RT with PBS/5% serum (horse/goat)/4% BSA. After the blocking step, sections were incubated with human-derived NI-308.18F7, NI-308.15O7, NI-308.5G2 and NI-308.4M1 antibodies at 5 nM concentration or C9RANT control antibody at 1:5000 dilution (Novus Biologicals, Littleton, USA) overnight at 4° C. Detection was performed with biotinylated donkey anti-human IgG (H+L) (1:350 dil, Jackson ImmunoResearch Laboratories, Inc., West Grove, USA) or anti-rabbit secondary antibody (1:250 dilution, Vector Laboratories; Burlingame, USA) and antibody signal was amplified with the Vectastain Elite ABC kit (Vector Laboratories, Burlingame, USA) and detected with diaminobenzidine (DAB, Thermo Scientific, Rockford, USA). Slides were mounted using Eukitt® mounting medium (O. Kindler GmbH; Freiburg, Germany). Bright-field imaging was performed using a Dotslide VS120 slide scanner (Olympus Schweiz AG, Switzerland). Binding of NI-308.18F7, NI-308.15O7, NI-308.5G2 and NI-308.4M1 to pathological C9orf72 dipeptide repeat proteins was assessed by immunohistochemical analysis of cerebellar sections from patients with FTLD and a non-neurological control subject. As shown in FIGS. 14A and 14B, human-derived NI-308.18F7, NI-308.15O7 and NI-308.5G2 antibodies revealed prominent neuronal cytoplasmic inclusions, neuronal intranuclear inclusions and dystrophic neurites in the granule cell layer of the cerebellum of all three C9orf72-FTLD cases tested. In contrast, non-neurological control cerebellum was negative for all antibodies tested (FIG. 14A). As shown in FIG. 14C, antibody NI-308.4M1 revealed neuronal cytoplasmic inclusions and neuronal intranuclear inclusions in the granule cell layer of the cerebellum of a C9orf72-FTLD case but not of a non-neurological control case. In conclusion, human-derived antibodies NI-308.18F7, NI-308.15O7, NI-308.5 G2 and NI-308.4M1 specifically detect C9orf72 dipeptide repeat protein aggregates in the granule cell layer of the cerebellum of C9orf72-FTLD cases while no staining is observed in control cerebellum demonstrating the high target specificity of the antibodies.

Example 13: Human Antibody Binding to Co-Aggregated DPR Species in FTLD

To assess the localization of distinct species of C9orf72 DPR proteins in post-mortem cerebellar tissues from human FTLD patients carrying C9orf72 hexanucleotide repeat expansions. In brief, antibody NI-308.18F7 was directly conjugated to the fluorescence dye Atto 488 by the use of the Atto 488 Protein labeling kit (Sigma-Aldrich, Buchs, Switzerland) according to the manufacturer's instructions. The antibody NI-308.5G2 was directly conjugated to Atto 550 by the use of the Atto 550 Protein labeling kit (Sigma-Aldrich, Buchs, Switzerland) according to the manufacturer's instructions. For immunofluorescence histochemistry experiments, formalin fixed, paraffin-embedded 5 μm sections of cerebellum from a FTLD patient with C9orf72 hexanucleotide repeat expansions (BiOBANC HCB-IDIBAPS, Barcelona, Spain) were pretreated for antigen retrieval by cooking in 1 mM EDTA buffer, pH 8.3, and microwave irradiation for 12 min (600 W). Non-specific binding sites were blocked for 1 h at room temperature with PBS/5% serum (horse/goat)/4% BSA. After the blocking step, sections were incubated with human antibodies NI-308.18F7-Atto 488 and NI-308.5G2-Atto 550 at 5 nM for 2 hrs at room temperature. After immunostaining, tissue sections were incubated with a 0.1% Sudan Black B solution for 10 min at room temperature for decreasing tissue autofluorescence. Nuclear counterstain was performed by the use of DAPI nucleic acid stain (1:1000 dilution of a 5 mg/ml stock solution, Molecular Probes®, Life Technologies Europe B.V., Zug, Switzerland). Slides were mounted using Hydromount (National Diagnostics, Atlanta, USA) medium. Fluorescence imaging was performed using a Dotslide VS120 slide scanner (Olympus Schweiz AG, Switzerland).

Figure 15:
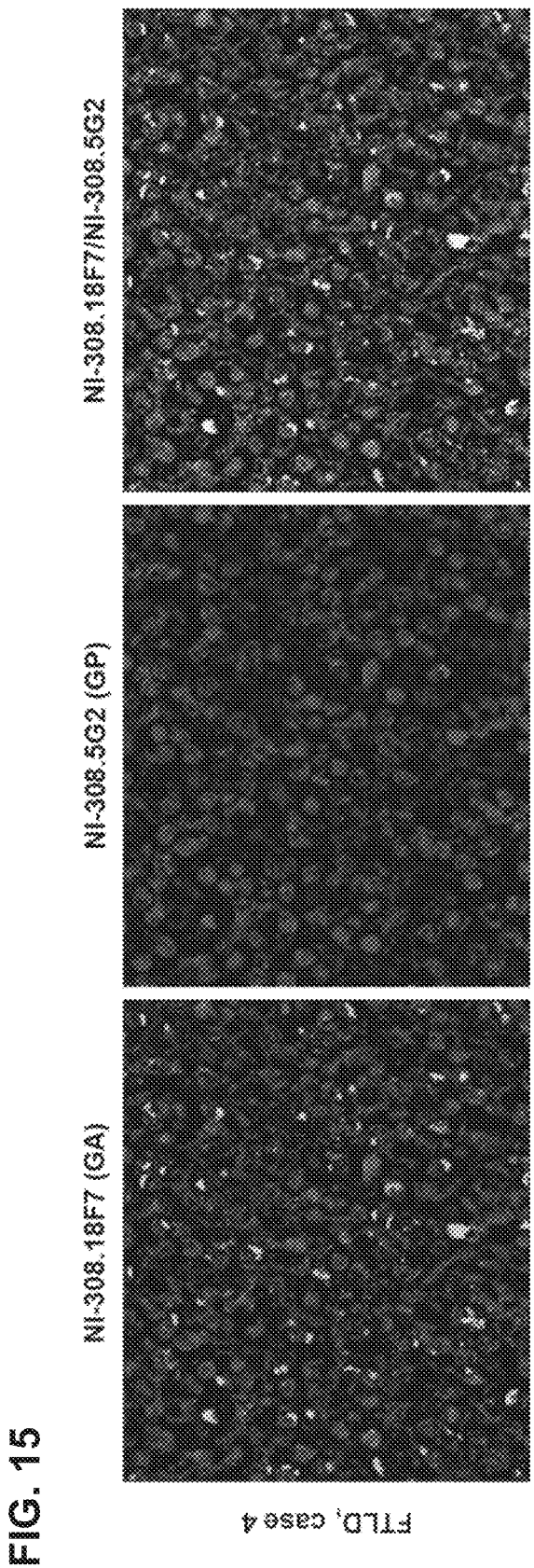
FIG. 15: C9orf72 Poly-GA and poly-GP DPR proteins form co-aggregates. Presence of pathological C9orf72 poly-GA and poly-GP DPR proteins co-aggregates in the granular layer of the cerebellum of a human FTLD patient carrying C9orf72 hexanucleotide repeat expansions. NI-308.18F7 recognized C9orf72 poly-GA whereas antibody NI-308.5G2 specifically detected C9orf72 poly-GP cytoplasmic and intranuclear inclusions. The vast majority of poly-GP DPR protein aggregates were co-localized with poly-GA aggregates. Representative images are shown.

The localization of C9orf72 poly-GA and poly-GP DPR proteins in the granular layer of the cerebellum of a human FTLD patient carrying C9orf72 hexanucleotide repeat expansions were assessed by fluorescence microscopy. As shown in FIG. 15, antibody NI-308.18F7 recognized widespread neuronal cytoplasmic and intranuclear C9orf72 poly-GA inclusions (left panel, green staining signal). Under the experimental conditions chosen NI-308.5G2 detected a more sparse pathology of cytoplasmic and intranuclear poly-GP inclusions (central panel, red staining signal). A substantial fraction of poly-GP DPR protein aggregates were co-localized with poly-GA DPR protein aggregates (left panel, yellow staining signal) suggesting that both DPR proteins can co-aggregate in pathological inclusions.

Example 14: Cell-Based Models for Studying the Pathogenic Mechanisms of C9orf72 DPR Proteins Recent reports in emerging cell culture and animal models provided evidence for the toxicity of aberrant C9orf72 DPR proteins. For example, in flies and some cell culture models, particularly arginine-rich DPR proteins (poly-GR and poly-PR) were found to be toxic (Kwon et al., Science 345 (2014), 1139-1145; Mizielinska et al., Science 345 (2014), 1192-1194; Tao et al., Hum. Mol. Genet. 24 (2015), 2426-2441; Wen et al., Neuron 84 (2014), 1213-1225; Yang et al., Acta Neuropathol. 130 (2015), 525-535) by inducing nuclear inclusions and nucleolar stress, while others reported toxicity for cytoplasmic poly-GA aggregates in cell culture systems (May et al., Acta Neuropathol. 128 (2014), 485-503; Zhang et al., Acta Neuropathol. 128 (2014), 505-524).

To determine if, as shown for tau (Yanamandra et al., Ann. Clin. Transl. Neurol. 2 (2013), 278-288) and α-synuclein (Tran et al., Cell Rep. 7 (2014), 2054-2065), spread of DPR pathology can be prevented by treatment with antibodies of the present invention, in vitro C9orf72 DPR toxicity assays are used similar in kind. In particular, synthetic DNA sequences were generated to drive the expression of individual DPR proteins harboring 150 dipeptide repeats in an ATG-dependent translation. A randomized codon strategy was employed to ensure the expression of only the selected individual DPR protein sequence. To drive expression of the DPR proteins in neuronal cells such as SH-SY5Y, NSC-34, Neuro-2a, iPSC-derived neurons and primary neurons, the synthetic DNA sequences were cloned into an expression vector regulated by the neuron specific Thy 1.2 promoter. For high-level expression in a wide range of eukaryotic cells such as HEK293T, U-2 OS, HeLa and Cos cells the synthetic DNA sequences were cloned into expression vectors regulated by the CMV promoter. Human iPSC-derived neurons and trans-differentiated neurons (iNeurons) derived from C9orf72 patient fibroblasts represents additional C9orf72 DPR proteins cell culture models.

These cellular models can be used for testing the therapeutic utility of the antibodies of the present invention. Evaluation and confirmation of the therapeutic effects of the antibodies of the present invention can be performed by monitoring cell viability by mitochondrial and/or caspase activity assays, cell toxicity by cytolysis and/or membrane leakage assays, and inhibition of cellular DPR proteins spreading by immunohistochemical assays.

Example 15: Transgenic Mouse Models for Studying the Pathogenic Mechanisms of C9orf72DPR Proteins Immunotherapy approaches developed against aggregation-prone and/or misfolded proteins have yielded promising results in preclinical and clinical studies of several neurodegenerative diseases. Transgenic mouse models that recapitulate pathological features of C9orf72 hexanucleotide repeat expansion-mediated ALS/FTLD have been recently developed ((Chew et al., Science 348 (2015), 1151-1154); and international application WO2014/159247 A1). For the generation of these mouse models, bacterial artificial chromosome constructs harboring either a full-length or truncated hexanucleotide repeat expanded C9orf72 gene (between ~450 to 500 hexanucleotide repeats) or an adeno-associated viral vector harbouring 66 C9orf72 hexanucleotide repeats sequence were used. In the these mouse models, C9orf72 hexanucleotide repeat expansion-mediated accumulation of nuclear RNA foci and DPR proteins has been detected in the central nervous system. Furthermore, pathological hallmarks of C9orf72 disease such as neuronal loss, behavioural abnormalities, motor deficits and decreased survival have been observed in the different transgenic mouse models. These mouse models can be used for testing the therapeutic utility of the antibodies of the present invention. In particular, the antibodies to be screened may be applied on diverse possible routes to the animals such as intraperitoneal antibody injection, intracranial injection, intraventricular brain infusion and tested for treatment effects.

Because of the evolutionarily optimization and affinity maturation within the human immune system antibodies of the present invention provide a valuable therapeutic tool due to being isolated from healthy human subjects with high probability for excellent safety profile and lack of immunogenicity. Confirmation of these expected therapeutic effects may be provided by test methods as described in the above mentioned publications with human instead of mouse antibodies.

The invention claimed is:

1. An antibody or antigen-binding fragment thereof that binds to a chromosome 9 open reading frame 72 (C9orf72) dipeptide repeat (DPR) protein with a poly-glycine-alanine $(GA)_{15}$ repeat, wherein the antibody or antigen-binding fragment thereof comprises:
   a heavy chain variable region (VH) comprising VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and
   a light chain variable region (VL) comprising VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively; and
   wherein the antibody or antigen-binding fragment thereof comprises a heterologous sequence that is heterologous to the VH CDRs 1, 2, and 3 and the VL CDRs 1, 2, and 3.

2. The antibody or antigen-binding fragment thereof of claim 1, wherein:
   the VH comprises an amino acid sequence that is at least 95% identical to the amino acid sequence set forth in SEQ ID NO:8; and
   the VL comprises an amino acid sequence that is at least 95% identical to the amino acid sequence set forth in SEQ ID NO:10.

3. The antibody or antigen-binding fragment thereof of claim 1, wherein:
   the VH comprises an amino acid sequence that is at least 99% identical to the amino acid sequence set forth in SEQ ID NO:8; and
   the VL comprises an amino acid sequence that is at least 99% identical to the amino acid sequence set forth in SEQ ID NO:10.

4. The antibody or antigen-binding fragment thereof of claim 1, wherein:
   the VH comprises the amino acid sequence set forth in SEQ ID NO:8 or a variant of the amino acid sequence set forth in SEQ ID NO:8 with one amino acid deletion; and
   the VL comprises the amino acid sequence set forth in SEQ ID NO:10 or a variant of the amino acid sequence set forth in SEQ ID NO:10 with one amino acid deletion.

5. The antibody or antigen-binding fragment thereof of claim 1, wherein the heterologous sequence is an immunoglobulin heavy chain constant region.

6. The antibody or antigen-binding fragment thereof of claim 1, wherein the heterologous sequence is an immunoglobulin light chain constant region.

7. The antibody or antigen-binding fragment thereof of claim 1, wherein the heterologous sequence is a heterologous mammalian secretory signal peptide.

8. An antibody or antigen-binding fragment thereof that binds to a chromosome 9 open reading frame 72 (C9orf72) dipeptide repeat (DPR) protein with a poly-glycine-alanine $(GA)_{15}$ repeat, wherein the antibody or antigen-binding fragment thereof comprises:
   a heavy chain variable region (VH) comprising VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and
   a light chain variable region (VL) comprising VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively,
wherein the antibody or antigen-binding fragment thereof comprises polyethylene glycol or a detectable label.

9. The antibody or antigen-binding fragment thereof of claim 8, wherein the detectable label is selected from the group consisting of an enzyme, a radioisotope, a fluorescent compound, a chemiluminescent compound, a bioluminescent compound, and a heavy metal.

10. The antibody or antigen-binding fragment thereof of claim 8, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

11. The antibody or antigen-binding fragment thereof of claim 8, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

12. The antibody or antigen-binding fragment thereof of claim 8, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

13. The antibody or antigen-binding fragment thereof of claim 8, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

14. A polynucleotide linked to a heterologous nucleic acid, wherein the polynucleotide is selected from the group consisting of:
a polynucleotide comprising a nucleic acid sequence encoding a heavy chain variable region (VH), wherein the VH comprises VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively, wherein the VH when paired with a light chain variable region (VL) comprising VL CDRs 1, 2, and 3 comprising the amino acid sequences set forth in amino acid positions 25-35 of SEQ ID NO:10, amino acid positions 51-57 of SEQ ID NO:10, and amino acid positions 90-98 of SEQ ID NO:10, respectively, binds to a chromosome 9 open reading frame 72 (C9orf72) dipeptide repeat (DPR) protein with a poly-glycine-alanine $(GA)_{15}$ repeat; and
a polynucleotide comprising a nucleic acid sequence encoding a VL, wherein the VL comprises VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively, wherein the VL when paired with a VH comprising VH CDRs 1, 2, and 3 comprising the amino acid sequences set forth in amino acid positions 32-36 of SEQ ID NO:8, amino acid positions 51-67 of SEQ ID NO:8, and amino acid positions 100-113 of SEQ ID NO:8, respectively, binds to a C9orf72 DPR protein with a poly-$(GA)_{15}$ repeat.

15. The polynucleotide of claim 14, wherein the heterologous nucleic acid is a regulatory element.

16. The polynucleotide of claim 15, wherein the regulatory element is a promoter, an enhancer, a ribosome binding site, or a transcription terminator.

17. The polynucleotide of claim 14, wherein the heterologous nucleic acid encodes a secretory signal peptide.

18. The polynucleotide of claim 17, wherein the secretory signal peptide is a mammalian signal peptide.

19. The polynucleotide of claim 14, wherein:
the VH comprises an amino acid sequence that is at least 95% identical to the amino acid sequence set forth in SEQ ID NO:8; or
the VL comprises an amino acid sequence that is at least 95% identical to the amino acid sequence set forth in SEQ ID NO:10.

20. The polynucleotide of claim 14, wherein:
the VH comprises an amino acid sequence that is at least 99% identical to the amino acid sequence set forth in SEQ ID NO:8; or
the VL comprises an amino acid sequence that is at least 99% identical to the amino acid sequence set forth in SEQ ID NO:10.

21. The polynucleotide of claim 14, wherein:
the VH comprises the amino acid sequence set forth in SEQ ID NO:8 or a variant of the amino acid sequence set forth in SEQ ID NO:8 with one amino acid deletion; or
the VL comprises the amino acid sequence set forth in SEQ ID NO:10 or a variant of the amino acid sequence set forth in SEQ ID NO:10 with one amino acid deletion.

22. The polynucleotide of claim 14, wherein:
the nucleic acid sequence encodes the VH, wherein the VH CDRs 1, 2, and 3 are encoded by the nucleotide sequences set forth in nucleotide positions 94 to 108 of SEQ ID NO:7, nucleotide positions 151 to 201 of SEQ ID NO:7, and nucleotide positions 298 to 339 of SEQ ID NO:7, respectively;
the nucleic acid sequence encodes the VL, wherein the VL CDRs 1, 2, and 3 are encoded by the nucleotide sequences set forth in nucleotide positions 73 to 105 of SEQ ID NO:9, nucleotide positions 151 to 171 of SEQ ID NO:9, and nucleotide positions 268 to 294 of SEQ ID NO:9, respectively;
the nucleic acid sequence encodes the VH, wherein the nucleic acid sequence is at least 95% identical to SEQ ID NO:7; or
the nucleic acid sequence encodes the VL, wherein the nucleic acid sequence is at least 95% identical to SEQ ID NO:9.

23. A cDNA comprising a polynucleotide encoding a polypeptide, wherein the polypeptide comprises:
a heavy chain variable region (VH), wherein the VH comprises VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively, wherein the VH when paired with a light chain variable region (VL) comprising VL CDRs 1, 2, and 3 comprising the amino acid sequences set forth in amino acid positions 25-35 of SEQ ID NO:10, amino acid positions 51-57 of SEQ ID NO:10, and amino acid positions 90-98 of SEQ ID NO:10, respectively, binds to a chromosome 9 open reading frame 72 (C9orf72) dipeptide repeat (DPR) protein with a poly-glycine-alanine $(GA)_{15}$ repeat; or a VL, wherein the VL comprises VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively, wherein the VL when paired with a VH comprising VH CDRs 1, 2, and 3 comprising the amino acid sequences set forth in amino acid positions 32-36 of SEQ ID NO:8, amino acid positions 51-67 of SEQ ID NO:8, and amino acid positions 100-113 of SEQ ID NO:8, respectively, binds to a C9orf72 DPR protein with a poly-$(GA)_{15}$ repeat.

24. The cDNA of claim 23, wherein:
the VH comprises an amino acid sequence that is at least 95% identical to the amino acid sequence set forth in SEQ ID NO:8; or
the VL comprises an amino acid sequence that is at least 95% identical to the amino acid sequence set forth in SEQ ID NO:10.

25. The cDNA of claim 23, wherein:
the VH comprises an amino acid sequence that is at least 99% identical to the amino acid sequence set forth in SEQ ID NO:8; or
the VL comprises an amino acid sequence that is at least 99% identical to the amino acid sequence set forth in SEQ ID NO:10.

26. The cDNA of claim 23, wherein:
the VH comprises the amino acid sequence set forth in SEQ ID NO:8 or a variant of the amino acid sequence set forth in SEQ ID NO:8 with one amino acid deletion; or
the VL comprises the amino acid sequence set forth in SEQ ID NO:10 or a variant of the amino acid sequence set forth in SEQ ID NO:10 with one amino acid deletion.

27. An expression vector comprising a promoter operably linked to a polynucleotide, wherein the polynucleotide encodes:
a polypeptide comprising an immunoglobulin heavy chain or a fragment thereof comprising a heavy chain variable region (VH), wherein the VH comprises VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively, wherein the VH when paired with a light chain variable region (VL) comprising VL CDRs 1, 2, and 3 comprising the amino acid sequences set forth in amino acid positions 25-35 of SEQ ID NO:10, amino acid positions 51-57 of SEQ ID NO:10, and amino acid positions 90-98 of SEQ ID NO:10, respectively, binds to a chromosome 9 open reading frame 72 (C9orf72) dipeptide repeat (DPR) protein with a poly-glycine-alanine $(GA)_{15}$ repeat; or
a polypeptide comprising an immunoglobulin light chain or a fragment thereof comprising a VL, wherein the VL comprises VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively, wherein the VL when paired with a VH comprising VH CDRs 1, 2, and 3 comprising the amino acid sequences set forth in amino acid positions 32-36 of SEQ ID NO:8, amino acid positions 51-67 of SEQ ID NO:8, and amino acid positions 100-113 of SEQ ID NO:8, respectively, binds to a C9orf72 DPR protein with a poly-$(GA)_{15}$ repeat.

28. The expression vector of claim 27, wherein:
the VH comprises an amino acid sequence that is at least 95% identical to the amino acid sequence set forth in SEQ ID NO:8; or
the VL comprises an amino acid sequence that is at least 95% identical to the amino acid sequence set forth in SEQ ID NO:10.

29. The expression vector of claim 27, wherein:
the VH comprises an amino acid sequence that is at least 99% identical to the amino acid sequence set forth in SEQ ID NO:8; or
the VL comprises an amino acid sequence that is at least 99% identical to the amino acid sequence set forth in SEQ ID NO:10.

30. The expression vector of claim 27, wherein:
the VH comprises the amino acid sequence set forth in SEQ ID NO:8 or a variant of the amino acid sequence set forth in SEQ ID NO:8 with one amino acid deletion; or
the VL comprises the amino acid sequence set forth in SEQ ID NO:10 or a variant of the amino acid sequence set forth in SEQ ID NO:10 with one amino acid deletion.

31. The expression vector of claim 27, wherein the promoter is a heterologous promoter.

32. The expression vector of claim 31, wherein the heterologous promoter is a cytomegalovirus, simian virus 40, or retroviral promoter.

33. The expression vector of claim 32, wherein the promoter is a cytomegalovirus immediate early promoter.

34. The expression vector of claim 27, wherein the polypeptide comprises a signal peptide.

35. The expression vector of claim 34, wherein the signal peptide is a heterologous signal peptide.

36. The expression vector of claim 27, wherein the expression vector is a plasmid, phage, virus, or retrovirus.

37. An expression vector comprising:
a first polynucleotide encoding a first polypeptide comprising an immunoglobulin heavy chain or a fragment thereof comprising a heavy chain variable region (VH), wherein the VH comprises VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and
a second polynucleotide encoding a second polypeptide comprising an immunoglobulin light chain or a fragment thereof comprising a light chain variable region (VL), wherein the VL comprises VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively;

wherein the immunoglobulin heavy chain or fragment thereof when paired with the immunoglobulin light chain or fragment thereof forms an antibody or antigen-binding fragment thereof that binds to a chromosome 9 open reading frame 72 (C9orf72) dipeptide repeat (DPR) protein with a poly-glycine-alanine $(GA)_{15}$ repeat.

38. The expression vector of claim 37, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

39. The expression vector of claim 37, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

40. The expression vector of claim 37, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

41. The expression vector of claim 37, wherein the first polypeptide comprises a human IgG1 heavy chain constant region and the second polypeptide comprises a human kappa light chain constant region.

42. The expression vector of claim 37, wherein the expression vector is a plasmid, phage, virus, or retrovirus.

43. A host cell comprising:
a first expression vector comprising a first polynucleotide encoding a first polypeptide comprising an immunoglobulin heavy chain or a fragment thereof comprising a heavy chain variable region (VH), wherein the VH comprises VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and
a second expression vector comprising a second polynucleotide encoding a second polypeptide comprising an immunoglobulin light chain or a fragment thereof comprising a light chain variable region (VL), wherein the VL comprises VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively,
wherein the immunoglobulin heavy chain or fragment thereof when paired with the immunoglobulin light chain or fragment thereof forms an antibody or antigen-binding fragment thereof that binds to a chromosome 9 open reading frame 72 (C9orf72) dipeptide repeat (DPR) protein with a poly-glycine-alanine $(GA)_{15}$ repeat.

44. The host cell of claim 43, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

45. The host cell of claim 43, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

46. The host cell of claim 43, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

47. The host cell of claim 43, wherein the first polypeptide comprises a human IgG1 heavy chain constant region and the second polypeptide comprises a human kappa light chain constant region.

48. The host cell of claim 43, wherein the host cell is a mammalian host cell.

49. The host cell of claim 43, wherein the host cell is a Chinese hamster ovary (CHO) cell, a HEK 293 cell, or a NSO cell.

50. The host cell of claim 43, wherein the first expression vector is a plasmid, phage, or virus, and the second expression vector is a plasmid, phage, or virus.

51. A host cell comprising the expression vector of claim 37.

52. The host cell of claim 51, wherein the first polypeptide comprises a human IgG1 heavy chain constant region and the second polypeptide comprises a human kappa light chain constant region.

53. The host cell of claim 51, wherein the host cell is a mammalian host cell.

54. The host cell of claim 51, wherein the host cell is a Chinese hamster ovary (CHO) cell, a HEK 293 cell, or a NSO cell.

55. The host cell of claim 51, wherein the expression vector is a plasmid, phage, or virus.

56. A pharmaceutical composition comprising the antibody or antigen-binding fragment thereof of claim 1, and a pharmaceutically acceptable carrier.

57. The pharmaceutical composition of claim 56, which is suitable for intrathecal, intravenous, or subcutaneous administration.

58. A method for preparing an antibody or antigen-binding fragment thereof that binds to a chromosome 9 open reading frame 72 (C9orf72) dipeptide repeat (DPR) protein with a poly-glycine-alanine $(GA)_{15}$ repeat, the method comprising:
culturing the host cell of claim 43 in a cell culture; and
isolating the antibody or antigen-binding fragment thereof from the cell culture.

59. The method of claim 58, further comprising formulating the antibody or antigen-binding fragment thereof into a sterile pharmaceutical composition suitable for administration to a human subject.

60. The method of claim 59, wherein the pharmaceutical composition is suitable for intrathecal, intravenous, or subcutaneous administration.

61. A method for preparing an antibody or antigen-binding fragment thereof that binds to a chromosome 9 open reading frame 72 (C9orf72) dipeptide repeat (DPR) protein with a poly-glycine-alanine $(GA)_{15}$ repeat, the method comprising:
culturing the host cell of claim 51 in a cell culture; and
isolating the antibody or antigen-binding fragment thereof from the cell culture.

62. The method of claim 61, further comprising formulating the antibody or antigen-binding fragment thereof into a sterile pharmaceutical composition suitable for administration to a human subject.

63. The method of claim 62, wherein the pharmaceutical composition is suitable for intrathecal, intravenous, or subcutaneous administration.

64. A method of preparing a pharmaceutical composition, the method comprising formulating an antibody or antigen-binding fragment thereof that binds to a chromosome 9 open reading frame 72 (C9orf72) dipeptide repeat (DPR) protein with a poly-glycine-alanine $(GA)_{15}$ repeat into a sterile pharmaceutical composition suitable for administration to a human subject, wherein the antibody or antigen-binding fragment thereof comprises (i) an immunoglobulin heavy chain or a fragment thereof comprising a heavy chain variable region (VH) comprising VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and (ii) an immunoglobulin light chain or a fragment thereof comprising a light chain variable region (VL) comprising VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively.

65. The method of claim 64, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

66. The method of claim 64, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

67. The method of claim 64, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

68. The method of claim 64, wherein the pharmaceutical composition is suitable for intrathecal, intravenous, or subcutaneous administration.

69. A method of treating a disease or disorder associated with poly-glycine-alanine (GA) dipeptide repeat (DPR) protein or aggregated forms thereof, wherein the disease or disorder is selected from the group consisting of Frontotemporal lobar degeneration (FTLD), amyotrophic lateral sclerosis (ALS), and FTLD-ALS, the method comprising administering to a human subject in need thereof a therapeutically effective amount of an antibody or antigen-binding fragment thereof that binds to a chromosome 9 open reading frame 72 (C9orf72) DPR protein with a poly-$(GA)_{15}$ repeat, wherein the antibody or antigen-binding fragment thereof comprises:
a heavy chain variable region (VH) comprising VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and
a light chain variable region (VL) comprising VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively.

70. The method of claim 69, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

71. The method of claim 69, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

72. The method of claim 69, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

73. The method of claim 69, wherein the antibody comprises a human IgG1 heavy chain constant region and a human kappa light chain constant region.

74. The method of claim 69, wherein the disease or disorder is Frontotemporal lobar degeneration (FTLD).

75. The method of claim 69, wherein the disease or disorder is amyotrophic lateral sclerosis (ALS).

76. The method of claim 69, wherein the disease or disorder is FTLD-ALS.

77. A method of diagnosing or monitoring the progression of a disease or disorder associated with poly-glycine-alanine (GA) dipeptide repeat (DPR) protein or aggregated forms thereof, wherein the disease or disorder is selected from the group consisting of Frontotemporal lobar degeneration (FTLD), amyotrophic lateral sclerosis (ALS), and FTLD-ALS, the method comprising:
measuring the level of pathologically modified or aggregated DPR protein in a sample from a human subject with an antibody or antigen-binding fragment thereof that binds to a chromosome 9 open reading frame 72 (C9orf72) DPR protein with a poly-(GA)$_{15}$ repeat, wherein the antibody or antigen-binding fragment thereof comprises: a heavy chain variable region (VH) comprising VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and a light chain variable region (VL) comprising VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively; and comparing the level of modified or aggregated DPR protein to a reference standard that indicates the level of the pathologically modified or aggregated DPR in one or more control subjects, wherein a difference or similarity between the level of pathologically modified or aggregated DPR protein and the reference standard indicates that the human subject has a disease or disorder associated with poly-GA DPR protein or aggregated forms thereof.

78. The method of claim 77, wherein the disease or disorder is Frontotemporal lobar degeneration (FTLD).

79. The method of claim 77, wherein the disease or disorder is amyotrophic lateral sclerosis (ALS).

80. The method of claim 77, wherein the disease or disorder is FTLD-ALS.

81. A method for in vivo detection of poly-glycine-alanine (GA) dipeptide repeat (DPR) protein deposition in the brain, the method comprising:

administering to a human subject an antibody or antigen-binding fragment thereof that binds to a chromosome 9 open reading frame 72 (C9orf72) DPR protein with a poly-(GA)$_{15}$ repeat, wherein the antibody or antigen-binding fragment thereof comprises: a heavy chain variable region (VH) comprising VH complementarity determining regions (CDRs) 1, 2, and 3, wherein the VH CDRs 1, 2, and 3 comprise the amino acid sequences set forth in amino acid positions 32-36 of SEQ ID NO:8, amino acid positions 51-67 of SEQ ID NO:8, and amino acid positions 100-113 of SEQ ID NO:8, respectively; and a light chain variable region (VL) comprising VL CDRs 1, 2, and 3, wherein the VL CDRs 1, 2, and 3 comprise the amino acid sequences set forth in amino acid positions 25-35 of SEQ ID NO:10, amino acid positions 51-57 of SEQ ID NO:10, and amino acid positions 90-98 of SEQ ID NO:10, respectively, wherein the antibody or antigen-binding fragment thereof is attached to a detectable label; and detecting the detectable label in the brain of the human subject, to thereby detect poly-GA DPR protein deposition in the brain of the human subject.

82. The method of claim 81, wherein the poly-GA DPR protein is detected by position emission tomography (PET), single photon emission tomography (SPECT), near infrared (NIR), optical imaging, or magnetic resonance imaging (MRI).

83. The method of claim 81, wherein the detectable label is selected from the group consisting of enzyme, a radioisotope, a fluorophore, and a heavy metal.

84. The method of claim 70, wherein the antibody comprises a human IgG1 heavy chain constant region and a human kappa light chain constant region.

85. The method of claim 70, wherein the disease or disorder is Frontotemporal lobar degeneration (FTLD).

86. The method of claim 70, wherein the disease or disorder is amyotrophic lateral sclerosis (ALS).

87. The method of claim 70, wherein the disease or disorder is FTLD-ALS.

88. The method of claim 71, wherein the antibody comprises a human IgG1 heavy chain constant region and a human kappa light chain constant region.

89. The method of claim 71, wherein the disease or disorder is Frontotemporal lobar degeneration (FTLD).

90. The method of claim 71, wherein the disease or disorder is amyotrophic lateral sclerosis (ALS).

91. The method of claim 71, wherein the disease or disorder is FTLD-ALS.

92. The method of claim 72, wherein the antibody comprises a human IgG1 heavy chain constant region and a human kappa light chain constant region.

93. The method of claim 72, wherein the disease or disorder is Frontotemporal lobar degeneration (FTLD).

94. The method of claim 72, wherein the disease or disorder is amyotrophic lateral sclerosis (ALS).

95. The method of claim 72, wherein the disease or disorder is FTLD-ALS.

96. The method of claim 69, wherein the antibody or antigen-binding fragment thereof is administered to the human subject via intrathecal, intravenous, or subcutaneous administration.

97. The method of claim 70, wherein the antibody or antigen-binding fragment thereof is administered to the human subject via intrathecal, intravenous, or subcutaneous administration.

98. The method of claim 71, wherein the antibody or antigen-binding fragment thereof is administered to the human subject via intrathecal, intravenous, or subcutaneous administration.

99. The method of claim 72, wherein the antibody or antigen-binding fragment thereof is administered to the human subject via intrathecal, intravenous, or subcutaneous administration.

100. The method of claim 73, wherein the antibody or antigen-binding fragment thereof is administered to the human subject via intrathecal, intravenous, or subcutaneous administration.

101. The method of claim 74, wherein the antibody or antigen-binding fragment thereof is administered to the human subject via intrathecal, intravenous, or subcutaneous administration.

102. The method of claim 75, wherein the antibody or antigen-binding fragment thereof is administered to the human subject via intrathecal, intravenous, or subcutaneous administration.

103. The method of claim 76, wherein the antibody or antigen-binding fragment thereof is administered to the human subject via intrathecal, intravenous, or subcutaneous administration.

104. The method of claim 69, wherein the antibody or antigen-binding fragment thereof is administered to the human subject via intravenous administration.

105. The method of claim 70, wherein the antibody or antigen-binding fragment thereof is administered to the human subject via intravenous administration.

106. The method of claim 71, wherein the antibody or antigen-binding fragment thereof is administered to the human subject via intravenous administration.

107. The method of claim 72, wherein the antibody or antigen-binding fragment thereof is administered to the human subject via intravenous administration.

108. The method of claim 73, wherein the antibody or antigen-binding fragment thereof is administered to the human subject via intravenous administration.

109. The method of claim 74, wherein the antibody or antigen-binding fragment thereof is administered to the human subject via intravenous administration.

110. The method of claim 75, wherein the antibody or antigen-binding fragment thereof is administered to the human subject via intravenous administration.

111. The method of claim 76, wherein the antibody or antigen-binding fragment thereof is administered to the human subject via intravenous administration.

112. The method of claim 81, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

113. The method of claim 81, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

114. The method of claim 81, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

115. The method of claim 82, wherein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

116. The method of claim 82, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

117. The method of claim 82, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

118. The method of claim 83 herein:
the VH comprises an amino acid sequence that is at least 95% identical to the amino acid sequence set forth in SEQ ID NO:8; and
the VL comprises an amino acid sequence that is at least 95% identical to the amino acid sequence set forth in SEQ ID NO:10.

119. The method of claim 83, wherein:
the VH comprises an amino acid sequence that is at least 99% identical to the amino acid sequence set forth in SEQ ID NO:8; and
the VL comprises an amino acid sequence that is at least 99% identical to the amino acid sequence set forth in SEQ ID NO:10.

120. The method of claim 83, wherein:
the VH comprises the amino acid sequence set forth in SEQ ID NO:8 or a variant of the amino acid sequence set forth in SEQ ID NO:8 with one amino acid deletion; and
the VL comprises the amino acid sequence set forth in SEQ ID NO:10 or a variant of the amino acid sequence set forth in SEQ ID NO:10 with one amino acid deletion.

\* \* \* \* \*

SEQUENCE LISTING

```
<160> NUMBER OF SEQ ID NOS: 86

<210> SEQ ID NO 1
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-308.18F7-VH variable heavy chain (VH)
      sequence
<220> FEATURE:
<221> NAME/KEY: V_region
<222> LOCATION: (94)..(108)
<223> OTHER INFORMATION: complementarity determining region (CDR) VH-
      CDR1
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(336)
<223> OTHER INFORMATION: complementarity determining region (CDR) VH-
      CDR3

<400> SEQUENCE: 1 tgc cag gtg cag ctg cag gag tcg ggc cca gga ctg gtg aag cct tcg      48
Cys Gln Val Gln Leu Gln Glu Ser Gly Pro Gly Leu Val Lys Pro Ser
1               5                   10                  15 gag acc ctg tcc gtc acg tgc act gtc tct ggt ggc tcc atc aat gat      96
Glu Thr Leu Ser Val Thr Cys Thr Val Ser Gly Gly Ser Ile Asn Asp
            20                  25                  30
```

```
tac tac tgg aac tgg atc cgg cag ccc gcc ggg aag gga ctg gag tgg         144
Tyr Tyr Trp Asn Trp Ile Arg Gln Pro Ala Gly Lys Gly Leu Glu Trp
        35                  40                  45 att ggg cgt ata tat gcc agt ggg acc atc aat tac aac cct tcc ctc         192
Ile Gly Arg Ile Tyr Ala Ser Gly Thr Ile Asn Tyr Asn Pro Ser Leu
 50                  55                  60 cag agt cga gtc acc atg tca att gac acg tcc aag aac cag ttc tcc         240
Gln Ser Arg Val Thr Met Ser Ile Asp Thr Ser Lys Asn Gln Phe Ser
65                  70                  75                  80 cta gac ctc atc tct gtg tcc gcc gcg gac acg gcc gtc tac tat tgt         288
Leu Asp Leu Ile Ser Val Ser Ala Ala Asp Thr Ala Val Tyr Tyr Cys
                85                  90                  95 gcg aga tgg ggc cag gtg gtc ggg gac tac tac tac ggg atg gac gtc         336
Ala Arg Trp Gly Gln Val Val Gly Asp Tyr Tyr Tyr Gly Met Asp Val
                    100                 105                 110 tgg ggc cag ggg acc acg gtc acc gtc tcc tcg                             369
Trp Gly Gln Gly Thr Thr Val Thr Val Ser Ser
            115                 120

<210> SEQ ID NO 2
<211> LENGTH: 123
<212> TYPE: PRT
<213> ORGANISM: Homo sapiens

<400> SEQUENCE: 2

Cys Gln Val Gln Leu Gln Glu Ser Gly Pro Gly Leu Val Lys Pro Ser
 1               5                  10                  15

Glu Thr Leu Ser Val Thr Cys Thr Val Ser Gly Gly Ser Ile Asn Asp
                20                  25                  30

Tyr Tyr Trp Asn Trp Ile Arg Gln Pro Ala Gly Lys Gly Leu Glu Trp
        35                  40                  45

Ile Gly Arg Ile Tyr Ala Ser Gly Thr Ile Asn Tyr Asn Pro Ser Leu
 50                  55                  60

Gln Ser Arg Val Thr Met Ser Ile Asp Thr Ser Lys Asn Gln Phe Ser
65                  70                  75                  80

Leu Asp Leu Ile Ser Val Ser Ala Ala Asp Thr Ala Val Tyr Tyr Cys
                85                  90                  95

Ala Arg Trp Gly Gln Val Val Gly Asp Tyr Tyr Tyr Gly Met Asp Val
                    100                 105                 110

Trp Gly Gln Gly Thr Thr Val Thr Val Ser Ser
            115                 120

<210> SEQ ID NO 3
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-308.18F7 VK variable light-kappa chain (VK)
      sequence
<220> FEATURE:
<221> NAME/KEY: V_region
<222> LOCATION: (73)..(120)
<223> OTHER INFORMATION: complementarity determining region (CDR) VK-
      CDR1
<220> FEATURE:
<221> NAME/KEY: V_region
<222> LOCATION: (166)..(186)
<223> OTHER INFORMATION: complementarity determining region (CDR) VK-
      CDR2
<220> FEATURE:
<221> NAME/KEY: V_region
<222> LOCATION: (283)..(306)
```

<223> OTHER INFORMATION: complementarity determining region (CDR) VK-
      CDR3

<400> SEQUENCE: 3

```
tgc gaa att gtg ctg act cag tct cca ctc tcc ctg tcc gtc acc cct      48
Cys Glu Ile Val Leu Thr Gln Ser Pro Leu Ser Leu Ser Val Thr Pro
1               5                   10                  15 gga gag ccg gcc tcc atc tcc tgc aag tct agt cag agc ctc caa cat      96
Gly Glu Pro Ala Ser Ile Ser Cys Lys Ser Ser Gln Ser Leu Gln His
            20                  25                  30 aca aat gga tac aat tac ttg gat tgg tac ctg ctg aag cca ggg cag     144
Thr Asn Gly Tyr Asn Tyr Leu Asp Trp Tyr Leu Leu Lys Pro Gly Gln
        35                  40                  45 tct cca caa ctc cta atc ttc ttg act tct aat cgg gcc tcc ggg gtc     192
Ser Pro Gln Leu Leu Ile Phe Leu Thr Ser Asn Arg Ala Ser Gly Val
    50                  55                  60 cct gac agg ttc agt ggc agt gga tca ggc aca aat ttt aca ctg aaa     240
Pro Asp Arg Phe Ser Gly Ser Gly Ser Gly Thr Asn Phe Thr Leu Lys
65                  70                  75                  80 atc agc aga gtg gag gct gag gat gtt ggg gtc tat tat tgc atg gaa     288
Ile Ser Arg Val Glu Ala Glu Asp Val Gly Val Tyr Tyr Cys Met Glu
                85                  90                  95 ggt ata caa ttg tgg acg ttc ggc caa ggg acc aag ctg gag atc aaa     336
Gly Ile Gln Leu Trp Thr Phe Gly Gln Gly Thr Lys Leu Glu Ile Lys
            100                 105                 110
```

<210> SEQ ID NO 4
<211> LENGTH: 112
<212> TYPE: PRT
<213> ORGANISM: Homo sapiens

<400> SEQUENCE: 4

```
Cys Glu Ile Val Leu Thr Gln Ser Pro Leu Ser Leu Ser Val Thr Pro
1               5                   10                  15

Gly Glu Pro Ala Ser Ile Ser Cys Lys Ser Ser Gln Ser Leu Gln His
            20                  25                  30

Thr Asn Gly Tyr Asn Tyr Leu Asp Trp Tyr Leu Leu Lys Pro Gly Gln
        35                  40                  45

Ser Pro Gln Leu Leu Ile Phe Leu Thr Ser Asn Arg Ala Ser Gly Val
    50                  55                  60

Pro Asp Arg Phe Ser Gly Ser Gly Ser Gly Thr Asn Phe Thr Leu Lys
65                  70                  75                  80

Ile Ser Arg Val Glu Ala Glu Asp Val Gly Val Tyr Tyr Cys Met Glu
                85                  90                  95

Gly Ile Gln Leu Trp Thr Phe Gly Gln Gly Thr Lys Leu Glu Ile Lys
            100                 105                 110
```

<210> SEQ ID NO 5
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-308.18F7 VK-PIMC variable light-kappa chain
      (VK) sequence after correction of primer induced mutations
<220> FEATURE:
<221> NAME/KEY: V_region
<222> LOCATION: (73)..(120)
<223> OTHER INFORMATION: complementarity determining region (CDR) VK-
      CDR1
<220> FEATURE:
<221> NAME/KEY: V_region

```
<222> LOCATION: (166)..(186)
<223> OTHER INFORMATION: complementarity determining region (CDR) VK-
      CDR2
<220> FEATURE:
<221> NAME/KEY: V_region
<222> LOCATION: (283)..(306)
<223> OTHER INFORMATION: complementarity determining region (CDR) VK-
      CDR3

<400> SEQUENCE: 5 tgc gac atc gtg atg acc cag tct cca ctc tcc ctg tcc gtc acc cct        48
Cys Asp Ile Val Met Thr Gln Ser Pro Leu Ser Leu Ser Val Thr Pro
1               5                   10                  15 gga gag ccg gcc tcc atc tcc tgc aag tct agt cag agc ctc caa cat        96
Gly Glu Pro Ala Ser Ile Ser Cys Lys Ser Ser Gln Ser Leu Gln His
            20                  25                  30 aca aat gga tac aat tac ttg gat tgg tac ctg ctg aag cca ggg cag       144
Thr Asn Gly Tyr Asn Tyr Leu Asp Trp Tyr Leu Leu Lys Pro Gly Gln
        35                  40                  45 tct cca caa ctc cta atc ttc ttg act tct aat cgg gcc tcc ggg gtc       192
Ser Pro Gln Leu Leu Ile Phe Leu Thr Ser Asn Arg Ala Ser Gly Val
    50                  55                  60 cct gac agg ttc agt ggc agt gga tca ggc aca aat ttt aca ctg aaa       240
Pro Asp Arg Phe Ser Gly Ser Gly Ser Gly Thr Asn Phe Thr Leu Lys
65                  70                  75                  80 atc agc aga gtg gag gct gag gat gtt ggg gtc tat tat tgc atg gaa       288
Ile Ser Arg Val Glu Ala Glu Asp Val Gly Val Tyr Tyr Cys Met Glu
                85                  90                  95 ggt ata caa ttg tgg acg ttc ggc caa ggg acc aag gtg gag atc aaa       336
Gly Ile Gln Leu Trp Thr Phe Gly Gln Gly Thr Lys Val Glu Ile Lys
            100                 105                 110

<210> SEQ ID NO 6
<211> LENGTH: 112
<212> TYPE: PRT
<213> ORGANISM: Homo sapiens

<400> SEQUENCE: 6

Cys Asp Ile Val Met Thr Gln Ser Pro Leu Ser Leu Ser Val Thr Pro
1               5                   10                  15

Gly Glu Pro Ala Ser Ile Ser Cys Lys Ser Ser Gln Ser Leu Gln His
            20                  25                  30

Thr Asn Gly Tyr Asn Tyr Leu Asp Trp Tyr Leu Leu Lys Pro Gly Gln
        35                  40                  45

Ser Pro Gln Leu Leu Ile Phe Leu Thr Ser Asn Arg Ala Ser Gly Val
    50                  55                  60

Pro Asp Arg Phe Ser Gly Ser Gly Ser Gly Thr Asn Phe Thr Leu Lys
65                  70                  75                  80

Ile Ser Arg Val Glu Ala Glu Asp Val Gly Val Tyr Tyr Cys Met Glu
                85                  90                  95

Gly Ile Gln Leu Trp Thr Phe Gly Gln Gly Thr Lys Val Glu Ile Lys
            100                 105                 110

<210> SEQ ID NO 7
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-308.15O7 VH variable heavy chain (VH)
      sequence
<220> FEATURE:
```

```
<221> NAME/KEY: V_region
<222> LOCATION: (94)..(108)
<223> OTHER INFORMATION: complementarity determining region (CDR) VH-
      CDR1
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(339)
<223> OTHER INFORMATION: complementarity determining region (CDR) VH-
      CDR3

<400> SEQUENCE: 7 tgc cag gtg cag ctg gtg gag tct ggg gga ggc gta gtc cag cct ggg      48
Cys Gln Val Gln Leu Val Glu Ser Gly Gly Gly Val Val Gln Pro Gly
1               5                   10                  15 agg tcc ctg aga ctg tcc tgt gca gcc tct gga ttc acc ttc agt aat      96
Arg Ser Leu Arg Leu Ser Cys Ala Ala Ser Gly Phe Thr Phe Ser Asn
            20                  25                  30 cat gct atg cac tgg gtc cgc cag gct cca ggc aag ggg ctg gag tgg     144
His Ala Met His Trp Val Arg Gln Ala Pro Gly Lys Gly Leu Glu Trp
        35                  40                  45 gtg gca gtt ata tca tat gat ggc gag aac aca tat tat gca gac tcc     192
Val Ala Val Ile Ser Tyr Asp Gly Glu Asn Thr Tyr Tyr Ala Asp Ser
    50                  55                  60 att gag ggc cga ttc acc att tcc aga gac aat ttc aag aac aca ctc     240
Ile Glu Gly Arg Phe Thr Ile Ser Arg Asp Asn Phe Lys Asn Thr Leu
65                  70                  75                  80 ttt cta caa atg tac agc ctg aca gct gat gac acg gct atg tac ttc     288
Phe Leu Gln Met Tyr Ser Leu Thr Ala Asp Asp Thr Ala Met Tyr Phe
                85                  90                  95 tgt gcg aga ggg ggc cgt cgg ggg cac ttc acc tca tac tac ctt gac     336
Cys Ala Arg Gly Gly Arg Arg Gly His Phe Thr Ser Tyr Tyr Leu Asp
            100                 105                 110 tac tgg ggc cag gga acc ctg gtc acc gtc tcc tcg                     372
Tyr Trp Gly Gln Gly Thr Leu Val Thr Val Ser Ser
        115                 120

<210> SEQ ID NO 8
<211> LENGTH: 124
<212> TYPE: PRT
<213> ORGANISM: Homo sapiens

<400> SEQUENCE: 8

Cys Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Asn
            20                  25                  30

His Ala Met His Trp Val Arg Gln Ala Pro Gly Lys Gly Leu Glu Trp
        35                  40                  45

Val Ala Val Ile Ser Tyr Asp Gly Glu Asn Thr Tyr Tyr Ala Asp Ser
    50                  55                  60

Ile Glu Gly Arg Phe Thr Ile Ser Arg Asp Asn Phe Lys Asn Thr Leu
65                  70                  75                  80

Phe Leu Gln Met Tyr Ser Leu Thr Ala Asp Asp Thr Ala Met Tyr Phe
                85                  90                  95

Cys Ala Arg Gly Gly Arg Arg Gly His Phe Thr Ser Tyr Tyr Leu Asp
            100                 105                 110

Tyr Trp Gly Gln Gly Thr Leu Val Thr Val Ser Ser
```

```
<210> SEQ ID NO 9
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-308.15O7 VK variable light-kappa chain (VK)
      sequence
<220> FEATURE:
<221> NAME/KEY: V_region
<222> LOCATION: (73)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 9 tgc gac atc cag atg acc cag tct cca tcc tcc ctg tct gca tct gta      48
Cys Asp Ile Gln Met Thr Gln Ser Pro Ser Ser Leu Ser Ala Ser Val
1               5                   10                  15 gga gac aga gtc acc atc act tgc cgg gca agc cag aac ata gac aag      96
Gly Asp Arg Val Thr Ile Thr Cys Arg Ala Ser Gln Asn Ile Asp Lys
            20                  25                  30 tac tta aat tgg tat cag cag ata ccg ggg aaa gcc cct aag ctc ctg     144
Tyr Leu Asn Trp Tyr Gln Gln Ile Pro Gly Lys Ala Pro Lys Leu Leu
        35                  40                  45 atc tat gct gca tcg agt ttg cac agt ggg gtc cca tca agg ttc agt     192
Ile Tyr Ala Ala Ser Ser Leu His Ser Gly Val Pro Ser Arg Phe Ser
    50                  55                  60 ggc agt gga tct ggg aca gat ttc tct ctc acc atc agc agt ctg caa     240
Gly Ser Gly Ser Gly Thr Asp Phe Ser Leu Thr Ile Ser Ser Leu Gln
65                  70                  75                  80 cct gaa gat ttt gca att tac tac tgt caa cag agt tac agt tcc ttc     288
Pro Glu Asp Phe Ala Ile Tyr Tyr Cys Gln Gln Ser Tyr Ser Ser Phe
                85                  90                  95 cgg acg ttc ggc caa ggg acc aag ctg gag atc aaa                     324
Arg Thr Phe Gly Gln Gly Thr Lys Leu Glu Ile Lys
            100                 105

<210> SEQ ID NO 10
<211> LENGTH: 108
<212> TYPE: PRT
<213> ORGANISM: Homo sapiens

<400> SEQUENCE: 10

Cys Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asn Ile Asp Lys
            20                  25                  30

Tyr Leu Asn Trp Tyr Gln Gln Ile Pro Gly Lys Ala Pro Lys Leu Leu
        35                  40                  45

Ile Tyr Ala Ala Ser Ser Leu His Ser Gly Val Pro Ser Arg Phe Ser
    50                  55                  60

Gly Ser Gly Ser Gly Thr Asp Phe Ser Leu Thr Ile Ser Ser Leu Gln
```

```
                   65                  70                  75                  80
Pro Glu Asp Phe Ala Ile Tyr Tyr Cys Gln Gln Ser Tyr Ser Phe
                           85                  90                  95

Arg Thr Phe Gly Gln Gly Thr Lys Leu Glu Ile Lys
                100                 105

<210> SEQ ID NO 11
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-308.15O7 VK-PIMC variable light-kappa chain
      (VK) sequence after correction of primer induced mutations
<220> FEATURE:
<221> NAME/KEY: V_region
<222> LOCATION: (73)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 11 tgc gac atc cag atg acc cag tct ccg tcc tcc ctg tct gca tct gta      48
Cys Asp Ile Gln Met Thr Gln Ser Pro Ser Ser Leu Ser Ala Ser Val
1               5                   10                  15 gga gac aga gtc acc atc act tgc cgg gca agc cag aac ata gac aag      96
Gly Asp Arg Val Thr Ile Thr Cys Arg Ala Ser Gln Asn Ile Asp Lys
            20                  25                  30 tac tta aat tgg tat cag cag ata ccg ggg aaa gcc cct aag ctc ctg     144
Tyr Leu Asn Trp Tyr Gln Gln Ile Pro Gly Lys Ala Pro Lys Leu Leu
        35                  40                  45 atc tat gct gca tcg agt ttg cac agt ggg gtc cca tca agg ttc agt     192
Ile Tyr Ala Ala Ser Ser Leu His Ser Gly Val Pro Ser Arg Phe Ser
    50                  55                  60 ggc agt gga tct ggg aca gat ttc tct ctc acc atc agc agt ctg caa     240
Gly Ser Gly Ser Gly Thr Asp Phe Ser Leu Thr Ile Ser Ser Leu Gln
65                  70                  75                  80 cct gaa gat ttt gca att tac tac tgt caa cag agt tac agt tcc ttc     288
Pro Glu Asp Phe Ala Ile Tyr Tyr Cys Gln Gln Ser Tyr Ser Ser Phe
                85                  90                  95 cgg acg ttc ggc caa ggg acc aag gtg gag atc aaa                     324
Arg Thr Phe Gly Gln Gly Thr Lys Val Glu Ile Lys
                100                 105

<210> SEQ ID NO 12
<211> LENGTH: 108
<212> TYPE: PRT
<213> ORGANISM: Homo sapiens

<400> SEQUENCE: 12

Cys Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asn Ile Asp Lys
            20                  25                  30

Tyr Leu Asn Trp Tyr Gln Gln Ile Pro Gly Lys Ala Pro Lys Leu Leu
```

```
                35                  40                  45
Ile Tyr Ala Ala Ser Ser Leu His Ser Gly Val Pro Ser Arg Phe Ser
 50                  55                  60

Gly Ser Gly Ser Gly Thr Asp Phe Ser Leu Thr Ile Ser Ser Leu Gln
 65                  70                  75                  80

Pro Glu Asp Phe Ala Ile Tyr Tyr Cys Gln Gln Ser Tyr Ser Ser Phe
                     85                  90                  95

Arg Thr Phe Gly Gln Gly Thr Lys Val Glu Ile Lys
                100                 105
```

<210> SEQ ID NO 13
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-308.5G2-VH variable heavy chain (VH)
      sequence
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(201)
<223> OTHER INFORMATION: complementarity determining region (CDR) VH-
      CDR1
<220> FEATURE:
<221> NAME/KEY: V_region
<222> LOCATION: (298)..(339)
<223> OTHER INFORMATION: complementarity determining region (CDR) VH-
      CDR1

<400> SEQUENCE: 13

```
tgc gag gtg cag ctg gtg cag tct ggg gct gac ttg cgg aac cct ggg      48
Cys Glu Val Gln Leu Val Gln Ser Gly Ala Asp Leu Arg Asn Pro Gly
 1               5                  10                  15 gcc tca gtg acg gtt tcc tgc acg gct tct gga tac cat ttc gct gac      96
Ala Ser Val Thr Val Ser Cys Thr Ala Ser Gly Tyr His Phe Ala Asp
                 20                  25                  30 aat gct ata aac tgg ctg cgc cag gcc ccc gga caa agg ctt gag tgg     144
Asn Ala Ile Asn Trp Leu Arg Gln Ala Pro Gly Gln Arg Leu Glu Trp
             35                  40                  45 atg ggg tgg atc aac att tac agt ggt aac aca aaa tat tca cag aac     192
Met Gly Trp Ile Asn Ile Tyr Ser Gly Asn Thr Lys Tyr Ser Gln Asn
 50                  55                  60 ttc cag ggc aga gtc acc ttt acc aga aac aca tcc gcg agc aca gcc     240
Phe Gln Gly Arg Val Thr Phe Thr Arg Asn Thr Ser Ala Ser Thr Ala
 65                  70                  75                  80 ttc atg cac ctg cgc agc ctg aga tca gaa gac acg gct gtg tat ttc     288
Phe Met His Leu Arg Ser Leu Arg Ser Glu Asp Thr Ala Val Tyr Phe
                 85                  90                  95 tgt gcg aga gac cct gat agc agt gga tat tac ttg ccc tat ttt gac     336
Cys Ala Arg Asp Pro Asp Ser Ser Gly Tyr Tyr Leu Pro Tyr Phe Asp
                100                 105                 110 tac tgg ggc caa gga acc ctg gtc acc gtc tcc tcg                     372
Tyr Trp Gly Gln Gly Thr Leu Val Thr Val Ser Ser
            115                 120
```

<210> SEQ ID NO 14
<211> LENGTH: 124
<212> TYPE: PRT
<213> ORGANISM: Homo sapiens

<400> SEQUENCE: 14

Cys Glu Val Gln Leu Val Gln Ser Gly Ala Asp Leu Arg Asn Pro Gly
1               5                   10                  15

Ala Ser Val Thr Val Ser Cys Thr Ala Ser Gly Tyr His Phe Ala Asp
            20                  25                  30

Asn Ala Ile Asn Trp Leu Arg Gln Ala Pro Gly Gln Arg Leu Glu Trp
        35                  40                  45

Met Gly Trp Ile Asn Ile Tyr Ser Gly Asn Thr Lys Tyr Ser Gln Asn
    50                  55                  60

Phe Gln Gly Arg Val Thr Phe Thr Arg Asn Thr Ser Ala Ser Thr Ala
65                  70                  75                  80

Phe Met His Leu Arg Ser Leu Arg Ser Glu Asp Thr Ala Val Tyr Phe
                85                  90                  95

Cys Ala Arg Asp Pro Asp Ser Ser Gly Tyr Tyr Leu Pro Tyr Phe Asp
            100                 105                 110

Tyr Trp Gly Gln Gly Thr Leu Val Thr Val Ser Ser
        115                 120

<210> SEQ ID NO 15
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: NI-308.5G2 VK variable light-kappa chain (VK)
      sequence
<220> FEATURE:
<221> NAME/KEY: V_region
<222> LOCATION: (73)..(123)
<223> OTHER INFORMATION: complementarity determining region (CDR) VK-
      CDR1
<220> FEATURE:
<221> NAME/KEY: V_region
<222> LOCATION: (169)..(189)
<223> OTHER INFORMATION: complementarity determining region (CDR) VK-
      CDR2
<220> FEATURE:
<221> NAME/KEY: V_region
<222> LOCATION: (286)..(312)
<223> OTHER INFORMATION: complementarity determining region (CDR) VK-
      CDR3

<400> SEQUENCE: 15 tgc gac atc cag ttg acc cag tct cca gac tcc ctg act ttg tct ctg     48
Cys Asp Ile Gln Leu Thr Gln Ser Pro Asp Ser Leu Thr Leu Ser Leu
1               5                   10                  15 ggc gag agg gcc acc atc aac tgc aag tcc agc cag agt gtt ttc tac     96
Gly Glu Arg Ala Thr Ile Asn Cys Lys Ser Ser Gln Ser Val Phe Tyr
            20                  25                  30 aac tcc aac aat aag aac tac tta gct tgg tat cag cag aaa cca gga    144
Asn Ser Asn Asn Lys Asn Tyr Leu Ala Trp Tyr Gln Gln Lys Pro Gly
        35                  40                  45 cag cct cct aag ttg ctc atg tac tgg gca tct acc cgg gag tcc ggg    192
Gln Pro Pro Lys Leu Leu Met Tyr Trp Ala Ser Thr Arg Glu Ser Gly
    50                  55                  60 gtc act gac cga ttc agt ggc agc ggg tct ggg aca gat ttt act ctc    240
Val Thr Asp Arg Phe Ser Gly Ser Gly Ser Gly Thr Asp Phe Thr Leu

```
                    65                  70                  75                  80
acc att acc aac ctg cag gct gaa gat gtg gca gtc tat tat tgt cag     288
Thr Ile Thr Asn Leu Gln Ala Glu Asp Val Ala Val Tyr Tyr Cys Gln
                    85                  90                  95 caa ttt tat agt tct cct ctc act ttc ggc gga ggg acc aag gtg gag     336
Gln Phe Tyr Ser Ser Pro Leu Thr Phe Gly Gly Gly Thr Lys Val Glu
            100                 105                 110 atc aaa                                                              342
Ile Lys <210> SEQ ID NO 16
<211> LENGTH: 114
<212> TYPE: PRT
<213> ORGANISM: Homo sapiens

<400> SEQUENCE: 16

Cys Asp Ile Gln Leu Thr Gln Ser Pro Asp Ser Leu Thr Leu Ser Leu
1               5                   10                  15

Gly Glu Arg Ala Thr Ile Asn Cys Lys Ser Ser Gln Ser Val Phe Tyr
            20                  25                  30

Asn Ser Asn Asn Lys Asn Tyr Leu Ala Trp Tyr Gln Gln Lys Pro Gly
        35                  40                  45

Gln Pro Pro Lys Leu Leu Met Tyr Trp Ala Ser Thr Arg Glu Ser Gly
    50                  55                  60

Val Thr Asp Arg Phe Ser Gly Ser Gly Ser Gly Thr Asp Phe Thr Leu
65                  70                  75                  80

Thr Ile Thr Asn Leu Gln Ala Glu Asp Val Ala Val Tyr Tyr Cys Gln
                85                  90                  95

Gln Phe Tyr Ser Ser Pro Leu Thr Phe Gly Gly Gly Thr Lys Val Glu
            100                 105                 110

Ile Lys

<210> SEQ ID NO 17
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-308.5G2 VH-PIMC variable heavy chain (VH)
      sequence after correction of primer induced mutations
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(339)
<223> OTHER INFORMATION: complementarity determining region (CDR) VH-
      CDR3

<400> SEQUENCE: 17 tgc cag gtg cag ctg gtg caa tct ggg gct gac ttg cgg aac cct ggg     48
```

```
Cys Gln Val Gln Leu Val Gln Ser Gly Ala Asp Leu Arg Asn Pro Gly
1               5                   10                  15 gcc tca gtg acg gtt tcc tgc acg gct tct gga tac cat ttc gct gac      96
Ala Ser Val Thr Val Ser Cys Thr Ala Ser Gly Tyr His Phe Ala Asp
            20                  25                  30 aat gct ata aac tgg ctg cgc cag gcc ccc gga caa agg ctt gag tgg     144
Asn Ala Ile Asn Trp Leu Arg Gln Ala Pro Gly Gln Arg Leu Glu Trp
        35                  40                  45 atg ggg tgg atc aac att tac agt ggt aac aca aaa tat tca cag aac     192
Met Gly Trp Ile Asn Ile Tyr Ser Gly Asn Thr Lys Tyr Ser Gln Asn
    50                  55                  60 ttc cag ggc aga gtc acc ttt acc aga aac aca tcc gcg agc aca gcc     240
Phe Gln Gly Arg Val Thr Phe Thr Arg Asn Thr Ser Ala Ser Thr Ala
65                  70                  75                  80 ttc atg cac ctg cgc agc ctg aga tca gaa gac acg gct gtg tat ttc     288
Phe Met His Leu Arg Ser Leu Arg Ser Glu Asp Thr Ala Val Tyr Phe
                85                  90                  95 tgt gcg aga gac cct gat agc agt gga tat tac ttg ccc tat ttt gac     336
Cys Ala Arg Asp Pro Asp Ser Ser Gly Tyr Tyr Leu Pro Tyr Phe Asp
            100                 105                 110 tac tgg ggc caa gga acc ctg gtc acc gtc tcc tcg                     372
Tyr Trp Gly Gln Gly Thr Leu Val Thr Val Ser Ser
        115                 120
```

<210> SEQ ID NO 18
<211> LENGTH: 124
<212> TYPE: PRT
<213> ORGANISM: Homo sapiens

<400> SEQUENCE: 18

```
Cys Gln Val Gln Leu Val Gln Ser Gly Ala Asp Leu Arg Asn Pro Gly
1               5                   10                  15

Ala Ser Val Thr Val Ser Cys Thr Ala Ser Gly Tyr His Phe Ala Asp
            20                  25                  30

Asn Ala Ile Asn Trp Leu Arg Gln Ala Pro Gly Gln Arg Leu Glu Trp
        35                  40                  45

Met Gly Trp Ile Asn Ile Tyr Ser Gly Asn Thr Lys Tyr Ser Gln Asn
    50                  55                  60

Phe Gln Gly Arg Val Thr Phe Thr Arg Asn Thr Ser Ala Ser Thr Ala
65                  70                  75                  80

Phe Met His Leu Arg Ser Leu Arg Ser Glu Asp Thr Ala Val Tyr Phe
                85                  90                  95

Cys Ala Arg Asp Pro Asp Ser Ser Gly Tyr Tyr Leu Pro Tyr Phe Asp
            100                 105                 110

Tyr Trp Gly Gln Gly Thr Leu Val Thr Val Ser Ser
        115                 120
```

<210> SEQ ID NO 19
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: NI-308.5G2 VK-PIMC variable light-kappa chain
      (VK) sequence after correction of primer induced mutations
<220> FEATURE:
<221> NAME/KEY: V_region
<222> LOCATION: (73)..(123)
<223> OTHER INFORMATION: complementarity determining region (CDR) VK-
      CDR1
<220> FEATURE:

```
<221> NAME/KEY: V_region
<222> LOCATION: (169)..(189)
<223> OTHER INFORMATION: complementarity determining region (CDR) VK-
      CDR2
<220> FEATURE:
<221> NAME/KEY: V_region
<222> LOCATION: (286)..(312)
<223> OTHER INFORMATION: complementarity determining region (CDR) VK-
      CDR3

<400> SEQUENCE: 19 tgc gac atc gtg atg acc cag tct cca gac tcc ctg act ttg tct ctg     48
Cys Asp Ile Val Met Thr Gln Ser Pro Asp Ser Leu Thr Leu Ser Leu
1               5                   10                  15 ggc gag agg gcc acc atc aac tgc aag tcc agc cag agt gtt ttc tac     96
Gly Glu Arg Ala Thr Ile Asn Cys Lys Ser Ser Gln Ser Val Phe Tyr
            20                  25                  30 aac tcc aac aat aag aac tac tta gct tgg tat cag cag aaa cca gga    144
Asn Ser Asn Asn Lys Asn Tyr Leu Ala Trp Tyr Gln Gln Lys Pro Gly
        35                  40                  45 cag cct cct aag ttg ctc atg tac tgg gca tct acc cgg gag tcc ggg    192
Gln Pro Pro Lys Leu Leu Met Tyr Trp Ala Ser Thr Arg Glu Ser Gly
    50                  55                  60 gtc act gac cga ttc agt ggc agc ggg tct ggg aca gat ttt act ctc    240
Val Thr Asp Arg Phe Ser Gly Ser Gly Ser Gly Thr Asp Phe Thr Leu
65                  70                  75                  80 acc att acc aac ctg cag gct gaa gat gtg gca gtc tat tat tgt cag    288
Thr Ile Thr Asn Leu Gln Ala Glu Asp Val Ala Val Tyr Tyr Cys Gln
                85                  90                  95 caa ttt tat agt tct cct ctc act ttc ggc gga ggg acc aag gtg gag    336
Gln Phe Tyr Ser Ser Pro Leu Thr Phe Gly Gly Gly Thr Lys Val Glu
            100                 105                 110 atc aaa                                                            342
Ile Lys

<210> SEQ ID NO 20
<211> LENGTH: 114
<212> TYPE: PRT
<213> ORGANISM: Homo sapiens

<400> SEQUENCE: 20

Cys Asp Ile Val Met Thr Gln Ser Pro Asp Ser Leu Thr Leu Ser Leu
1               5                   10                  15

Gly Glu Arg Ala Thr Ile Asn Cys Lys Ser Ser Gln Ser Val Phe Tyr
            20                  25                  30

Asn Ser Asn Asn Lys Asn Tyr Leu Ala Trp Tyr Gln Gln Lys Pro Gly
        35                  40                  45

Gln Pro Pro Lys Leu Leu Met Tyr Trp Ala Ser Thr Arg Glu Ser Gly
    50                  55                  60

Val Thr Asp Arg Phe Ser Gly Ser Gly Ser Gly Thr Asp Phe Thr Leu
65                  70                  75                  80

Thr Ile Thr Asn Leu Gln Ala Glu Asp Val Ala Val Tyr Tyr Cys Gln
                85                  90                  95

Gln Phe Tyr Ser Ser Pro Leu Thr Phe Gly Gly Gly Thr Lys Val Glu
            100                 105                 110

Ile Lys

<210> SEQ ID NO 21
<211> LENGTH: 369
<212> TYPE: DNA
<213> ORGANISM: Homo sapiens
```

```
<220> FEATURE:
<221> NAME/KEY: CDS
<222> LOCATION: (1)..(369)
<223> OTHER INFORMATION: NI-308.28G1-VH variable heavy chain (VH)
      sequence
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(336)
<223> OTHER INFORMATION: complementarity determining region (CDR) VH-
      CDR3

<400> SEQUENCE: 21 tgc cag gtg cag ctg cag gag tcg ggc cca aga ctg gtg aag ccc tcg       48
Cys Gln Val Gln Leu Gln Glu Ser Gly Pro Arg Leu Val Lys Pro Ser
1               5                   10                  15 gag acc ctg tcg ctc acg tgc act gtc gct ggc ggc tcc gtc aat agt       96
Glu Thr Leu Ser Leu Thr Cys Thr Val Ala Gly Gly Ser Val Asn Ser
            20                  25                  30 tac tat tgg acc tgg atc cag cag tcc ccc ggg aag gga ctg gag tgg      144
Tyr Tyr Trp Thr Trp Ile Gln Gln Ser Pro Gly Lys Gly Leu Glu Trp
        35                  40                  45 ctt ggg cgt atc tat atc gct ggg agg acc aac tat aac ccc tcc ctc      192
Leu Gly Arg Ile Tyr Ile Ala Gly Arg Thr Asn Tyr Asn Pro Ser Leu
    50                  55                  60 acg agt cga atc gcc ctg tca gtg gac acg tcc agg aac cag ttg tcc      240
Thr Ser Arg Ile Ala Leu Ser Val Asp Thr Ser Arg Asn Gln Leu Ser
65                  70                  75                  80 ctg aag ctg acg tct gtg acc gcc gcg gac acg gcc ata tat tat tgt      288
Leu Lys Leu Thr Ser Val Thr Ala Ala Asp Thr Ala Ile Tyr Tyr Cys
                85                  90                  95 gcg aga tgg gga gcg gag agt ggt gac tac tac tat gga gtg gac gtc      336
Ala Arg Trp Gly Ala Glu Ser Gly Asp Tyr Tyr Tyr Gly Val Asp Val
            100                 105                 110 tgg ggc cca ggc acc ctg gtc acc gtc tcc tcg                          369
Trp Gly Pro Gly Thr Leu Val Thr Val Ser Ser
        115                 120

<210> SEQ ID NO 22
<211> LENGTH: 123
<212> TYPE: PRT
<213> ORGANISM: Homo sapiens

<400> SEQUENCE: 22

Cys Gln Val Gln Leu Gln Glu Ser Gly Pro Arg Leu Val Lys Pro Ser
1               5                   10                  15

Glu Thr Leu Ser Leu Thr Cys Thr Val Ala Gly Gly Ser Val Asn Ser
            20                  25                  30

Tyr Tyr Trp Thr Trp Ile Gln Gln Ser Pro Gly Lys Gly Leu Glu Trp
        35                  40                  45

Leu Gly Arg Ile Tyr Ile Ala Gly Arg Thr Asn Tyr Asn Pro Ser Leu
```

```
                    50                  55                  60
Thr Ser Arg Ile Ala Leu Ser Val Asp Thr Ser Arg Asn Gln Leu Ser
 65                  70                  75                  80

Leu Lys Leu Thr Ser Val Thr Ala Ala Asp Thr Ala Ile Tyr Tyr Cys
                 85                  90                  95

Ala Arg Trp Gly Ala Glu Ser Gly Asp Tyr Tyr Gly Val Asp Val
            100                 105                 110

Trp Gly Pro Gly Thr Leu Val Thr Val Ser Ser
        115                 120

<210> SEQ ID NO 23
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-308.28G1 VK variable light-kappa chain (VK)
      sequence
<220> FEATURE:
<221> NAME/KEY: V_region
<222> LOCATION: (73)..(120)
<223> OTHER INFORMATION: complementarity determining region (CDR) VK-
      CDR1
<220> FEATURE:
<221> NAME/KEY: V_region
<222> LOCATION: (166)..(186)
<223> OTHER INFORMATION: complementarity determining region (CDR) VK-
      CDR2
<220> FEATURE:
<221> NAME/KEY: V_region
<222> LOCATION: (283)..(309)
<223> OTHER INFORMATION: complementarity determining region (CDR) VK-
      CDR3

<400> SEQUENCE: 23 tgc gaa att gtg atg acg cag tct cca ctc tcc ctg ccc gtc acc cct         48
Cys Glu Ile Val Met Thr Gln Ser Pro Leu Ser Leu Pro Val Thr Pro
  1               5                  10                  15 gga gag ccg gcc tcc atc tcc tgc aag tct agt gag gga ctc ctg cat         96
Gly Glu Pro Ala Ser Ile Ser Cys Lys Ser Ser Glu Gly Leu Leu His
             20                  25                  30 agt aat ggt tac acc tat ttg gat tgg tac ctg cag aag cca ggg cag        144
Ser Asn Gly Tyr Thr Tyr Leu Asp Trp Tyr Leu Gln Lys Pro Gly Gln
         35                  40                  45 gct ccg cag ctc ctg atc ttt ctg gct tct aat cgg gcc gcc ggg gtc        192
Ala Pro Gln Leu Leu Ile Phe Leu Ala Ser Asn Arg Ala Ala Gly Val
     50                  55                  60 cct gac agg ttc agt ggc agt gga tca ggc aca gat ttt aca ctg aag        240
Pro Asp Arg Phe Ser Gly Ser Gly Ser Gly Thr Asp Phe Thr Leu Lys
 65                  70                  75                  80 atc agc aga gtg gag gct gag gat gtt ggc gtt tat tac tgc atg cag        288
Ile Ser Arg Val Glu Ala Glu Asp Val Gly Val Tyr Tyr Cys Met Gln
                 85                  90                  95 gct ata caa agt cct tgg acg ttc ggc cca ggg acc aag gtg gaa atc        336
Ala Ile Gln Ser Pro Trp Thr Phe Gly Pro Gly Thr Lys Val Glu Ile
            100                 105                 110 aaa                                                                    339
Lys

<210> SEQ ID NO 24
<211> LENGTH: 113
<212> TYPE: PRT
<213> ORGANISM: Homo sapiens
```

<400> SEQUENCE: 24

Cys Glu Ile Val Met Thr Gln Ser Pro Leu Ser Leu Pro Val Thr Pro
1               5                   10                  15

Gly Glu Pro Ala Ser Ile Ser Cys Lys Ser Ser Glu Gly Leu Leu His
            20                  25                  30

Ser Asn Gly Tyr Thr Tyr Leu Asp Trp Tyr Leu Gln Lys Pro Gly Gln
        35                  40                  45

Ala Pro Gln Leu Leu Ile Phe Leu Ala Ser Asn Arg Ala Ala Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Ile Gln Ser Pro Trp Thr Phe Gly Pro Gly Thr Lys Val Glu Ile
            100                 105                 110

Lys

<210> SEQ ID NO 25
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-308.28G1 VH-PIMC variable heavy chain (VH)
      sequence after correction of primer induced mutations
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(336)
<223> OTHER INFORMATION: complementarity determining region (CDR) VH-
      CDR3

<400> SEQUENCE: 25 tgc cag gtg cag ctg cag gag tcg ggc cca aga ctg gtg aag ccc tcg    48
Cys Gln Val Gln Leu Gln Glu Ser Gly Pro Arg Leu Val Lys Pro Ser
1               5                   10                  15 gag acc ctg tcg ctc acg tgc act gtc gct ggc ggc tcc gtc aat agt    96
Glu Thr Leu Ser Leu Thr Cys Thr Val Ala Gly Gly Ser Val Asn Ser
            20                  25                  30 tac tat tgg acc tgg atc cag cag tcc ccc ggg aag gga ctg gag tgg   144
Tyr Tyr Trp Thr Trp Ile Gln Gln Ser Pro Gly Lys Gly Leu Glu Trp
        35                  40                  45 ctt ggg cgt atc tat atc gct ggg agg acc aac tat aac ccc tcc ctc   192
Leu Gly Arg Ile Tyr Ile Ala Gly Arg Thr Asn Tyr Asn Pro Ser Leu
    50                  55                  60 acg agt cga atc gcc ctg tca gtg gac acg tcc agg aac cag ttg tcc   240
Thr Ser Arg Ile Ala Leu Ser Val Asp Thr Ser Arg Asn Gln Leu Ser
65                  70                  75                  80

```
ctg aag ctg acg tct gtg acc gcc gcg gac acg gcc ata tat tat tgt    288
Leu Lys Leu Thr Ser Val Thr Ala Ala Asp Thr Ala Ile Tyr Tyr Cys
                85                  90                  95 gcg aga tgg gga gcg gag agt ggt gac tac tac tat gga gtg gac gtc    336
Ala Arg Trp Gly Ala Glu Ser Gly Asp Tyr Tyr Tyr Gly Val Asp Val
            100                 105                 110 tgg ggc cca ggg acc acg gtc acc gtc tcc tca                        369
Trp Gly Pro Gly Thr Thr Val Thr Val Ser Ser
        115                 120

<210> SEQ ID NO 26
<211> LENGTH: 123
<212> TYPE: PRT
<213> ORGANISM: Homo sapiens

<400> SEQUENCE: 26

Cys Gln Val Gln Leu Gln Glu Ser Gly Pro Arg Leu Val Lys Pro Ser
1               5                   10                  15

Glu Thr Leu Ser Leu Thr Cys Thr Val Ala Gly Gly Ser Val Asn Ser
            20                  25                  30

Tyr Tyr Trp Thr Trp Ile Gln Gln Ser Pro Gly Lys Gly Leu Glu Trp
        35                  40                  45

Leu Gly Arg Ile Tyr Ile Ala Gly Arg Thr Asn Tyr Asn Pro Ser Leu
    50                  55                  60

Thr Ser Arg Ile Ala Leu Ser Val Asp Thr Ser Arg Asn Gln Leu Ser
65                  70                  75                  80

Leu Lys Leu Thr Ser Val Thr Ala Ala Asp Thr Ala Ile Tyr Tyr Cys
                85                  90                  95

Ala Arg Trp Gly Ala Glu Ser Gly Asp Tyr Tyr Tyr Gly Val Asp Val
            100                 105                 110

Trp Gly Pro Gly Thr Thr Val Thr Val Ser Ser
        115                 120

<210> SEQ ID NO 27
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-308.28G1 VK-PIMC variable light-kappa chain
      (VK) sequence after correction of primer induced mutations
<220> FEATURE:
<221> NAME/KEY: V-region
<222> LOCATION: (73)..(120)
<223> OTHER INFORMATION: complementarity determining region (CDR) VK-
      CDR1
<220> FEATURE:
<221> NAME/KEY: V-region
<222> LOCATION: (166)..(186)
<223> OTHER INFORMATION: complementarity determining region (CDR) VK-
      CDR2
<220> FEATURE:
<221> NAME/KEY: V-region
<222> LOCATION: (283)..(309)
<223> OTHER INFORMATION: complementarity determining region (CDR) VK-
      CDR3

<400> SEQUENCE: 27 tgc gat att gtg atg act cag tct cca ctc tcc ctg ccc gtc acc cct    48
Cys Asp Ile Val Met Thr Gln Ser Pro Leu Ser Leu Pro Val Thr Pro
1               5                   10                  15 gga gag ccg gcc tcc atc tcc tgc aag tct agt gag gga ctc ctg cat    96
Gly Glu Pro Ala Ser Ile Ser Cys Lys Ser Ser Glu Gly Leu Leu His
            20                  25                  30
```

```
agt aat ggt tac acc tat ttg gat tgg tac ctg cag aag cca ggg cag        144
Ser Asn Gly Tyr Thr Tyr Leu Asp Trp Tyr Leu Gln Lys Pro Gly Gln
         35                  40                  45 gct ccg cag ctc ctg atc ttt ctg gct tct aat cgg gcc gcc ggg gtc        192
Ala Pro Gln Leu Leu Ile Phe Leu Ala Ser Asn Arg Ala Ala Gly Val
 50                  55                  60 cct gac agg ttc agt ggc agt gga tca ggc aca gat ttt aca ctg aag        240
Pro Asp Arg Phe Ser Gly Ser Gly Ser Gly Thr Asp Phe Thr Leu Lys
 65                  70                  75                  80 atc agc aga gtg gag gct gag gat gtt ggc gtt tat tac tgc atg cag        288
Ile Ser Arg Val Glu Ala Glu Asp Val Gly Val Tyr Tyr Cys Met Gln
                 85                  90                  95 gct ata caa agt cct tgg acg ttc ggc cca ggg acc aag gtg gaa atc        336
Ala Ile Gln Ser Pro Trp Thr Phe Gly Pro Gly Thr Lys Val Glu Ile
            100                 105                 110 aaa                                                                     339
Lys

<210> SEQ ID NO 28
<211> LENGTH: 113
<212> TYPE: PRT
<213> ORGANISM: Homo sapiens

<400> SEQUENCE: 28

Cys Asp Ile Val Met Thr Gln Ser Pro Leu Ser Leu Pro Val Thr Pro
 1               5                  10                  15

Gly Glu Pro Ala Ser Ile Ser Cys Lys Ser Ser Glu Gly Leu Leu His
                 20                  25                  30

Ser Asn Gly Tyr Thr Tyr Leu Asp Trp Tyr Leu Gln Lys Pro Gly Gln
         35                  40                  45

Ala Pro Gln Leu Leu Ile Phe Leu Ala Ser Asn Arg Ala Ala Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Ile Gln Ser Pro Trp Thr Phe Gly Pro Gly Thr Lys Val Glu Ile
            100                 105                 110

Lys

<210> SEQ ID NO 29
<211> LENGTH: 387
<212> TYPE: DNA
<213> ORGANISM: Homo sapiens
<220> FEATURE:
<221> NAME/KEY: CDS
<222> LOCATION: (1)..(387)
<223> OTHER INFORMATION: NI-308.45C2-VH variable heavy chain (VH)
      sequence
<220> FEATURE:
<221> NAME/KEY: V_region
<222> LOCATION: (79)..(114)
<223> OTHER INFORMATION: complementarity determining region (CDR) VH-
      CDR1
<220> FEATURE:
<221> NAME/KEY: V_region
<222> LOCATION: (94)..(114)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (157)..(210)
```

```
<223> OTHER INFORMATION: complementarity determining region (CDR) VH-
      CDR2
<220> FEATURE:
<221> NAME/KEY: V_region
<222> LOCATION: (307)..(354)
<223> OTHER INFORMATION: complementarity determining region (CDR) VH-
      CDR3

<400> SEQUENCE: 29 tgc cag ctg cag ctg cag gag tcg ggt cca gga ctg gtg aag ccc tcg     48
Cys Gln Leu Gln Leu Gln Glu Ser Gly Pro Gly Leu Val Lys Pro Ser
1               5                   10                  15 cag atc ctc tca ctc acc tgt gcc atc tcc ggg gac agt gtc ttc agc     96
Gln Ile Leu Ser Leu Thr Cys Ala Ile Ser Gly Asp Ser Val Phe Ser
            20                  25                  30 aac agt gct gct tgg aac tgg atc agg cag tcc cca tcg aga ggc ctt    144
Asn Ser Ala Ala Trp Asn Trp Ile Arg Gln Ser Pro Ser Arg Gly Leu
        35                  40                  45 gag tgg ctg gga agg aca tac tac agg tcc aag tgg gat aat gat tat    192
Glu Trp Leu Gly Arg Thr Tyr Tyr Arg Ser Lys Trp Asp Asn Asp Tyr
    50                  55                  60 gca cca tct gtg aaa agt cga ata agt atc aac cca gac aca tcc aag    240
Ala Pro Ser Val Lys Ser Arg Ile Ser Ile Asn Pro Asp Thr Ser Lys
65                  70                  75                  80 aac cag ttc tcc ctg cag ttg aat tct gtg act ccc gag gac acg gct    288
Asn Gln Phe Ser Leu Gln Leu Asn Ser Val Thr Pro Glu Asp Thr Ala
                85                  90                  95 gtg tat tat tgt gca aga gag gtc gca tat tgt ggt ggt gac tgc tat    336
Val Tyr Tyr Cys Ala Arg Glu Val Ala Tyr Cys Gly Gly Asp Cys Tyr
            100                 105                 110 tct gtt tcc ttt gac tac tgg ggc cag gga acc ctg gtc acc gtc tcc    384
Ser Val Ser Phe Asp Tyr Trp Gly Gln Gly Thr Leu Val Thr Val Ser
        115                 120                 125 tcg                                                                 387
Ser

<210> SEQ ID NO 30
<211> LENGTH: 129
<212> TYPE: PRT
<213> ORGANISM: Homo sapiens

<400> SEQUENCE: 30

Cys Gln Leu Gln Leu Gln Glu Ser Gly Pro Gly Leu Val Lys Pro Ser
1               5                   10                  15

Gln Ile Leu Ser Leu Thr Cys Ala Ile Ser Gly Asp Ser Val Phe Ser
            20                  25                  30

Asn Ser Ala Ala Trp Asn Trp Ile Arg Gln Ser Pro Ser Arg Gly Leu
        35                  40                  45

Glu Trp Leu Gly Arg Thr Tyr Tyr Arg Ser Lys Trp Asp Asn Asp Tyr
    50                  55                  60

Ala Pro Ser Val Lys Ser Arg Ile Ser Ile Asn Pro Asp Thr Ser Lys
65                  70                  75                  80

Asn Gln Phe Ser Leu Gln Leu Asn Ser Val Thr Pro Glu Asp Thr Ala
                85                  90                  95

Val Tyr Tyr Cys Ala Arg Glu Val Ala Tyr Cys Gly Gly Asp Cys Tyr
            100                 105                 110

Ser Val Ser Phe Asp Tyr Trp Gly Gln Gly Thr Leu Val Thr Val Ser
        115                 120                 125

Ser
```

```
<210> SEQ ID NO 31
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-308.45C2 VK variable light-kappa chain (VK)
      sequence
<220> FEATURE:
<221> NAME/KEY: V_region
<222> LOCATION: (73)..(120)
<223> OTHER INFORMATION: complementarity determining region (CDR) VK-
      CDR1
<220> FEATURE:
<221> NAME/KEY: V_region
<222> LOCATION: (166)..(186)
<223> OTHER INFORMATION: complementarity determining region (CDR) VK-
      CDR2
<220> FEATURE:
<221> NAME/KEY: V_region
<222> LOCATION: (283)..(309)
<223> OTHER INFORMATION: complementarity determining region (CDR) VK-
      CDR3

<400> SEQUENCE: 31 tgc gaa att gtg atg aca cag tct cca ctc tcc ctg ccc gtc acc cct        48
Cys Glu Ile Val Met Thr Gln Ser Pro Leu Ser Leu Pro Val Thr Pro
1               5                   10                  15 gga gag ccg gcc tcc atc tcc tgc agg tct agt cag agc ctc ctc cag        96
Gly Glu Pro Ala Ser Ile Ser Cys Arg Ser Ser Gln Ser Leu Leu Gln
            20                  25                  30 agt aat gga tac acc tat ttg gat tgg tac ctg cag aag cca ggg cag       144
Ser Asn Gly Tyr Thr Tyr Leu Asp Trp Tyr Leu Gln Lys Pro Gly Gln
        35                  40                  45 tct cca cag ctc ctg atc tat ttg ggt tct aat cgg gcc tcc ggg gtc       192
Ser Pro Gln Leu Leu Ile Tyr Leu Gly Ser Asn Arg Ala Ser Gly Val
    50                  55                  60 cct gac agg ttc agt ggc agt gga tca ggc aca gat ttt aca ctg aaa       240
Pro Asp Arg Phe Ser Gly Ser Gly Ser Gly Thr Asp Phe Thr Leu Lys
65                  70                  75                  80 atc agc aga gtg gag gct gag gat gtt ggg gtt tat tac tgc atg caa       288
Ile Ser Arg Val Glu Ala Glu Asp Val Gly Val Tyr Tyr Cys Met Gln
                85                  90                  95 gct cta caa act ccg ctc act ttc ggc gga ggg acc aag gtg gag atc       336
Ala Leu Gln Thr Pro Leu Thr Phe Gly Gly Gly Thr Lys Val Glu Ile
            100                 105                 110 aaa                                                                   339
Lys

<210> SEQ ID NO 32
<211> LENGTH: 113
<212> TYPE: PRT
<213> ORGANISM: Homo sapiens

<400> SEQUENCE: 32

Cys Glu Ile Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu Gln
            20                  25                  30

Ser Asn Gly Tyr Thr Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60
```

```
Pro Asp Arg Phe Ser Gly Ser Gly Ser Gly Thr Asp Phe Thr Leu Lys
65              70                  75                  80

Ile Ser Arg Val Glu Ala Glu Asp Val Gly Val Tyr Tyr Cys Met Gln
                85                  90                  95

Ala Leu Gln Thr Pro Leu Thr Phe Gly Gly Gly Thr Lys Val Glu Ile
                100                 105                 110

Lys
```

<210> SEQ ID NO 33
<211> LENGTH: 387
<212> TYPE: DNA
<213> ORGANISM: Homo sapiens
<220> FEATURE:
<221> NAME/KEY: CDS
<222> LOCATION: (1)..(387)
<223> OTHER INFORMATION: NI-308.45C2 VH-PIMC variable heavy chain (VH) sequence after correction of primer induced mutations
<220> FEATURE:
<221> NAME/KEY: V_region
<222> LOCATION: (79)..(114)
<223> OTHER INFORMATION: complementarity determining region (CDR) VH-CDR1
<220> FEATURE:
<221> NAME/KEY: V_region
<222> LOCATION: (94)..(114)
<223> OTHER INFORMATION: complementarity determining region (CDR) VH-CDR1 according to the numbering conventions set forth by Kabat et al. 1983
<220> FEATURE:
<221> NAME/KEY: V_region
<222> LOCATION: (157)..(210)
<223> OTHER INFORMATION: complementarity determining region (CDR) VH-CDR2
<220> FEATURE:
<221> NAME/KEY: V_region
<222> LOCATION: (307)..(354)
<223> OTHER INFORMATION: complementarity determining region (CDR) VH-CDR3

<400> SEQUENCE: 33

```
tgc cag ctg cag ctg cag cag tca ggt cca gga ctg gtg aag ccc tcg        48
Cys Gln Leu Gln Leu Gln Gln Ser Gly Pro Gly Leu Val Lys Pro Ser
1               5                   10                  15 cag atc ctc tca ctc acc tgt gcc atc tcc ggg gac agt gtc ttc agc        96
Gln Ile Leu Ser Leu Thr Cys Ala Ile Ser Gly Asp Ser Val Phe Ser
            20                  25                  30 aac agt gct gct tgg aac tgg atc agg cag tcc cca tcg aga ggc ctt       144
Asn Ser Ala Ala Trp Asn Trp Ile Arg Gln Ser Pro Ser Arg Gly Leu
        35                  40                  45 gag tgg ctg gga agg aca tac tac agg tcc aag tgg gat aat gat tat       192
Glu Trp Leu Gly Arg Thr Tyr Tyr Arg Ser Lys Trp Asp Asn Asp Tyr
    50                  55                  60 gca cca tct gtg aaa agt cga ata agt atc aac cca gac aca tcc aag       240
Ala Pro Ser Val Lys Ser Arg Ile Ser Ile Asn Pro Asp Thr Ser Lys
65                  70                  75                  80 aac cag ttc tcc ctg cag ttg aat tct gtg act ccc gag gac acg gct       288
Asn Gln Phe Ser Leu Gln Leu Asn Ser Val Thr Pro Glu Asp Thr Ala
                85                  90                  95 gtg tat tat tgt gca aga gag gtc gca tat tgt ggt ggt gac tgc tat       336
Val Tyr Tyr Cys Ala Arg Glu Val Ala Tyr Cys Gly Gly Asp Cys Tyr
            100                 105                 110 tct gtt tcc ttt gac tac tgg ggc cag gga acc ctg gtc acc gtc tcc       384
Ser Val Ser Phe Asp Tyr Trp Gly Gln Gly Thr Leu Val Thr Val Ser
        115                 120                 125 tcg                                                                    387
Ser
```

```
<210> SEQ ID NO 34
<211> LENGTH: 129
<212> TYPE: PRT
<213> ORGANISM: Homo sapiens

<400> SEQUENCE: 34

Cys Gln Leu Gln Leu Gln Gln Ser Gly Pro Gly Leu Val Lys Pro Ser
1               5                   10                  15

Gln Ile Leu Ser Leu Thr Cys Ala Ile Ser Gly Asp Ser Val Phe Ser
            20                  25                  30

Asn Ser Ala Ala Trp Asn Trp Ile Arg Gln Ser Pro Ser Arg Gly Leu
        35                  40                  45

Glu Trp Leu Gly Arg Thr Tyr Tyr Arg Ser Lys Trp Asp Asn Asp Tyr
50                  55                  60

Ala Pro Ser Val Lys Ser Arg Ile Ser Ile Asn Pro Asp Thr Ser Lys
65                  70                  75                  80

Asn Gln Phe Ser Leu Gln Leu Asn Ser Val Thr Pro Glu Asp Thr Ala
                85                  90                  95

Val Tyr Tyr Cys Ala Arg Glu Val Ala Tyr Cys Gly Gly Asp Cys Tyr
            100                 105                 110

Ser Val Ser Phe Asp Tyr Trp Gly Gln Gly Thr Leu Val Thr Val Ser
        115                 120                 125

Ser

<210> SEQ ID NO 35
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-308.45C2 VK-PIMC variable light-kappa chain
      (VK) sequence after correction of primer induced mutations
<220> FEATURE:
<221> NAME/KEY: V_region
<222> LOCATION: (73)..(120)
<223> OTHER INFORMATION: complementarity determining region (CDR) VK-
      CDR1
<220> FEATURE:
<221> NAME/KEY: V_region
<222> LOCATION: (166)..(186)
<223> OTHER INFORMATION: complementarity determining region (CDR) VK-
      CDR2
<220> FEATURE:
<221> NAME/KEY: V_region
<222> LOCATION: (283)..(309)
<223> OTHER INFORMATION: complementarity determining region (CDR) VK-
      CDR3

<400> SEQUENCE: 35 tgc gat att gtg atg act cag tct cca ctc tcc ctg ccc gtc acc cct      48
Cys Asp Ile Val Met Thr Gln Ser Pro Leu Ser Leu Pro Val Thr Pro
1               5                   10                  15 gga gag ccg gcc tcc atc tcc tgc agg tct agt cag agc ctc ctc cag      96
Gly Glu Pro Ala Ser Ile Ser Cys Arg Ser Ser Gln Ser Leu Leu Gln
            20                  25                  30 agt aat gga tac acc tat ttg gat tgg tac ctg cag aag cca ggg cag     144
Ser Asn Gly Tyr Thr Tyr Leu Asp Trp Tyr Leu Gln Lys Pro Gly Gln
        35                  40                  45 tct cca cag ctc ctg atc tat ttg ggt tct aat cgg gcc tcc ggg gtc     192
Ser Pro Gln Leu Leu Ile Tyr Leu Gly Ser Asn Arg Ala Ser Gly Val
    50                  55                  60
```

```
cct gac agg ttc agt ggc agt gga tca ggc aca gat ttt aca ctg aaa    240
Pro Asp Arg Phe Ser Gly Ser Gly Ser Gly Thr Asp Phe Thr Leu Lys
 65              70                  75                  80 atc agc aga gtg gag gct gag gat gtt ggg gtt tat tac tgc atg caa    288
Ile Ser Arg Val Glu Ala Glu Asp Val Gly Val Tyr Tyr Cys Met Gln
             85                  90                  95 gct cta caa act ccg ctc act ttc ggc gga ggg acc aag gtg gag atc    336
Ala Leu Gln Thr Pro Leu Thr Phe Gly Gly Gly Thr Lys Val Glu Ile
            100                 105                 110 aaa                                                                339
Lys

<210> SEQ ID NO 36
<211> LENGTH: 113
<212> TYPE: PRT
<213> ORGANISM: Homo sapiens

<400> SEQUENCE: 36

Cys Asp Ile Val Met Thr Gln Ser Pro Leu Ser Leu Pro Val Thr Pro
 1               5                  10                  15

Gly Glu Pro Ala Ser Ile Ser Cys Arg Ser Ser Gln Ser Leu Leu Gln
             20                  25                  30

Ser Asn Gly Tyr Thr Tyr Leu Asp Trp Tyr Leu Gln Lys Pro Gly Gln
         35                  40                  45

Ser Pro Gln Leu Leu Ile Tyr Leu Gly Ser Asn Arg Ala Ser Gly Val
     50                  55                  60

Pro Asp Arg Phe Ser Gly Ser Gly Ser Gly Thr Asp Phe Thr Leu Lys
 65              70                  75                  80

Ile Ser Arg Val Glu Ala Glu Asp Val Gly Val Tyr Tyr Cys Met Gln
             85                  90                  95

Ala Leu Gln Thr Pro Leu Thr Phe Gly Gly Gly Thr Lys Val Glu Ile
            100                 105                 110

Lys

<210> SEQ ID NO 37
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-308.24E11-VH variable heavy chain (VH)
      sequence
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(348)
<223> OTHER INFORMATION: complementarity determining region (CDR) VH-
      CDR3

<400> SEQUENCE: 37
```

```
tgc cag gtg cag ctg cag gag tcg ggc cca gga ctg gtg aag cct tcg        48
Cys Gln Val Gln Leu Gln Glu Ser Gly Pro Gly Leu Val Lys Pro Ser
1               5                   10                  15 gag acc ctg tcc ctc acc tgc act gtc tct act act tcc ctc aga agt        96
Glu Thr Leu Ser Leu Thr Cys Thr Val Ser Thr Thr Ser Leu Arg Ser
                20                  25                  30 tat ttc tgg agt tgg atc cgg cag ccc cca ggg aag ggg ctg gag tgg       144
Tyr Phe Trp Ser Trp Ile Arg Gln Pro Pro Gly Lys Gly Leu Glu Trp
            35                  40                  45 att ggg tat gtc tat tac agt ggg agt acc atc tac aat ccg tcc ctc       192
Ile Gly Tyr Val Tyr Tyr Ser Gly Ser Thr Ile Tyr Asn Pro Ser Leu
        50                  55                  60 aag aat cga gtc acc ata tcc ata gac acg tcc aag aac cag ttc tcc       240
Lys Asn Arg Val Thr Ile Ser Ile Asp Thr Ser Lys Asn Gln Phe Ser
65                  70                  75                  80 ctg aac ctg cgc tct gtg acc gct gcg gat acg gcc atg tat ttc tgt       288
Leu Asn Leu Arg Ser Val Thr Ala Ala Asp Thr Ala Met Tyr Phe Cys
                85                  90                  95 gcg aga ggc gtc ccg gct gag act gat gcg cgg gac ttc ccg ccc tac       336
Ala Arg Gly Val Pro Ala Glu Thr Asp Ala Arg Asp Phe Pro Pro Tyr
            100                 105                 110 tac ttt gat cac tgg ggc cag gga acc ctg gtc acc gtc tcc tcg           381
Tyr Phe Asp His Trp Gly Gln Gly Thr Leu Val Thr Val Ser Ser
        115                 120                 125

<210> SEQ ID NO 38
<211> LENGTH: 127
<212> TYPE: PRT
<213> ORGANISM: Homo sapiens

<400> SEQUENCE: 38

Cys Gln Val Gln Leu Gln Glu Ser Gly Pro Gly Leu Val Lys Pro Ser
1               5                   10                  15

Glu Thr Leu Ser Leu Thr Cys Thr Val Ser Thr Thr Ser Leu Arg Ser
                20                  25                  30

Tyr Phe Trp Ser Trp Ile Arg Gln Pro Pro Gly Lys Gly Leu Glu Trp
            35                  40                  45

Ile Gly Tyr Val Tyr Tyr Ser Gly Ser Thr Ile Tyr Asn Pro Ser Leu
        50                  55                  60

Lys Asn Arg Val Thr Ile Ser Ile Asp Thr Ser Lys Asn Gln Phe Ser
65                  70                  75                  80

Leu Asn Leu Arg Ser Val Thr Ala Ala Asp Thr Ala Met Tyr Phe Cys
                85                  90                  95

Ala Arg Gly Val Pro Ala Glu Thr Asp Ala Arg Asp Phe Pro Pro Tyr
            100                 105                 110

Tyr Phe Asp His Trp Gly Gln Gly Thr Leu Val Thr Val Ser Ser
        115                 120                 125

<210> SEQ ID NO 39
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-308.24E11 VK variable light-kappa chain (VK)
      sequence
<220> FEATURE:
<221> NAME/KEY: V_region
<222> LOCATION: (73)..(105)
<223> OTHER INFORMATION: complementarity determining region (CDR) VK-
```

CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 39

```
tgc gac atc cag ttg acc cag tct cca tcc tcc ctg tct gcg tca gta    48
Cys Asp Ile Gln Leu Thr Gln Ser Pro Ser Ser Leu Ser Ala Ser Val
1               5                   10                  15 gga aac aga atc acc ttc act tgc cag gcg agt cag gac att aga tat    96
Gly Asn Arg Ile Thr Phe Thr Cys Gln Ala Ser Gln Asp Ile Arg Tyr
            20                  25                  30 tat tta aat tgg tat cag cag aaa cca ggg aaa gcc cct aaa ctc ctg   144
Tyr Leu Asn Trp Tyr Gln Gln Lys Pro Gly Lys Ala Pro Lys Leu Leu
        35                  40                  45 atc tac gat gtg tcc aat ttg gat aca ggg gtg cca cca agg ttc agt   192
Ile Tyr Asp Val Ser Asn Leu Asp Thr Gly Val Pro Pro Arg Phe Ser
    50                  55                  60 gga agt gga tct ggg aca aat ttc act ttc acc atc agc agc ctg cag   240
Gly Ser Gly Ser Gly Thr Asn Phe Thr Phe Thr Ile Ser Ser Leu Gln
65                  70                  75                  80 cct gaa gat att gca gtt tat tac tgt caa cag tat gaa gga ctc cct   288
Pro Glu Asp Ile Ala Val Tyr Tyr Cys Gln Gln Tyr Glu Gly Leu Pro
                85                  90                  95 gtg acc ttc ggc ggg ggg acc aag gtg gag atc aaa                    324
Val Thr Phe Gly Gly Gly Thr Lys Val Glu Ile Lys
            100                 105
```

<210> SEQ ID NO 40
<211> LENGTH: 108
<212> TYPE: PRT
<213> ORGANISM: Homo sapiens

<400> SEQUENCE: 40

```
Cys Asp Ile Gln Leu Thr Gln Ser Pro Ser Ser Leu Ser Ala Ser Val
1               5                   10                  15

Gly Asn Arg Ile Thr Phe Thr Cys Gln Ala Ser Gln Asp Ile Arg Tyr
            20                  25                  30

Tyr Leu Asn Trp Tyr Gln Gln Lys Pro Gly Lys Ala Pro Lys Leu Leu
        35                  40                  45

Ile Tyr Asp Val Ser Asn Leu Asp Thr Gly Val Pro Pro Arg Phe Ser
    50                  55                  60

Gly Ser Gly Ser Gly Thr Asn Phe Thr Phe Thr Ile Ser Ser Leu Gln
65                  70                  75                  80

Pro Glu Asp Ile Ala Val Tyr Tyr Cys Gln Gln Tyr Glu Gly Leu Pro
                85                  90                  95

Val Thr Phe Gly Gly Gly Thr Lys Val Glu Ile Lys
            100                 105
```

<210> SEQ ID NO 41
<211> LENGTH: 324
<212> TYPE: DNA
<213> ORGANISM: Homo sapiens
<220> FEATURE:
<221> NAME/KEY: CDS
<222> LOCATION: (1)..(324)

<223> OTHER INFORMATION: NI-308.24E11 VK-PIMC variable light-kappa chain
(VK) sequence after correction of primer induced mutations
<220> FEATURE:
<221> NAME/KEY: V_region
<222> LOCATION: (73)..(105)
<223> OTHER INFORMATION: complementarity determining region (CDR) VK-
CDR1
<220> FEATURE:
<221> NAME/KEY: V_region
<222> LOCATION: (151)..(171)
<223> OTHER INFORMATION: complementarity determining region (CDR) VK-
CDR2
<220> FEATURE:
<221> NAME/KEY: V_region
<222> LOCATION: (268)..(294)
<223> OTHER INFORMATION: complementarity determining region (CDR) VK-
CDR3

<400> SEQUENCE: 41

```
tgc gac atc cag atg acc cag tct cca tcc tcc ctg tct gcg tca gta      48
Cys Asp Ile Gln Met Thr Gln Ser Pro Ser Ser Leu Ser Ala Ser Val
1               5                   10                  15 gga aac aga atc acc ttc act tgc cag gcg agt cag gac att aga tat      96
Gly Asn Arg Ile Thr Phe Thr Cys Gln Ala Ser Gln Asp Ile Arg Tyr
            20                  25                  30 tat tta aat tgg tat cag cag aaa cca ggg aaa gcc cct aaa ctc ctg     144
Tyr Leu Asn Trp Tyr Gln Gln Lys Pro Gly Lys Ala Pro Lys Leu Leu
        35                  40                  45 atc tac gat gtg tcc aat ttg gat aca ggg gtg cca cca agg ttc agt     192
Ile Tyr Asp Val Ser Asn Leu Asp Thr Gly Val Pro Pro Arg Phe Ser
    50                  55                  60 gga agt gga tct ggg aca aat ttc act ttc acc atc agc agc ctg cag     240
Gly Ser Gly Ser Gly Thr Asn Phe Thr Phe Thr Ile Ser Ser Leu Gln
65                  70                  75                  80 cct gaa gat att gca gtt tat tac tgt caa cag tat gaa gga ctc cct     288
Pro Glu Asp Ile Ala Val Tyr Tyr Cys Gln Gln Tyr Glu Gly Leu Pro
                85                  90                  95 gtg acc ttc ggc ggg ggg acc aag gtg gag atc aaa                     324
Val Thr Phe Gly Gly Gly Thr Lys Val Glu Ile Lys
            100                 105
```

<210> SEQ ID NO 42
<211> LENGTH: 108
<212> TYPE: PRT
<213> ORGANISM: Homo sapiens

<400> SEQUENCE: 42

```
Cys Asp Ile Gln Met Thr Gln Ser Pro Ser Ser Leu Ser Ala Ser Val
1               5                   10                  15

Gly Asn Arg Ile Thr Phe Thr Cys Gln Ala Ser Gln Asp Ile Arg Tyr
            20                  25                  30

Tyr Leu Asn Trp Tyr Gln Gln Lys Pro Gly Lys Ala Pro Lys Leu Leu
        35                  40                  45

Ile Tyr Asp Val Ser Asn Leu Asp Thr Gly Val Pro Pro Arg Phe Ser
    50                  55                  60

Gly Ser Gly Ser Gly Thr Asn Phe Thr Phe Thr Ile Ser Ser Leu Gln
65                  70                  75                  80

Pro Glu Asp Ile Ala Val Tyr Tyr Cys Gln Gln Tyr Glu Gly Leu Pro
                85                  90                  95

Val Thr Phe Gly Gly Gly Thr Lys Val Glu Ile Lys
            100                 105
```

<210> SEQ ID NO 43

-continued

```
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-308.46E9-VH variable heavy chain (VH)
      sequence
<220> FEATURE:
<221> NAME/KEY: V_region
<222> LOCATION: (79)..(114)
<223> OTHER INFORMATION: complementarity determining region (CDR) VH-
      CDR1
<220> FEATURE:
<221> NAME/KEY: V_region
<222> LOCATION: (94)..(114)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (157)..(204)
<223> OTHER INFORMATION: complementarity determining region (CDR) VH-
      CDR2
<220> FEATURE:
<221> NAME/KEY: V_region
<222> LOCATION: (301)..(339)
<223> OTHER INFORMATION: complementarity determining region (CDR) VH-
      CDR3
```

<400> SEQUENCE: 43

| tgc cag gtg cag ctg cag gag tcg ggc cca gga ctg gtg aag cct tcg | 48 |
|---|---|
| Cys Gln Val Gln Leu Gln Glu Ser Gly Pro Gly Leu Val Lys Pro Ser | |
| 1               5                   10                  15 | |

| gag acc ctg tcc ctc act tgc act gtc tct ggt gcc tcc atc agc ggt | 96 |
|---|---|
| Glu Thr Leu Ser Leu Thr Cys Thr Val Ser Gly Ala Ser Ile Ser Gly | |
|             20                  25                  30 | |

| agt acc tac tac tgg ggc tgg atc cgc cag ccc cca ggg aag ggg ctg | 144 |
|---|---|
| Ser Thr Tyr Tyr Trp Gly Trp Ile Arg Gln Pro Pro Gly Lys Gly Leu | |
|         35                  40                  45 | |

| gag tat att ggg aga atc tac tat agt ggg agc acc tac tac aac ccg | 192 |
|---|---|
| Glu Tyr Ile Gly Arg Ile Tyr Tyr Ser Gly Ser Thr Tyr Tyr Asn Pro | |
|     50                  55                  60 | |

| tcc ctc aag agt cga gcc acc ata tct gta gac acg tcc aag aac cag | 240 |
|---|---|
| Ser Leu Lys Ser Arg Ala Thr Ile Ser Val Asp Thr Ser Lys Asn Gln | |
| 65                  70                  75                  80 | |

| ctc tcc ctg aca ctg agt tct gtg acc gcc gca gat acg gct gtg tat | 288 |
|---|---|
| Leu Ser Leu Thr Leu Ser Ser Val Thr Ala Ala Asp Thr Ala Val Tyr | |
|                 85                  90                  95 | |

| tat tgt gtg aga ccc ttt tac gct ggt tcg ggg aac tcc ccc ttt gac | 336 |
|---|---|
| Tyr Cys Val Arg Pro Phe Tyr Ala Gly Ser Gly Asn Ser Pro Phe Asp | |
|             100                 105                 110 | |

| tac tgg ggc cag gga acc ctg gtc acc gtc tcc tcg | 372 |
|---|---|
| Tyr Trp Gly Gln Gly Thr Leu Val Thr Val Ser Ser | |
|         115                 120 | |

```
<210> SEQ ID NO 44
<211> LENGTH: 124
<212> TYPE: PRT
<213> ORGANISM: Homo sapiens
```

<400> SEQUENCE: 44

Cys Gln Val Gln Leu Gln Glu Ser Gly Pro Gly Leu Val Lys Pro Ser
1               5                   10                  15

Glu Thr Leu Ser Leu Thr Cys Thr Val Ser Gly Ala Ser Ile Ser Gly
            20                  25                  30

Ser Thr Tyr Tyr Trp Gly Trp Ile Arg Gln Pro Pro Gly Lys Gly Leu

```
                    35                  40                  45
Glu Tyr Ile Gly Arg Ile Tyr Tyr Ser Gly Ser Thr Tyr Tyr Asn Pro
 50                  55                  60

Ser Leu Lys Ser Arg Ala Thr Ile Ser Val Asp Thr Ser Lys Asn Gln
 65                  70                  75                  80

Leu Ser Leu Thr Leu Ser Ser Val Thr Ala Ala Asp Thr Ala Val Tyr
                 85                  90                  95

Tyr Cys Val Arg Pro Phe Tyr Ala Gly Ser Gly Asn Ser Pro Phe Asp
            100                 105                 110

Tyr Trp Gly Gln Gly Thr Leu Val Thr Val Ser Ser
        115                 120

<210> SEQ ID NO 45
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-308.46E9 VK variable light-kappa chain (VK)
      sequence
<220> FEATURE:
<221> NAME/KEY: V_region
<222> LOCATION: (73)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 45 tgc gaa att gtg ctg act cag tct cca gcc acc gtg tct gtg tct cca      48
Cys Glu Ile Val Leu Thr Gln Ser Pro Ala Thr Val Ser Val Ser Pro
  1               5                  10                  15 ggg gag aga gcc acc ctc tcc tgc agg gcc agc cag agt gtt agc acc      96
Gly Glu Arg Ala Thr Leu Ser Cys Arg Ala Ser Gln Ser Val Ser Thr
             20                  25                  30 aac tta gcc tgg tac cag cag aaa cct ggc cag cct ccc agg ctc ctc     144
Asn Leu Ala Trp Tyr Gln Gln Lys Pro Gly Gln Pro Pro Arg Leu Leu
         35                  40                  45 att tat ggt gca tcc acc agg gcc act ggt atc cca gcc agg ttc agt     192
Ile Tyr Gly Ala Ser Thr Arg Ala Thr Gly Ile Pro Ala Arg Phe Ser
 50                  55                  60 ggc agt ggg tct ggg gca gag ttc acc ctc acc atc agc agc ctg cag     240
Gly Ser Gly Ser Gly Ala Glu Phe Thr Leu Thr Ile Ser Ser Leu Gln
 65                  70                  75                  80 tct gaa gat ttt gtt gtt tat tac tgt cag caa tat aat aac tgg cct     288
Ser Glu Asp Phe Val Val Tyr Tyr Cys Gln Gln Tyr Asn Asn Trp Pro
                 85                  90                  95 ccg gct ttc ggc gga ggg acc aag gtg gaa atc aaa                     324
Pro Ala Phe Gly Gly Gly Thr Lys Val Glu Ile Lys
            100                 105

<210> SEQ ID NO 46
<211> LENGTH: 108
<212> TYPE: PRT
<213> ORGANISM: Homo sapiens
```

-continued

```
<400> SEQUENCE: 46

Cys Glu Ile Val Leu Thr Gln Ser Pro Ala Thr Val Ser Val Ser Pro
1               5                  10                  15

Gly Glu Arg Ala Thr Leu Ser Cys Arg Ala Ser Gln Ser Val Ser Thr
            20                  25                  30

Asn Leu Ala Trp Tyr Gln Gln Lys Pro Gly Gln Pro Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Ala Glu Phe Thr Leu Thr Ile Ser Ser Leu Gln
65                  70                  75                  80

Ser Glu Asp Phe Val Val Tyr Tyr Cys Gln Gln Tyr Asn Asn Trp Pro
                85                  90                  95

Pro Ala Phe Gly Gly Gly Thr Lys Val Glu Ile Lys
            100                 105

<210> SEQ ID NO 47
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-308.46E9 VH-PIMC variable heavy chain (VH)
      sequence after correction of primer induced mutations
<220> FEATURE:
<221> NAME/KEY: V_region
<222> LOCATION: (79)..(114)
<223> OTHER INFORMATION: complementarity determining region (CDR) VH-
      CDR1
<220> FEATURE:
<221> NAME/KEY: V_region
<222> LOCATION: (94)..(114)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (157)..(204)
<223> OTHER INFORMATION: complementarity determining region (CDR) VH-
      CDR2
<220> FEATURE:
<221> NAME/KEY: V_region
<222> LOCATION: (301)..(339)
<223> OTHER INFORMATION: complementarity determining region (CDR) VH-
      CDR3

<400> SEQUENCE: 47 tgc cag ctg cag ctg cag gag tcg ggc cca gga ctg gtg aag cct tcg      48
Cys Gln Leu Gln Leu Gln Glu Ser Gly Pro Gly Leu Val Lys Pro Ser
1               5                  10                  15 gag acc ctg tcc ctc act tgc act gtc tct ggt gcc tcc atc agc ggt      96
Glu Thr Leu Ser Leu Thr Cys Thr Val Ser Gly Ala Ser Ile Ser Gly
            20                  25                  30 agt acc tac tac tgg ggc tgg atc cgc cag ccc cca ggg aag ggg ctg     144
Ser Thr Tyr Tyr Trp Gly Trp Ile Arg Gln Pro Pro Gly Lys Gly Leu
        35                  40                  45 gag tat att ggg aga atc tac tat agt ggg agc acc tac tac aac ccg     192
Glu Tyr Ile Gly Arg Ile Tyr Tyr Ser Gly Ser Thr Tyr Tyr Asn Pro
    50                  55                  60 tcc ctc aag agt cga gcc acc ata tct gta gac acg tcc aag aac cag     240
Ser Leu Lys Ser Arg Ala Thr Ile Ser Val Asp Thr Ser Lys Asn Gln
65                  70                  75                  80 ctc tcc ctg aca ctg agt tct gtg acc gcc gca gat acg gct gtg tat     288
Leu Ser Leu Thr Leu Ser Ser Val Thr Ala Ala Asp Thr Ala Val Tyr
```

```
                                85                  90                  95
tat tgt gtg aga ccc ttt tac gct ggt tcg ggg aac tcc ccc ttt gac         336
Tyr Cys Val Arg Pro Phe Tyr Ala Gly Ser Gly Asn Ser Pro Phe Asp
        100                 105                 110 tac tgg ggc cag gga acc ctg gtc acc gtc tcc tcg                         372
Tyr Trp Gly Gln Gly Thr Leu Val Thr Val Ser Ser
        115                 120

<210> SEQ ID NO 48
<211> LENGTH: 124
<212> TYPE: PRT
<213> ORGANISM: Homo sapiens

<400> SEQUENCE: 48

Cys Gln Leu Gln Leu Gln Glu Ser Gly Pro Gly Leu Val Lys Pro Ser
1               5                   10                  15

Glu Thr Leu Ser Leu Thr Cys Thr Val Ser Gly Ala Ser Ile Ser Gly
            20                  25                  30

Ser Thr Tyr Tyr Trp Gly Trp Ile Arg Gln Pro Pro Gly Lys Gly Leu
        35                  40                  45

Glu Tyr Ile Gly Arg Ile Tyr Tyr Ser Gly Ser Thr Tyr Tyr Asn Pro
    50                  55                  60

Ser Leu Lys Ser Arg Ala Thr Ile Ser Val Asp Thr Ser Lys Asn Gln
65                  70                  75                  80

Leu Ser Leu Thr Leu Ser Ser Val Thr Ala Ala Asp Thr Ala Val Tyr
                85                  90                  95

Tyr Cys Val Arg Pro Phe Tyr Ala Gly Ser Gly Asn Ser Pro Phe Asp
            100                 105                 110

Tyr Trp Gly Gln Gly Thr Leu Val Thr Val Ser Ser
        115                 120

<210> SEQ ID NO 49
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-308.46E9 VK-PIMC variable light-kappa chain
      (VK) sequence after correction of primer induced mutations
<220> FEATURE:
<221> NAME/KEY: V_region
<222> LOCATION: (73)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 49 tgc gaa ata gtg atg acg cag tct cca gcc acc gtg tct gtg tct cca        48
Cys Glu Ile Val Met Thr Gln Ser Pro Ala Thr Val Ser Val Ser Pro
1               5                   10                  15 ggg gag aga gcc acc ctc tcc tgc agg gcc agc cag agt gtt agc acc        96
Gly Glu Arg Ala Thr Leu Ser Cys Arg Ala Ser Gln Ser Val Ser Thr
            20                  25                  30 aac tta gcc tgg tac cag cag aaa cct ggc cag cct ccc agg ctc ctc        144
```

```
                Asn Leu Ala Trp Tyr Gln Gln Lys Pro Gly Gln Pro Arg Leu Leu
                             35                  40                  45 att tat ggt gca tcc acc agg gcc act ggt atc cca gcc agg ttc agt        192
Ile Tyr Gly Ala Ser Thr Arg Ala Thr Gly Ile Pro Ala Arg Phe Ser
 50                  55                  60 ggc agt ggg tct ggg gca gag ttc acc ctc acc atc agc agc ctg cag        240
Gly Ser Gly Ser Gly Ala Glu Phe Thr Leu Thr Ile Ser Ser Leu Gln
 65                  70                  75                  80 tct gaa gat ttt gtt gtt tat tac tgt cag caa tat aat aac tgg cct        288
Ser Glu Asp Phe Val Val Tyr Tyr Cys Gln Gln Tyr Asn Asn Trp Pro
                     85                  90                  95 ccg gct ttc ggc gga ggg acc aag gtg gag atc aaa                        324
Pro Ala Phe Gly Gly Gly Thr Lys Val Glu Ile Lys
                 100                 105

<210> SEQ ID NO 50
<211> LENGTH: 108
<212> TYPE: PRT
<213> ORGANISM: Homo sapiens

<400> SEQUENCE: 50

Cys Glu Ile Val Met Thr Gln Ser Pro Ala Thr Val Ser Val Ser Pro
 1               5                  10                  15

Gly Glu Arg Ala Thr Leu Ser Cys Arg Ala Ser Gln Ser Val Ser Thr
             20                  25                  30

Asn Leu Ala Trp Tyr Gln Gln Lys Pro Gly Gln Pro Pro Arg Leu Leu
             35                  40                  45

Ile Tyr Gly Ala Ser Thr Arg Ala Thr Gly Ile Pro Ala Arg Phe Ser
 50                  55                  60

Gly Ser Gly Ser Gly Ala Glu Phe Thr Leu Thr Ile Ser Ser Leu Gln
 65                  70                  75                  80

Ser Glu Asp Phe Val Val Tyr Tyr Cys Gln Gln Tyr Asn Asn Trp Pro
                     85                  90                  95

Pro Ala Phe Gly Gly Gly Thr Lys Val Glu Ile Lys
                 100                 105

<210> SEQ ID NO 51
<211> LENGTH: 387
<212> TYPE: DNA
<213> ORGANISM: Homo sapiens
<220> FEATURE:
<221> NAME/KEY: CDS
<222> LOCATION: (1)..(387)
<223> OTHER INFORMATION: NI-308.6B11-VH variable heavy chain (VH)
      sequence
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(354)
<223> OTHER INFORMATION: complementarity determining region (CDR) VH-
      CDR3
```

```
<400> SEQUENCE: 51 tgc gag gtg cag ctg gtg cag tct ggg gct gag gtg aag agg cct ggg      48
Cys Glu Val Gln Leu Val Gln Ser Gly Ala Glu Val Lys Arg Pro Gly
1               5                   10                  15 gcc tca gtg aag gtc tcc tgc aag gtt tcc gga tac acc ctc act gaa      96
Ala Ser Val Lys Val Ser Cys Lys Val Ser Gly Tyr Thr Leu Thr Glu
            20                  25                  30 tta tcc atg cac tgg gtg cga cag gct cct gga aaa ggg ctt gag tgg     144
Leu Ser Met His Trp Val Arg Gln Ala Pro Gly Lys Gly Leu Glu Trp
        35                  40                  45 atg gga ggt ttt gat cct gaa gat ggt gaa aca gtc tac gca cag aag     192
Met Gly Gly Phe Asp Pro Glu Asp Gly Glu Thr Val Tyr Ala Gln Lys
    50                  55                  60 ttc cag ggc aga gtc acc atg acc gag gac aca tct aca gac aca gcc     240
Phe Gln Gly Arg Val Thr Met Thr Glu Asp Thr Ser Thr Asp Thr Ala
65                  70                  75                  80 tac atg gag ctg agc agc ctg aga tct gag gac acg gcc ttg tat cac     288
Tyr Met Glu Leu Ser Ser Leu Arg Ser Glu Asp Thr Ala Leu Tyr His
                85                  90                  95 tgt gca aca tac ggc agc agc tgg cac tgg aat gag gga aat gag ggg     336
Cys Ala Thr Tyr Gly Ser Ser Trp His Trp Asn Glu Gly Asn Glu Gly
            100                 105                 110 tcc tac tac ttt gac tac tgg ggc cag gga acc ctg gtc acc gtc tcc     384
Ser Tyr Tyr Phe Asp Tyr Trp Gly Gln Gly Thr Leu Val Thr Val Ser
        115                 120                 125 tcg                                                                  387
Ser

<210> SEQ ID NO 52
<211> LENGTH: 129
<212> TYPE: PRT
<213> ORGANISM: Homo sapiens

<400> SEQUENCE: 52

Cys Glu Val Gln Leu Val Gln Ser Gly Ala Glu Val Lys Arg Pro Gly
1               5                   10                  15

Ala Ser Val Lys Val Ser Cys Lys Val Ser Gly Tyr Thr Leu Thr Glu
            20                  25                  30

Leu Ser Met His Trp Val Arg Gln Ala Pro Gly Lys Gly Leu Glu Trp
        35                  40                  45

Met Gly Gly Phe Asp Pro Glu Asp Gly Glu Thr Val Tyr Ala Gln Lys
    50                  55                  60

Phe Gln Gly Arg Val Thr Met Thr Glu Asp Thr Ser Thr Asp Thr Ala
65                  70                  75                  80

Tyr Met Glu Leu Ser Ser Leu Arg Ser Glu Asp Thr Ala Leu Tyr His
                85                  90                  95

Cys Ala Thr Tyr Gly Ser Ser Trp His Trp Asn Glu Gly Asn Glu Gly
            100                 105                 110

Ser Tyr Tyr Phe Asp Tyr Trp Gly Gln Gly Thr Leu Val Thr Val Ser
        115                 120                 125

Ser

<210> SEQ ID NO 53
<211> LENGTH: 324
<212> TYPE: DNA
<213> ORGANISM: Homo sapiens
<220> FEATURE:
<221> NAME/KEY: CDS
```

```
<222> LOCATION: (1)..(324)
<223> OTHER INFORMATION: NI-308.6B11 VK variable light-kappa chain (VK)
      sequence
<220> FEATURE:
<221> NAME/KEY: V_region
<222> LOCATION: (73)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 53 tgc gac atc cag atg acc cag tct cca tcc tcc ctg tct gca tct gta        48
Cys Asp Ile Gln Met Thr Gln Ser Pro Ser Ser Leu Ser Ala Ser Val
1               5                   10                  15 gga gac aga gtc acc atc act tgc cag gcg agt cag gac att agc att        96
Gly Asp Arg Val Thr Ile Thr Cys Gln Ala Ser Gln Asp Ile Ser Ile
            20                  25                  30 tat tta aat tgg tat cag caa aaa cca ggg aaa gcc cct aag ctc ctg       144
Tyr Leu Asn Trp Tyr Gln Gln Lys Pro Gly Lys Ala Pro Lys Leu Leu
        35                  40                  45 atc tac gat gca tcc aat ttg gaa aca ggg gtc cca tca agg ttc agt       192
Ile Tyr Asp Ala Ser Asn Leu Glu Thr Gly Val Pro Ser Arg Phe Ser
    50                  55                  60 gga agt gga tct ggg aca gat ttt act ttc acc atc agc ggc ctg cag       240
Gly Ser Gly Ser Gly Thr Asp Phe Thr Phe Thr Ile Ser Gly Leu Gln
65                  70                  75                  80 cct gaa gat gtt gca aga tat tat tgt caa cag tat gat gat ctc ccc       288
Pro Glu Asp Val Ala Arg Tyr Tyr Cys Gln Gln Tyr Asp Asp Leu Pro
                85                  90                  95 atc acc ttc ggc caa ggg aca cga ctg gag att aaa                       324
Ile Thr Phe Gly Gln Gly Thr Arg Leu Glu Ile Lys
            100                 105

<210> SEQ ID NO 54
<211> LENGTH: 108
<212> TYPE: PRT
<213> ORGANISM: Homo sapiens

<400> SEQUENCE: 54

Cys Asp Ile Gln Met Thr Gln Ser Pro Ser Ser Leu Ser Ala Ser Val
1               5                   10                  15

Gly Asp Arg Val Thr Ile Thr Cys Gln Ala Ser Gln Asp Ile Ser Ile
            20                  25                  30

Tyr Leu Asn Trp Tyr Gln Gln Lys Pro Gly Lys Ala Pro Lys Leu Leu
        35                  40                  45

Ile Tyr Asp Ala Ser Asn Leu Glu Thr Gly Val Pro Ser Arg Phe Ser
    50                  55                  60

Gly Ser Gly Ser Gly Thr Asp Phe Thr Phe Thr Ile Ser Gly Leu Gln
65                  70                  75                  80

Pro Glu Asp Val Ala Arg Tyr Tyr Cys Gln Gln Tyr Asp Asp Leu Pro
                85                  90                  95

Ile Thr Phe Gly Gln Gly Thr Arg Leu Glu Ile Lys
            100                 105
```

```
<210> SEQ ID NO 55
<211> LENGTH: 387
<212> TYPE: DNA
<213> ORGANISM: Homo sapiens
<220> FEATURE:
<221> NAME/KEY: CDS
<222> LOCATION: (1)..(387)
<223> OTHER INFORMATION: NI-308.6B11 VH-PIMC variable heavy chain (VH)
      sequence after correction of primer induced mutations
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(354)
<223> OTHER INFORMATION: complementarity determining region (CDR) VH-
      CDR3

<400> SEQUENCE: 55 tgc cag gtc cag ctg gta cag tct ggg gct gag gtg aag agg cct ggg      48
Cys Gln Val Gln Leu Val Gln Ser Gly Ala Glu Val Lys Arg Pro Gly
1               5                   10                  15 gcc tca gtg aag gtc tcc tgc aag gtt tcc gga tac acc ctc act gaa      96
Ala Ser Val Lys Val Ser Cys Lys Val Ser Gly Tyr Thr Leu Thr Glu
            20                  25                  30 tta tcc atg cac tgg gtg cga cag gct cct gga aaa ggg ctt gag tgg     144
Leu Ser Met His Trp Val Arg Gln Ala Pro Gly Lys Gly Leu Glu Trp
        35                  40                  45 atg gga ggt ttt gat cct gaa gat ggt gaa aca gtc tac gca cag aag     192
Met Gly Gly Phe Asp Pro Glu Asp Gly Glu Thr Val Tyr Ala Gln Lys
    50                  55                  60 ttc cag ggc aga gtc acc atg acc gag gac aca tct aca gac aca gcc     240
Phe Gln Gly Arg Val Thr Met Thr Glu Asp Thr Ser Thr Asp Thr Ala
65                  70                  75                  80 tac atg gag ctg agc agc ctg aga tct gag gac acg gcc ttg tat cac     288
Tyr Met Glu Leu Ser Ser Leu Arg Ser Glu Asp Thr Ala Leu Tyr His
                85                  90                  95 tgt gca aca tac ggc agc agc tgg cac tgg aat gag gga aat gag ggg     336
Cys Ala Thr Tyr Gly Ser Ser Trp His Trp Asn Glu Gly Asn Glu Gly
            100                 105                 110 tcc tac tac ttt gac tac tgg ggc cag gga acc ctg gtc acc gtc tcc     384
Ser Tyr Tyr Phe Asp Tyr Trp Gly Gln Gly Thr Leu Val Thr Val Ser
        115                 120                 125 tcg                                                                  387
Ser

<210> SEQ ID NO 56
<211> LENGTH: 129
<212> TYPE: PRT
<213> ORGANISM: Homo sapiens

<400> SEQUENCE: 56

Cys Gln Val Gln Leu Val Gln Ser Gly Ala Glu Val Lys Arg Pro Gly
1               5                   10                  15
```

```
Ala Ser Val Lys Val Ser Cys Lys Val Ser Gly Tyr Thr Leu Thr Glu
            20                  25                  30

Leu Ser Met His Trp Val Arg Gln Ala Pro Gly Lys Gly Leu Glu Trp
        35                  40                  45

Met Gly Gly Phe Asp Pro Glu Asp Gly Glu Thr Val Tyr Ala Gln Lys
    50                  55                  60

Phe Gln Gly Arg Val Thr Met Thr Glu Asp Thr Ser Thr Asp Thr Ala
65                  70                  75                  80

Tyr Met Glu Leu Ser Ser Leu Arg Ser Glu Asp Thr Ala Leu Tyr His
                85                  90                  95

Cys Ala Thr Tyr Gly Ser Ser Trp His Trp Asn Glu Gly Asn Glu Gly
            100                 105                 110

Ser Tyr Tyr Phe Asp Tyr Trp Gly Gln Gly Thr Leu Val Thr Val Ser
        115                 120                 125

Ser

<210> SEQ ID NO 57
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-308.46F8-VH variable heavy chain (VH)
      sequence
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(345)
<223> OTHER INFORMATION: complementarity determining region (CDR) VH-
      CDR3

<400> SEQUENCE: 57 tgc cag gtg cag ctg gtg gag tct ggg gga ggt gtg gta cgg cct ggg    48
Cys Gln Val Gln Leu Val Glu Ser Gly Gly Gly Val Val Arg Pro Gly
1               5                   10                  15 ggg tcc ctg aga ctc tcc tgt aca gcc tct gga ttc acg ttt gat gaa    96
Gly Ser Leu Arg Leu Ser Cys Thr Ala Ser Gly Phe Thr Phe Asp Glu
            20                  25                  30 tat ggc atg agc tgg gtc cgc caa gtt cca ggg aag ggg ctg gag tgg   144
Tyr Gly Met Ser Trp Val Arg Gln Val Pro Gly Lys Gly Leu Glu Trp
        35                  40                  45 gtc tct ggc att aat tgg aat gga gca acc aca cgt tat gca gac tct   192
Val Ser Gly Ile Asn Trp Asn Gly Ala Thr Thr Arg Tyr Ala Asp Ser
    50                  55                  60 gtg aag ggc cga ttc acc atc tcc aga gac aac gcc aag aac tcc ctc   240
Val Lys Gly Arg Phe Thr Ile Ser Arg Asp Asn Ala Lys Asn Ser Leu
65                  70                  75                  80 tat ctg caa atg aac agt ctg aga gcc gag gac acg gcc ttg tat cac   288
Tyr Leu Gln Met Asn Ser Leu Arg Ala Glu Asp Thr Ala Leu Tyr His
```

-continued

```
                 85                  90                  95
tgt gcg aga gat ggg tgt agg aat acc agc tgc tat atc tgg gac tgg      336
Cys Ala Arg Asp Gly Cys Arg Asn Thr Ser Cys Tyr Ile Trp Asp Trp
            100                 105                 110 ttc gat ccc tgg ggc cag gga acc ctg gtc acc gtc tcc tcg              378
Phe Asp Pro Trp Gly Gln Gly Thr Leu Val Thr Val Ser Ser
        115                 120                 125

<210> SEQ ID NO 58
<211> LENGTH: 126
<212> TYPE: PRT
<213> ORGANISM: Homo sapiens

<400> SEQUENCE: 58

Cys Gln Val Gln Leu Val Glu Ser Gly Gly Gly Val Val Arg Pro Gly
1               5                   10                  15

Gly Ser Leu Arg Leu Ser Cys Thr Ala Ser Gly Phe Thr Phe Asp Glu
            20                  25                  30

Tyr Gly Met Ser Trp Val Arg Gln Val Pro Gly Lys Gly Leu Glu Trp
        35                  40                  45

Val Ser Gly Ile Asn Trp Asn Gly Ala Thr Thr Arg Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Leu Tyr His
                85                  90                  95

Cys Ala Arg Asp Gly Cys Arg Asn Thr Ser Cys Tyr Ile Trp Asp Trp
            100                 105                 110

Phe Asp Pro Trp Gly Gln Gly Thr Leu Val Thr Val Ser Ser
        115                 120                 125

<210> SEQ ID NO 59
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-308.46F8 VL variable light-lambda chain (VL)
      sequence
<220> FEATURE:
<221> NAME/KEY: V_region
<222> LOCATION: (70)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(303)
<223> OTHER INFORMATION: complementarity determining region (CDR) VL-
      CDR3

<400> SEQUENCE: 59 tgc cag tct gtg ttg acg cag ccg ccc tca gtg tct gcg gcc cca gga      48
Cys Gln Ser Val Leu Thr Gln Pro Pro Ser Val Ser Ala Ala Pro Gly
1               5                   10                  15 cag aag gtc acc atc tcc tgc tct gga agc agc tcc aac att gga aat      96
Gln Lys Val Thr Ile Ser Cys Ser Gly Ser Ser Ser Asn Ile Gly Asn
            20                  25                  30 aat tat gta tgc tgg tac cag aac ctc cca gga aca gcc ccc aaa ctc      144
```

```
                Asn Tyr Val Cys Trp Tyr Gln Asn Leu Pro Gly Thr Ala Pro Lys Leu
                                35                  40                  45 ctc att tat gac gat aat aag cga ccc tca ggg att cct gac cga ttc            192
Leu Ile Tyr Asp Asp Asn Lys Arg Pro Ser Gly Ile Pro Asp Arg Phe
     50                  55                  60 tct ggc tcc aag tct ggc acg tca gcc acc ctg ggc atc acc gga ctc            240
Ser Gly Ser Lys Ser Gly Thr Ser Ala Thr Leu Gly Ile Thr Gly Leu
 65                  70                  75                  80 cag act ggg gac gag gcc gat tat tac tgc gga aca tgg gac agc agc            288
Gln Thr Gly Asp Glu Ala Asp Tyr Tyr Cys Gly Thr Trp Asp Ser Ser
                     85                  90                  95 ctg agt gtt gtg gta ttc ggc gga ggg acc aag ctg acc gtc cta                333
Leu Ser Val Val Val Phe Gly Gly Gly Thr Lys Leu Thr Val Leu
                100                 105                 110

<210> SEQ ID NO 60
<211> LENGTH: 111
<212> TYPE: PRT
<213> ORGANISM: Homo sapiens

<400> SEQUENCE: 60

Cys Gln Ser Val Leu Thr Gln Pro Pro Ser Val Ser Ala Ala Pro Gly
 1               5                  10                  15

Gln Lys Val Thr Ile Ser Cys Ser Gly Ser Ser Ser Asn Ile Gly Asn
                20                  25                  30

Asn Tyr Val Cys Trp Tyr Gln Asn Leu Pro Gly Thr Ala Pro Lys Leu
                35                  40                  45

Leu Ile Tyr Asp Asp Asn Lys Arg Pro Ser Gly Ile Pro Asp Arg Phe
     50                  55                  60

Ser Gly Ser Lys Ser Gly Thr Ser Ala Thr Leu Gly Ile Thr Gly Leu
 65                  70                  75                  80

Gln Thr Gly Asp Glu Ala Asp Tyr Tyr Cys Gly Thr Trp Asp Ser Ser
                     85                  90                  95

Leu Ser Val Val Val Phe Gly Gly Gly Thr Lys Leu Thr Val Leu
                100                 105                 110

<210> SEQ ID NO 61
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-308.46F8 VH-PIMC variable heavy chain (VH)
      sequence after correction of primer induced mutations
<220> FEATURE:
<221> NAME/KEY: V_region
<222> LOCATION: (79)..(108)
<223> OTHER INFORMATION: complementarity determining region (CDR) VH-
      CDR1
<220> FEATURE:
<221> NAME/KEY: V_region
<222> LOCATION: (94)..(108)
<223> OTHER INFORMATION: complementarity determining region (CDR) VH-
      CDR1 according to the numbering conventions set forth by Kabat et
      al. 1983
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(345)
<223> OTHER INFORMATION: complementarity determining region (CDR) VH-
      CDR3
```

<400> SEQUENCE: 61

| tgc | gag | gtg | cag | ctg | gtg | gag | tct | ggg | gga | ggt | gtg | gta | cgg | cct | ggg | 48 |
|---|---|---|---|---|---|---|---|---|---|---|---|---|---|---|---|---|
| Cys | Glu | Val | Gln | Leu | Val | Glu | Ser | Gly | Gly | Gly | Val | Val | Arg | Pro | Gly | |
| 1 | | | | 5 | | | | | 10 | | | | | 15 | | |

| ggg | tcc | ctg | aga | ctc | tcc | tgt | aca | gcc | tct | gga | ttc | acg | ttt | gat | gaa | 96 |
|---|---|---|---|---|---|---|---|---|---|---|---|---|---|---|---|---|
| Gly | Ser | Leu | Arg | Leu | Ser | Cys | Thr | Ala | Ser | Gly | Phe | Thr | Phe | Asp | Glu | |
| | | | 20 | | | | | 25 | | | | | 30 | | | |

| tat | ggc | atg | agc | tgg | gtc | cgc | caa | gtt | cca | ggg | aag | ggg | ctg | gag | tgg | 144 |
|---|---|---|---|---|---|---|---|---|---|---|---|---|---|---|---|---|
| Tyr | Gly | Met | Ser | Trp | Val | Arg | Gln | Val | Pro | Gly | Lys | Gly | Leu | Glu | Trp | |
| | | 35 | | | | | 40 | | | | | 45 | | | | |

| gtc | tct | ggc | att | aat | tgg | aat | gga | gca | acc | aca | cgt | tat | gca | gac | tct | 192 |
|---|---|---|---|---|---|---|---|---|---|---|---|---|---|---|---|---|
| Val | Ser | Gly | Ile | Asn | Trp | Asn | Gly | Ala | Thr | Thr | Arg | Tyr | Ala | Asp | Ser | |
| 50 | | | | | 55 | | | | | 60 | | | | | | |

| gtg | aag | ggc | cga | ttc | acc | atc | tcc | aga | gac | aac | gcc | aag | aac | tcc | ctc | 240 |
|---|---|---|---|---|---|---|---|---|---|---|---|---|---|---|---|---|
| Val | Lys | Gly | Arg | Phe | Thr | Ile | Ser | Arg | Asp | Asn | Ala | Lys | Asn | Ser | Leu | |
| 65 | | | | 70 | | | | | 75 | | | | | 80 | | |

| tat | ctg | caa | atg | aac | agt | ctg | aga | gcc | gag | gac | acg | gcc | ttg | tat | cac | 288 |
|---|---|---|---|---|---|---|---|---|---|---|---|---|---|---|---|---|
| Tyr | Leu | Gln | Met | Asn | Ser | Leu | Arg | Ala | Glu | Asp | Thr | Ala | Leu | Tyr | His | |
| | | | | 85 | | | | | 90 | | | | | 95 | | |

| tgt | gcg | aga | gat | ggg | tgt | agg | aat | acc | agc | tgc | tat | atc | tgg | gac | tgg | 336 |
|---|---|---|---|---|---|---|---|---|---|---|---|---|---|---|---|---|
| Cys | Ala | Arg | Asp | Gly | Cys | Arg | Asn | Thr | Ser | Cys | Tyr | Ile | Trp | Asp | Trp | |
| | | | 100 | | | | | 105 | | | | | 110 | | | |

| ttc | gat | ccc | tgg | ggc | cag | gga | acc | ctg | gtc | acc | gtc | tcc | tcg | | | 378 |
|---|---|---|---|---|---|---|---|---|---|---|---|---|---|---|---|---|
| Phe | Asp | Pro | Trp | Gly | Gln | Gly | Thr | Leu | Val | Thr | Val | Ser | Ser | | | |
| | | 115 | | | | | 120 | | | | | 125 | | | | |

<210> SEQ ID NO 62
<211> LENGTH: 126
<212> TYPE: PRT
<213> ORGANISM: Homo sapiens

<400> SEQUENCE: 62

Cys Glu Val Gln Leu Val Glu Ser Gly Gly Gly Val Val Arg Pro Gly
1               5                   10                  15

Gly Ser Leu Arg Leu Ser Cys Thr Ala Ser Gly Phe Thr Phe Asp Glu
            20                  25                  30

Tyr Gly Met Ser Trp Val Arg Gln Val Pro Gly Lys Gly Leu Glu Trp
        35                  40                  45

Val Ser Gly Ile Asn Trp Asn Gly Ala Thr Thr Arg Tyr Ala Asp Ser
50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Leu Tyr His
                85                  90                  95

Cys Ala Arg Asp Gly Cys Arg Asn Thr Ser Cys Tyr Ile Trp Asp Trp
            100                 105                 110

Phe Asp Pro Trp Gly Gln Gly Thr Leu Val Thr Val Ser Ser
        115                 120                 125

<210> SEQ ID NO 63
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-308.4M1-VH variable heavy chain (VH)
      sequence
<220> FEATURE:
<221> NAME/KEY: V_region

```
<222> LOCATION: (94)..(108)
<223> OTHER INFORMATION: complementarity determining region (CDR) VH-
      CDR1
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(348)
<223> OTHER INFORMATION: complementarity determining region (CDR) VH-
      CDR3

<400> SEQUENCE: 63 tgc gag gtg cag ctg gtg gag act ggg gga ggc gtg gtc cag ccg ggg        48
Cys Glu Val Gln Leu Val Glu Thr Gly Gly Gly Val Val Gln Pro Gly
1               5                   10                  15 ggg tcc ctg cga ctc tcc tgt gaa gcc tct gga ttc acc atc ggc acc        96
Gly Ser Leu Arg Leu Ser Cys Glu Ala Ser Gly Phe Thr Ile Gly Thr
            20                  25                  30 tat gcc atg cac tgg gtc cgc cag ttt cca ggc aag ggc ctg gat tgg       144
Tyr Ala Met His Trp Val Arg Gln Phe Pro Gly Lys Gly Leu Asp Trp
        35                  40                  45 gtg gca gta ata tcg ttc gat gga act act gag tac tac aca gac gcc       192
Val Ala Val Ile Ser Phe Asp Gly Thr Thr Glu Tyr Tyr Thr Asp Ala
    50                  55                  60 gtg aag ggc cga ttc acc atc tcc aga gac aat gcc aag aac aca ctg       240
Val Lys Gly Arg Phe Thr Ile Ser Arg Asp Asn Ala Lys Asn Thr Leu
65                  70                  75                  80 tat ctg caa atg aac tac ttg aga ggt gac gac acg gct ata tat ttc       288
Tyr Leu Gln Met Asn Tyr Leu Arg Gly Asp Asp Thr Ala Ile Tyr Phe
                85                  90                  95 tgt gcg cga gat ttc acc tcc tcg ggg gag acc ggt tcg tgg aca caa       336
Cys Ala Arg Asp Phe Thr Ser Ser Gly Glu Thr Gly Ser Trp Thr Gln
            100                 105                 110 gta cct gat ctc tgg ggc cag ggc acc ctg gtc acc gtc tcc tcg           381
Val Pro Asp Leu Trp Gly Gln Gly Thr Leu Val Thr Val Ser Ser
        115                 120                 125

<210> SEQ ID NO 64
<211> LENGTH: 127
<212> TYPE: PRT
<213> ORGANISM: Homo sapiens

<400> SEQUENCE: 64

Cys Glu Val Gln Leu Val Glu Thr Gly Gly Gly Val Val Gln Pro Gly
1               5                   10                  15

Gly Ser Leu Arg Leu Ser Cys Glu Ala Ser Gly Phe Thr Ile Gly Thr
            20                  25                  30

Tyr Ala Met His Trp Val Arg Gln Phe Pro Gly Lys Gly Leu Asp Trp
        35                  40                  45

Val Ala Val Ile Ser Phe Asp Gly Thr Thr Glu Tyr Tyr Thr Asp Ala
    50                  55                  60

Val Lys Gly Arg Phe Thr Ile Ser Arg Asp Asn Ala Lys Asn Thr Leu
65                  70                  75                  80

Tyr Leu Gln Met Asn Tyr Leu Arg Gly Asp Asp Thr Ala Ile Tyr Phe
                85                  90                  95

Cys Ala Arg Asp Phe Thr Ser Ser Gly Glu Thr Gly Ser Trp Thr Gln
            100                 105                 110

Val Pro Asp Leu Trp Gly Gln Gly Thr Leu Val Thr Val Ser Ser
        115                 120                 125
```

<210> SEQ ID NO 65
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-308.4M1 VK variable light-kappa chain (VK) sequence
<220> FEATURE:
<221> NAME/KEY: V_region
<222> LOCATION: (73)..(105)
<223> OTHER INFORMATION: complementarity determining region (CDR) VK-CDR1
<220> FEATURE:
<221> NAME/KEY: V_region
<222> LOCATION: (151)..(171)
<223> OTHER INFORMATION: complementarity determining region (CDR) VK-CDR2
<220> FEATURE:
<221> NAME/KEY: V_region
<222> LOCATION: (268)..(297)
<223> OTHER INFORMATION: complementarity determining region (CDR) VK-CDR3

<400> SEQUENCE: 65

```
tgc gaa att gtg atg aca cag tct cca gcc acc ctg tct ctg tct cca      48
Cys Glu Ile Val Met Thr Gln Ser Pro Ala Thr Leu Ser Leu Ser Pro
1               5                  10                  15 ggg gaa aga gcc acg ctc tcc tgc agg gcc agt cag agt gtt act aaa      96
Gly Glu Arg Ala Thr Leu Ser Cys Arg Ala Ser Gln Ser Val Thr Lys
            20                  25                  30 tac tta gcc tgg tac caa cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat gat gta tct tac agg gcc gct ggc acc cca gcc agg ttc agt     192
Ile Tyr Asp Val Ser Tyr Arg Ala Ala Gly Thr Pro Ala Arg Phe Ser
    50                  55                  60 ggc agt ggg tct ggg aca gac ttc act ctc acc atc agc agc cta gag     240
Gly Ser Gly Ser Gly Thr Asp Phe Thr Leu Thr Ile Ser Ser Leu Glu
65                  70                  75                  80 cct gaa gat ttt gca gtt tat tac tgt cac caa cgt agc agc tgg cct     288
Pro Glu Asp Phe Ala Val Tyr Tyr Cys His Gln Arg Ser Ser Trp Pro
                85                  90                  95 ccg gtc act ttc ggc gga ggg acc aag gtg gag atc aaa                 327
Pro Val Thr Phe Gly Gly Gly Thr Lys Val Glu Ile Lys
            100                 105
```

<210> SEQ ID NO 66
<211> LENGTH: 109
<212> TYPE: PRT
<213> ORGANISM: Homo sapiens

<400> SEQUENCE: 66

```
Cys Glu Ile Val Met Thr Gln Ser Pro Ala Thr Leu Ser Leu Ser Pro
1               5                  10                  15

Gly Glu Arg Ala Thr Leu Ser Cys Arg Ala Ser Gln Ser Val Thr Lys
            20                  25                  30

Tyr Leu Ala Trp Tyr Gln Gln Lys Pro Gly Gln Ala Pro Arg Leu Leu
        35                  40                  45

Ile Tyr Asp Val Ser Tyr Arg Ala Ala Gly Thr Pro Ala Arg Phe Ser
    50                  55                  60

Gly Ser Gly Ser Gly Thr Asp Phe Thr Leu Thr Ile Ser Ser Leu Glu
65                  70                  75                  80
```

```
Pro Glu Asp Phe Ala Val Tyr Tyr Cys His Gln Arg Ser Ser Trp Pro
                85                  90                  95

Pro Val Thr Phe Gly Gly Gly Thr Lys Val Glu Ile Lys
            100                 105

<210> SEQ ID NO 67
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-308.4M1 VH-PIMC variable heavy chain (VH)
      sequence after correction of primer induced mutations
<220> FEATURE:
<221> NAME/KEY: V_region
<222> LOCATION: (94)..(108)
<223> OTHER INFORMATION: complementarity determining region (CDR) VH-
      CDR1
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(348)
<223> OTHER INFORMATION: complementarity determining region (CDR) VH-
      CDR3

<400> SEQUENCE: 67 tgc cag gtg cag ctg gtg gag tct ggg gga ggc gtg gtc cag ccg ggg      48
Cys Gln Val Gln Leu Val Glu Ser Gly Gly Gly Val Val Gln Pro Gly
1               5                   10                  15 ggg tcc ctg cga ctc tcc tgt gaa gcc tct gga ttc acc atc ggc acc      96
Gly Ser Leu Arg Leu Ser Cys Glu Ala Ser Gly Phe Thr Ile Gly Thr
                20                  25                  30 tat gcc atg cac tgg gtc cgc cag ttt cca ggc aag ggc ctg gat tgg     144
Tyr Ala Met His Trp Val Arg Gln Phe Pro Gly Lys Gly Leu Asp Trp
            35                  40                  45 gtg gca gta ata tcg ttc gat gga act act gag tac tac aca gac gcc     192
Val Ala Val Ile Ser Phe Asp Gly Thr Thr Glu Tyr Tyr Thr Asp Ala
        50                  55                  60 gtg aag ggc cga ttc acc atc tcc aga gac aat gcc aag aac aca ctg     240
Val Lys Gly Arg Phe Thr Ile Ser Arg Asp Asn Ala Lys Asn Thr Leu
65                  70                  75                  80 tat ctg caa atg aac tac ttg aga ggt gac gac acg gct ata tat ttc     288
Tyr Leu Gln Met Asn Tyr Leu Arg Gly Asp Asp Thr Ala Ile Tyr Phe
                85                  90                  95 tgt gcg cga gat ttc acc tcc tcg ggg gag acc ggt tcg tgg aca caa     336
Cys Ala Arg Asp Phe Thr Ser Ser Gly Glu Thr Gly Ser Trp Thr Gln
            100                 105                 110 gta cct gat ctc tgg ggc cag ggc acc ctg gtc acc gtc tcc tcg         381
Val Pro Asp Leu Trp Gly Gln Gly Thr Leu Val Thr Val Ser Ser
        115                 120                 125

<210> SEQ ID NO 68
<211> LENGTH: 127
<212> TYPE: PRT
<213> ORGANISM: Homo sapiens

<400> SEQUENCE: 68

Cys Gln Val Gln Leu Val Glu Ser Gly Gly Gly Val Val Gln Pro Gly
1               5                   10                  15

Gly Ser Leu Arg Leu Ser Cys Glu Ala Ser Gly Phe Thr Ile Gly Thr
```

```
                     20                  25                  30
Tyr Ala Met His Trp Val Arg Gln Phe Pro Gly Lys Gly Leu Asp Trp
             35                  40                  45

Val Ala Val Ile Ser Phe Asp Gly Thr Thr Glu Tyr Tyr Thr Asp Ala
 50                  55                  60

Val Lys Gly Arg Phe Thr Ile Ser Arg Asp Asn Ala Lys Asn Thr Leu
 65                  70                  75                  80

Tyr Leu Gln Met Asn Tyr Leu Arg Gly Asp Asp Thr Ala Ile Tyr Phe
                 85                  90                  95

Cys Ala Arg Asp Phe Thr Ser Ser Gly Glu Thr Gly Ser Trp Thr Gln
                100                 105                 110

Val Pro Asp Leu Trp Gly Gln Gly Thr Leu Val Thr Val Ser Ser
            115                 120                 125
```

```
<210> SEQ ID NO 69
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-308.4M1 VK-PIMC variable light-kappa chain
      (VK) sequence after correction of primer induced mutations
<220> FEATURE:
<221> NAME/KEY: V_region
<222> LOCATION: (73)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(297)
<223> OTHER INFORMATION: complementarity determining region (CDR) VK-
      CDR3

<400> SEQUENCE: 69 tgc gaa att gtg ttg aca cag tct cca gcc acc ctg tct ctg tct cca      48
Cys Glu Ile Val Leu Thr Gln Ser Pro Ala Thr Leu Ser Leu Ser Pro
 1               5                  10                  15 ggg gaa aga gcc acg ctc tcc tgc agg gcc agt cag agt gtt act aaa      96
Gly Glu Arg Ala Thr Leu Ser Cys Arg Ala Ser Gln Ser Val Thr Lys
             20                  25                  30 tac tta gcc tgg tac caa cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat gat gta tct tac agg gcc gct ggc acc cca gcc agg ttc agt     192
Ile Tyr Asp Val Ser Tyr Arg Ala Ala Gly Thr Pro Ala Arg Phe Ser
 50                  55                  60 ggc agt ggg tct ggg aca gac ttc act ctc acc atc agc agc cta gag     240
Gly Ser Gly Ser Gly Thr Asp Phe Thr Leu Thr Ile Ser Ser Leu Glu
 65                  70                  75                  80 cct gaa gat ttt gca gtt tat tac tgt cac caa cgt agc agc tgg cct     288
Pro Glu Asp Phe Ala Val Tyr Tyr Cys His Gln Arg Ser Ser Trp Pro
                 85                  90                  95 ccg gtc act ttc ggc gga ggg acc aag gtg gag atc aaa                 327
Pro Val Thr Phe Gly Gly Gly Thr Lys Val Glu Ile Lys
                100                 105

<210> SEQ ID NO 70
<211> LENGTH: 109
```

```
<212> TYPE: PRT
<213> ORGANISM: Homo sapiens

<400> SEQUENCE: 70

Cys Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Thr Lys
                20                  25                  30

Tyr Leu Ala Trp Tyr Gln Gln Lys Pro Gly Gln Ala Pro Arg Leu Leu
            35                  40                  45

Ile Tyr Asp Val Ser Tyr Arg Ala Ala Gly Thr Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Arg Ser Ser Trp Pro
                85                  90                  95

Pro Val Thr Phe Gly Gly Gly Thr Lys Val Glu Ile Lys
                100                 105

<210> SEQ ID NO 71
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-308.12A3-VH variable heavy chain (VH)
      sequence
<220> FEATURE:
<221> NAME/KEY: V_region
<222> LOCATION: (94)..(108)
<223> OTHER INFORMATION: complementarity determining region (CDR) VH-
      CDR1
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(348)
<223> OTHER INFORMATION: complementarity determining region (CDR) VH-
      CDR3

<400> SEQUENCE: 71 tgc gag gtg cag ctg gtg gag act ggg gga ggc ttg gta cag cct gga       48
Cys Glu Val Gln Leu Val Glu Thr Gly Gly Gly Leu Val Gln Pro Gly
1               5                   10                  15 ggg tcc ctg aga ctc tcc tgc gta ggc tct gga ttt ctc ttc agt gat       96
Gly Ser Leu Arg Leu Ser Cys Val Gly Ser Gly Phe Leu Phe Ser Asp
                20                  25                  30 ttt gaa atg gac tgg gtc cgc cag gct cca ggg aag ggg ctg gag tgg      144
Phe Glu Met Asp Trp Val Arg Gln Ala Pro Gly Lys Gly Leu Glu Trp
            35                  40                  45 att tca tat att agt ggt gac ggt aat atc ata tat cag aca gac tct      192
Ile Ser Tyr Ile Ser Gly Asp Gly Asn Ile Ile Tyr Gln Thr Asp Ser
    50                  55                  60 gtg aag ggc cga ttc acc atc tcc aga gac aac gcc aag aat tca ctg      240
Val Lys Gly Arg Phe Thr Ile Ser Arg Asp Asn Ala Lys Asn Ser Leu
65                  70                  75                  80 ttt cta caa atg gac agc ctg acc gtc gag gac acg gct gta tat tac      288
Phe Leu Gln Met Asp Ser Leu Thr Val Glu Asp Thr Ala Val Tyr Tyr
                85                  90                  95 tgt gcg aga gac gcc cgt gaa aac tgt ggt ggt gac tgc tat tcc acg      336
```

```
Cys Ala Arg Asp Ala Arg Glu Asn Cys Gly Gly Asp Cys Tyr Ser Thr
            100                 105                 110 tcc ttt gat ttt tgg ggc cag ggc acc ctg gtc acc gtc tcc tcg        381
Ser Phe Asp Phe Trp Gly Gln Gly Thr Leu Val Thr Val Ser Ser
            115                 120                 125

<210> SEQ ID NO 72
<211> LENGTH: 127
<212> TYPE: PRT
<213> ORGANISM: Homo sapiens

<400> SEQUENCE: 72

Cys Glu Val Gln Leu Val Glu Thr Gly Gly Gly Leu Val Gln Pro Gly
1               5                   10                  15

Gly Ser Leu Arg Leu Ser Cys Val Gly Ser Gly Phe Leu Phe Ser Asp
            20                  25                  30

Phe Glu Met Asp Trp Val Arg Gln Ala Pro Gly Lys Gly Leu Glu Trp
        35                  40                  45

Ile Ser Tyr Ile Ser Gly Asp Gly Asn Ile Ile Tyr Gln Thr Asp Ser
    50                  55                  60

Val Lys Gly Arg Phe Thr Ile Ser Arg Asp Asn Ala Lys Asn Ser Leu
65                  70                  75                  80

Phe Leu Gln Met Asp Ser Leu Thr Val Glu Asp Thr Ala Val Tyr Tyr
                85                  90                  95

Cys Ala Arg Asp Ala Arg Glu Asn Cys Gly Gly Asp Cys Tyr Ser Thr
            100                 105                 110

Ser Phe Asp Phe Trp Gly Gln Gly Thr Leu Val Thr Val Ser Ser
        115                 120                 125

<210> SEQ ID NO 73
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: NI-308.12A3 VK  variable light-kappa chain (VK)
      sequence
<220> FEATURE:
<221> NAME/KEY: V_region
<222> LOCATION: (73)..(123)
<223> OTHER INFORMATION: complementarity determining region (CDR) VK-
      CDR1
<220> FEATURE:
<221> NAME/KEY: V_region
<222> LOCATION: (169)..(189)
<223> OTHER INFORMATION: complementarity determining region (CDR) VK-
      CDR2
<220> FEATURE:
<221> NAME/KEY: V_region
<222> LOCATION: (286)..(312)
<223> OTHER INFORMATION: complementarity determining region (CDR) VK-
      CDR3

<400> SEQUENCE: 73 tgc gac atc cag atg acc cag tct cca gac tcc ctg gct gtg tct ctg     48
Cys Asp Ile Gln Met Thr Gln Ser Pro Asp Ser Leu Ala Val Ser Leu
1               5                   10                  15 ggc gag agg gcc acc atc aac tgc aag tcc agc cag agt ctt tta tac    96
Gly Glu Arg Ala Thr Ile Asn Cys Lys Ser Ser Gln Ser Leu Leu Tyr
            20                  25                  30 act gcc aac aat agg aac tac tta gcc tgg tac cag aaa aaa gca gga   144
Thr Ala Asn Asn Arg Asn Tyr Leu Ala Trp Tyr Gln Lys Lys Ala Gly
        35                  40                  45
```

-continued

```
cag cct cct aag ctc ctc att cac tgg gca tct acc cgg gca tcc ggg      192
Gln Pro Pro Lys Leu Leu Ile His Trp Ala Ser Thr Arg Ala Ser Gly
    50                  55                  60 gtc cct gac cga ttc agt ggc agc ggg tct ggg aca gat ttc att ctc      240
Val Pro Asp Arg Phe Ser Gly Ser Gly Ser Gly Thr Asp Phe Ile Leu
65                  70                  75                  80 acc atc agc agc ctg cag gct gaa gat gtg gca gtt tat ttt tgt caa      288
Thr Ile Ser Ser Leu Gln Ala Glu Asp Val Ala Val Tyr Phe Cys Gln
                85                  90                  95 cat tat tat aat tct ccc cgg acg ttc ggc caa ggg acc aag gtg gag      336
His Tyr Tyr Asn Ser Pro Arg Thr Phe Gly Gln Gly Thr Lys Val Glu
            100                 105                 110 atc aaa                                                              342
Ile Lys
```

<210> SEQ ID NO 74
<211> LENGTH: 114
<212> TYPE: PRT
<213> ORGANISM: Homo sapiens

<400> SEQUENCE: 74

```
Cys Asp Ile Gln Met Thr Gln Ser Pro Asp Ser Leu Ala Val Ser Leu
1               5                   10                  15

Gly Glu Arg Ala Thr Ile Asn Cys Lys Ser Ser Gln Ser Leu Leu Tyr
            20                  25                  30

Thr Ala Asn Asn Arg Asn Tyr Leu Ala Trp Tyr Gln Lys Lys Ala Gly
        35                  40                  45

Gln Pro Pro Lys Leu Leu Ile His Trp Ala Ser Thr Arg Ala Ser Gly
    50                  55                  60

Val Pro Asp Arg Phe Ser Gly Ser Gly Ser Gly Thr Asp Phe Ile Leu
65                  70                  75                  80

Thr Ile Ser Ser Leu Gln Ala Glu Asp Val Ala Val Tyr Phe Cys Gln
                85                  90                  95

His Tyr Tyr Asn Ser Pro Arg Thr Phe Gly Gln Gly Thr Lys Val Glu
            100                 105                 110

Ile Lys
```

<210> SEQ ID NO 75
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-308.12A3 VH-PIMC variable heavy chain (VH) sequence after correction of primer induced mutations
<220> FEATURE:
<221> NAME/KEY: V_region
<222> LOCATION: (94)..(108)
<223> OTHER INFORMATION: complementarity determining region (CDR) VH-CDR1
<220> FEATURE:
<221> NAME/KEY: V_region
<222> LOCATION: (151)..(201)
<223> OTHER INFORMATION: complementarity determining region (CDR) VH-CDR2
<220> FEATURE:
<221> NAME/KEY: V_region
<222> LOCATION: (298)..(348)
<223> OTHER INFORMATION: complementarity determining region (CDR) VH-CDR3

<400> SEQUENCE: 75

```
tgc gag gtg cag ctg gtg gag tct ggg gga ggc ttg gta cag cct gga      48
```

```
                Cys Glu Val Gln Leu Val Glu Ser Gly Gly Gly Leu Val Gln Pro Gly
                1               5                   10                  15 ggg tcc ctg aga ctc tcc tgc gta ggc tct gga ttt ctc ttc agt gat            96
Gly Ser Leu Arg Leu Ser Cys Val Gly Ser Gly Phe Leu Phe Ser Asp
                20                  25                  30 ttt gaa atg gac tgg gtc cgc cag gct cca ggg aag ggg ctg gag tgg           144
Phe Glu Met Asp Trp Val Arg Gln Ala Pro Gly Lys Gly Leu Glu Trp
            35                  40                  45 att tca tat att agt ggt gac ggt aat atc ata tat cag aca gac tct           192
Ile Ser Tyr Ile Ser Gly Asp Gly Asn Ile Ile Tyr Gln Thr Asp Ser
        50                  55                  60 gtg aag ggc cga ttc acc atc tcc aga gac aac gcc aag aat tca ctg           240
Val Lys Gly Arg Phe Thr Ile Ser Arg Asp Asn Ala Lys Asn Ser Leu
    65                  70                  75                  80 ttt cta caa atg gac agc ctg acc gtc gag gac acg gct gta tat tac           288
Phe Leu Gln Met Asp Ser Leu Thr Val Glu Asp Thr Ala Val Tyr Tyr
                85                  90                  95 tgt gcg aga gac gcc cgt gaa aac tgt ggt ggt gac tgc tat tcc acg           336
Cys Ala Arg Asp Ala Arg Glu Asn Cys Gly Gly Asp Cys Tyr Ser Thr
            100                 105                 110 tcc ttt gat ttt tgg ggc cag ggc acc ctg gtc acc gtc tcc tcg               381
Ser Phe Asp Phe Trp Gly Gln Gly Thr Leu Val Thr Val Ser Ser
        115                 120                 125

<210> SEQ ID NO 76
<211> LENGTH: 127
<212> TYPE: PRT
<213> ORGANISM: Homo sapiens

<400> SEQUENCE: 76

Cys Glu Val Gln Leu Val Glu Ser Gly Gly Gly Leu Val Gln Pro Gly
1               5                   10                  15

Gly Ser Leu Arg Leu Ser Cys Val Gly Ser Gly Phe Leu Phe Ser Asp
            20                  25                  30

Phe Glu Met Asp Trp Val Arg Gln Ala Pro Gly Lys Gly Leu Glu Trp
        35                  40                  45

Ile Ser Tyr Ile Ser Gly Asp Gly Asn Ile Ile Tyr Gln Thr Asp Ser
    50                  55                  60

Val Lys Gly Arg Phe Thr Ile Ser Arg Asp Asn Ala Lys Asn Ser Leu
65                  70                  75                  80

Phe Leu Gln Met Asp Ser Leu Thr Val Glu Asp Thr Ala Val Tyr Tyr
                85                  90                  95

Cys Ala Arg Asp Ala Arg Glu Asn Cys Gly Gly Asp Cys Tyr Ser Thr
            100                 105                 110

Ser Phe Asp Phe Trp Gly Gln Gly Thr Leu Val Thr Val Ser Ser
        115                 120                 125

<210> SEQ ID NO 77
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: NI-308.12A3 VK-PIMC variable light-kappa chain
      (VK) sequence after correction of primer induced mutations
<220> FEATURE:
<221> NAME/KEY: V_region
<222> LOCATION: (73)..(123)
<223> OTHER INFORMATION: complementarity determining region (CDR) VK-
      CDR1
<220> FEATURE:
```

```
<221> NAME/KEY: V_region
<222> LOCATION: (169)..(189)
<223> OTHER INFORMATION: complementarity determining region (CDR) VK-
      CDR2
<220> FEATURE:
<221> NAME/KEY: V_region
<222> LOCATION: (286)..(312)
<223> OTHER INFORMATION: complementarity determining region (CDR) VK-
      CDR3

<400> SEQUENCE: 77 tgc gac atc gtg atg acc cag tct cca gac tcc ctg gct gtg tct ctg      48
Cys Asp Ile Val Met Thr Gln Ser Pro Asp Ser Leu Ala Val Ser Leu
1               5                   10                  15 ggc gag agg gcc acc atc aac tgc aag tcc agc cag agt ctt tta tac      96
Gly Glu Arg Ala Thr Ile Asn Cys Lys Ser Ser Gln Ser Leu Leu Tyr
            20                  25                  30 act gcc aac aat agg aac tac tta gcc tgg tac cag aaa aaa gca gga     144
Thr Ala Asn Asn Arg Asn Tyr Leu Ala Trp Tyr Gln Lys Lys Ala Gly
        35                  40                  45 cag cct cct aag ctc ctc att cac tgg gca tct acc cgg gca tcc ggg     192
Gln Pro Pro Lys Leu Leu Ile His Trp Ala Ser Thr Arg Ala Ser Gly
    50                  55                  60 gtc cct gac cga ttc agt ggc agc ggg tct ggg aca gat ttc att ctc     240
Val Pro Asp Arg Phe Ser Gly Ser Gly Ser Gly Thr Asp Phe Ile Leu
65                  70                  75                  80 acc atc agc agc ctg cag gct gaa gat gtg gca gtt tat ttt tgt caa     288
Thr Ile Ser Ser Leu Gln Ala Glu Asp Val Ala Val Tyr Phe Cys Gln
                85                  90                  95 cat tat tat aat tct ccc cgg acg ttc ggc caa ggg acc aag gtg gag     336
His Tyr Tyr Asn Ser Pro Arg Thr Phe Gly Gln Gly Thr Lys Val Glu
            100                 105                 110 atc aaa                                                              342
Ile Lys <210> SEQ ID NO 78
<211> LENGTH: 114
<212> TYPE: PRT
<213> ORGANISM: Homo sapiens

<400> SEQUENCE: 78

Cys Asp Ile Val Met Thr Gln Ser Pro Asp Ser Leu Ala Val Ser Leu
1               5                   10                  15

Gly Glu Arg Ala Thr Ile Asn Cys Lys Ser Ser Gln Ser Leu Leu Tyr
            20                  25                  30

Thr Ala Asn Asn Arg Asn Tyr Leu Ala Trp Tyr Gln Lys Lys Ala Gly
        35                  40                  45

Gln Pro Pro Lys Leu Leu Ile His Trp Ala Ser Thr Arg Ala Ser Gly
    50                  55                  60

Val Pro Asp Arg Phe Ser Gly Ser Gly Ser Gly Thr Asp Phe Ile Leu
65                  70                  75                  80

Thr Ile Ser Ser Leu Gln Ala Glu Asp Val Ala Val Tyr Phe Cys Gln
                85                  90                  95

His Tyr Tyr Asn Ser Pro Arg Thr Phe Gly Gln Gly Thr Lys Val Glu
            100                 105                 110

Ile Lys

<210> SEQ ID NO 79
<211> LENGTH: 375
<212> TYPE: DNA
<213> ORGANISM: Homo sapiens
```

```
-continued

<220> FEATURE:
<221> NAME/KEY: CDS
<222> LOCATION: (1)..(375)
<223> OTHER INFORMATION: NI-308.16C10-VH variable heavy chain (VH)
       sequence
<220> FEATURE:
<221> NAME/KEY: V_region
<222> LOCATION: (94)..(108)
<223> OTHER INFORMATION: complementarity determining region (CDR) VH-
       CDR1
<220> FEATURE:
<221> NAME/KEY: V_region
<222> LOCATION: (151)..(201)
<223> OTHER INFORMATION: complementarity determining region (CDR) VH-
       CDR2
<220> FEATURE:
<221> NAME/KEY: V_region
<222> LOCATION: (298)..(342)
<223> OTHER INFORMATION: complementarity determining region (CDR) VH-
       CDR3

<400> SEQUENCE: 79 tgc gag gtg cag ctg gtg gag act ggg gga ggc gtg gtc cag cct ggg    48
Cys Glu Val Gln Leu Val Glu Thr Gly Gly Gly Val Val Gln Pro Gly
1               5                   10                  15 atg tcc ctg agc ctc tcc tgt gca gcg act gga ttc acc ttc agc agt    96
Met Ser Leu Ser Leu Ser Cys Ala Ala Thr Gly Phe Thr Phe Ser Ser
            20                  25                  30 tat ggc atg cac tgg gtc cgc caa ggt cca ggc aag ggg ccg gag tgg    144
Tyr Gly Met His Trp Val Arg Gln Gly Pro Gly Lys Gly Pro Glu Trp
        35                  40                  45 gtg gcg ggt ata tgg tac gat gga aca aat aag tat tat gga gac tcc    192
Val Ala Gly Ile Trp Tyr Asp Gly Thr Asn Lys Tyr Tyr Gly Asp Ser
    50                  55                  60 gtg acg ggc aga gtc acc atc tcc aga gac aac tcc aag aac acg ctg    240
Val Thr Gly Arg Val Thr Ile Ser Arg Asp Asn Ser Lys Asn Thr Leu
65                  70                  75                  80 ttt ctg caa atg atc aac gtg aga gtc gag gac acg gct gtg tat tac    288
Phe Leu Gln Met Ile Asn Val Arg Val Glu Asp Thr Ala Val Tyr Tyr
                85                  90                  95 tgt gtg aag gat gca gag cgc gtc cag aaa tgg gct agt tac att atg    336
Cys Val Lys Asp Ala Glu Arg Val Gln Lys Trp Ala Ser Tyr Ile Met
            100                 105                 110 gac gtg tgg ggc caa ggg acc acg gtc acc gtc tcc tcg                375
Asp Val Trp Gly Gln Gly Thr Thr Val Thr Val Ser Ser
        115                 120                 125

<210> SEQ ID NO 80
<211> LENGTH: 125
<212> TYPE: PRT
<213> ORGANISM: Homo sapiens

<400> SEQUENCE: 80

Cys Glu Val Gln Leu Val Glu Thr Gly Gly Gly Val Val Gln Pro Gly
1               5                   10                  15

Met Ser Leu Ser Leu Ser Cys Ala Ala Thr Gly Phe Thr Phe Ser Ser
            20                  25                  30

Tyr Gly Met His Trp Val Arg Gln Gly Pro Gly Lys Gly Pro Glu Trp
        35                  40                  45

Val Ala Gly Ile Trp Tyr Asp Gly Thr Asn Lys Tyr Tyr Gly Asp Ser
    50                  55                  60

Val Thr Gly Arg Val Thr Ile Ser Arg Asp Asn Ser Lys Asn Thr Leu
65                  70                  75                  80

Phe Leu Gln Met Ile Asn Val Arg Val Glu Asp Thr Ala Val Tyr Tyr
```

```
                85                  90                  95
Cys Val Lys Asp Ala Glu Arg Val Gln Lys Trp Ala Ser Tyr Ile Met
            100                 105                 110

Asp Val Trp Gly Gln Gly Thr Thr Val Thr Val Ser Ser
            115                 120                 125

<210> SEQ ID NO 81
<211> LENGTH: 315
<212> TYPE: DNA
<213> ORGANISM: Homo sapiens
<220> FEATURE:
<221> NAME/KEY: CDS
<222> LOCATION: (1)..(315)
<223> OTHER INFORMATION: NI-308.16C10 VK  variable light-kappa chain
      (VK) sequence
<220> FEATURE:
<221> NAME/KEY: V_region
<222> LOCATION: (73)..(108)
<223> OTHER INFORMATION: complementarity determining region (CDR) VK-
      CDR1
<220> FEATURE:
<221> NAME/KEY: V_region
<222> LOCATION: (154)..(174)
<223> OTHER INFORMATION: complementarity determining region (CDR) VK-
      CDR2
<220> FEATURE:
<221> NAME/KEY: V_region
<222> LOCATION: (271)..(285)
<223> OTHER INFORMATION: complementarity determining region (CDR) VK-
      CDR3

<400> SEQUENCE: 81 tgc gaa att gtg ctg act cag tct cca ggc atc ctg tct ttg tct cga        48
Cys Glu Ile Val Leu Thr Gln Ser Pro Gly Ile Leu Ser Leu Ser Arg
1               5                   10                  15 ggg aat cgg gtc gcc ctc tcc tgc agg gcc agt cgg agt gtt aat agc        96
Gly Asn Arg Val Ala Leu Ser Cys Arg Ala Ser Arg Ser Val Asn Ser
            20                  25                  30 agc tac tta aat tgg tac cag caa aaa cca ggc cag gct ccc aga ctc       144
Ser Tyr Leu Asn Trp Tyr Gln Gln Lys Pro Gly Gln Ala Pro Arg Leu
        35                  40                  45 ctc atc tat ggt gca tct aaa agg gcc act ggc atc tca gac agg ttc       192
Leu Ile Tyr Gly Ala Ser Lys Arg Ala Thr Gly Ile Ser Asp Arg Phe
    50                  55                  60 cgt ggc act ggg tct ggg aca gac ttc act ctc acc gtc gcc aga ctg       240
Arg Gly Thr Gly Ser Gly Thr Asp Phe Thr Leu Thr Val Ala Arg Leu
65                  70                  75                  80 gag cct gaa gat att gcg gtt tac tac tgt cag cac tat ggt gcc ttc       288
Glu Pro Glu Asp Ile Ala Val Tyr Tyr Cys Gln His Tyr Gly Ala Phe
                85                  90                  95 ggc caa ggg acc aag ctg gag atc aaa                                   315
Gly Gln Gly Thr Lys Leu Glu Ile Lys
            100                 105

<210> SEQ ID NO 82
<211> LENGTH: 105
<212> TYPE: PRT
<213> ORGANISM: Homo sapiens

<400> SEQUENCE: 82

Cys Glu Ile Val Leu Thr Gln Ser Pro Gly Ile Leu Ser Leu Ser Arg
1               5                   10                  15

Gly Asn Arg Val Ala Leu Ser Cys Arg Ala Ser Arg Ser Val Asn Ser
            20                  25                  30

Ser Tyr Leu Asn Trp Tyr Gln Gln Lys Pro Gly Gln Ala Pro Arg Leu
```

```
                35                  40                  45
Leu Ile Tyr Gly Ala Ser Lys Arg Ala Thr Gly Ile Ser Asp Arg Phe
        50                  55                  60

Arg Gly Thr Gly Ser Gly Thr Asp Phe Thr Leu Thr Val Ala Arg Leu
65                  70                  75                  80

Glu Pro Glu Asp Ile Ala Val Tyr Tyr Cys Gln His Tyr Gly Ala Phe
                85                  90                  95

Gly Gln Gly Thr Lys Leu Glu Ile Lys
            100                 105

<210> SEQ ID NO 83
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-308.16C10 VH-PIMC variable heavy chain (VH)
      sequence after correction of primer induced mutations
<220> FEATURE:
<221> NAME/KEY: V_region
<222> LOCATION: (94)..(108)
<223> OTHER INFORMATION: complementarity determining region (CDR) VH-
      CDR1
<220> FEATURE:
<221> NAME/KEY: V_region
<222> LOCATION: (151)..(201)
<223> OTHER INFORMATION: complementarity determining region (CDR) VH-
      CDR2
<220> FEATURE:
<221> NAME/KEY: V_region
<222> LOCATION: (298)..(342)
<223> OTHER INFORMATION: complementarity determining region (CDR) VH-
      CDR3

<400> SEQUENCE: 83 tgc cag gtg cag ctg gtg gag tct ggg gga ggc gtg gtc cag cct ggg      48
Cys Gln Val Gln Leu Val Glu Ser Gly Gly Gly Val Val Gln Pro Gly
1               5                   10                  15 atg tcc ctg agc ctc tcc tgt gca gcg act gga ttc acc ttc agc agt      96
Met Ser Leu Ser Leu Ser Cys Ala Ala Thr Gly Phe Thr Phe Ser Ser
            20                  25                  30 tat ggc atg cac tgg gtc cgc caa ggt cca ggc aag ggg ccg gag tgg     144
Tyr Gly Met His Trp Val Arg Gln Gly Pro Gly Lys Gly Pro Glu Trp
        35                  40                  45 gtg gcg ggt ata tgg tac gat gga aca aat aag tat tat gga gac tcc     192
Val Ala Gly Ile Trp Tyr Asp Gly Thr Asn Lys Tyr Tyr Gly Asp Ser
    50                  55                  60 gtg acg ggc aga gtc acc atc tcc aga gac aac tcc aag aac acg ctg     240
Val Thr Gly Arg Val Thr Ile Ser Arg Asp Asn Ser Lys Asn Thr Leu
65                  70                  75                  80 ttt ctg caa atg atc aac gtg aga gtc gag gac acg gct gtg tat tac     288
Phe Leu Gln Met Ile Asn Val Arg Val Glu Asp Thr Ala Val Tyr Tyr
            85                  90                  95 tgt gtg aag gat gca gag cgc gtc cag aaa tgg gct agt tac att atg     336
Cys Val Lys Asp Ala Glu Arg Val Gln Lys Trp Ala Ser Tyr Ile Met
        100                 105                 110 gac gtg tgg ggc caa ggg acc acg gtc acc gtc tcc tcg                 375
Asp Val Trp Gly Gln Gly Thr Thr Val Thr Val Ser Ser
    115                 120                 125

<210> SEQ ID NO 84
<211> LENGTH: 125
<212> TYPE: PRT
<213> ORGANISM: Homo sapiens
```

<400> SEQUENCE: 84

Cys Gln Val Gln Leu Val Glu Ser Gly Gly Val Val Gln Pro Gly
1               5                   10                  15

Met Ser Leu Ser Leu Ser Cys Ala Ala Thr Gly Phe Thr Phe Ser Ser
            20                  25                  30

Tyr Gly Met His Trp Val Arg Gln Gly Pro Gly Lys Gly Pro Glu Trp
        35                  40                  45

Val Ala Gly Ile Trp Tyr Asp Gly Thr Asn Lys Tyr Tyr Gly Asp Ser
50                  55                  60

Val Thr Gly Arg Val Thr Ile Ser Arg Asp Asn Ser Lys Asn Thr Leu
65                  70                  75                  80

Phe Leu Gln Met Ile Asn Val Arg Val Glu Asp Thr Ala Val Tyr Tyr
                85                  90                  95

Cys Val Lys Asp Ala Glu Arg Val Gln Lys Trp Ala Ser Tyr Ile Met
            100                 105                 110

Asp Val Trp Gly Gln Gly Thr Thr Val Thr Val Ser Ser
            115                 120                 125

<210> SEQ ID NO 85
<211> LENGTH: 315
<212> TYPE: DNA
<213> ORGANISM: Homo sapiens
<220> FEATURE:
<221> NAME/KEY: CDS
<222> LOCATION: (1)..(315)
<223> OTHER INFORMATION: NI-308.16C10 VK-PIMC variable light-kappa chain
    (VK) sequence after correction of primer induced mutations
<220> FEATURE:
<221> NAME/KEY: V_region
<222> LOCATION: (73)..(108)
<223> OTHER INFORMATION: complementarity determining region (CDR) VK-
    CDR1
<220> FEATURE:
<221> NAME/KEY: V_region
<222> LOCATION: (154)..(174)
<223> OTHER INFORMATION: complementarity determining region (CDR) VK-
    CDR2
<220> FEATURE:
<221> NAME/KEY: V_region
<222> LOCATION: (271)..(285)
<223> OTHER INFORMATION: complementarity determining region (CDR) VK-
    CDR3

<400> SEQUENCE: 85 tgc gaa att gtg ttg acg cag tct cca ggc acc ctg tct ttg tct cga    48
Cys Glu Ile Val Leu Thr Gln Ser Pro Gly Thr Leu Ser Leu Ser Arg
1               5                   10                  15 ggg aat cgg gtc gcc ctc tcc tgc agg gcc agt cgg agt gtt aat agc    96
Gly Asn Arg Val Ala Leu Ser Cys Arg Ala Ser Arg Ser Val Asn Ser
            20                  25                  30 agc tac tta aat tgg tac cag caa aaa cca ggc cag gct ccc aga ctc   144
Ser Tyr Leu Asn Trp Tyr Gln Gln Lys Pro Gly Gln Ala Pro Arg Leu
        35                  40                  45 ctc atc tat ggt gca tct aaa agg gcc act ggc atc tca gac agg ttc   192
Leu Ile Tyr Gly Ala Ser Lys Arg Ala Thr Gly Ile Ser Asp Arg Phe
50                  55                  60 cgt ggc act ggg tct ggg aca gac ttc act ctc acc gtc gcc aga ctg   240
Arg Gly Thr Gly Ser Gly Thr Asp Phe Thr Leu Thr Val Ala Arg Leu
65                  70                  75                  80 gag cct gaa gat att gcg gtt tac tac tgt cag cac tat ggt gcc ttc   288
Glu Pro Glu Asp Ile Ala Val Tyr Tyr Cys Gln His Tyr Gly Ala Phe
                85                  90                  95

```
ggc caa ggg acc aag gtg gaa atc aaa                              315
Gly Gln Gly Thr Lys Val Glu Ile Lys
            100             105

<210> SEQ ID NO 86
<211> LENGTH: 105
<212> TYPE: PRT
<213> ORGANISM: Homo sapiens

<400> SEQUENCE: 86

Cys Glu Ile Val Leu Thr Gln Ser Pro Gly Thr Leu Ser Leu Ser Arg
1               5                   10                  15

Gly Asn Arg Val Ala Leu Ser Cys Arg Ala Ser Arg Ser Val Asn Ser
                20                  25                  30

Ser Tyr Leu Asn Trp Tyr Gln Gln Lys Pro Gly Gln Ala Pro Arg Leu
        35                  40                  45

Leu Ile Tyr Gly Ala Ser Lys Arg Ala Thr Gly Ile Ser Asp Arg Phe
    50                  55                  60

Arg Gly Thr Gly Ser Gly Thr Asp Phe Thr Leu Thr Val Ala Arg Leu
65                  70                  75                  80

Glu Pro Glu Asp Ile Ala Val Tyr Tyr Cys Gln His Tyr Gly Ala Phe
                85                  90                  95

Gly Gln Gly Thr Lys Val Glu Ile Lys
            100             105
```

UNITED STATES PATENT AND TRADEMARK OFFICE
CERTIFICATE OF CORRECTION

| | | |
|---|---|---|
| PATENT NO. | : 10,392,447 B2 | Page 1 of 1 |
| APPLICATION NO. | : 15/508343 | |
| DATED | : August 27, 2019 | |
| INVENTOR(S) | : Fabio Montrasio and Jan Grimm | |

It is certified that error appears in the above-identified patent and that said Letters Patent is hereby corrected as shown below:

In the Claims

<u>Column 214, Claim 118:</u>
Line 19, delete "83 herein:" and insert -- 83, wherein: --.

Signed and Sealed this
Twelfth Day of November, 2019

Andrei Iancu
*Director of the United States Patent and Trademark Office*